United States Patent
Chen et al.

(10) Patent No.: US 6,806,365 B2
(45) Date of Patent: Oct. 19, 2004

(54) N-ALKANOYLPHENYLALAMINE DERIVATIVES

(75) Inventors: Li Chen, Westfield, NJ (US); Robert William Guthrie, Saddle Brook, NJ (US); Tai-Nang Huang, Lexington, MA (US); Achytharao Sidduri, Livingston, NJ (US); Jefferson Wright Tilley, North Caldwell, NJ (US); Kenneth Gregory Hull, Cambridge, MA (US)

(73) Assignee: Hoffmann-La Rocher Inc., Nutley, NJ (US)

( * ) Notice: Subject to any disclaimer, the term of this patent is extended or adjusted under 35 U.S.C. 154(b) by 0 days.

(21) Appl. No.: 10/117,616

(22) Filed: Apr. 5, 2002

(65) Prior Publication Data

US 2003/0109459 A1 Jun. 12, 2003

Related U.S. Application Data

(62) Division of application No. 09/138,353, filed on Aug. 21, 1998, now Pat. No. 6,455,550.
(60) Provisional application No. 60/056,929, filed on Aug. 22, 1997, and provisional application No. 60/094,591, filed on Jul. 29, 1998.

(51) Int. Cl.⁷ ............................................. C07C 229/02
(52) U.S. Cl. ........................ 544/169; 546/323; 548/214; 548/253; 548/374.1; 548/536; 549/436; 552/10; 558/406; 558/415; 560/30; 562/426; 562/429; 562/430; 562/435; 562/441; 562/448; 562/449
(58) Field of Search .................. 544/169; 546/323; 548/214, 253, 374.1, 536; 549/436; 552/10; 558/406, 415; 560/30; 562/426, 429, 430, 435, 441, 448, 449, 450; 514/19, 239.5, 354, 378, 381, 403, 423, 466, 487, 521, 522, 562, 563

(56) References Cited

U.S. PATENT DOCUMENTS 6,455,550 B1 * 9/2002 Chen et al. .................. 514/341

FOREIGN PATENT DOCUMENTS

| DE | 19548709 | 7/1997 |
|---|---|---|
| DE | 19654483 | 1/1998 |
| WO | WO 95/35296 | 12/1995 |
| WO | WO 96/22966 | 8/1996 |
| WO | WO 97/36859 | 10/1997 |
| WO | WO 97/36862 | 10/1997 |
| WO | 9906435 | 2/1999 |

OTHER PUBLICATIONS

Patani, et al. Chem. Reviews vol. 96, No. 8, 1996 pp. 3147–3176.

Abstract corresponding to DE19654483, 1998.

Abstract corresponding to DE 19548709 (B1), 1997.

* cited by examiner

*Primary Examiner*—Richard L. Raymond
(74) *Attorney, Agent, or Firm*—George W. Johnston; Dennis P. Tramaloni

(57) ABSTRACT

Compounds of the formula:

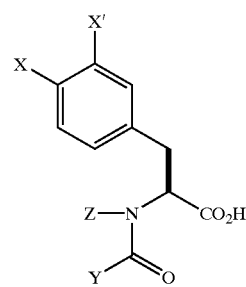

are disclosed which have activity as inhibitors of binding between VCAM-1 and cells expressing VLA-4. Such compounds are useful for treating diseases whose symptoms and/or damage are related to the binding of VCAM-1 to cells expressing VLA-4.

305 Claims, No Drawings

N-ALKANOYLPHENYLALAMINE DERIVATIVES

This application is a divisional of Ser. No. 09/138,353, filed Aug. 21, 1998, now U.S. Pat. No. 6,455,550, issued Sep. 24, 2002, which claims benefit of Provisional Application No. 60/056,929, filed Aug. 22, 1997 and provisional Application No. 60/094,591, filed Jul. 29, 1998.

BACKGROUND OF THE INVENTION

Vascular cell adhesion molecule-1 (VCAM-1), a member of the immunoglobulin (Ig) supergene family, is expressed on activated, but not resting, endothelium. The integrin VLA-4 ($a_4b_1$), which is expressed on many cell types including circulating lymphocytes, eosinophils, basophils, and monocytes, but not neutrophils, is the principal receptor for VCAM-1. Antibodies to VCAM-1 or VLA-4 can block the adhesion of these mononuclear leukocytes, as well as melanoma cells, to activated endothelium in vitro. Antibodies to either protein have been effective at inhibiting leukocyte infiltration and preventing tissue damage in several animal models of inflammation. Anti-VLA-4 monoclonal antibodies have been shown to block T-cell emigration in adjuvant-induced arthritis, prevent eosinophil accumulation and bronchoconstriction in models of asthma, and reduce paralysis and inhibit monocyte and lymphocyte infiltration in experimental autoimmune encephalitis (EAE). Anti-VCAM-1 monoclonal antibodies have been shown to prolong the survival time of cardiac allografts. Recent studies have demonstrated that anti-VLA-4 mAbs can prevent insulitis and diabetes in non-obese diabetic mice, and significantly attenuate inflammation in the cotton-top tamarin model of colitis.

Thus, compounds which inhibit the interaction between $\alpha_4$-containing integrins, such as VLA-4 and VCAM-1, will be useful as therapeutic agents for the treatment of chronic inflammatory diseases such as rheumatoid arthritis (RA), multiple sclerosis (MS), pulmonary inflammation (e.g., asthma), and inflammatory bowel disease (IBD).

SUMMARY OF THE INVENTION

It has been discovered that compounds of the formula:

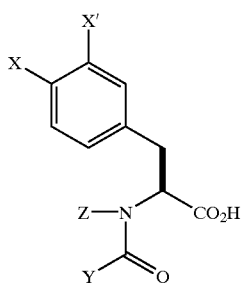

1 and the pharmaceutically acceptable salts and esters thereof wherein X, X', Z and Y are as defined below, inhibit the binding of VCAM-1 to VLA-4 and so would be useful in treating inflammatory diseases in which such binding acts to bring on the disease.

DETAILED DESCRIPTION OF THE INVENTION

As used in this specification, the term "lower alkyl", alone or in combination (for example, as part of "lower alkanoyl," below), means a straight-chain or branched-chain alkyl group containing a maximum of six carbon atoms, such as methyl, ethyl, n-propyl, isopropyl, n-butyl, sec.butyl, isobutyl, tert.butyl, n-pentyl, n-hexyl and the like. Lower alkyl groups may be unsubstituted or substituted by one or more groups selected independently from cycloalkyl, nitro, aryloxy, aryl, hydroxy, halogen, cyano, lower alkoxy, lower alkoxycarbonyl, lower alkanoyl, lower alkylthio, lower alkyl sulfinyl, lower alkyl sulfonyl, and substituted amino, e.g., lower alkoxycarbonyl amino. Examples of substituted lower alkyl groups include 2-hydroxyethyl, 2-methoxypropyl, 3-oxobutyl, cyanomethyl, trifluoromethyl, 2-nitropropyl, benzyl, including p-chloro-benzyl and p-methoxy-benzyl, and 2-phenyl ethyl.

The term "cycloalkyl" means an unsubstituted or substituted 3- to 7-membered carbacyclic ring. Substitutents useful in accordance with the present invention are hydroxy, halogen, cyano, lower alkoxy, lower alkanoyl, lower alkyl, aroyl, lower alkylthio, lower alkyl sulfinyl, lower alkyl sulfonyl, aryl, heteroaryl and substituted amino.

The term "heterocycloalkyl" means an unsubstituted or substituted 5- to 6-membered carbacyclic ring in which one or two of the carbon atoms has been replaced by heteroatoms independently selected from O, S and N. Preferred heterocycloalkyl groups are pyrrolidinyl and morpholinyl.

The term "lower alkoxy" means a lower alkyl group (as defined above) bonded through an oxygen atom. Examples of unsubstituted lower alkoxy groups are methoxy, ethoxy, n-propoxy, isopropoxy, n-butoxy, tert-butoxy and the like.

The term "lower alkylthio" means a lower alkyl group bonded through a divalent sulfur atom, for example, a methyl mercapto or a isopropyl mercapto group.

The term "aryl" means a mono- or bicylic aromatic group, such as phenyl or naphthyl, which is unsubstituted or substituted by conventional substituent groups. Preferred subsituents are lower alkyl, lower alkoxy, hydroxy lower alkyl, hydroxy, hydroxyalkoxy, halogen, lower alkylthio, lower alkylsulfinyl, lower alkylsulfonyl, cyano, nitro, perfluoroalkyl, alkanoyl, aroyl, aryl alkynyl, heteroaryl (especially tetrazolyl), lower alkynyl and lower alkanoylamino. Examples of aryl groups that may be used in accordance with this invention are unsubstituted phenyl, m- or o-nitrophenyl, p-tolyl, m- or p-methoxyphenyl, 3,4-dimethoxyphenyl, p-chlorophenyl, p-cyanophenyl, m-methylthiophenyl, 2-methyl-5-nitrophenyl, 2,6-dichlorophenyl, m-perfluorophenyl, 1-naphthyl, m- or p-2-methyltetraozolyl, and the like.

The term "arylalkyl" means a lower alkyl group as hereinbefore defined in which one or more hydrogen atoms is/are replaced by an aryl or heteroaryl group as herein defined. Any conventional arylalkyl may be used in accordance with this invention, such as benzyl, 2-phenyl ethyl, and the like.

The term "aryloxy" means an aryl group, as hereinbefore defined which is bonded via an oxygen atom. The preferred aryloxy group is phenoxy.

The term "heteroaryl" means an unsubstituted or substituted 5- or 6-membered monocyclic hetereoaromatic ring or a 9- or 10-membered bicyclic hetereoaromatic ring containing 1, 2, 3 or 4 hetereoatoms which are independently N, S or O. Examples of hetereoaryl rings are pyridine, benzimidazole, indole, imidazole, thiophene, isoquinoline, quinzoline, tetrazole, and the like. Substituents as defined above for "aryl" are included in the definition of heteroaryl. The wide variety of heteroaryl groups useful in accordance with the invention is illustrated by Examples 56, 57, 74, 364 and 381–386.

The term "lower alkoxycarbonyl" means a lower alkoxy group bonded via a carbonyl group. Examples of alkoxycarbonyl groups are methoxycarbony, ethoxycarbonyl, t-butoxycarbonyl and the like.

The term "lower alkylcarbonyloxy" means lower alkylcarbonyl groups bonded via an oxygen atom, for example an acetoxy group.

The term "lower alkanoyl" means lower alkyl groups bonded via a carbonyl group and embraces in the sense of the foregoing definition groups such as acetyl, propionyl and the like. Where the lower alkyl portion of the lower alkanoyl group is substituted, the preferred substitutents are methoxy, trifluoro, phenyl, cyclopentyl, methoxycarbonyl, amino and t-butoxycarbonylamino.

The term "lower alkylcarbonylamino" means lower alkylcarbonyl groups bonded via a nitrogen atom, such as acetylamino.

The term "aroyl" means an mono- or bicyclic aryl or heteroaryl group bonded via a carbonyl group. Examples of aroyl groups are benzoyl, 3-cyanobenzoyl, m-perfluromethyl-benzoyl, p-methoxy-benzoyl, 2-naphthoyl, groups of the formula:

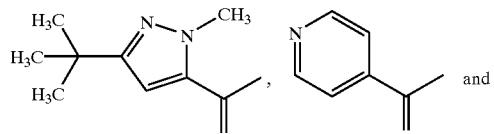

and

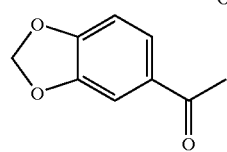

and the like.

The present invention comprises a compound of the formula:

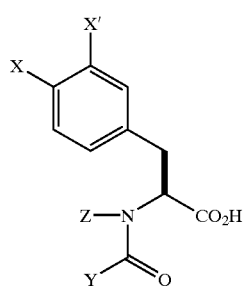

1 and the pharmaceutically acceptable salts and esters thereof.

In accordance with the invention, Z is hydrogen or lower alkyl (preferably hydrogen), one of X and X' is hydrogen, halogen, or lower alkyl (X' is preferably hydrogen), and the other (preferably X) is a group X-6, X-7 or X-10 as described below. Y is a group Y-1 or Y-2 as described below.

Y-1 is a group of the formula:

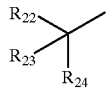

Y-1 wherein:
$R_{22}$ and $R_{23}$ are independently aryl, heteroaryl or lower alkyl which is unsubstituted or substituted by one or more chloro, bromo, nitro, hydroxy, lower alkoxy, aryl, lower alkanoyl, aroyl or cyano,
$R_{24}$ is aryl, cyano, alkylsulfonyl or lower alkyl or alkenyl unsubstituted or substituted by an aryl or heteroaryl ring, and when $R_{22}$ is aryl and $R_{23}$ is aryl or lower alkyl, hydrogen, and
the total number of carbon atoms in $R_{22}$, $R_{23}$ and $R_{24}$ is from 6 to 14.
In Y-1, $R_{22}$ and $R_{23}$ are preferably lower alkyl or phenyl, and $R_{24}$ is preferably lower alkyl except when $R_{22}$ is aryl and $R_{23}$ is aryl or lower alkyl, then $R_{24}$ is preferably hydrogen.

However, Y is preferably the group Y-2 which is a 3–7 membered ring of the formula:

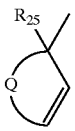

Y-2 wherein:
$R_{25}$ is lower alkyl, unsubstituted or fluorine substituted lower alkenyl, or a group of formula $R_{26}-(CH_2)_e-$,
$R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula $-NR_{28}R_{29}$, wherein:
$R_{28}$ is hydrogen or lower alkyl,
$R_{29}$ is hydrogen, lower alkyl, lower alkoxycarbonyl, lower alkoxycarbonylaminocarbonyl, lower alkanoyl, aroyl, heteroaroyl, perfluoro lower alkanoyl, lower alkyl sulfonyl, lower alkylaminocarbonyl, arylaminocarbonyl, or lower alkylaminothiocarbonyl, or
$R_{28}$ and $R_{29}$ taken together with the nitrogen atom to which they are attached form a 4, 5 or 6-membered saturated heterocyclic ring containing one or two heteroatoms with the second heteroatom being O, S, or N—$R_{27}$;
Q is $-(CH_2)_fO-$, $-(CH_2)_fS-$, $-(CH_2)_f-$, or when f=0, a bond, the dotted line is a second bond which is present or absent,
$R_{27}$ is hydrogen, lower alkyl, aryl, lower alkanoyl, aroyl, or lower alkoxycarbony, the carbon atoms in the ring are unsubstituted or substituted by lower alkyl or halogen,
e is an integer from 0 to 4, and
f is an integer from 0 to 3.
Q is preferably $-(CH_2)_f-$ or, when f=0, a bond. When $R_{25}$ is a group of formula $R_{26}-(CH_2)_e-$, $R_{26}$ is preferably aryl, heteroaryl, azido, cyano, hydroxy, lower alkoxy, lower alkoxycarbonyl, lower alkanoyl, lower alkylthio, lower alkyl sulfonyl, lower alkyl sulfinyl, nitro, or $R_{26}$ is a group of formula —$NR_{28}R_{29}$ wherein $R_{28}$ is hydrogen or lower alkyl, $R_{29}$ is hydrogen, lower alkyl, lower alkoxycarbonyl, lower alkanoyl, aroyl, perfluoro lower alkanoyl, lower alkyl sulfonyl, lower alkylaminocarbonyl, heterocycloalkyl carbonyl, arylaminocarbonyl, or $R_{28}$ and $R_{29}$ taken together with the nitrogen to which they are attached form a 4, 5 or 6-membered saturated heterocyclic ring which can contain one oxygen atom. When $R_{26}$ is aryl, it is especially phenyl unsubstituted, mono-substituted by chloro, methoxy, cyano, or tetrazolyl which is unsubstituted or substituted by methyl, or is phenyl di-substituted by methoxy.

The group X-6 is of the formula:

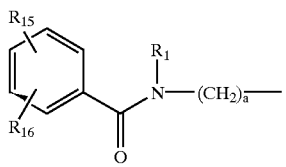

wherein:

$R_1$ is hydrogen or lower alkyl, $R_{15}$ is hydrogen, halogen, nitro, lower alkyl sulfonyl, cyano, lower alkyl, lower alkoxy, lower alkoxycarbonyl, carboxy, lower alkyl aminosulfonyl, perfluorolower alkyl, lower alkylthio, hydroxy lower alkyl, alkoxy lower alkyl, alkylthio lower alkyl, alkylsulfinyl lower alkyl, alkylsufonyl lower alkyl, lower alkylsulfinyl, lower alkanoyl, aroyl, aryl, aryloxy or a group of the formula $R_{17}$—C≡C—, $R_{16}$ is hydrogen, halogen, nitro, cyano, lower alkyl, OH, perfluorolower alkyl, or lower alkylthio, $R_{17}$ is hydrogen, aryl, heteroaryl, or lower alkyl which is unsubstituted or substituted by OH, aryl, or heteroaryl, and a is 0 or 1.

The groups $R_{15}$ and $R_{16}$ are preferably independently hydrogen, lower alkyl, nitro, halogen (especially chloro or fluoro), perfluoromethyl, cyano or phenoxy. $R_1$ is preferably hydrogen and a is preferably 0.

X-7 is a group of the formula:

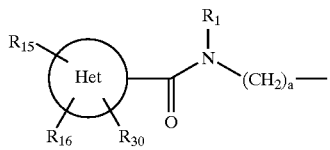

wherein Het is a 5- or 6-membered heteroaromatic ring containing 1, 2 or 3 heteroatoms selected from N,O, and S, or Het is a 9- or 10-membered bicyclic heteroaromatic ring containing 1, 2, 3 or 4 heteroatoms selected from O, S, and N;

a, $R_1$, $R_{15}$ and $R_{16}$ are as above, and $R_{30}$ is absent or is hydrogen or lower alkyl.

Het is preferably a 5- or 6-membered monocyclic heteroaromatic ring containing 1, 2 or 3 nitrogens, or a nitrogen and a sulfur, or a nitrogen and an oxygen. When Het is a bicyclic heteroaromatic ring, it preferably contains from 1 to 3 nitrogens as the heteroatoms. $R_{15}$ is preferably, nitro, lower alkyl sulfonyl, cyano, lower alkyl, lower alkoxy, perfluorolower alkyl, lower alkylthio, lower alkanoyl, or aryl (especially unsubstituted phenyl); $R_{16}$ is perferably hydrogen, halogen, nitro, cyano, lower alkyl, perfluoro lower alkyl; and $R_{30}$, when present, is preferably hydrogen or lower alkyl.

The group X-10 is of the formula:

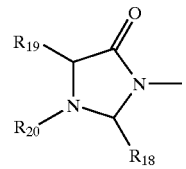

wherein:

$R_{18}$ is hydrogen, substituted or unsubstituted lower alkyl, aryl, heteroaryl, arylalkyl, heteroaryl alkyl, $R_{19}$ is substituted or unsubstituted lower alkyl, aryl, heteroaryl, arylalkyl, heteroaryl alkyl, and $R_{20}$ is subituted or unsubstituted lower alkyl, substituted or unsubstituted lower alkanoyl, carboxyl lower alkanoyl, aroyl, aryloxylower alkanoyl.

$R_{18}$ is preferably phenyl wherein the phenyl ring is unsubstituted or monosubstituted by lower alkoxy or halogen, or is phenyl lower alkyl. $R_{19}$ is preferably lower alkyl, which is unsubstituted or substituted by pyridyl or phenyl wherein the phenyl ring is unsubstituted or monosubstituted by lower alkoxy or halogen. $R_{20}$ is preferably lower alkanoyl The compounds of the invention include the pharmaceutically acceptable salts and esters thereof. Certain prefered esters of the invention were discovered which are useful to improve bioavailabilty of compounds of this invention. These preferred esters are of the formula:

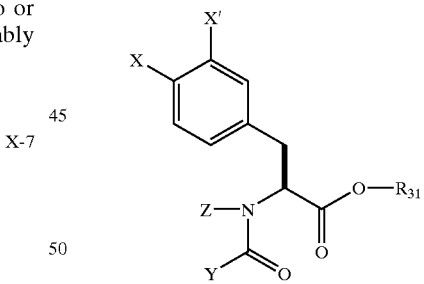

wherein X, X', Z and Y are as described above, and $R_{31}$ is lower alkyl, or $R_{31}$ is a group of formula P-1:

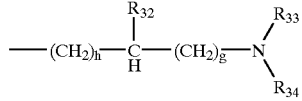

wherein:

$R_{32}$ is hydrogen or lower alkyl, $R_{33}$ is hyrogen, lower alkyl, aryl, $R_{34}$ is hydrogen or lower alkyl, h is an integer from 0 to 2,
g is an integer from 0 to 2,
the sum of h and g is 1 to 3; or
$R_{31}$ is a group of formula P-2:

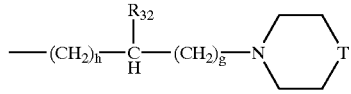

P-2 wherein:
$R_{32}$, g, and h are as previously defined,
T is O, S, —$(CH_2)_j$—, a bond (when j=0) or a group of the formula N—$R_{35}$,
$R_{35}$, is hydrogen, lower alkyl, lower alkanoyl, lower alkoxycarbonyl, and
j is 0, 1 or 2.
$R_{31}$ is preferably ethyl or 2-(4-morpholinyl)ethyl.

The compounds of the invention can exist as stereoisomers and diastereomers, all of which are encompassed within the scope of the present invention.

The especially preferred groups Y-1 are of the formula:

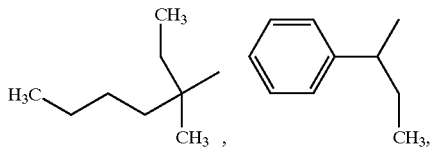

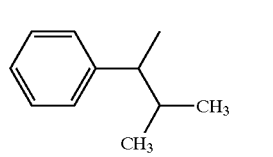 and 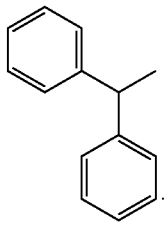.

The especially preferred groups Y-2 are of the formulas shown in the following table:

TABLE 1

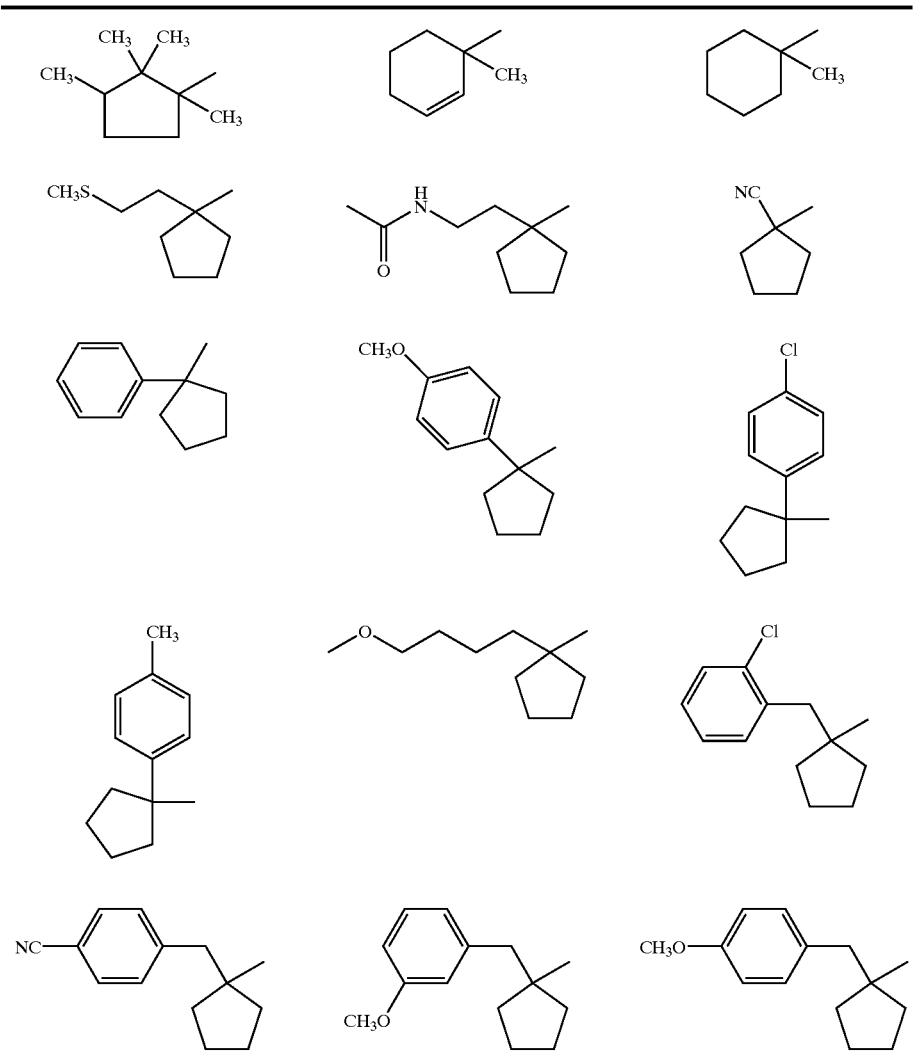

TABLE 1-continued
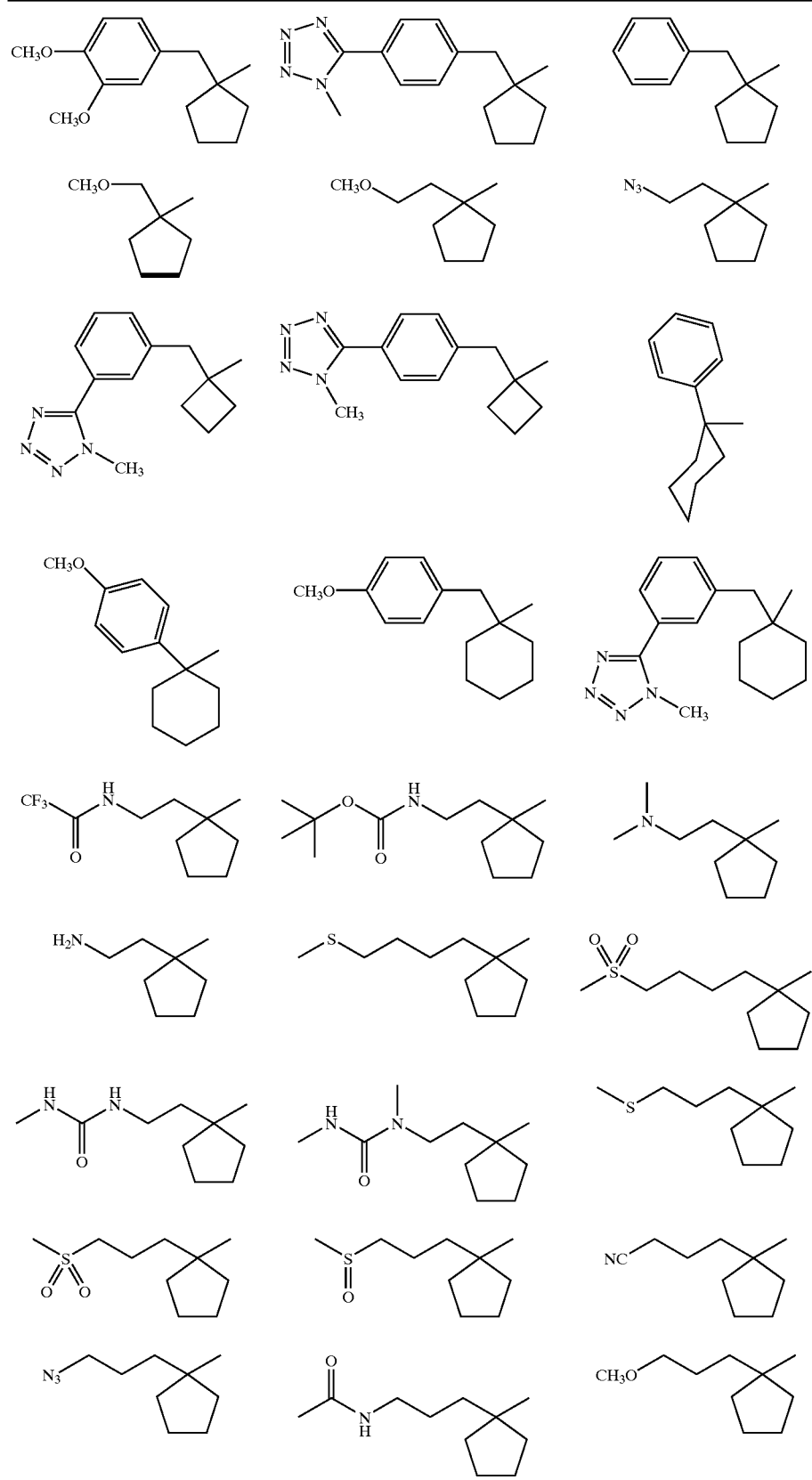

TABLE 1-continued
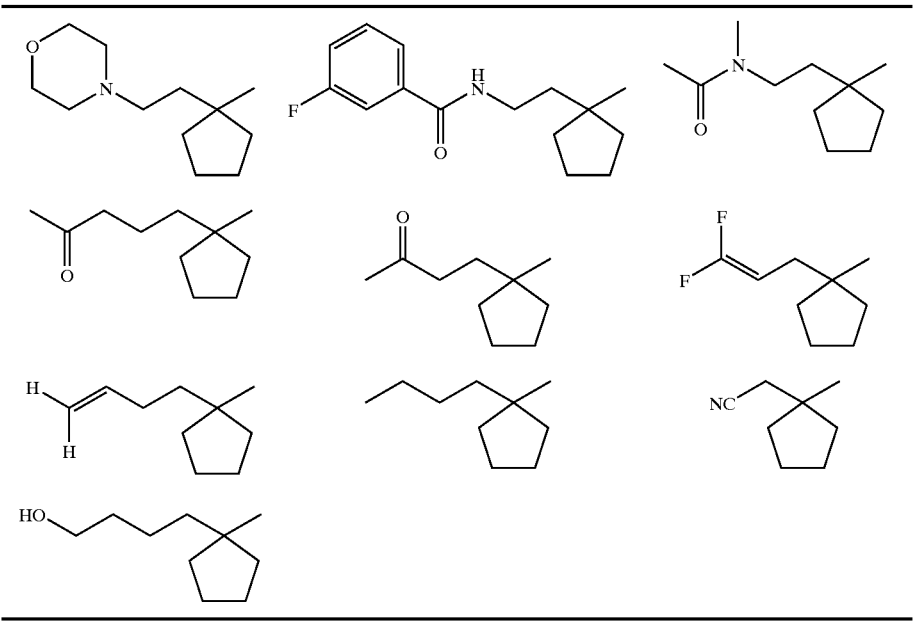
The especially preferred groups X-6 are of the formula:
The expecially preferred groups X-7 are of the formula:
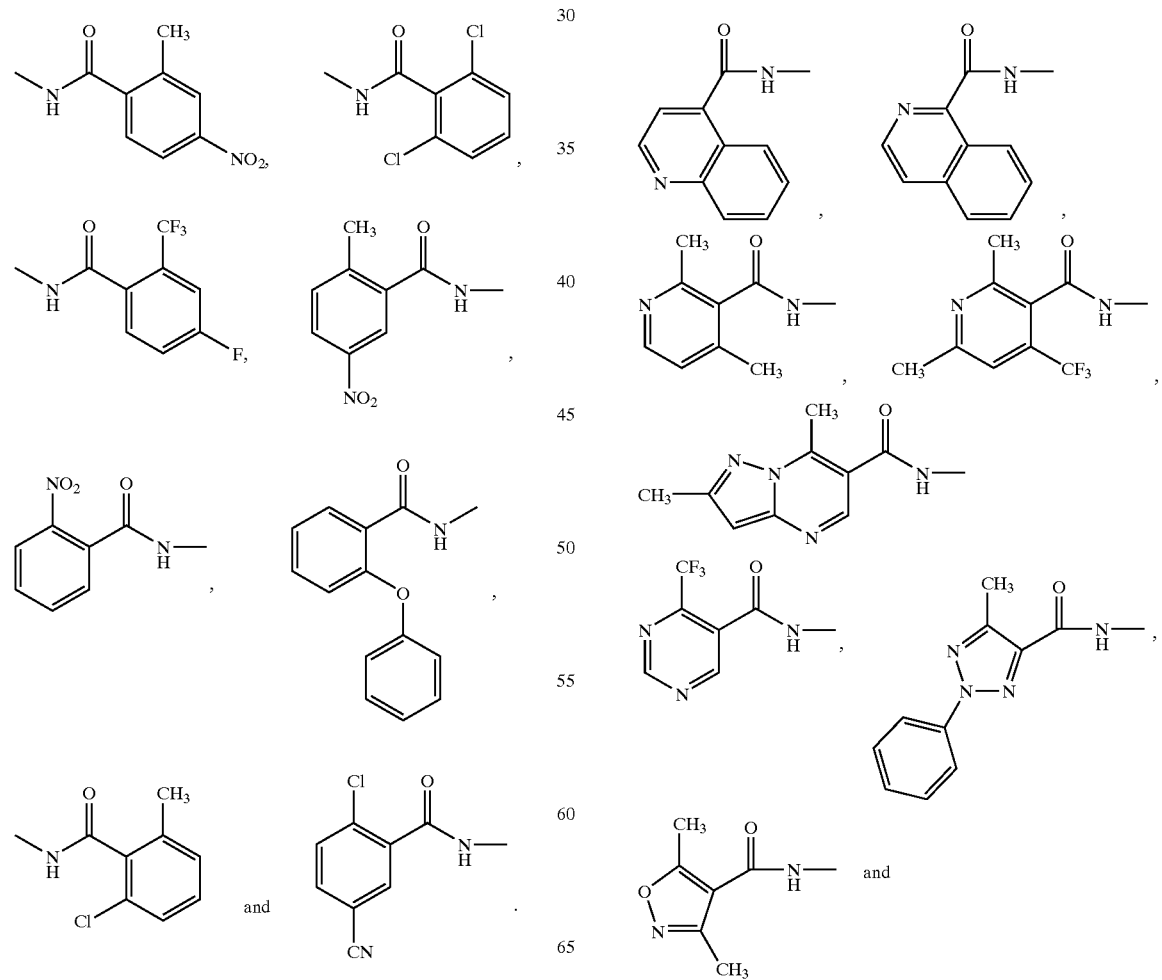

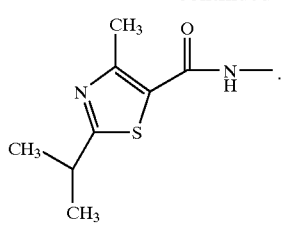
The especially preferred groups X-10 are of the formula:
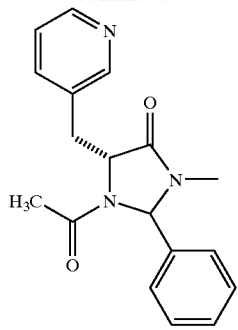
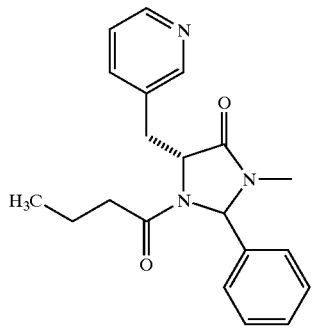
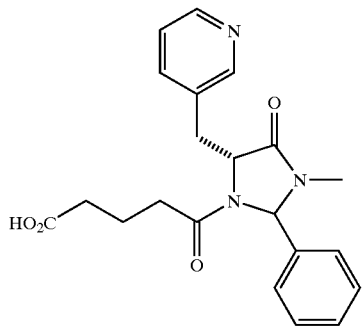
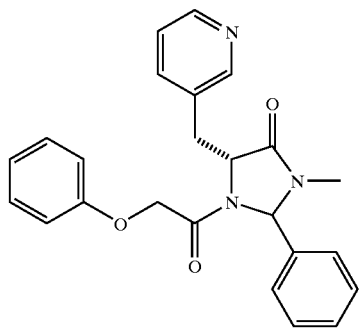
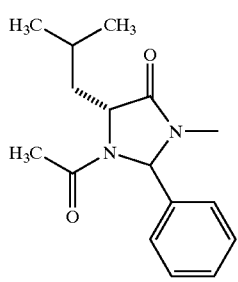

-continued
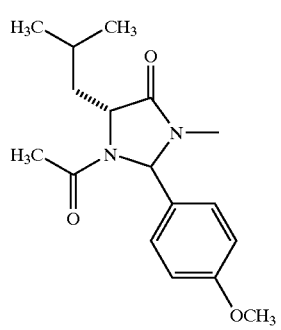
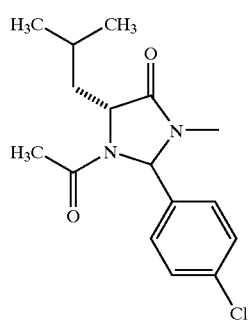
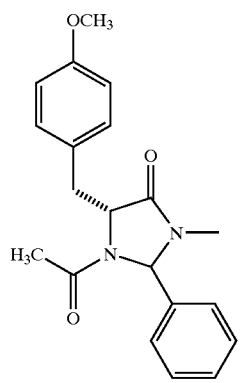
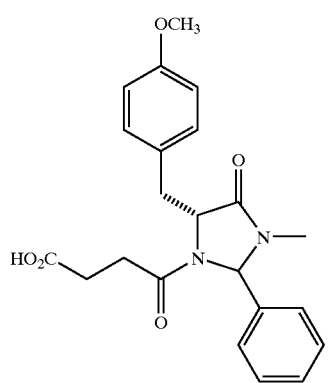
-continued
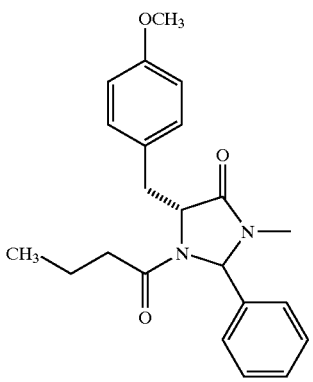
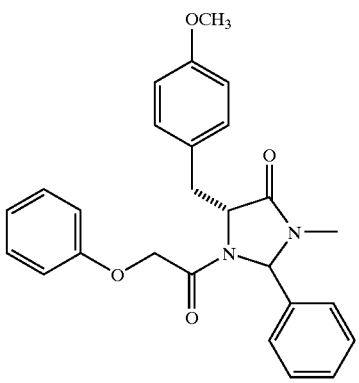
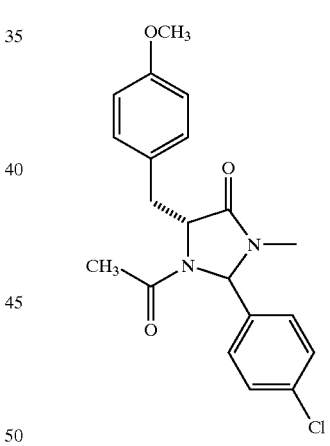
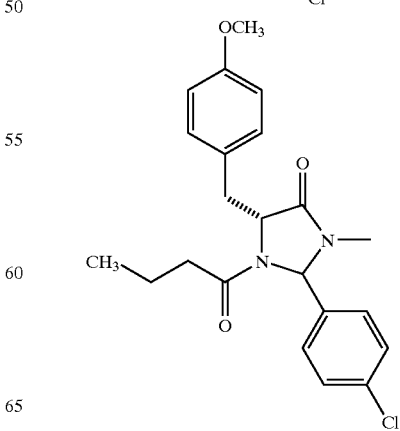

-continued
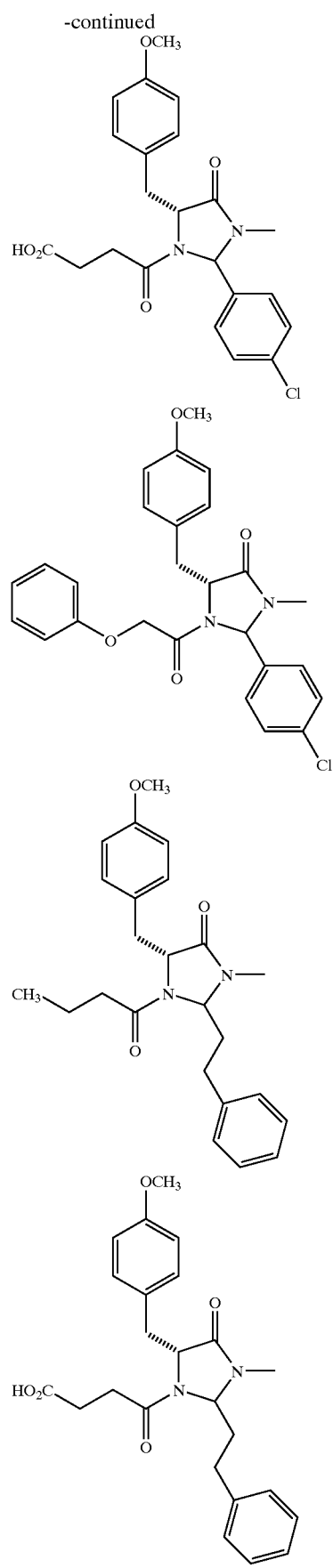

-continued
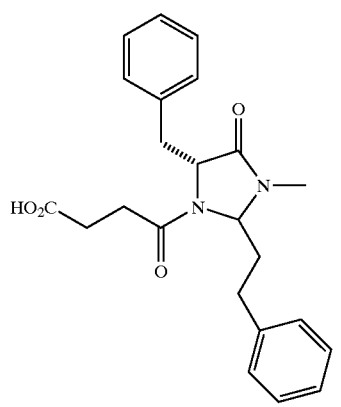
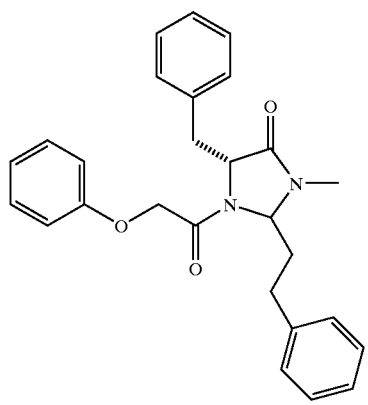
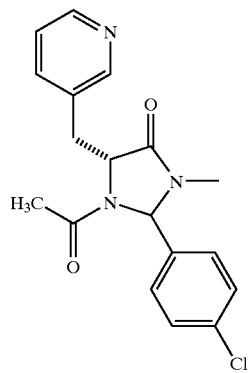
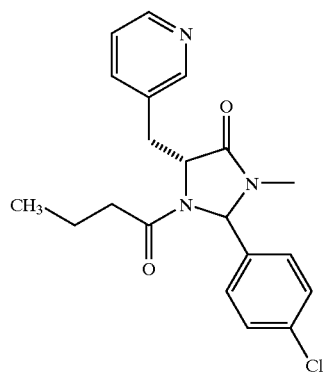
-continued
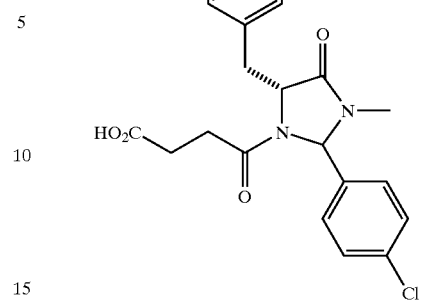
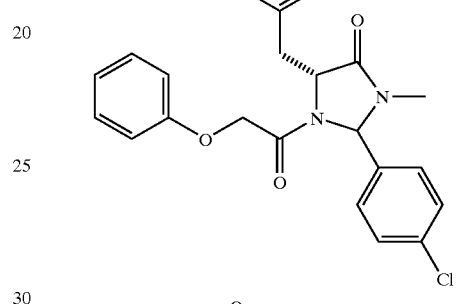
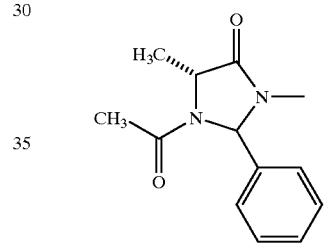
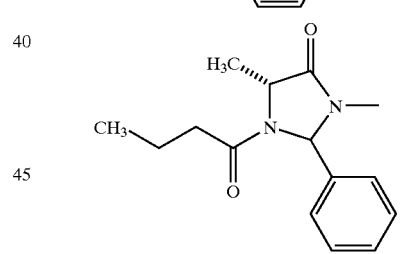
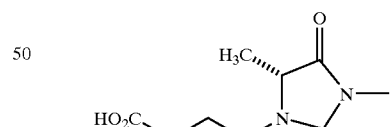
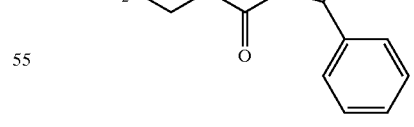

-continued
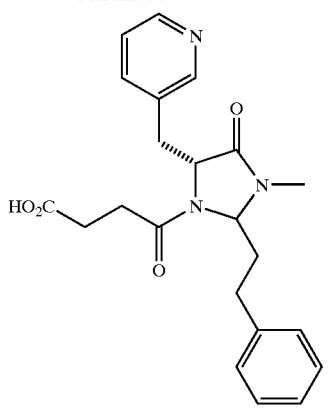
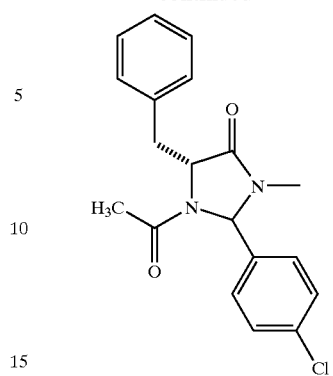
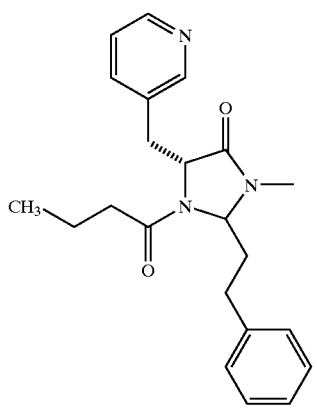
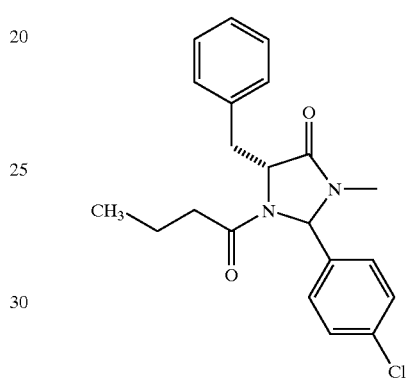
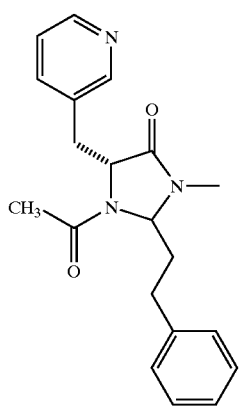
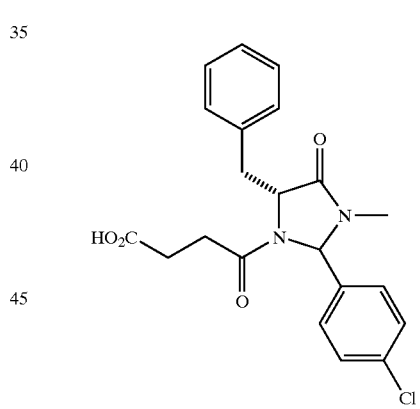
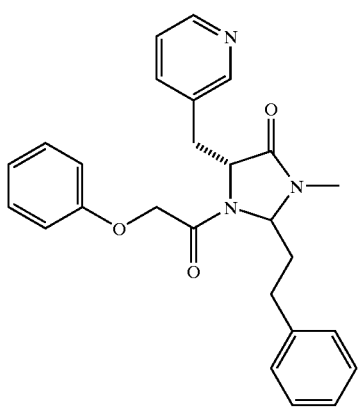
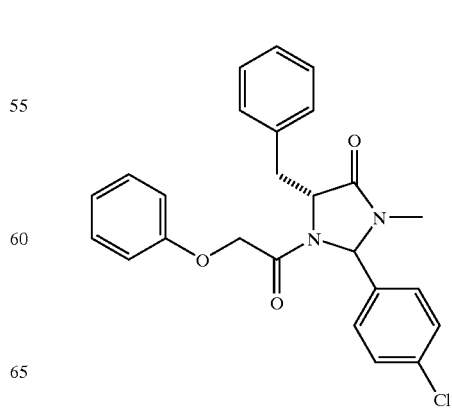

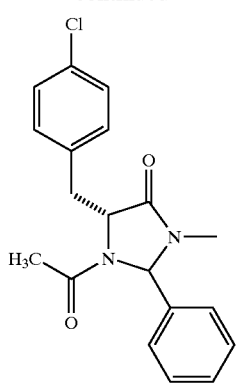
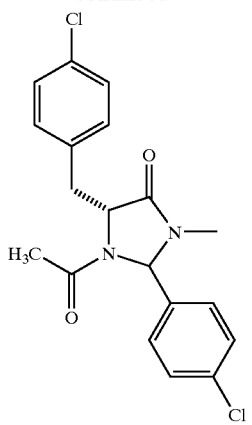
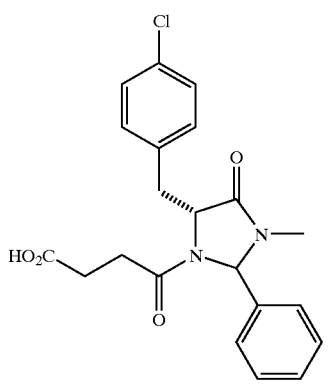
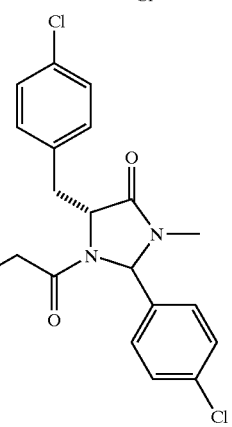
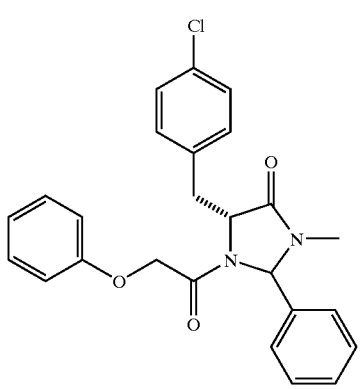
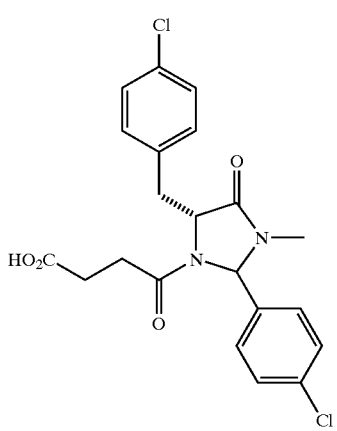
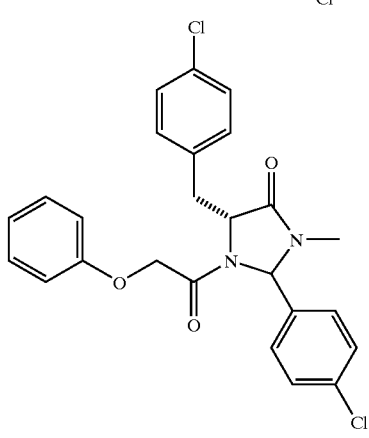

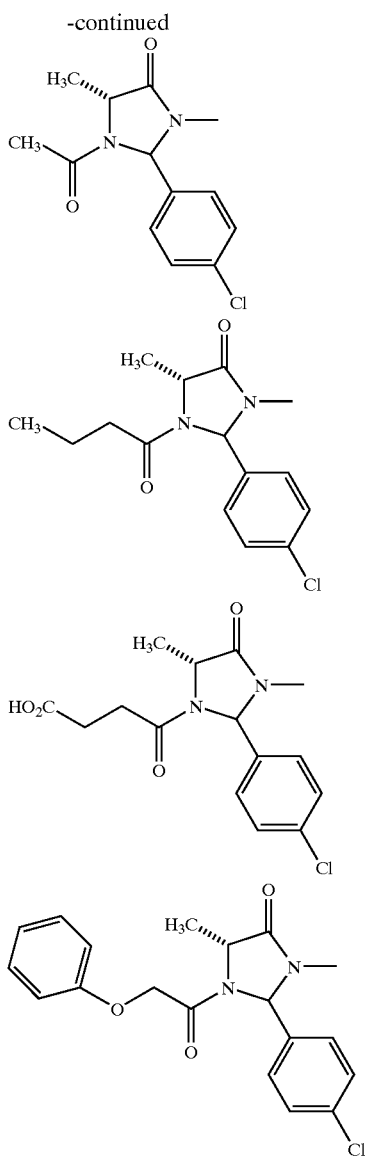

The compounds of the invention inhibit the binding of VCAM-1 and fibronectin to VLA-4 on circulating lymphocytes, eosinophils, basophils, and monocytes ("VLA-4-expressing cells"). The binding of VCAM-1 and fibronectin to VLA-4 on such cells is known to be implicated in certain disease states, such as rheumatoid arthritis, multiple sclerosis, inflammatory bowel disease, and particularly in the binding of eosinophils to pulmonary endothelium which is the cause of the pulmonary inflammation which occurs in asthma. Thus, the compounds of the present invention can be used as medicaments for the treatment of disorders which are known to be associated with such binding, and especially would be useful for the treatment of asthma.

Furthermore, compounds of the invention also inhibit the binding of VCAM-1 and MadCAM to the cellular receptor alpha4-beta7, also known as LPAM, which is expressed on lymphocytes, eosinophiles and T-cells. While the precise role of alpha4-beta7 interaction with various ligands in inflammatory conditions such as asthma is not completely understood, compounds of the invention which inhibit both alpha4-beta1 and alpha4-beta7 receptor binding are particularly effective in animal models of asthma. Furthermore, work with monoclonal antibodies to alpha4-beta7 indicate that compounds which inhibit alpha4-beta7 binding to MadCAM or VCAM are useful for the treatment of inflammatory bowel disease. They would also be useful in the treatment of other diseases in which such binding is implicated as a cause of disease damage or symptoms.

The compounds of the invention can be administered orally, rectally, or parentally, e.g., intravenously, intramuscularly, subcutaneously, intrathecally or transdermally; or sublingually, or as opthalmalogical preparations, or as an aerosol for the treatment of pulmonary inflammation. Capsules, tablets, suspensions or solutions for oral administration, suppositories, injection solutions, eye drops, salves or spray solutions are examples of administration forms.

Intravenous, intramuscular, oral or inhalation administration is a preferred form of administration. The dosages in which the compounds of the invention are administered in effective amounts depend on the nature of the specific active ingredient, the age and the requirements of the patient and the mode of administration. Dosages may be determined by any conventional means, e.g., by dose-limiting clinical trials. Thus, the invention further comprises a method of treating a host suffering from a disease in which VCAM-1 or fibronectin binding to VLA-4-expressing cells is a causative factor in the disease symptoms or damage by administering an amount of a compound of the invention sufficient to inhibit VCAM-1 or fibronectin binding to VLA-4-expressing cells so that said symptoms or said damage is reduced. In general, dosages of about 0.1–100 mg/kg body weight per day are preferred, with dosages of 1–25 mg/kg per day being particularly preferred, and dosages of 1–10 mg/kg body weight per day being especially preferred.

The invention further comprises pharmaceutical compositions which contain a pharmaceutically effective amount of a compound of the invention and a pharmaceutically acceptable carrier. Such compositions may be formulated by any conventional means. Tablets or granulates can contain a series of binders, fillers, carriers or diluents. Liquid compositions can be, for example, in the form of a sterile water-miscible solution. Capsules can contain a filler or thickener in addition to the active ingredient. Furthermore, flavour-improving additives as well as substances usually used as preserving, stabilizing, moisture-retaining and emulsifying agents as well as salts for varying the osmotic pressure, buffers and other additives can also be present.

The previously mentioned carrier materials and diluents can comprise any conventional pharmaceutically acceptable organic or inorganic substances, e.g., water, gelatine, lactose, starch, magnesium stearate, talc, gum arabic, polyalkylene glycols and the like.

Oral unit dosage forms, such as tablets and capsules, preferably contain from 25 mg to 1000 mg of a compound of the invention.

The compounds of the present invention may be prepared by any conventional means. In reaction Scheme 1, a compound of formula 1 in which $R_1$ is hydrogen or lower alkyl, and which is a known compound or can be prepared by standard methodology, is treated with a reducing agent capable of selectively reducing a nitro group in the presence of a benzylic alcohol. This procedure is advantageously carried out in the presence of a derivatizing agent of the formula $R_2$-OCOX wherein X is a leaving group and $R_2$ is tert-alkyl, benzyl or the like so as to form a readily cleavable protecting group, thus leading directly to a compound of formula 2. For example, this procedure can be conveniently carried out by catalytic hydrogenation of 1 over Pd(C) in ethyl acetate in the presence of di-tert-butyl dicarbonate to give a derivative of 2 in which $R_2$ is tert-butyl.

Conversion to an aldehyde of formula 3 can be carried out using an one of a variety of oxidizing agents capable of oxidizing a benzylic alcohol to the corresponding aldehyde, for example activated manganese dioxide in a suitable solvent, for example dichloromethane. Reaction of 3 to give a dehydroamino acid of formula 5 can be effected by treatment with a Wittig reagent of formula 4 in which $R_3$ is lower alkyl and $R_4$ is an alkoxy group, for example benzyloxy- or tert-butoxy- or represents a portion of one of the acyl groups of the compounds of the invention, for example substituted lower alkyl or substituted cycloalkyl. For example treatment of 3 with (±)-N-(benzyloxycarbonyl)-α-phosphonoglycine trimethyl ester in the presence of a suitable base for example tetramethyl guanidine leads directly to a dehydroamino acid of formula 5, $R_3$=methyl and $R_4$=benzyloxy. Enantioselective reduction of 5 to the L-amino acid 6 can be effected by use of a number of reducing agents suitable for the purpose, for example, the recently described ethyl-DuPHOS rhodium reagent (Burk, M. J., Feaster, J. E.; Nugent, W. A.; Harlow, R. L. *J. Am. Chem. Soc.* 1993, 115, 10125) using essentially the literature procedure.

Reaction Scheme 1

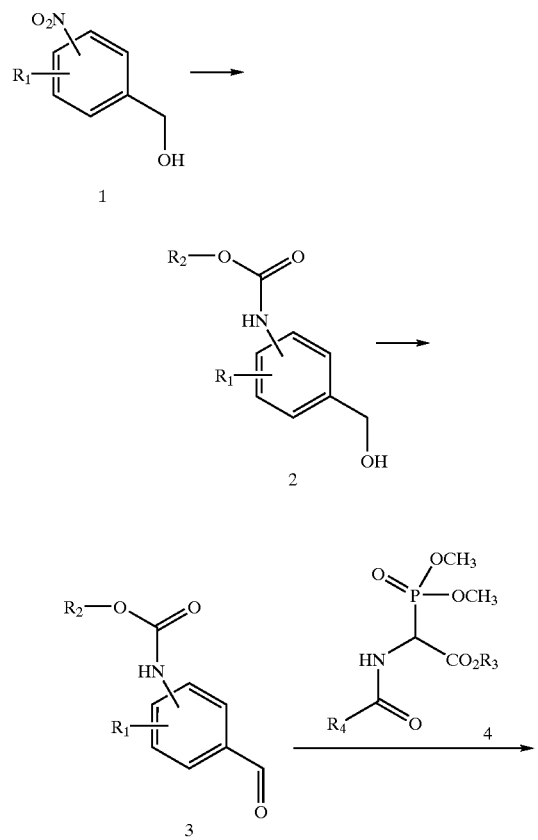

One process for the conversion of compounds of structure 6 into compounds of the invention is shown in Reaction Scheme 2. The protecting group incorporating $R_2$ can be removed under conditions dependent on the particular choice of $R_2$ as well as $R_3$ and $R_4$. The choice of these groups will be dependent on the particular target compound. A variety of common protecting groups and their use are described in "T. W. Green and P. G. M. Wuts, Protective Groups in Organic Synthesis, 2nd edition, Wiley Interscience, New York, 1991" For example when $R_2$ is a tert-butyl group and $R_3$ is lower alkyl and $R_4$ is either a benzyloxy group or represents a portion of one of the acyl groups of the compounds of the invention, for example substituted lower alkyl or substituted cycloalkyl, treatment with trifluoroacetic acid either neat or in dichloromethane solution in the presence of suitable scavengers, for example, triethylsilane or anisol leads to a compound of formula 7. This compound can be coupled with a carboxylic acid of formula 8 using standard peptide coupling conditions, for example HBTU in the presence of DIPEA in a polar, aprotic solvent such as DMF at a temperature between 0° C. and room temperature to give a compound of formula 9. In the carboxylic acid of formula 8, $R_5$ may represent a substituted alkyl group, a substituted aromatic ring, or a substituted heteroaromatic ring. $R_5$ may also incorporate suitably protected reactive functionalities to permit final conversion into compounds of the invention. The choice and use of such groups will be apparent to those skilled in the art.

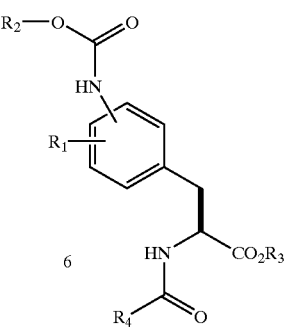

Reaction Scheme 2

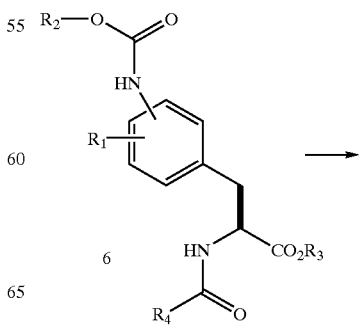

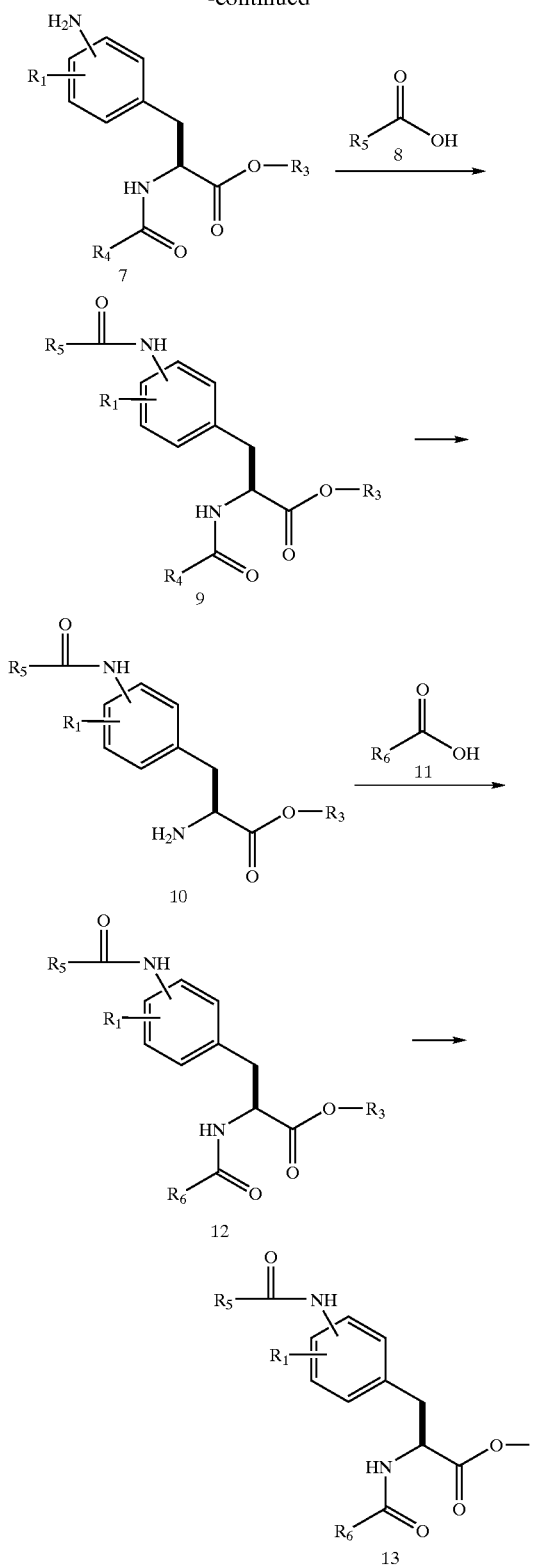

Depending on the choice of $R_4$ and whether an ester or acid is the final goal of the synthesis, compound 9 may be a compound of the invention or in the case that $R_4$ is a protecting group, for example, a benzyloxy group, it may be removed under appropriate conditions, for example by catalytic hydrogenation over Pd(C) in a suitable solvent such as a lower alcohol to give a compound of formula 10. This intermediate can be coupled with a carboxylic acid of formula 11 using standard peptide coupling conditions, for example HBTU in the presence of DIPEA in a polar, aprotic solvent such as DMF at a temperature between 0° C. and room temperature to give a compound of formula 12. In the carboxylic acid of formula 11, $R_6$ may represent a portion of a compound of the invention, for example, a substituted alkyl or substituted cycloalkyl. These compounds are known compounds or can be prepared by known methods. R6 may also incorporate suitably protected reactive functionalities to permit final conversion into compounds of the invention. The choice and use of such groups will be apparent to those skilled in the art. General methods for the preparation of such compounds are illustrated in Reaction Scheme 13. If the acid 13 is the target compound, conversion of a compound of formula 12 can be effected using standard hydrolysis conditions appropriate for the particular choice of $R_3$ and any functional groups present as part of $R_5$ and $R_6$. In the case where $R_3$ is lower alkyl, treatment with an alkali metal hydroxide, for example lithium hydroxide in aqueous THF is generally effective.

In reaction Scheme 3, a compound of formula 14 in which $R_7$ is a lower alkyl group which may serve as a protecting group or a group suitable for use in a prodrug for example methyl, ethyl, tert-butyl or the like or represents a connection to a solid phase resin, for example a Wang resin, is coupled with a carboxylic acid of formula 11 using standard peptide coupling conditions, for example HBTU in the presence of DIPEA in a polar, aprotic solvent such as DMF at a temperature between 0° C. and room temperature to give a compound of formula 15. Reduction of the nitro group of 15 can be effected by catalytic hydrogenation for example using Pd(C) as a catalyst or by treatment with a standard reducing agent, for example $SnCl_2$. The resulting compound of structure 16 is useful as a key intermediate for several series of compounds. In the instance highlighted in Scheme 3, it can be coupled with an acid of formula 8 using standard peptide coupling conditions, for example HBTU in the presence of DIPEA in a polar, aprotic solvent such as DMF at a temperature between 0° C. and room temperature to give a compound of formula 17. Compound 17 may be a compound of the invention depending on the nature of $R_7$ or may be converted to a compound of the invention by an appropriate hydrolysis procedure, for example in the case where $R_7$ is lower alkyl, by hydrolysis by treatment with excess alkali metal hydroxide, such as lithium hydroxide in aqueous alcohol. When $R_7$ represents a resin suitable for solid phase synthesis, appropriate hydrolysis conditions will depend on the choice of resin. In the case of Wang resin, treatment with trifluoroacetic acid in the presence of appropriate scavengers will lead to an acid of formula 18.

Reaction Scheme 3

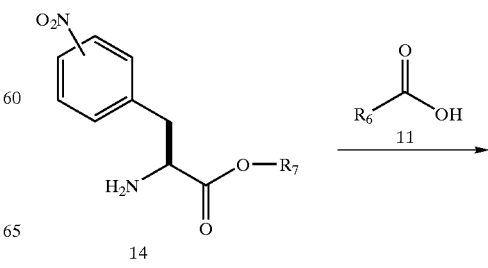

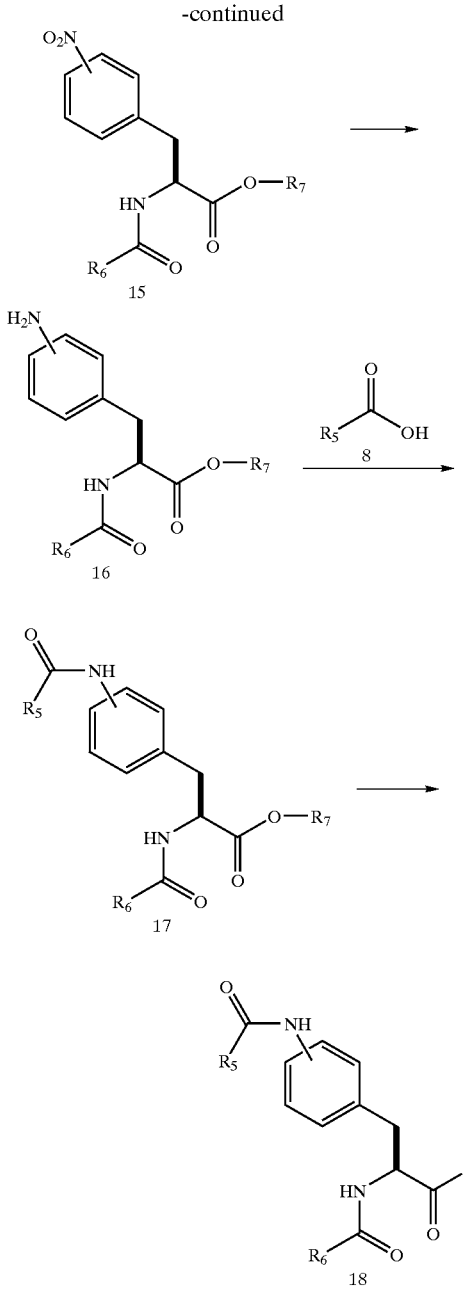

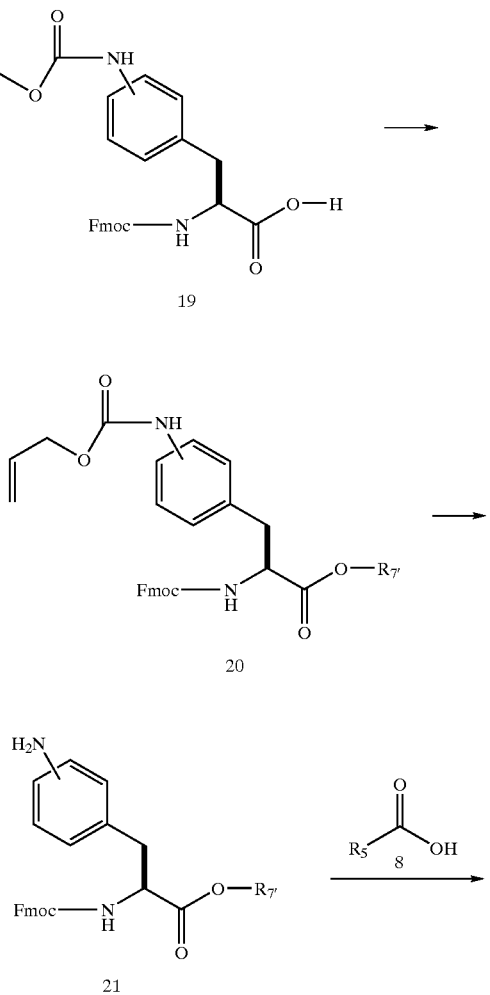

room temperature to give a compound of formula 22. The Fmoc protecting group may be removed from 22 using standard base treatment well known to those practicing peptide chemistry, for example with piperidine in DMF, to afford an amine of formula 23. The resulting compound 23 can be coupled with a carboxylic acid of formula 11 using standard peptide coupling conditions, for example HBTU in the presence of DIPEA in a polar, aprotic solvent such as DMF at a temperature between 0° C. and room temperature to give a compound of formula 24. Finally the compound of structure 24 can be cleaved from the resin under conditions dependent on the particular choice of resin. For example, in the case of a Wang resin, acid treatment with trifluoroacetic acid in dichloromethane in the presence of scavengers as necessary will afford a compound of formula 18.

Depending on the particular synthetic target, the order of removal of the protecting groups from 19 may be altered so that the Fmoc group is first removed, coupling of the resulting amine with an acid of formula 11 is carried out followed by removal of the Alloc group and coupling of the product with an acid of formula 8 and cleavage from the resin. Also the choice of protecting groups can be modified to reflect the reactivities of the resin and the nature of any functional groups incorporated into $R_5$ and $R_6$.

Reaction Scheme 4

In a method particularly well suited for solid phase synthesis, an N'-Alloc-amino-$N^\alpha$-Fmoc protected phenylalanine derivative of formula 19 can be coupled to a resin suitable for solid phase synthesis, for example, a Wang resin using standard coupling procedures, for example, by forming a mixed anhydride with 2,6-dichlorobenzoyl chloride and carrying out the coupling reaction in a polar, aprotic solvent such as N-methyl pyrrolidinone to give a compound of structure 20 in which $R_{7'}$ represents the resin. The Alloc group may be removed by standard methods, for example by treatment with a reducing agent such as $nBu_3SnH$ in the presence of a catalyst which is a source of $Pd^o$, for instance, $Pd(Ph_3P)_2Cl_2$ to give an amine derivative of structure 21. This compound can be coupled with a carboxylic acid of formula 8 using standard peptide coupling conditions, for example HBTU in the presence of DIPEA in a polar, aprotic solvent such as DMF at a temperature between 0° C. and

Reaction Scheme 5

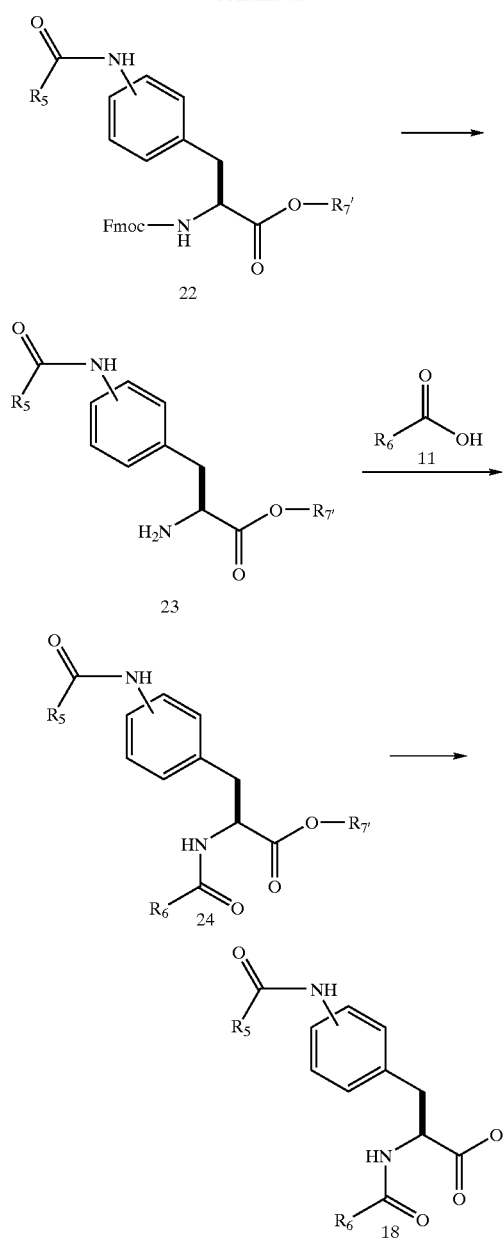

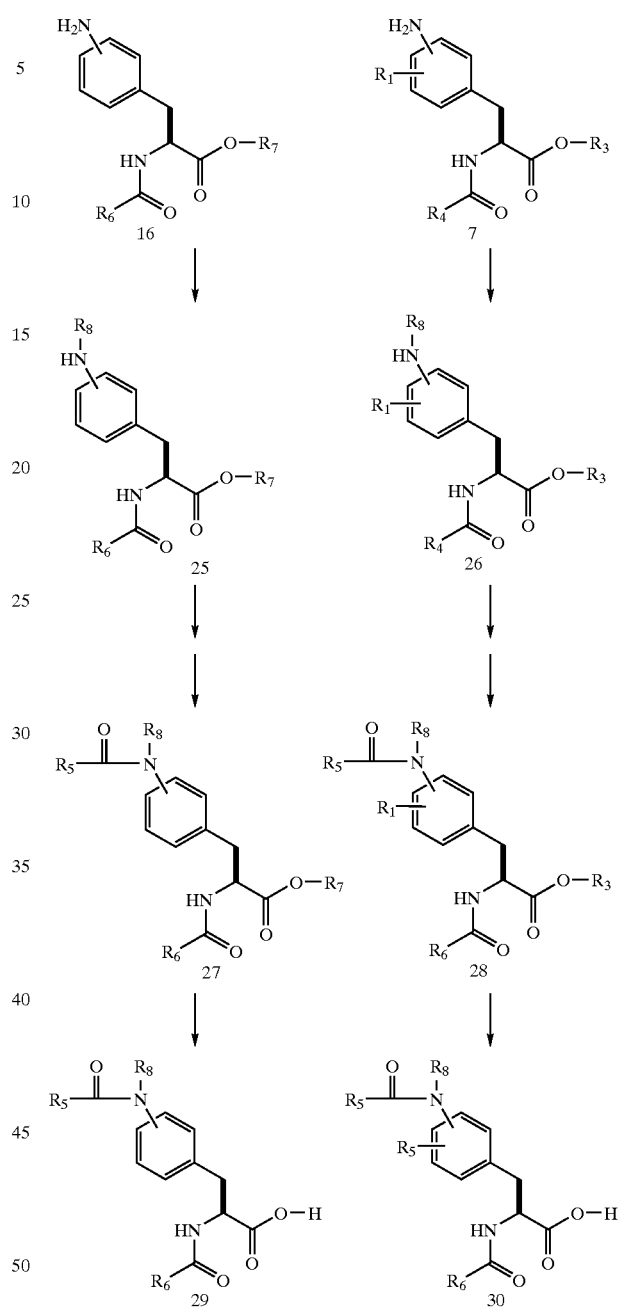

Compounds derived from 3- or 4-(alkylamino) phenylalanine derivatives can be prepared as outlined in Reaction Scheme 5. A compound of formula 16 or 7 may be treated with diazomethane in a suitable solvent, for example, ethyl ether to give products of formulas 25 and 26 respectively in which $R_8$ is methyl. Alternatively, the compound of structure 16 or 7 may be treated with an lower alkyl aldehyde or ketone, for example acetone, to give an intermediate Schiff's base which is in turn subjected to catalytic hydrogenation or reduction with sodium cyanoborohydride in the presence of an organic acid, for example acetic acid to give a compound of formula 25 or 26 in which $R_8$ is lower alkyl other than methyl. Conversion of compounds 25 or 26 to prodrug esters 27 or 28 or to the corresponding acids 29 or 30 respectively can be carried out as described above in Reaction Schemes 2 and 3.

For the preparation of 3- or 4-sulfonylamino phenylalanine derivatives, compounds of formula 7, 16, 25 or 26 may be reacted with a sulfonyl chloride of formula 31, in which $R_9$ is a substituted aryl or heteroaryl moiety, in an inert solvent, for example dichloromethane in the presence of a non-nucleophilic base, for example triethylamine or pyridine at about 0° C. to room temperature to give compounds of structure 32 or 33 respectively as illustrated in Reaction Scheme 6 for compounds 7 and 26. These can be further converted to compounds of formulas 34 and 35 if desired using the general methods described above in Reaction Schemes 2 and 3. Furthermore, the group R4CO—may replaced by a group R6CO— using the general chemistry described in scheme 2.

For the preparation of compounds derived from 3- or 4-aminomethylphenylalanine, the procedure shown in Reaction Scheme 7 may be employed. A 3- or 4-hydroxymethyl benzoate of formula 36 in which $R_{10}$ is lower alkyl, which are known compounds, or can be prepared by known methods, is treated with a silylating agent in which $R_{11}$–$R_{13}$ are lower alkyl or phenyl, for example tert-butyldimethylsilyl chloride in an inert solvent, for example dimethylformamide in the presence of imidazole at about 0° C. to give a silyl protected compound of formula 37. Reduction of 37 may be carried out using a variety of suitable reducing agents, for example, lithium aluminum hydride in an inert solvent such as ether or tetrahydrofuran at a temperature of about 0° C. followed by an aqueous workup to give an intermediate alcohol which can be oxidized by any of several oxidizing agents suitable for oxidizing benzyl alcohols to the corresponding aldehydes, for example activated manganese dioxide, to give an aldehyde of formula 38. Monosilyl protected diols are alternatively available from 3- or 4-hydroxymethylbenzylalcohols by monosilylation and separation of the side products. Alternatively, an ester of formula 37 may be reduced directly to an aldehyde of formula 38 using diisobutylaluminum hydride at low temperature, for example at −78° C.

Reaction of 38 to give a dehydroamino acid of formula 39 can be effected by treatment with a Wittig reagent of formula 4 in which $R_3$ is lower alkyl and $R_4$ is an alkoxy group, for example benzyloxy- or tert-butoxy- or represents a portion of one of the acyl groups of the compounds of the invention, for example substituted lower alkyl or substituted cycloalkyl. For example treatment of 38 with (±)-N-(benzyloxycarbonyl)-α-phosphonoglycine trimethyl ester in the presence of a suitable base for example tetramethyl guanidine leads directly to a dehydroamino acid of formula 39, $R_3$=methyl and $R_4$=benzyloxy. Enantioselective reduction of 39 to the L-amino acid 40 can be effected by use of one of a number of reducing agents suitable for the purpose, for example, the recently described ethyl-DuPHOS rhodium reagent. It will be readily apparent to those skilled in the art that the optimal procedure for the further conversion of 40 into compounds of the invention will depend on the choices of $R_4$ and $R_3$. For the case wherein $R_3$ is lower alkyl and $R_4$ is benzyloxy, conversion to an amine of formula 41 can be conveniently effected by catalytic transfer hydrogenation of 40 over Pd(C) in a suitable solvent, for example, methanol in the presence of ammonium formate as the reducing agent. Acylation of 41 with a carboxylic acid of formula 11 can be carried as described above in Reaction Scheme 2 to give a compound of formula 42. Conditions for removal of the silyl protecting group will depend on the particular choice of $R_{11}$–$R_{13}$. In the case of $R_{11}$, $R_{12}$=methyl and $R_{13}$=tert-butyl, this group is readily removed by treatment with a strong acid, for example hydrochloric acid in an appropriate solvent for the choice of $R_3$, for example where $R_3$ is methyl, methanol.

The resulting benzylic alcohol of formula 43 can be converted to an amine of formula 45 using procedures well established for similar transformations. For example, the alcohol of formula 43 can be converted to a leaving group, for example a mesylate by treatment with methane sulfonyl chloride in the presence of a proton acceptor, for example pyridine, followed by displacement with an alkali metal azide, for example sodium azide in a polar aprotic solvent such as dimethylformamide. Alternatively, the transformation from 43 to an azide of formula 44 can be carried out directly by treatment with diphenyl phosphorazidate as described in: Thompson, A. S.; Humphrey, G R.; DeMarco, A. M.; Mathre, D. J.; Grabowski, E. J. J. *J. Org. Chem.* 1993, 58, 5886–5888. Reduction of the azide 44 to an amine of formula 45 can be carried out by a number of means suitable for the conversion of azides to amines, for example by treatment with a phosphine, for example triphenyl phosphine in an inert solvent such as dichloromethane or THF followed by an aqueous workup or by catalytic hydrogenation over an appropriate catalyst, for example Pd(C) in a solvent suitable for catalytic hydrogenations such as a lower alkanol or tetrahydrofuran. The resulting amine of formula 45 can be converted into the corresponding compounds of the invention using the procedures applicable to free amines described in the other reaction schemes. For example, coupling of 45 with a carboxylic acid of formula 8 under the conditions described in Reaction Scheme 2 leads to an amide of formula 46 which may be further converted to an acid of formula 47 if desired by base catalyzed hydrolysis as described in Reaction Scheme 2.

Reaction Scheme 6

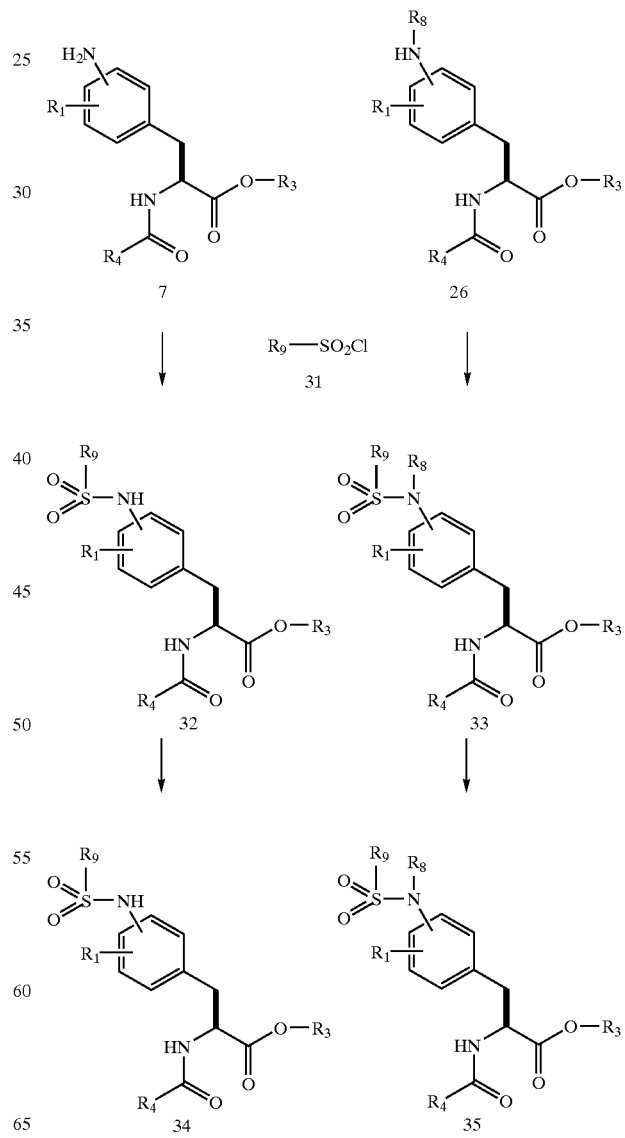

Reaction Scheme 7
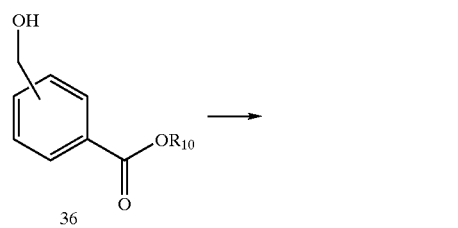
36
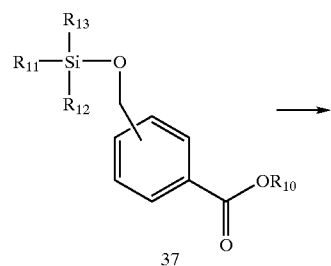
37
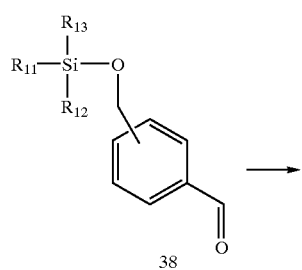
38
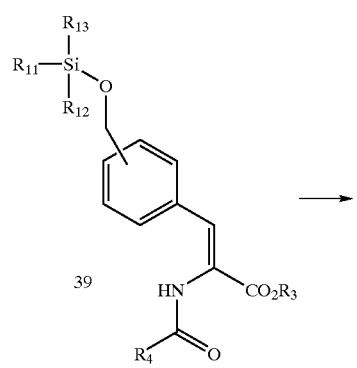
39
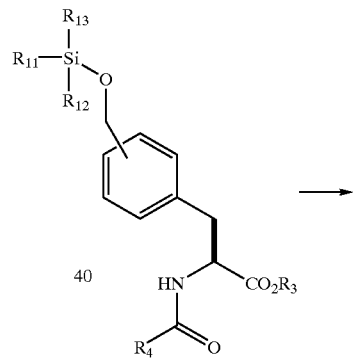
40
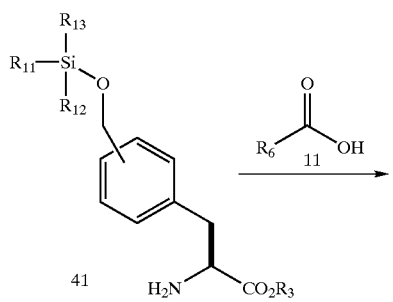
41
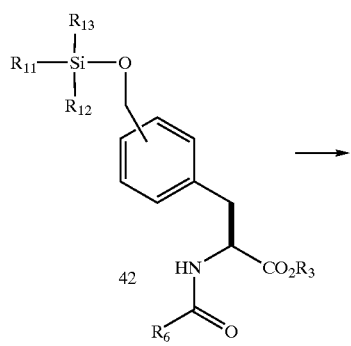
42
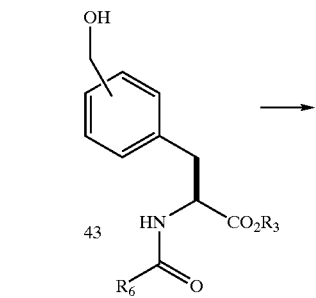
43
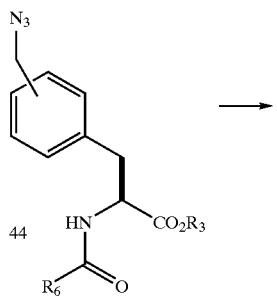
44

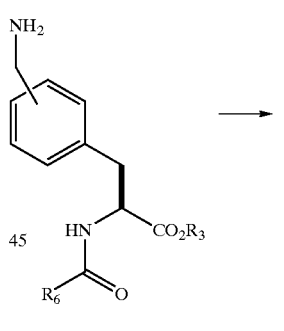

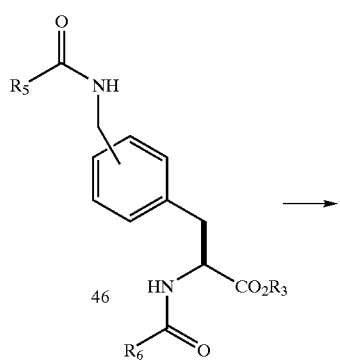

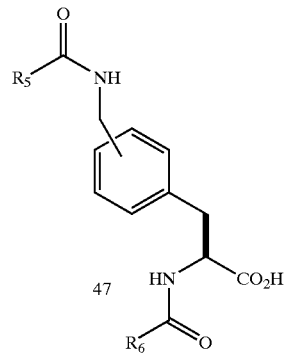

For the synthesis of urea derivatives, a compound of formula 26 can be treated with an isocyanate of formula 49, wherein $R_{14}$ is substituted aryl, substituted heteroaryl or substituted lower alkyl with potentially reactive substituents protected as appropriate using conventional protecting group strategies, in a suitable inert solvent, for example dichloromethane, to give a urea of formula 50. More generally, a compound of formula 26 can be treated with a phosgene equivalent, for example, triphosgene in an inert solvent such as dichloromethane in the presence of a non-nucleophilic proton acceptor, for example diisopropylethylamine, to give an intermediate of formula 48. Subsequent treatment of a compound of formula 48 with an amine of formula 51 in which $R_{15}$ and $R_{16}$ are independently hydrogen, substituted lower alkyl, substituted aryl, substituted heteroaryl or taken together form a substituted 5, 6 or 7 membered ring leads to a compound of formula 52. Further conversion, if necessary, of 50 or 52 to compounds of the invention can be carried out as described in Reaction Scheme 5.

Reaction Scheme 8

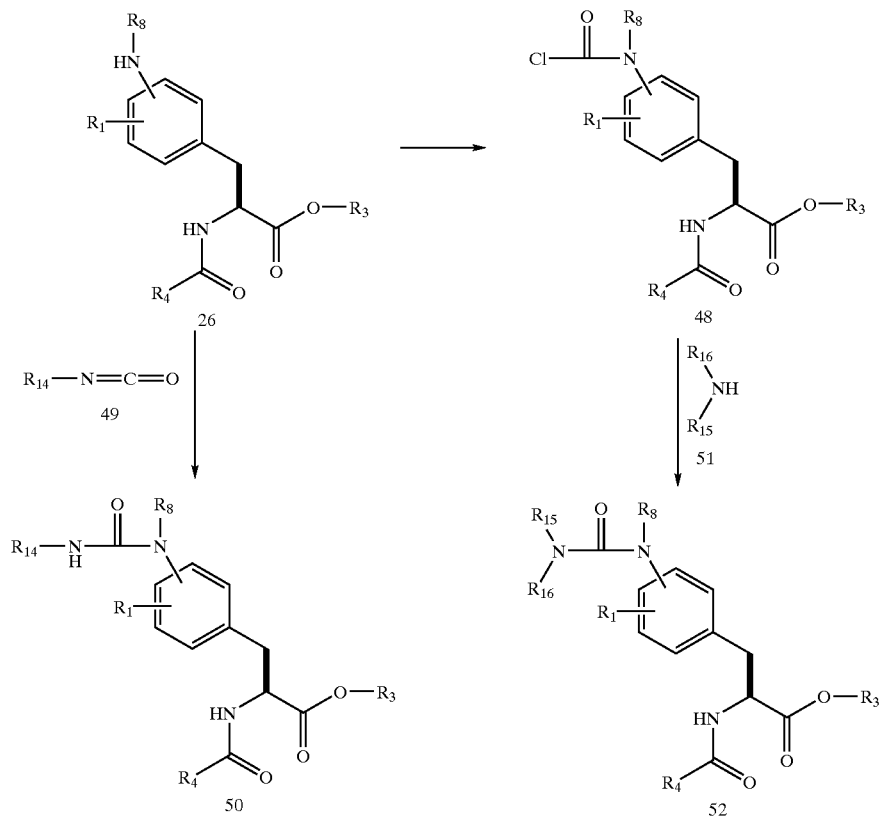

For the synthesis of imides, an aminophenylalanine derivative of structure 53 in which $R_1$ is hydrogen or lower alkyl, $R_6$ is as previously defined and $R_{7''}$ is hydrogen or a readily cleavable group such as substituted benzyl, tert-butyl, allyl, or the like, or in the event that a prodrug ester is desired as the final product, is that ester group, for example ethyl, is employed. Compounds of formula 53 can be readily obtained from intermediates described above in Reaction Scheme 2. Reaction of a compound of formula 53 with a cyclic anhydride of formula 54 in an inert solvent, for example dichloromethane leads to a ring opened intermediate of formula 55. The structure implied by 54 includes bicyclic molecules which may incorporate fused aromatic or heteroaromatic rings. In place of 54, it is also possible to use dicarboxylic acids which are capable of forming cyclic imides. In the latter case, a condensing agent must be employed in the first step, for example carbonyl diimidazole. Treatment of the compound of formula 55 with a reagent such as carbonyl diimidazole capable of effecting cyclodehydration leads to an imide of formula 56. Further manipulation of functional groups which were present on the anhydride of formula 54 and modification of $R_{7''}$ may be carried out on compound 56 as desired to obtain further analogs using standard chemistry which is compatible with the presence of the imide functionality.

For the synthesis of compounds of the invention in which $R_1$ is halogen, preferably chloro, the appropriate halogen atom can be incorpoarted into the starting material or inserted at various points during the course of the synthesis depending on the nature of the additional functionality in the molecule. A chlorine atom can be incorporated into the compound of structure 1, shown in scheme 1 and carried through to the compounds of the invention by avoiding reagents which would be expected to react with a halogen atom For example a compound of formula 6 in which $R_1$ is hydrogen can be treated with a mild chlorinating agent, for example, N-chlorosuccinimide in the presence of a proton acceptor, for example, sodium acetate to give the corresponding compound of formula 6 in which $R_1$ is chloro. In the case where 6 is derived from 3-amino-L-phenylalanine, a mixture of regioisomers may ensue which may be separated at a convenient point in the overall synthesis. Other intermediates described in the above schemes may be more suitable starting materials for halogenation for a particular target molecule. The particular merits of individual candidate starting materials will be apparent to those skilled in the art.

Reaction Scheme 9

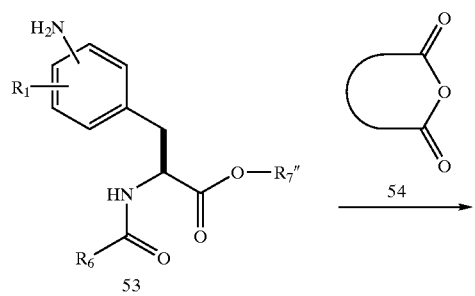

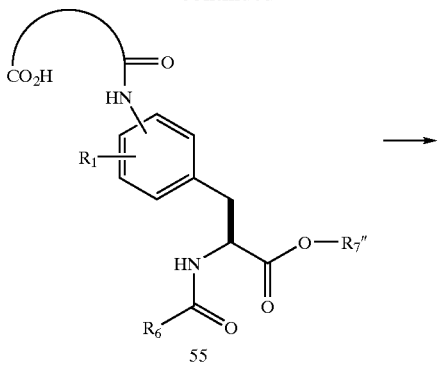

55

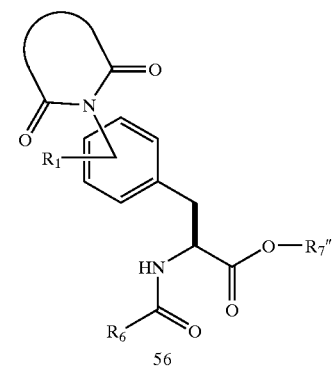

56

For the synthesis of the thiazolidinones of formula 62 described in reaction scheme 10, an aminophenylalanine derivative of structure 16, in which $R_6$ and $R_7$ are as previously defined may be employed. Reaction of 16 with an α-mercapto carboxylic acid of formula 59 in which $R_{20}$ can be hydrogen, lower alkyl or aryl, for example α-mercapto acetic acid, and an aldehyde of formula 60 in which $R_{21}$ can be lower alkyl, arylalkyl or a substituted aryl group, for example benzaldehyde, in an appropriate solvent such as benzene, THF or a lower alcohol, for example methanol, in the presence of a water scavenger such as 4 Å molecular sieves at 60 to 80° C. provides compound of formula 61. Compound 61 may be a compound of the invention depending on the nature of $R_7$ or may be converted to a compound of the invention by an appropriate hydrolysis procedure, for example in the case where $R_7$ is lower alkyl, by treatment with excess alkali metal hydroxide, such as sodium hydroxide in aqueous alcohol. When $R_7$ represents a resin suitable for solid phase synthesis, the appropriate hydrolysis conditions will depend on the choice of resin. In the case of Wang resin, treatment with trifluoroacetic acid in the presence of appropriate scavengers will lead to an acid of formula 62. The sequence may be initiated with related anilines, for example a compound of formula 7 in which $R_1$ is lower alkyl or halogen to give the corresponding thiazolidinones.

Reaction Scheme 10

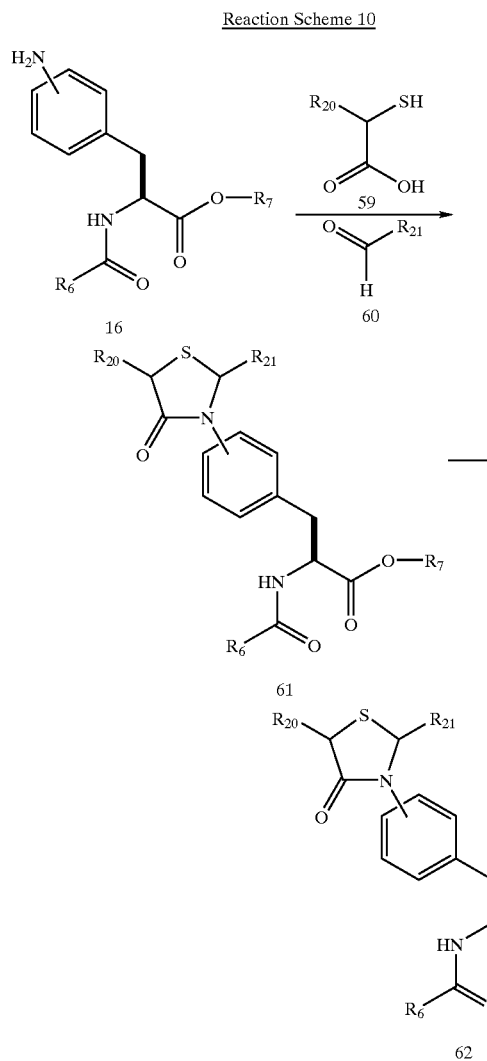

C. in an appropriate solvent, for example THF, provides a compound of formula 66. Compound 66 may be a compound of the invention depending on the nature of $R_7$ or may be converted to a compound of the invention by an appropriate hydrolysis procedure, for example in the case where $R_7$ is lower alkyl, by hydrolysis by treatment with an alkali metal hydroxide, such as sodium hydroxide in aqueous alcohol to give a carboxylic acid of formula 67.

Reaction Scheme 11

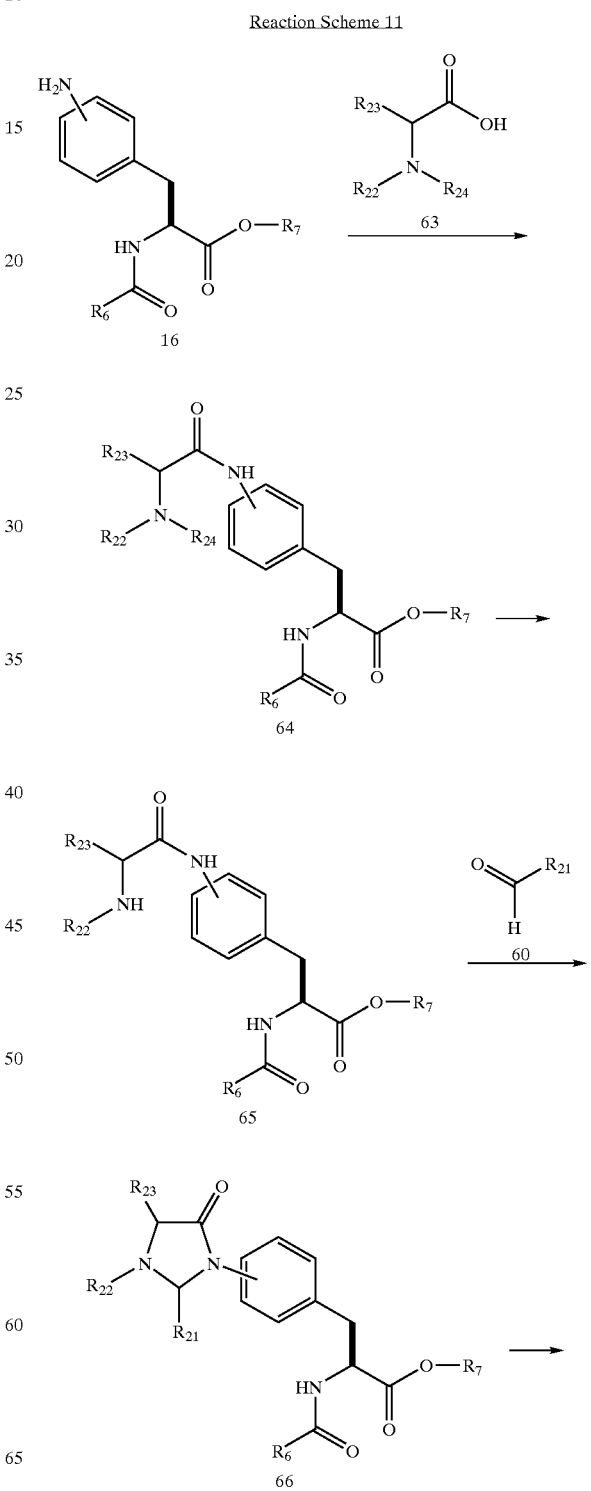

For the synthesis of imidazolidinones of formula 67 shown in reaction scheme 11, an aminophenylalanine derivative of structure 16 in which $R_6$ and $R_7$ are as previously defined may be employed. Compound 16 can be readily obtained through the synthesis described in reaction scheme 3. This compound can be coupled with a N-protected α-amino acid of formula 63, in which $R_{22}$ can be a lower alkyl or an aryl group, $R_{23}$ can be a natural or unnatural D- or L-α-amino acid side chain or $R_{22}$ and $R_{23}$ together can form a ring, for example a proline or pipicolinic acid ring and $R_{24}$ may be a standard amine protecting group suitable for the particular selection of $R_6$, $R_7$, $R_{22}$, and $R_{23}$ for example tert-butoxycarbonyl. The coupling reaction can be effected using standard peptide coupling conditions, for example HBTU in the presence of DIPEA in a polar, aprotic solvent such as DMF at a temperature between 0° C. and room temperature to give a compound of formula 64. Depending on the nature of protecting group $R_{24}$, an appropriate deprotection method is employed to give a compound of formula 65. In the event that the protecting group $R_{24}$ is a Boc group, the deprotection can be carried out by the reaction of 64 with HCl in dioxane at room temperature. Reaction of compound 65 with an aldehyde of formula 60, in which the $R_{21}$ is as defined above, in the presence of a water scavenger such as 4 Å molecular sieves at 60 to 80°

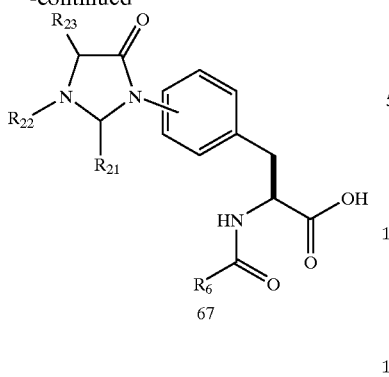

67

For the synthesis of imidazolidinones of formula 68 described in reaction scheme 12, an aminophenylalanine derivative of structure 16 in which $R_6$ and $R_7$ are as previously defined is employed. Compound 16 can be readily obtained through the synthesis described in reaction scheme 3 in the case of $R_7$ is lower alkyl. This compound can be coupled with a N-protected α-amino acid of formula 69, in which $R_{25}$ can be a natural or unnatural, D- or L-α-amino acid side chain and $R_{26}$ is a nitrogen protecting group of the type conventionally used in peptide chemistry, for example, a Fmoc group, using standard peptide coupling conditions, for example HBTU in the presence of DIPEA in a polar, aprotic solvent such as DMF at a temperature between 0° C. and room temperature to give a compound of formula 70. Depending on the nature of protecting group $R_{26}$, an appropriate deprotection method is employed to give compound of formula 71. In the case of the protecting group $R_{26}$ is Fmoc group, it may be removed from 70 using standard base treatment well known to those practicing peptide chemistry, for example with piperidine in DMF, to afford an amine of formula 71. The compound 71 can then react with an aldehyde 60, in which $R_{21}$ is as previously defined, in the presence of a water scavenger such as 4 Å molecular sieves in an appropriate solvent such as dichloromethane or THF at 25–80° C. (bath termperature) to give an imine of formula 72. The imine 72 may then be treated with an acylating agent such as the acyl chloride of formula 74 in which $R_{27}$ can be an alkyl or aryl group in the presence of a base such DIPEA or DBU in an appropriate solvent such as dichloromethane or THF at 25–80° C. (bath temperature) to give an acyl imidazolidinone of formula 73. Other acylating groups may be employed for example, acid anhydrides, and where appropriate, 74 may bear protected substituents which can later be removed at the neccessary point in the synthesis. Compound 73 may be a compound of the invention, or depending on the nature of $R_7$ may be converted to a compound of the invention by an appropriate hydrolysis procedure, for example in the case where $R_7$ is lower alkyl, by hydrolysis by treatment with an alkali metal hydroxide, for example sodium hydroxide in aqueous alcohol to give, after acidification, a carboxylic acid of formula 68. The sequence may be initiated with related anilines, for example a compound of formula 7 in which $R_1$ is lower alkyl or halogen to give the corresponding 3-acyl imidazolidinones.

Reaction Scheme 12

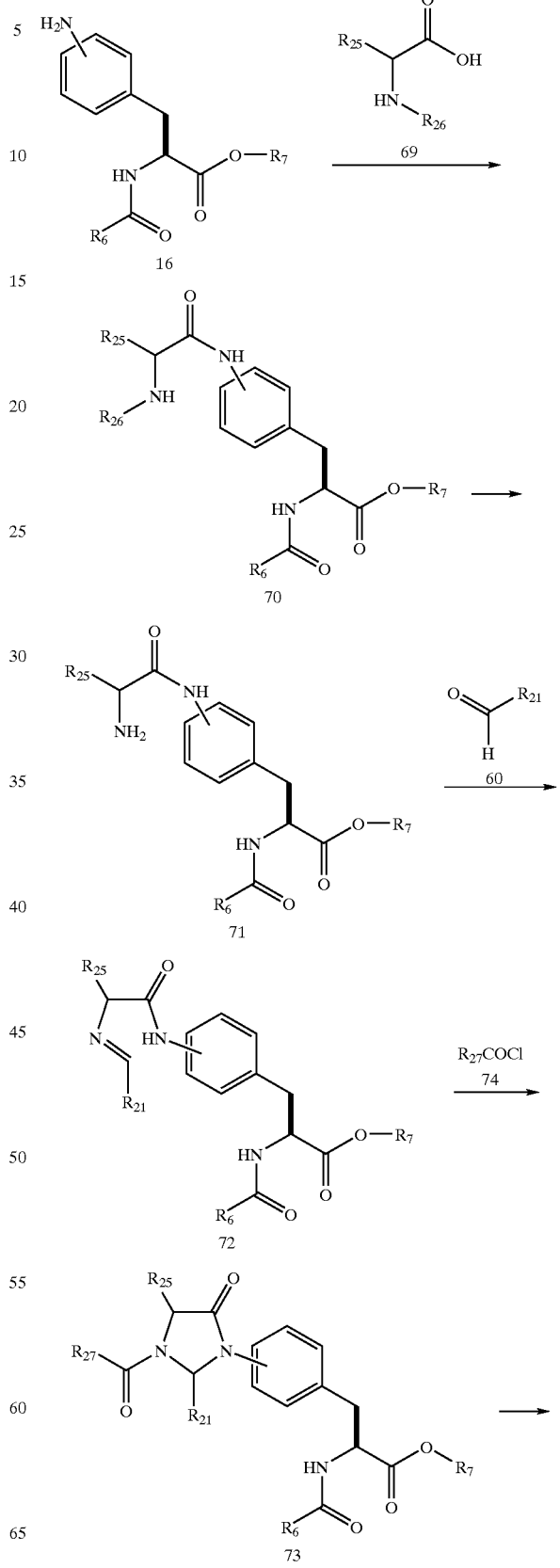

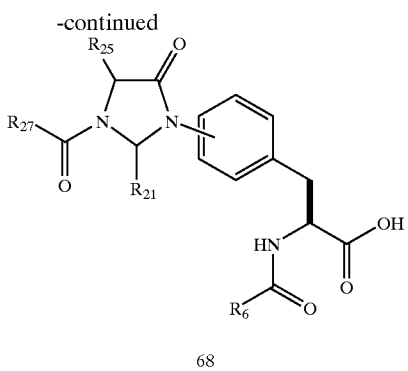

68

The acids of formula 11 are known compounds or can be prepared using standard methodologies. For the preparation of substituted alkyl- or cycloalkylcarboxylic acids, alkylation reactions can be employed using an alkali metal dianion of the acid or monoanion of the corresponding ester. For example, a cycloalkyl carboxylic acid ester of formula 75 can be treated with a strong base, for example, lithium diisopropylamide in an inert solvent, for example THF followed by addition of group $R_{28}$-Lv wherein $R_{28}$ represents a desired side chain, such as a substituted benzyl, lower alkyl, lower alkoxy alkyl, azidolower alkyl and the like and Lv represents a leaving group such as a bromide, iodide, mesylate or similar group known to participate in ester enolate alkylation reactions. The product ester 76 may be hydrolyzed to the acid 77 using alkali metal hydroxide in a suitable solvent, for example aqueous alcohol. Depending on the nature of $R_{28}$ and the eventual target, the compound 77 may be a coupled to an amine such as compound 23 and converted to the target directly or $R_{28}$ may be subject to further manipulation at a suitable point in the synthesis. For example, if $R_{28}$ is an azido lower alkyl moiety, the azide may be reduced using for example a trialkyl phosphine reagent followed by functionalization of the product amine by alkylation, acylation, sulfonylation and related procedures well known to those skilled in the art. If $R_{28}$ incorparates a leaving group, for example, a terminal bromine atom, this group may be displaced by an appropriate nucleophile, for example, sodium methyl mercaptide to give in this case, a thioether which may be the desired product or can be itself further manipulated, for example by oxidation to a sulfoxide or sulfone using standard reaction conditions. Other nucleophiles which may be employed to produce intermediates leading to compounds of this invention include: sodium cyanide, sodium methoxide, sodium azide, morpholine and others. When $R_{28}$ incorporates a ketal group, this group may be hydrolzyed at a convenient point in the synthesis to provide a keto group. This group in turn may be further manipulated, for example by reduction to an alcohol or conversion to derivative such as an oxime.

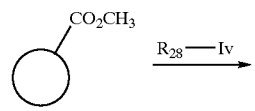

75

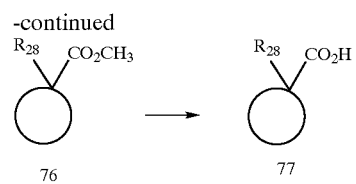

General Melting points were taken on a Thomas-Hoover apparatus and are uncorrected. Optical rotations were determined with a Perkin-Elmer model 241 polarimeter. $^1$H-NMR spectra were recorded with Varian XL-200 and Unityplus 400 MHz spectrometers, using tetramethylsilane (TMS) as internal standard. Electron impact (EI, 70 ev) and fast atom bombardment (FAB) mass spectra were taken on VG Autospec or VG 70E-HF mass spectrometers. Silica gel used for column chromatography was Mallinkrodt SiliCar 230–400 mesh silica gel for flash chromatography; columns were run under a 0–5 psi head of nitrogen to assist flow. Thin layer chromatograms were run on glass thin layer plates coated with silica gel as supplied by E. Merck (E. Merck # 1.05719) and were visualized by viewing under 254 nm UV light in a view box, by exposure to $I_2$ vapor, or by spaying with either phosphomolybdic acid (PMA) in aqueous ethanol, or after exposure to $Cl_2$, with a 4,4'-tetramethyldiaminodiphenylmethane reagent prepared according to E. Von Arx, M. Faupel and M Brugger, *J. Chromatography*, 1976, 120, 224–228.

Reversed phase high pressure liquid chromatography (RP-HPLC)was carried out using either a Waters Delta Prep 4000 employing a 3×30 cm, Waters Delta Pak 15 μM C-18 column at a flow of 40 mL/min employing a gradient of acetonitrile:water (each containing 0.75% TFA) typically from 5 tp 95% acetonitrile over 35–40 min or a Rainin HPLC employing a 41.4 mm×30 cm, 8 μM, Dynamax™ C-18 column at a flow of 49 mL/min and a similar gradient of acetonitrile:water as noted above.

Dichloromethane ($CH_2Cl_2$), 2-propanol, DMF, THF, toluene, hexane, ether, and methanol, were Fisher reagent grade and were used without additional purification except as noted, acetonitrile was Fisher hplc grade and was used as is.

DEFINITIONS

THF is tetrahydrofuran,
DMF is N,N-dimethylformamide,
HOBT is 1-hydroxybenzotriazole,
BOP is [(benzotriazole-1-yl)oxy]tris-(dimethylamino)phosphonium hexafluorophosphate,
HATU is O-(7-azabenzotriazol-1-yl)-1,1,3,3-tetramethyluronium hexafluorophosphate
HBTU is O-benzotriazole-N,N,N',N',-tetramethyluronium hexafluorophosphate,
DIPEA is diisopropylethylamine,
DMAP is 4-(N,N-dimethylamino)pyridine
DPPA is diphenylphosphoryl azide
DBU is 1,8-diazabicyclo[5.4.0]undec-7-ene
NaH is sodium hydride
brine is saturated aqueous sodium chloride solution
TLC is thin layer chromatography
LDA is lithium diisopropylamide
BOP-Cl is bis(2-oxo-3-oxazolidinyl)phosphinic chloride
NMP is N-methyl pyrrolidinone

EXAMPLES

Example 1

Synthesis of 1-Benzylcyclopentane Carboxylic Acid Ethyl Ester

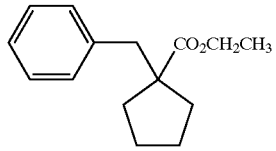

$C_{15}H_{20}O_2$
Mol. Wt: 232.32

A solution of diisopropylamine (1.0 mL, 7.7 mmol) in 20 mL of dry THF was cooled to −78° C. in a dry ice-acetone bath under argon. n-Butyl lithium in hexanes (2.5 M, 3.6 mL, 7.7 mmol) was added all at once and the mixture was stirred for 0.5 hour and transferred to a precooled (−30° C.) solution of 1.0 g (7.0 mmol) of ethyl cyclopentane carboxylate in 10 mL of THF. After a further 45 min, benzyl bromide (0.92 mL, 7.7 mmol) was added and the mixture was allowed to warm to room temperature over night. The resulting mixture was concentrated, and the residue was taken up in 70 mL of ether, washed with water, 1 N HCl, water, saturated brine and was dried (MgSO$_4$). The residue obtained after filtration and evaporation was purified by flash chromatography over 100 g of silica gel, eluting with 3% ethyl acetate-hexane to give 1-benzylcyclopentane carboxylic acid ethyl ester (0.80 g, 45%) as a colorless oil.

Example 2

Synthesis of 1-Benzylcyclopentane Carboxylic Acid

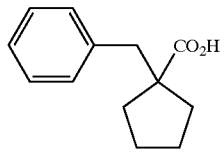

$C_{13}H_{16}O_2$
Mol. Wt: 204.26

A solution of 1-benzylcyclopentane carboxylic acid ethyl ester (0.40 g, 1.7 mmol) in 10 mL of THF and 5 mL of methanol was treated with a solution of 200 mg of lithium hydroxide hydrate in 5 mL of water and the mixture was stirred for 3 days at room temperature and at 40° C. for 3 days. The mixture was diluted with water, washed with ether and acidified with excess 6 N HCl. The aqueous layer was extracted with ether and the combined extracts were washed with water and brine and were dried (MgSO$_4$). Evaporation gave 0.34 g (96%) of 1-benzylcyclopentane carboxylic acid as a thick yellow oil.

Example 3

Synthesis of 1-[(4-Methoxyphenyl)Methyl] Cyclopentane Carboxylic Acid

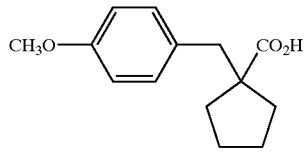

$C_{14}H_{18}O_3$
Mol. Wt: 234.29

A solution of diisopropylamine (58 mL, 0.44 mol) in THF 400 mL was cooled to below 0° C. and n-butyl lithium in hexane (170 mL, 2.5 N, 0.43 mol) was added dropwise maintaining the temperature below 0° C. Upon completion of the addition, ethyl cyclopentylcarboxylate (55 g, 0.39 mol) in THF (175 mL) was added dropwise maintaining the internal temperature between −60 and −70° C. Upon completion of the addition, the internal temperature was allowed to rise to −40° C. and was held there for 20 min and lowered back to −70° C. A solution of 4-methoxybenzyl bromide (75 g, 0.48 mol) in 175 mL of THF was added dropwise and the mixture was allowed to warm to room temperature overnight. A solution of 20% ammonium chloride in water (225 mL) was added followed by 450 mL of ethyl acetate, the layers were separated, the aqueous layer was extracted with ethyl acetate (450 mL) and the combined organic layers were washed with saturated brine (2×450 mL) and were dried (MgSO4). The crude product was chromatographed on silica gel, eluting with 1–5% ether in hexane to give 1-[(4-methoxyphenyl)methyl]cyclo-pentane carboxylic acid ethyl ester (80.8 g, 79%) as an oil.

The material obtained above was dissolved in methanol (620 mL) and 2 N sodium hydroxide (350 mL) and the mixture was heated to reflux overnight. The mixture was allowed to cool and was concentrated. The yellow, basic residue was washed with ether (2×500 mL) and was acidified with excess 6 N hydrochloric acid to pH<2. This solution was extracted with dichloromethane (2×500 mL), the extracts were combined, dried (MgSO$_4$) and evaporated to a white solid (69.6 g, 89%), mp 63.5–64.5° C.

Example 4

Synthesis of 1-(2-Azidoethyl)Cyclopentane Carboxylic Acid

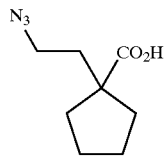

$C_8H_{13}N_3O_2$
Mol. Wt: 183.21

To an ice cold solution of diisopropylamine (56 mL, 0.396 mol) in THF 85 (mL) was added n-butyl lithium in hexane solution (240 mL, 1.6 M, 0.393 mol) over 20 min. The mixture was stirred at 0° C. for 30 min, cooled to a bath temperature of −65° C. and ethyl cyclopentane carboxylate (37.4 g, 0.263 mol) in THF (50 mL) was added over 20 min.

After 1 hr, a solution of 1,2-dibromoethane (47 mL, 0.545 mol) in THF (50 mL) was added, the mixture was held at −65° C. for 3 hr and allowed to warm to room temperature overnight. The reaction was quenched by addition of saturated ammonium chloride solution (200 mL), the layers were separated and the aqueous layer was extracted with ethyl acetate (100 mL). The combined extracts were washed with 1:1 brine:water (250 mL) and were dried ($Na_2SO_4$). The solution was filtered and concentrated, diluted with toluene (100 mL) and concentrated. The dilution and concentration was repeated twice to give ethyl 1-(2-bromoethyl) cyclopentane carboxylate (52.5 g).

A solution of the above bromide (52.5 g, 0.211 mol) and sodium azide (54 g, 0.831 mol) in DMF (200 mL) was stirred at 50° C. for 5 hr under a nitrogen atmosphere and was filtered. The filtrate was concentrated to near dryness, diluted with ethyl acetate (500 mL), filtered and concentrated to give crude ethyl 1-(2-azidoethyl)cyclopentane carboxylate (40.9 g) as a brown oil. This material was combined with product from a previous run (total 63.5 g) and was purified by chromatography over 250 g of silica gel, eluting with 5% ethyl acetate in hexane to give 50.3 g of product as a light brown oil.

The oil from above (50.3 g, 0.238 mol) was dissolved in THF (750 mL) and methanol (375 mL) and a solution of LiOH hydrate (15 g, 0.357 mol) in water (300 mL) was added. The resulting solution was stirred at 40° C. overnight and concentrated. The residue was dissolved in 2 L of water containing 40 mL of 1N NaOH and was washed with hexane (1 L). The aqueous layer was acidified with 1 N HCl (375 mL) and was extracted with ether (2×1 L). The combined extracts were dried ($Na_2SO_4$) and concentrated to give 1-(2-azidoethyl)cyclopentane carboxylic acid (37.5 g) as an amber liquid.

Example 5

Synthesis of 4-(Chloromethyl)-N-Methylbenzamide

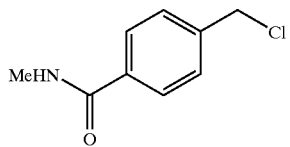

To a solution of 4-chloromethyl benzoic acid (17.05 g, 100 mmol) in toluene (dried over molecular sieves 4A) was added thionyl chloride (11 mL, 150 mmol). The mixture was heated to 80° C. and stirred overnight and then 3 h at 105° C. The reaction mixture was cooled to room temperature and excess thionyl chloride and toluene were removed under vacuum. The resulting oily residue was azeotroped with toluene (50 mL), then dried under high vacuum for 45 min to give the crude acid chloride.

To the crude acid chloride in dichloromethane (200 mL, dried over molecular sieves 4A) was added methylamine hydrochloride (7.5 g, 110 mmol) at −10° C. in one portion. To the mixture diisopropylamine (35 mL, 201 mmol) was added dropwise over 15 min while maintaining the temperature of the reaction mixture below 2° C. After addition, the suspension was allowed to warm to room temperature and stirred for 30 min. Then, the reaction mixture was diluted with water (125 mL) and the layers were separated. The aqueous layer was extracted with dichloromethane (2×60 mL) and the combined extracts were washed successively with water (150 mL) and brine solution (150 mL). After drying over anhydrous magnesium sulfate, the solution was concentrated to 50 mL. The precipitated white solid was collected by filtration and washed with dichloromethane and hexane to obtain 4-(chloromethyl)-N-methylbenzamide (12.02 g) as a white solid. A second crop material (3.05 g) was obtained from mother liquor by concetration and dilution with hexane to give a total of 15.07 g, 82%, mp 138–139.5° C.

Example 6

Synthesis of 4-(1-Methyltetrazol-5-yl)Benzyl Chloride

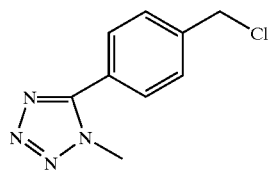

To a suspension of 4-(chloromethyl)-N-methylbenzamide (12 g, 65.3 mmol) in toluene (dried over molecular sieves 4A) was added thionyl chloride (7.15 mL, 98 mmol). The mixture was heated to reflux (~90° C.) and the resulting light yellow solution was stirred at reflux overnight. The reaction mixture was cooled to room temperature and excess thionyl chloride and toluene were removed under vacuum. The resulting oily residue was azeotroped with toluene (50 mL), then dried under high vacuum for 1.5 h to give the crude imidoyl chloride.

To a suspension of sodium azide (5.1 g, 78.5 mmol) in acetonitrile (62 mL) was added chlorotrimethylsilane (10.5 mL, 82.5 mmol) and the mixture was stirred for 1.5 h at room temperature. After cooling to 0° C., a solution of the crude imidoyl chloride prepared above in acetonitrile (20 mL) was added. This mixture was stirred for 1.5 h at 0° C., then allowed to warm to room temperature and stirred for 18 h. TLC analysis indicated the presence of traces of starting amide. Then, the reaction mixture was diluted with water (70 mL) and ethyl acetate (70 mL) and was poured into a mixture of saturated ammonium chloride (70 mL) and ethyl acetate (70 mL). The two layers were separated and the aqueous layer was extracted with ethyl acetate (2×50 mL). The combined extracts were washed successively with water (90 mL) and brine solution (90 mL). After drying over anhydrous magnesium sulfate, the solution was concentrated to 40 mL to afford a white precipitate. The solid was collected by filtration washing with hexane. Attempted purification by crystallization in various solvents were unsuccessful. Thus, it was purified by preparative HPLC using ethyl acetate and hexane in 1:2 ratio as eluent to afford 4-(1-methyltetrazol-5-yl)benzyl chloride (11.35 g, 83%) as a white solid; mp 90–92° C.

Example 7

Synthesis of 1-[[4-(1-Methyltetrazol-5-yl)Phenyl]Methyl]Cyclobutane Carboxylic Acid

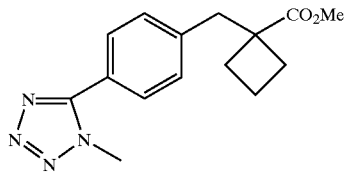

A solution of diisopropylamine (1.05 mL, 7.5 mmol) in THF (5 mL) was colled to −10° C. and a solution of n-butyl lithium (2.9 mL, 7.25 mmol) in hexanes was added dropwise while maintaining the temperature below 0° C. After addition, the solution was stirred for 30 min at 0° C. The solution was cooled to −70° C. and a solution of methyl cyclobutane carboxylate (0.57 g, 5 mmol) in THF (2 mL) was added dropwise maintaining the internal temperature between −60 to −70° C. After addition, the reaction mixture was stirred for 30 min at −50 to −60° C. Then, a solution of 4-(1-methyltetrazol-5-yl)benzyl chloride (0.94 g, 4.5 mmol) in THF (5 mL) was added dropwise and the reaction mixture was stirred for 1 h at −60 to −70° C. Then, it was allowed to warm to room temperature and stirred overnight at which point TLC analysis indicated the absence of 4-(1-methyltetrazol-5-yl)benzyl chloride (Note: the product and 4-(1-methyltetrazol-5-yl)benzyl chloride has the same Rf value, however they were differentiated by spraying with PMA). The mixture was poured into a mixture of water (70 mL) and ethyl acetate (70 mL). An emulsion formed and was filtered through celite. The resulting two layers were separated and the aqueous layer was extracted with ethyl acetate (2×50 mL). The combined extracts were washed with saturated brine and dried over anhydrous magnesium sulfate. After filtration, the solution was concentrated under vacuum and the residue was purified by silica gel chromatography eluting with 1:2 ethyl acetate:hexane to give methyl 1-[[4-(1-methyltetrazol-5-yl)phenyl]methyl]cyclobutane carboxylate (0.42 g, 32%) as a syrup. HR MS: obs. mass, 301.1668. Calcd mass, 301.1664.

Example 8–14

Using the procedure described in example 7, the cyclopentane carboxylate derivatives shown below were prepared.

| Example | R | Yield % | HR MS Obs. | HR MS Calcd |
|---|---|---|---|---|
| 8 | 3-CH₃O-C₆H₄-(CH₂)— | 66 | 248.1406 | 248.1412 |
| 9 | 2-Cl-C₆H₄-(CH₂)— | 99 | 252.0921 | 252.0917 |
| 9 | 4-NC-C₆H₄-(CH₂)— | 59 | 243.1253 | 243.1259 |
| 10 | 3,4-(CH₃O)₂-C₆H₃-(CH₂)— | 71 | 278.1518 | 278.1518 |
| 11 | 3-(1-methyltetrazol-5-yl)-C₆H₄-(CH₂)— | 53 | 301.1669 | 301.1664 |

-continued

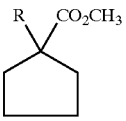

| Example | R | Yield % | HR MS Obs. | HR MS Calcd |
|---|---|---|---|---|
| 12 | ![structure with CH3-tetrazole-phenyl-(CH2)-] | 18 | 301.1668 | 301.1664 |
| 13 | CH3O(CH2)2— | 36 | 186.1257 | 187.1256 |
| 14 | CH3OCH2— | 45 | | |

Example 15

Synthesis of 1-[[4-(1-Methyl-5-Tetrazolyl)Phenyl]Methyl]Cyclobutane Carboxylic Acid

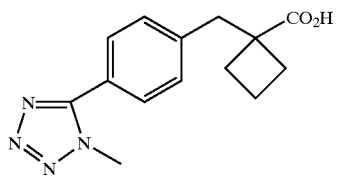

To a solution of methyl 1-[[4-(1-methyltetrazol-5-yl)phenyl]methyl]cyclobutane carboxylate (0.33 g, 1.15 mmol) in a mixture of THF (7 mL) and methanol (7 mL) was added 1 N sodium hydroxide (7 mL). The mixture was heated to 55° C. and stirred for 4 h at which point TLC analysis indicated the absence of starting material. After cooling to room temperature, the solvent was removed under vacuum and the residue was diluted with water and extracted with ethyl acetate to remove any neutral impurities. Then, the aqueous layer was neutralized with 1 N hydrochloric acid and the product was extracted with ethyl acetate (2×50 mL). The combined extracts were washed with saturated brine and dried over sodium sulfate. After filtration, the solution was concentrated under vacuum and the residue was dried under high vacuum to afford 1-[[4-(1-methyl-5-tetrazolyl)phenyl]methyl]cyclobutane carboxylic acid (180 mg, 57%) as a light yellow syrup.

Examples 16–23

Using the procedure described in example 15, the following cyclopentane carboxylic acids were prepared from the corresponding methyl esters:

| Example | R | Yield % | HR MS Obs. | HR MS Calcd |
|---|---|---|---|---|
| 16 | 3-methoxyphenyl-(CH2)— | 90 | 234.1264 | 234.1256 |
| 17 | 2-chlorophenyl-(CH2)— | 73* | 238.0757 | 238.0761 |
| 18 | 4-cyanophenyl-(CH2)— | 79 | 230.1173 | 230.1181 |

-continued

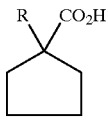

| Example | R | Yield % | HR MS Obs. | HR MS Calcd |
|---|---|---|---|---|
| 19 | 3,4-dimethoxybenzyl (CH₃O, CH₃O-C₆H₃-(CH₂)—) | 96 | 264.1361 | 264.1362 |
| 20 | 3-(1-methyltetrazol-5-yl)benzyl—(CH₂)— | 95 | 267.1508 | 267.1508 |
| 21 | 4-(1-methyltetrazol-5-yl)benzyl—(CH₂)— | 100 | 286.1433 | 286.1430 |
| 22 | CH3O(CH2)2— | 92 | 172.1095 | 172.1099 |
| 23 | CH3OCH2— | 73 | 158.0948 | 158.0943 | yield is the two steps according to the procedures described in examples 13 and 15.

Example 24

Synthesis of 1-[(4-Methoxyphenyl)Methyl]Cyclohexane Carboxylic Acid

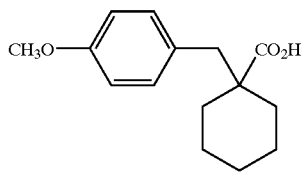

$C_{15}H_{20}O_3$
Mol. Wt: 248.32

Using the procedures described in examples 7 and 15, starting with 4-methoxybenzyl chloride, 1-[(4-methoxyphenyl)methyl]cyclohexane carboxylic acid was prepared in 23% overall yield. HRMS: obs. mass, 248.1426. Calcd. mass, 248.1412 (M+).

Example 25

Synthesis of 1-[3-(1-Methyl-5-Tetrazolyl)Phenyl]Methyl]Cyclohexane Carboxylic Acid

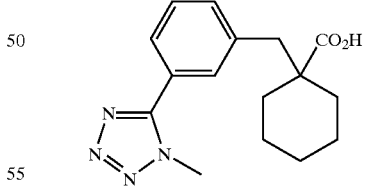

$C_{16}H_{20}N_4O_2$
Mol. Wt: 300.36

Using the procedures described in examples 7 and 15, starting with 1-[3-(1-methyl-5-tetrazolyl)benzyl chloride, 1-[3-(1-methyl-5-tetrazolyl)phenyl]methyl]cyclohexane carboxylic acid was prepared in 77% overall yield. HRMS: obs. mass, 301.1667. Calcd. mass, 301.1664 (M+H).

Example 26

Synthesis of N-[(1-Phenylcyclopentyl)Carbonyl]-4-Amino-L-Phenylalanine Methyl Ester

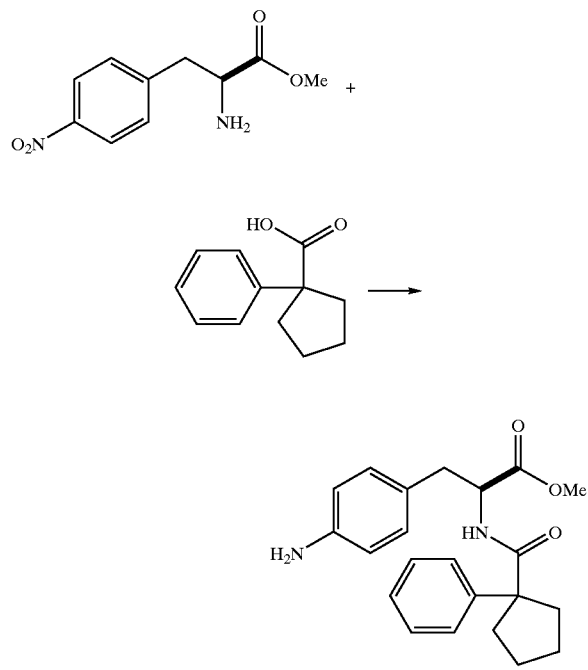

Example 27

Synthesis of N-[(1-Phenylcyclopentyl)Carbonyl]-4-[(4-Quinolinylcarbonyl)Amino]-L-Phenylalanine Sodium Salt

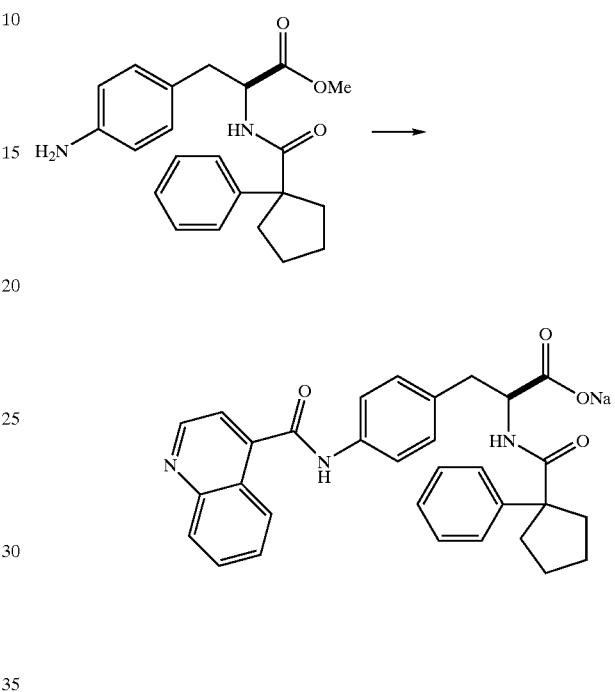

To a solution of 4-nitrophenylalanine hydrochloride methyl ester (3.90 g, 15 mmol) and 1-phenylcyclopentane carboxylic acid (3.4 g, 18 mmol) in 30 mL of DMF was added HBTU (6.8 g, 18 mmol) and diisopropylethyl amine (6.4 mL, 30 mmol) at room temperature. The mixture was then stirred at this temperature for 8 hr. The reaction was then diluted with 250 mL of ethyl acetate and was washed with 0.5 N HCl (40 mL), saturated NaHCO3 (2×40 mL) and saturated brine (2×40 mL). After removal of the solvent, the residue was purified on a silica gel column eluting with ethyl acetate:hexane (1:3) to give N-[(1-phenylcyclopentyl)carbonyl]-4-nitro-L-phenylalanine methyl ester (4.5 g, 75.7%).

A suspension of N-[(1-phenylcyclopentyl)carbonyl]-4-nitro-L-phenylalanine methyl ester (3.5 g, 8.88 mmol) and stannous chloride (10 g, 44 mmol) in 60 mL of ethanol was refluxed for 50 min under argon. The ethanol was then removed under reduced pressure and the residue was treated with 50 mL of saturated NaHCO3 followed by sodium carbonate to adjust pH above 9. The white slurry was extracted with ethyl acetate (3×300 mL). The combined extracts were washed with water (100 mL) and brine (100 mL) and were dried (MgSO4). Removal of the solvent afforded 4-amino-N-[(1-phenylcyclopentyl)carbonyl]-L-phenylalanine methyl ester (2.9 g, 89%).

To a solution of 4-amino-N-[(1-phenylcyclopentyl) carbonyl]-L-phenylalanine methyl ester (81 mg, 0.2 mmol) and 4-quinolinecarboxylic acid (43.3 mg, 0.25 mmol) in 1 mL of DMF was added HBTU (95 mg, 0.25 mmol) and diisopropylethylamine (65 µL, 0.5 mmol) at room temperature. The mixture was then stirred at this temperature for overnight. The reaction was then diluted with 15 mL of ethyl acetate and was washed with water (2 mL), saturated NaHCO3 (2×2 mL) and saturated brine (2×2 mL). The solution was dried (MgSO4) and concentrated. The residue was hydrolyzed with 0.5 mL of 1N NaOH in 5 mL of ethanol at 25° C. overnight. The crude product was purified by passing through an open C-18 column eluting with water (200 mL), 30% methanol in water (200 mL), 40% methanol in water (200 mL) and pure methanol (200 mL). The fractions containing product were concentrated and lyophilized to give N-[(1-phenylcyclopenyl)carbonyl]-4-[(4-quinolinylcarbonyl)amino]-L-phenylalanine sodium salt (79.5 mg, 75%), HR—FABMS: obs. mass, 530.2056. Calcd. mass, 530.2058.

Examples 28–31

Using the general method described in Example 27, the following analogs were prepared starting with the product from example 26 and the appropriate benzoic or hetereoaromatic carboxylic acids:

| Example | R' | HRMS calcd. | (M + H) found |
|---|---|---|---|
| 28 | 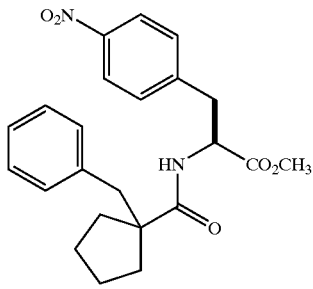 | 457.2127 | 457.2135 |
| 29 | | 496.1848 | 496.1844 |
| 30 | 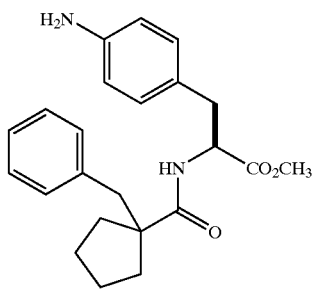 | 572.2161 | 572.2144 |
| 31 | | 530.2056 | 530.2057 |

Example 32
Synthesis of 4-Nitro-N-[[1-(Phenylmethyl) Cyclopentyl]Carbonyl]-L-Phenylalanine Methyl Ester A solution of 1-benzylcyclopentane carboxylic acid (0.135 g, 0.66 mmol), 4-nitro-L-phenylalanine methyl ester (0.187 g, 0.72 mmol), and HBTU (0.272 g, 0.72 mmol) in 2 mL of DMF was treated with diisopropylethylamine (0.35 mL, 2 mmol). The mixture was stirred over night, concentrated, diluted with ethyl acetate, washed with water, 1 N HCl, water, saturated NaHCO3 and dried (MgSO4). The residue obtained after evaporation was purified by chromatography over 30 g of silica gel, eluting with 40% ethyl acetate:hexane to give 4-nitro-N-[[1-(phenylmethyl) cyclopentyl]carbonyl]-L-phenylalanine methyl ester (194 mg, 71%), as a white foam.

Example 33

Synthesis of 4-Amino-N-[[1-(Phenylmethyl) Cyclopentyl]Carbonyl]-L-Phenylalanine Methyl Ester A solution of 4-nitro-N-[[1-(phenylmethyl)cyclopentyl] carbonyl]-L-phenylalanine methyl ester (185 mg, 0.45 mmol) in 10 mL of ethanol was hydrogenated at atmospheric pressure over 47 mg of 10% Pd(C.) for 3 hours. The reaction mixture was filtered through a pad of celite and evaporated to dryness to give 4-amino-N-[[1-(phenylmethyl) cyclopentyl]carbonyl]-L-phenylalanine methyl ester (170 mg, 99%) of as a white solid suitable for use in the next step.

Example 34

Synthesis of N-[[1-(Phenylmethyl)Cyclopentyl] Carbonyl]-4-[(4-Quinolinylcarbonyl)Amino)-L-Phenylalanine

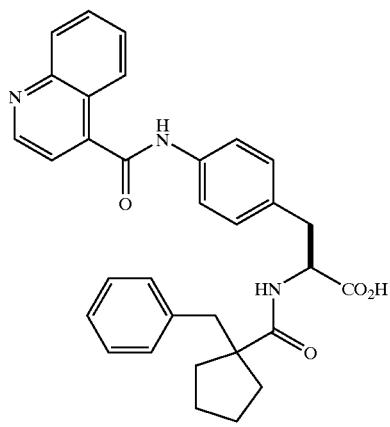

A solution of 4-amino-N-[[1-(phenylmethyl)cyclopentyl] carbonyl]-L-phenylalanine methyl ester (29.5 mg, 0.078 mmol), quinoline-4-carboxylic acid (17 mg, 0.10 mmol), and HBTU (38 mg, 0.10 mmol) in 1 mL of DMF was treated with diisopropylethylamine (30 μL, 0.17 mmol). The mixture was stirred over night and was diluted with 15 mL of ethyl acetate and 10 mL of ether and was washed with portions of water (2×10 mL), saturated NaHCO3 (10 mL) and was dried (MgSO4). Concentration gave 48 mg which was dissolved in 3 mL of methanol. Sodium hydroxide solution (0.10 mL, 4 N, 0.4 mmol) was added and the mixture was stirred for 2 hr. The excess base was quenched by addition of 0.1 mL of acetic acid, the solution was filtered through a 0.2μ nylon filter and the filtrate was purified by RP-HPLC on a 4×30 cm Rainin C-18 column using a gradient of 5 to 95% acetonitrile:water containing 0.75% trifluoroacetic acid at a flow of 49 mL/min over 30 min. The peak eluting at 74.5% acetonitrile was the acid N-[[1-(phenylmethyl)cyclopentyl]carbonyl]-4-[(4-quinolinylcarbonyl)amino)-L-phenylalanine (15 mg), HR—FAB—MS: obs. mass 522.2393. Calcd. mass 522.2393 (M+H), the peak eluting at 83% acetonitrile was recovered N-[[1-(phenylmethyl)cyclopentyl]carbonyl]-4-[(4-quinolinylcarbonyl)amino]-L-phenylalanine methyl ester (15 mg), HR—FAB—MS: obs. mass 536.2556. Calcd. mass 536.2549 (M+H).

Example 35

Synthesis of 4-[[(2-Nitrophenyl)Carbonyl]Amino]-N-[[1-(Phenylmethyl)Cyclopentyl]Carbonyl]-L-Phenylalanine

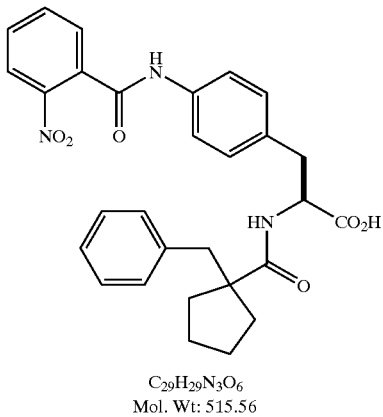

C29H29N3O6
Mol. Wt: 515.56

4-Amino-N-[[1-(phenylmethyl)cyclopentyl]carbonyl]-L-phenylalanine methyl ester (31.7 mg, 0.083 mmol) and 2-nitrobenzoic acid (38 mg, 0.10 mmol) were reacted as described in example 34 to give 26.7 mg of 4-[[(2-nitrophenyl)carbonyl]amino]-N-[[1-(phenylmethyl) cyclopentyl]carbonyl]-L-phenylalanine, HR—FAB—MS: obs. mass 516.2113. Calcd. mass 516.2134 (M+H).

Example 36

Synthesis of 4-[[(2-Methyl-5-Nitrophenyl)Carbonyl]amino]-N-[[1-(Phenylmethyl)Cyclopentyl]Carbonyl]-L-Phenylalanine

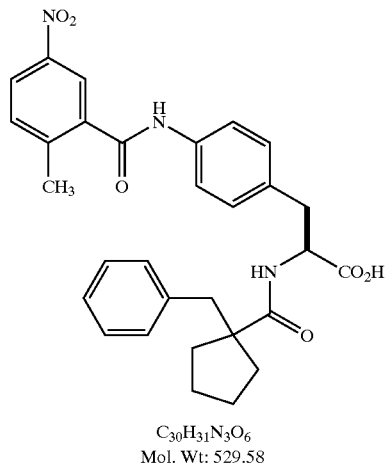

C30H31N3O6
Mol. Wt: 529.58

4-Amino-N-[[1-(phenylmethyl)cyclopentyl]carbonyl]-L-phenylalanine methyl ester (35.3 mg, 0.093 mmol) and 2-methyl-5-nitrobenzoic acid 20 mg, 0.11 mmol) were reacted as described in example 34 to give 4-[[(2-methyl-5-nitrophenyl)carbonyl]amino]-N-[[1-(phenylmethyl) cyclopentyl]carbonyl]-L-phenylalanine (34 mg, 69%), HR—FAB—MS: obs. mass 530.2298. Calcd. mass 530.2291 (M+H).

Example 37

Synthesis of 4-[[(2,6-Dichlorophenyl)Carbonyl]Amino]-N-[[1-(Phenylmethyl)Cyclopentyl]Carbonyl]-L-Phenylalanine

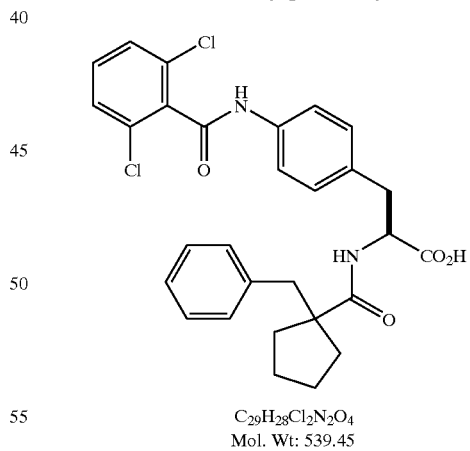

C29H28Cl2N2O4
Mol. Wt: 539.45

4-Amino-N-[[1-(phenylmethyl)cyclopentyl]carbonyl]-L-phenylalanine methyl ester (67 mg, 0.176 mmol) and 2,6-dichlorobenzoyl chloride (50 mg, 0.23 mmol) were dissolved in 5 mL of dichloromethane and 2,6-lutidine (50 μL, 0.43 mmol) were added. After 4 hours, the mixture was diluted with ether and dichloromethane and washed with 1 N HCl, water, and saturated NaHCO3 and was dried (MgSO4). The crude product was dissolved in 4 mL of methanol and treated with 4 N NaOH (0.1 mL). After 2 hours, the excess base was quenched with 0.1 mL of acetic acid, the solution was filtered through a 0.2μ nylon filter and the filtrate was purified by RP-HPLC on a 4×30 cm Rainin C-18 column using a gradient of 5 to 95% acetonitrile:water containing 0.75% trifluoroacetic acid at a flow of 49 mL/min over 30 min. The peak eluting at 87% acetonitrile was concentrated and lyophilized to give 4-[[(2,6-dichlorophenyl)carbonyl]amino]-N-[[1-(phenylmethyl)cyclopentyl]carbonyl]-L-phenylalanine (46 mg), LR(+) LSIMS: m/z 539 (M+H) (2 Cl)

Example 38

Synthesis of N-[[1-[(4-Methoxyphenyl)Methyl]Cyclopentyl]Carbonyl]-4-Nitro-L-Phenylalanine Methyl Ester

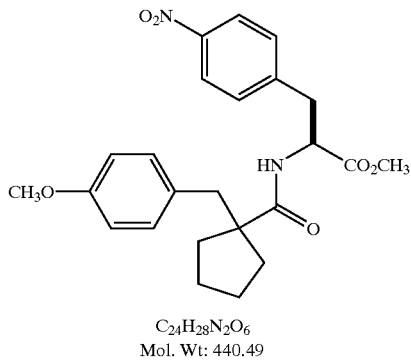

$C_{24}H_{28}N_2O_6$
Mol. Wt: 440.49

A solution of 1-(4-methoxy)benzylcyclopentane carboxylic acid (0.0.20 g, 0.86 mmol), 4-nitro-L-phenylalanine methyl ester (0.24 g, 0.94 mmol), and HBTU (0.36 g, 0.94 mmol) in 3 mL of DMF was treated with 0.52 mL (3 mmol) of diisopropylethylamine. The mixture was stirred over night, concentrated, diluted with ethyl acetate, washed with water, 1 N HCl, water, saturated NaHCO3 and dried (MgSO4). The residue obtained after evaporation was purified by chromatography over 30 g of silica gel, eluting with 40% ethyl acetate:hexane to give N-[[1-[(4-methoxyphenyl)methyl]cyclopentyl]carbonyl]-4-nitro-L-phenylalanine methyl ester (256 mg, 68%), as a white foam, HR—FAB—MS: Obs mass, 441.2027. Calcd mass, 441.2025 (M+H).

Example 39

Synthesis of 4-Amino-N-[[1-[(4-Methoxyphenyl)Methyl]Cyclopentyl]Carbonyl]-L-Phenylalanine Methyl Ester

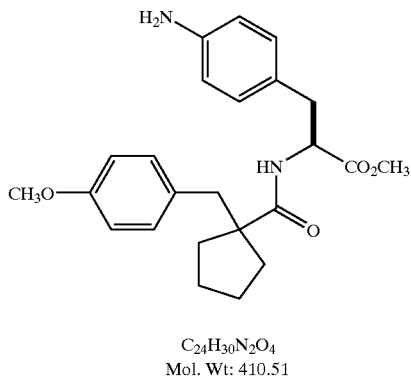

$C_{24}H_{30}N_2O_4$
Mol. Wt: 410.51

A solution of N-[[1-[(4-methoxyphenyl)methyl]cyclopentyl]carbonyl]-4-nitro-L-phenylalanine methyl ester (253 mg, 0.575 mmol) in 10 mL of ethanol was hydrogenated at atmospheric pressure over 45 mg of 10% Pd(C) for 3 hours. The reaction mixture was filtered through a pad of celite and evaporated to dryness to give 4-amino-N-[[1-[(4-methoxyphenyl)methyl]cyclopentyl]carbonyl]-L-phenylalanine methyl ester (225 mg, 95%) as a white solid suitable for use in the next step, HR—FAB—MS: Obs mass, 410.2196. Calcd mass, 410.2200 (M+).

Example 40

Synthesis of N-[[1-[(4-Methoxyphenyl)Methyl]Cyclopentyl]Carbonyl]-4-[(4-Quinolinylcarbonyl)Amino]-L-phenylalanine

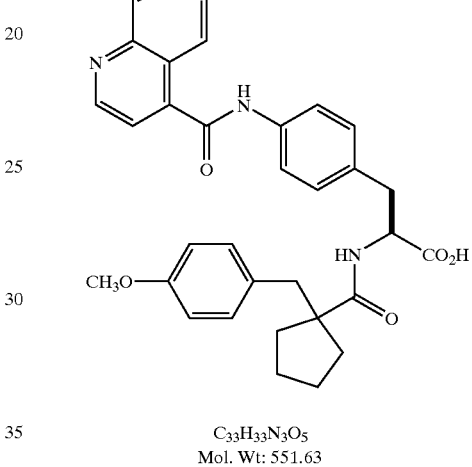

$C_{33}H_{33}N_3O_5$
Mol. Wt: 551.63

A solution of 4-amino-N-[[1-[(4-methoxyphenyl)methyl]cyclopentyl]carbonyl]-L-phenylalanine methyl ester (30.7 mg, 0.075 mmol), quinoline-4-carboxylic acid (17 mg, 0.10 mmol), and HBTU (38 mg, 0.10 mmol) in 1 mL of DMF was treated with diisopropylethylamine (30 μL, 0.17 mmol). The mixture was stirred over night and was diluted with 15 mL of ethyl acetate and 10 mL of ether and was washed with water (2×10 mL), saturated NaHCO3 (1×10 mL) and was dried (MgSO4). Concentration gave 42 mg which was dissolved in 3 mL of methanol. Sodium hydroxide (0.10 mL, 4 N, 0.4 mmol) was added and the mixture was stirred for 2 hours. The excess base was quenched by addition of acetic acid (0.1 mL), the solution was filtered through a 0.2μ nylon filter and the filtrate was purified by RP-HPLC on a 4×30 cm Rainin C-18 column using a gradient of 5 to 95% acetonitrile:water containing 0.75% trifluoroacetic acid at a flow of 49 mL/min over 30 min. The peak eluting at 74% acetonitrile was concentrated and lyophilized to give N-[[1-[(4-methoxyphenyl)methyl]cyclopentyl]carbonyl]-4-[(4-quinolinylcarbonyl)amino]-L-phenylalanine (22.8 mg), HR—FAB—MS: obs. mass 552.2482. Calcd. mass 552.2498 (M+H). The peak eluting at 82.6% acetonitrile was recovered N-[[1-[(4-methoxyphenyl)methyl]cyclopentyl]carbonyl]-4-[(4-quinolinylcarbonyl)amino]-L-phenylalanine methyl ester (11.2 mg), HR—FAB—MS: obs. mass 566.2675. Calcd. mass 566.2655 (M+H).

Example 41

Synthesis of N-[[1-[(4-Methoxyphenyl)Methyl]Cyclopentyl]Carbonyl]-4-[[(2-Nitrophenyl)Carbonyl]Amino]-L-Phenylalanine

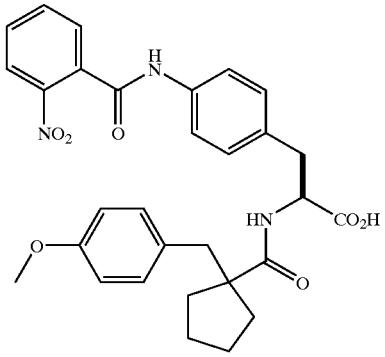

C30H31N3O7
Mol. Wt: 545.58

4-Amino-N-[[1-[(4-methoxyphenyl)methyl]cyclopentyl]carbonyl]-L-phenylalanine methyl ester (32.3 mg, 0.079 mmol) and 2-nitrobenzoic acid (17 mg, 0.10 mmol) were reacted as described in example 40 to give 22 mg of N-[[1-[(4-methoxyphenyl)methyl]cyclopentyl]carbonyl]-4-[[(2-nitrophenyl)carbonyl]amino]-L-phenylalanine, HR—FAB—MS: obs. mass 546.2235. Calcd. mass 546.2240 (M+H).

Example 42

Synthesis of N-[[1-[(4-Methoxyphenyl)Methyl]Cyclopentyl]Carbonyl]-4-[[(2-Methyl-5-Nitrophenyl)Carbonyl]Amino]-L-Phenylalanine

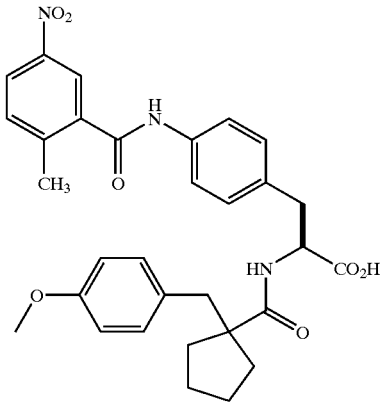

C31H33N3O7
Mol. Wt: 559.61

4-Amino-N-[[1-[(4-methoxyphenyl)methyl]cyclopentyl]carbonyl]-L-phenylalanine methyl ester (23.4 mg, 0.057 mmol) and 2-methyl-5-nitrobenzoic acid 13 mg, 0.07 mmol) were reacted as described in example 40 to give 23 mg (69%) of N-[[1-[(4-methoxyphenyl)methyl]cyclopentyl]carbonyl]-4-[[(2-methyl-5-nitrophenyl)carbonyl]amino]-L-phenylalanine, HR—FAB—MS: obs. mass 560.2413. Calcd. mass 560.2397 (M+H).

Example 43

Synthesis of 4-[[(2,6-Dichlorophenyl)Carbonyl]Amino]-N-[[1-[(4-Methoxyphenyl)methyl]Cyclopentyl]Carbonyl]-L-Phenylalanine

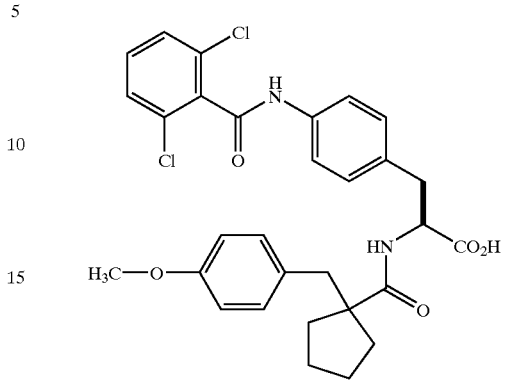

C30H30Cl2N2O5
Mol. Wt: 569.48

4-Amino-N-[[1-[(4-methoxyphenyl)methyl]cyclopentyl]carbonyl]-L-phenylalanine methyl ester (66 mg, 0.17 mmol) and 2,6-dichlorobenzoyl chloride (50 mg, 0.23 mmol) were dissolved in 5 mL of dichloromethane and 2,6-lutidine (50 μL, 0.43 mmol) were added. After 4 hours, the mixture was diluted with ether and dichloromethane and washed with 1 N HCl, water, and saturated NaHCO3 and was dried (MgSO4). The crude product was dissolved in methanol (4 mL) and treated with 4 N NaOH (0.1 mL). After 2 hours, the excess base was quenched with acetic acid (0.1 mL), the solution was filtered through a 0.2μ nylon filter and the filtrate was purified by RP-HPLC on a 4×30 cm Rainin C-18 column using a gradient of 5 to 95% acetonitrile:water containing 0.75% trifluoroacetic acid at a flow of 49 mL/min over 35 min. The peak eluting at 79% acetonitrile was concentrated and lyophilized to give 4-[[(2,6-dichlorophenyl)carbonyl]amino]-N-[[1-[(4-methoxyphenyl)methyl]cyclopentyl]carbonyl]-L-phenylalanine (28.2 mg), HR—FABMS: obs. mass 591.1445. Calcd. mass 591.1430 (M+Na).

Example 44

Synthesis of 4-[[(2,6-Dichlorophenyl)Carbonyl]Amino]-N-[(1,1-Dimethylethoxy)Carbonyl]-L-Phenylalanine Methyl Ester

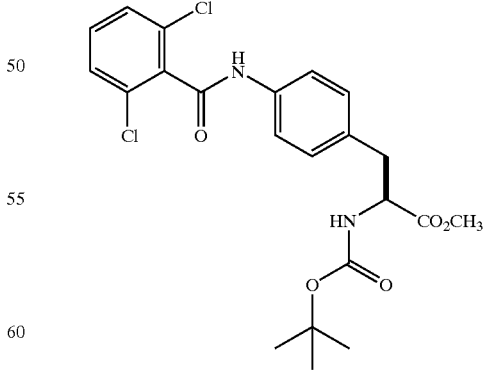

C22H24Cl2N2O5
Mol. Wt: 467.34

To a solution of 4-(amino)-N-[(1,1-dimethylethoxy)carbonyl]-L-phenylalanine methyl ester (2.6 g, 8.6 mmol) in dichloromethane (20 mL) were added diisopropylethylamine (2.3 mL, 13 mmol) followed by 2,6-dichlorobenzoyl chloride (1.99 g, 9.5 mmol) at room temperature. The mixture was stirred for 15 h at which time a white precipitate was formed. The mixture was diluted with 30 mL of dichloromethane and 50 mL of water. The layers were separated and the aqueous layer was extracted with 100 mL (2×50 mL) of dichloromethane. The combined organic extracts were washed with brine and dried over anhydrous magnesium sulfate. Filtration and concentration of the solvent gave 4.03 g (quantitative) of 4-[[(2,6-dichlorophenyl)carbonyl]amino]-N-[(1,1-dimethylethoxy)-carbonyl]-L-phenylalanine methyl ester as a white solid, mp 148–151° C.

Example 45

Synthesis of 4-[[(2,6-Dichlorophenyl)Carbonyl]Amino]-L-Phenylalanine Methyl Ester Hydrochloride Salt

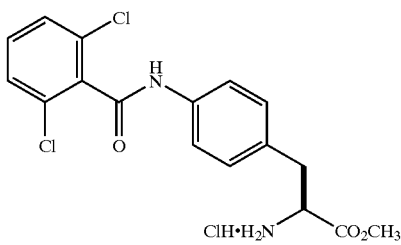

4-[[(2,6-Dichlorophenyl)carbonyl]amino]-N-[(1,1-dimethylethoxy)carbonyl]-L-phenylalanine methyl ester (1.86 g, 4.0 mmol) was treated with 4 N hydrochloric acid in dioxane (10 mL) at room temperature. After 5 minutes, the solids went into solution and the mixture was stirred for 1 h. Then, 25 mL of ethyl ether was added to precipitate the product. The solids were collected by filtration and washed with hexane. The resulting solid was very hydroscopic and became gummy. This material was dissolved in 50 mL of methanol and concentrated. After drying under high vacuum, 4-[[(2,6-dichlorophenyl)carbony]amino]-L-phenylalanine methyl ester hydrochloride salt. (1.64 g, 97%) was obtained as a light yellow solid: mp 158–161° C.

Example 46

Synthesis of 4-[[(2,6-Dichlorophenyl)Carbonyl]Amino]-N-[[1-(4-Methoxyphenyl-Methyl)Cycloheyl]Carbonyl]-L-Phenylalanine Methyl Ester

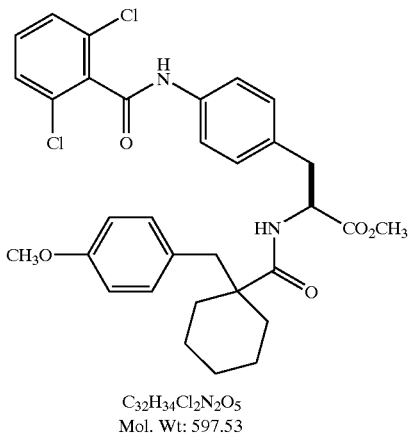

C$_{32}$H$_{34}$Cl$_2$N$_2$O$_5$
Mol. Wt: 597.53

To a solution of 4-[[(2,6-dichlorophenyl)carbonyl]amino]-L-phenylalanine methyl ester hydrochloride salt (0.2 g, 0.5 mmol) and 1-(4-methoxyphenylmethyl)cyclohexane-carboxylic acid (0.15 g, 0.60 mmol) in DMF (2 mL) were added HBTU (0.23 g, 0.60 mmol) and diisopropylethylamine (0.20 mL, 1.2 mmol) at room temperature. The mixture was stirred overnight and diluted with 25 mL of ethyl acetate. The ethyl acetate layer was washed successively with 0.5N hydrochloric acid (2×20 mL), saturated sodium bicarbonate solution (2×20 mL), brine (1×20 mL) and dried over anhydrous magnesium sulfate. Filtration and concentration gave 350 mg of white solid which was purified by column chromatography over 15 g of silica gel, eluting with 20–30% ethyl acetate in hexane to give 4-[[(2,6-dichlorophenyl)carbonyl]amino]-N-[[1-(4-methoxyphenylmethyl)cycloheyl]carbonyl]-L-phenylalanine methyl ester (0.25 g, 84%) as a white solid, mp 85–87° C. HR MS: Obs mass, 597.1913. Calcd mass, 597.1923 (M+H).

Example 47

Synthesis of 4-[[(2,6-Dichlorophenyl)Carbonyl]Amino]-N-[[1-(4-Methoxyphenylmethyl)Cycloheyl]Carbonyl]-L-Phenylalanine

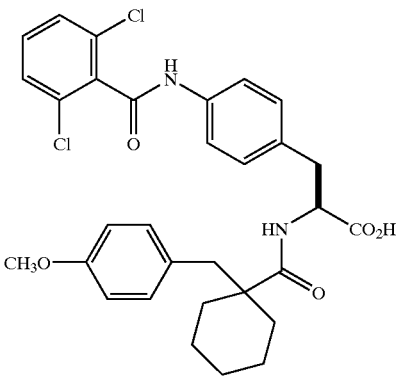

C$_{31}$H$_{32}$Cl$_2$N$_2$O$_5$
Mol. Wt.: 583.50

To a suspension of 4-[[(2,6-dichlorophenyl)carbonyl]amino]-N-[[1-(4-methoxyphenyl-methyl)cyclohexy]carbonyl]-L-phenylalanine methyl ester (0.15 g, 0.25 mmol) in ethanol (2 mL) was added aqueous 1.0 N sodium hydroxide (1.5 mL, 3 mmol) at room temperature. The mixture was heated to 50° C. and the resulting clear solution was stirred overnight. The mixture was concentrated, the residue was diluted with 5 mL of water and extracted with 25 mL of ether to remove any neutral impurities. The aqueous layer was acidified with 1 N HCl and the precipitated white solid was collected by filtration and washed with water (20 mL) and hexane (20 mL). After air-drying, 4-[[(2,6-dichlorophenyl)carbonyl]amino]-N-[[1-(4-methoxyphenylmethyl)cyclohexyl]carbonyl]-L-phenylalanine (0.12 g, 82%) was obtained as a white solid, mp 136–140° C. HR MS: Obs mass, 583.1763. Calcd mass, 583.1766 (M+H).

Examples 48 to 60

The compounds shown below were prepared according to the procedures given in examples 46 and 47.

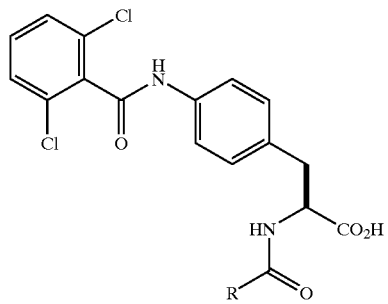
| Example | Starting Material From Example | R | Yield % | HRMS (M + H) calcd. | obs. |
|---|---|---|---|---|---|
| 48 | 20 | 3-(1-methyltetrazol-5-yl)phenyl-CH2-C(CH3)(cyclopentyl) | 92 | 621.1784 | 621.1758 |
| 49 | commercial | camphor-derived | 93 | 517.1297 | 517.1285 |
| 50 | 25 | 3-(1-methyltetrazol-5-yl)phenyl-CH2-C(CH3)(cyclohexyl) | 89 | 635.1940 | 635.1967 |
| 51 | 17 | 2-chlorophenyl-CH2-C(CH3)(cyclopentyl) | 84 | 573.1114 | 573.1113 |
| 52 | 16 | 3-methoxyphenyl-CH2-C(CH3)(cyclopentyl) | 99 | 569.1610 | 569.1620 |
| 53 | 18 | 4-cyanophenyl-CH2-C(CH3)(cyclopentyl) | 91 | 586.1277 | 586.1285 |

-continued
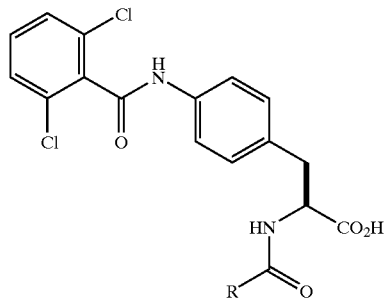
| Example | Starting Material From Example | R | Yield % | HRMS (M + H) calcd. | obs. |
|---|---|---|---|---|---|
| 54 | 19 | 3,4-dimethoxybenzyl-1-methylcyclopentyl | 87 | 599.1715 | 599.1714 |
| 55 | 21 | 4-(1-methyltetrazol-5-yl)benzyl-1-methylcyclopentyl | 91 | 621.1784 | 621.1782 |
| 56 | 401 | 3-(1-methyltetrazol-5-yl)benzyl-1-methylcyclobutyl | 95 | 607.1627 | 607.1644 |
| 57 | 15 | 4-(1-methyltetrazol-5-yl)benzyl-1-methylcyclobutyl | 80 | 607.1627 | 607.1640 |
| 58 | 4 | N₃-CH₂CH₂-1-methylcyclopentyl | 99 | 518.1362 | 518.1345 |
| 59 | 22 | CH₃O-CH₂CH₂-1-methylcyclopentyl | 93 | 507.1454 | 507.1464 |
| 60 | 23 | CH₃O-CH₂-1-methylcyclopentyl | 99 | 493.1297 | 493.1300 |

Example 61

Coupling of N-[(9H-fluoren-9-ylmethoxy)carbonyl]-4-[[(2-propenyloxy)carbonyl]amino]-L-phenylalanine to Wang resin

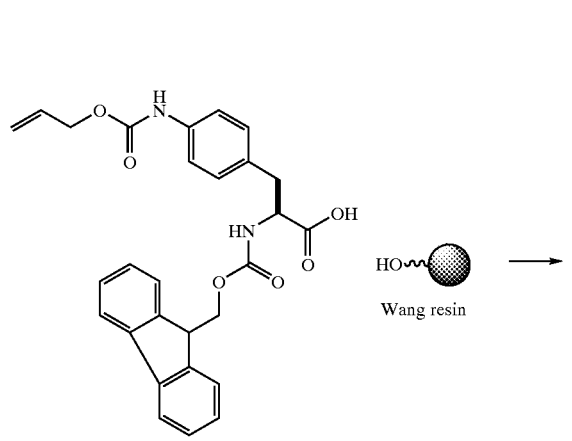

A 250 mL cylindrical glass vessel equipped with a coarse glass frit was charged with 10 g of Wang resin, (loading factor: 1.15 mmol/g, 300 mesh). The resin was washed with dichloromethane (2×100 mL), methanol (2×100 mL) and dimethylformamide (2×100 mL). To the swollen resin was added N-[(9H-fluoren-9-ylmethoxy)carbonyl]-4-[[(2-propenyloxy)carbonyl]amino]-L-phenylalanine (11.2 g, 23 mmol) and 2,6-dichlorobenzoyl chloride (8.06 mL, 57.5 mmol) in N-methylpyrrolidone (70 mL) and the mixture was agitated for 30 minutes. Pyridine (6.45 mL, 80.5 mmol) was added and the resulting mixture was agitated for 24 hr. The substitution was determined to be 0.75 mmol of N-[(9H-fluoren-9-ylmethoxy)carbonyl]-4-[[(2-propenyloxy)carbonyl]amino]-L-phenylalanine per gram of resin by quantitative UV measurement of the fmoc present on the resin.

Example 62

Synthesis of 4-Amino-N-[(9H-fluoren-9-ylmethoxy)Carbonyl]-L-Phenylalanine On Wang Resin

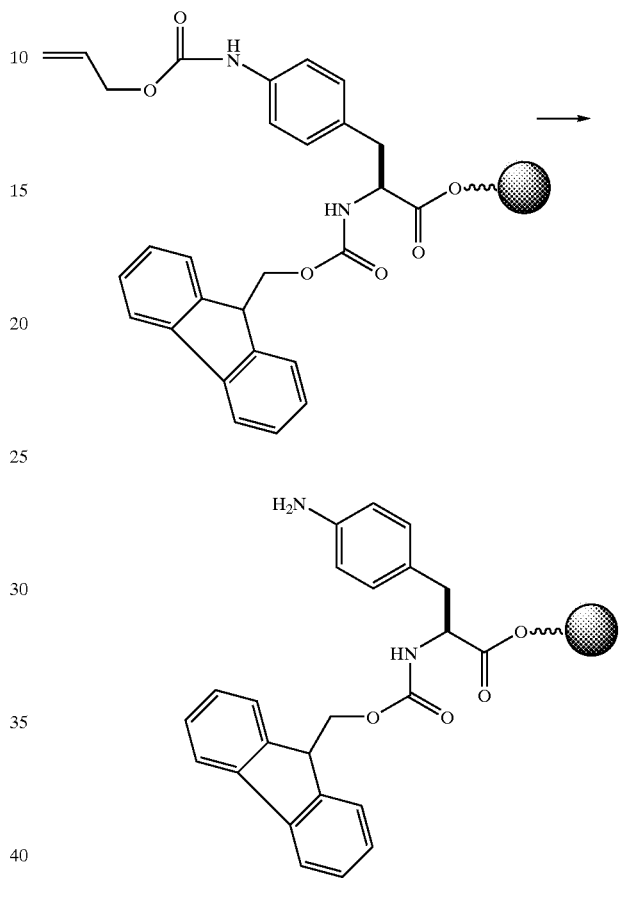

A 500 mL cylindrical glass vessel equipped with a coarse glass frit was charged with N-[(9H-fluoren-9-ylmethoxy)carbonyl]-4-[[(2-propenyloxy)carbonyl]amino]-L-phenylalanine substituted Wang resin (10 g, 7.5 mmol) obtained from Example 61 and a solution prepared from bis(triphenylphosphine)palladium dichloride (1.6 g, 2.3 mmol) and acetic acid (5 mL, 83 mmol) in dried dichloromethane (150 mL). The resulting mixture was agitated for 30 minutes followed by the addition of tri-n-butyl tin hydride (20 mL, 74.3 mmol). The resulting mixture was agitated for 1 hr. To the mixture was added tri-n-butyl tin hydride (10 mL, 37 mmol). Agitation was continued for 1 hour and the mixture was filtered. To the resulting resin was added a solution prepared from bis(triphenylphosphine) palladium dichloride (1.6 g, 2.3 mmol) and acetic acid (5 mL, 83 mmol) in dry dichloromethane (150 mL). The mixture was agitated for 30 minutes followed by the addition of tri-n-butyl tin hydride (20 mL, 74.3 mmol). The resulting mixture was agitated 1 hour. To the mixture was added additional tri-n-butyl tin hydride (10 mL, 37.15 mmol). Agitation was continued for 1 hour. After the second deprotection cycle, the mixture was washed with dichloromethane (2×100 mL), methanol (2×100 mL) and dimethylformamide (2×100 mL) to give 4-amino-N-[(9H-fluoren-9-ylmethoxy)carbonyl]-L-phenylalanine on Wang resin suitable for use in subsequent steps.

Example 63

Synthesis of 4-[(4-Quinolinylcarbonyl)Amino]-L-Phenylalanine on Wang Resin

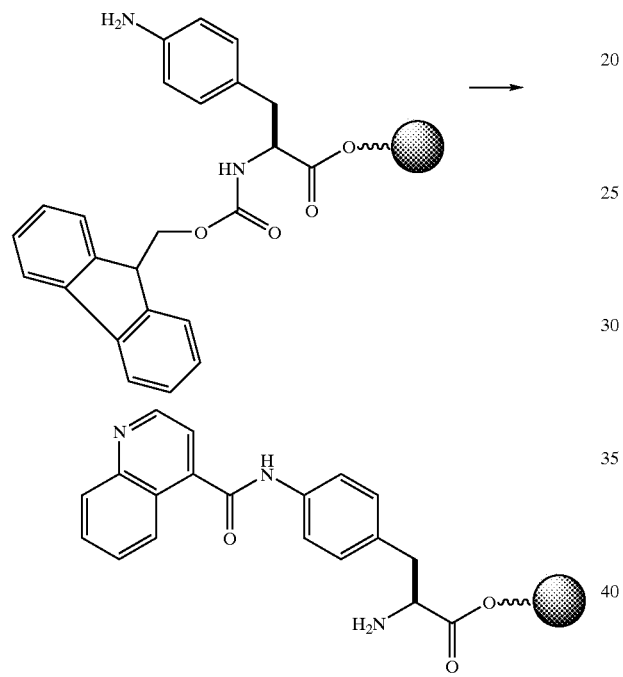

A 250 mL cylindrical glass vessel equipped with a coarse glass frit was charged with 4-amino-N-[(9H-fluoren-9-ylmethoxy)carbonyl]-L-phenylalanine (10 g) obtained in Example 62 and a solution prepared from quinoline-4-carboxylic acid (5.2 g, 30 mmol), BOP (13.75 g, 30 mmol) and diisopropylethylamine (6.8 mL) in 70 mL of N-methylpyrrolidinone. The slurry was agitated for 4 hr. The mixture was filtered and washed with dichloromethane (2×100 mL), methanol (2×100 mL) and dimethylformamide (2×100 mL). To the washed resin was added a solution of 25% piperidine in N-methylpyrrolidinone (80 mL), the mixture was agitated at room temperature for 20 minutes and filtered. The process was repeated and the resulting slurry was filtered and washed with dichloromethane (2×100 mL), methanol (2×100 mL) and dimethylformamide (2×100 mL). Filtration afforded 4-[(4-quinolinylcarbonyl)amino]-L-phenylalanine on Wang resin suitable for use in the next step.

Example 64

Synthesis of N-[(2,2-Dichloro-1-Methylcyclopropyl)Carbonyl]-4-[(4-Quinolinylcarbonyl)Amino]-L-Phenylalanine

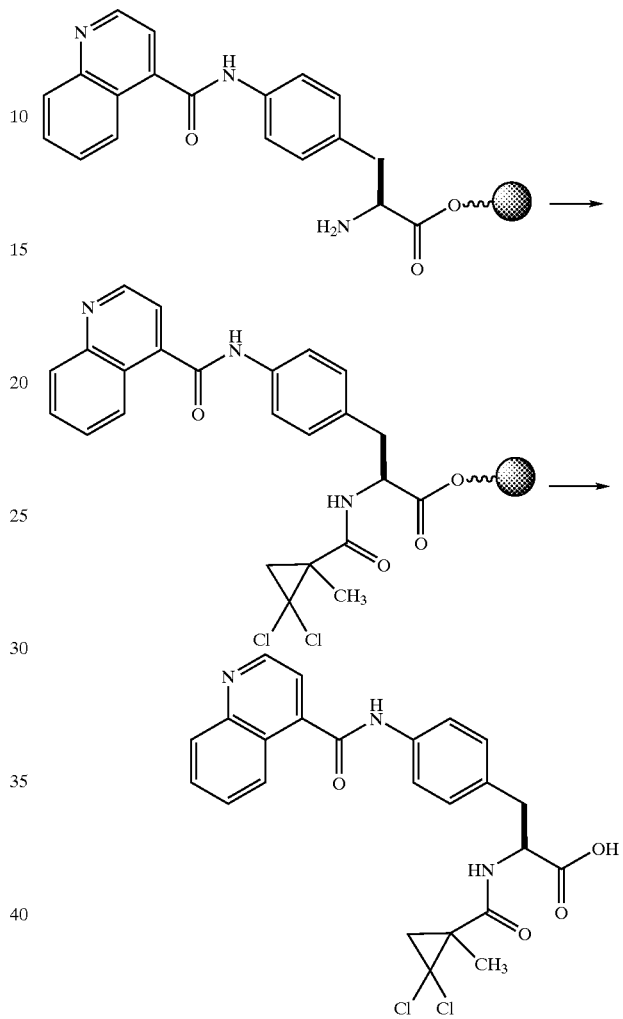

4-[(4-Quinolinylcarbonyl)amino]-L-phenylalanine on Wang resin (300 mg) obtained from Example 63 was washed with dichloromethane (2×10 mL), methanol (2×10 mL) and dimethylformamide (2×10 mL). To the resin was added a solution prepared from 2,2-dichloro-1-methylcyclopropylcarboxylic acid (180 mg, 1.02 mmol), BOP (450 mg, 1.02 mmol) and diisopropylethylamine (0.23 mL) in 4 mL of N-methylpyrrolidinone at room temperature. The resulting mixture was agitated for 2 hours. The reaction mixture was then filtered and washed with dichloromethane (2×10 mL), methanol (2×10 mL) and dichloromethane (2×10 mL). Cleavage was effected with 90% trifluoroacetic acid (TFA) in dichloromethane for 5 minutes. The mixture was filtered and the TFA was removed under high vacuum. Addition of ether (25 mL) effected precipitation of N-[(2,2-dichloro-1-methylcyclopropyl)carbonyl]-4-[(4-quinolinylcarbonyl)amino]-L-phenylalanine. The compound was purified by reverse phase HPLC (DuPont, Rx C18, 7 μM, 2.12 cm×25 cm) using acetonitrile and water as the mobile phase with a linear gradient from 20–50% of acetonitrile over 180 minutes. LRMS (M+H) obs. mass, 486.5. Calcd. mass 486.3.

Examples 65–81
Using the procedure described in Example 64, the compounds shown below were prepared.
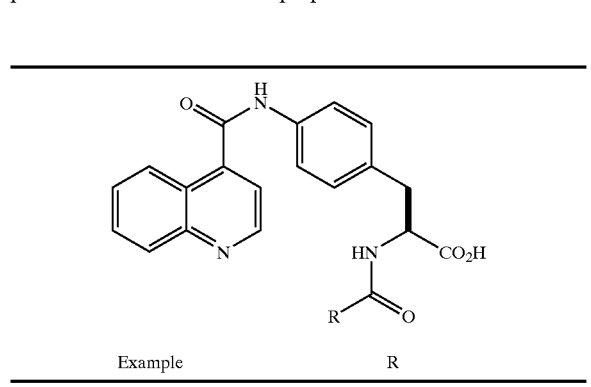
| Example | R |
|---|---|
| 65 | |
| 66 | |
| 67 | |
| 68 | |
| 69 | |
| 70 | |
| 71 | |
| 72 | |
-continued
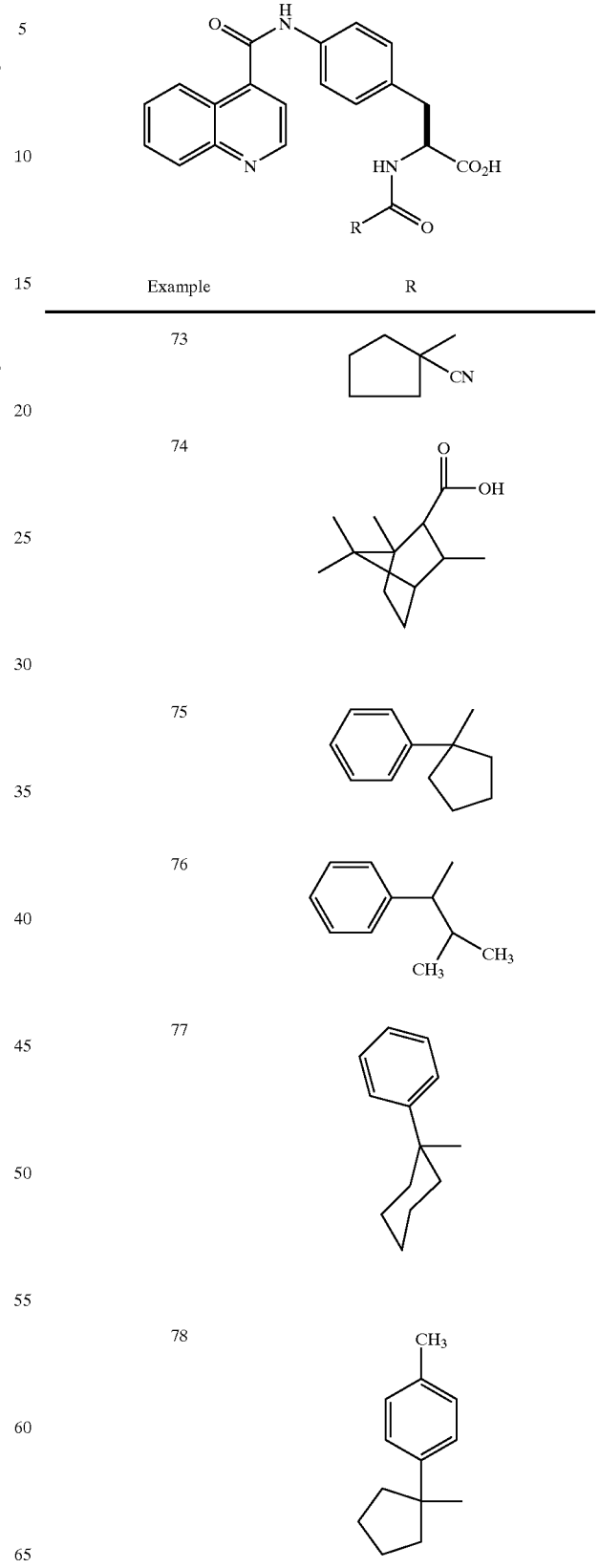
| Example | R |
|---|---|
| 73 | |
| 74 | |
| 75 | |
| 76 | |
| 77 | |
| 78 | |

-continued
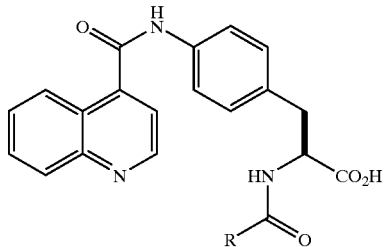
| Example | R |
|---|---|
| 79 | 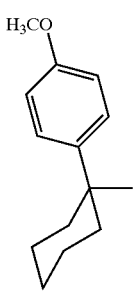 |
| 80 | 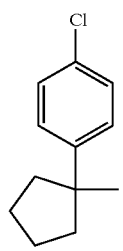 |
-continued
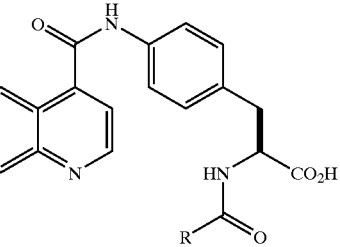
| Example | R |
|---|---|
| 81 | 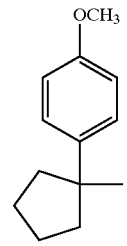 |
Examples 82 to 106
Using the method described in examples 63 and 64, the following derivatives were prepared:
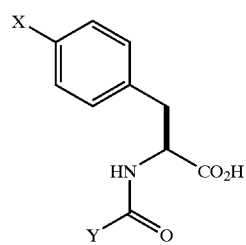
| Example | Y | X |
|---|---|---|
| 82 |  | 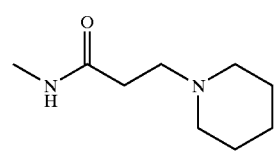 |

-continued

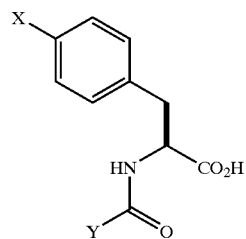

| Example | Y | X |
|---|---|---|
| 83 | 1-adamantyl | N-methyl-2,6-dichlorobenzamide |
| 84 | 1-adamantyl | N-methyl-2-trifluoromethyl-4-fluorobenzamide |
| 85 | 1-adamantyl | N-methyl-2-methyl-5-nitrobenzamide |
| 86 | 1-adamantyl | N-methyl-2-acetamido-3-(4-hydroxyphenyl)propanamide |
| 87 | 3,3-dimethylhexyl | N-methyl-3-(piperidin-1-yl)propanamide |
| 88 | 3,3-dimethylhexyl | N-methyl-2,6-dichlorobenzamide |
| 89 | 3,3-dimethylhexyl | N-methyl-2-trifluoromethyl-4-fluorobenzamide |

-continued

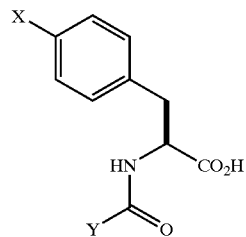

| Example | Y | X |
|---|---|---|
| 90 | (3,3-dimethylheptyl) | 2-methyl-5-nitro-N-methylbenzamide |
| 91 | (3,3-dimethylheptyl) | (S)-2-acetamido-3-(4-hydroxyphenyl)-N-methylpropanamide |
| 92 | 1-methyl-1-cyanocyclopentyl | N-methyl-3-(piperidin-1-yl)propanamide |
| 93 | 1-(4-methoxyphenyl)-1-methylcyclopentyl | N-methyl-3-(piperidin-1-yl)propanamide |
| 94 | 1-(4-methoxybenzyl)-1-methylcyclopentyl | N-methyl-3-(piperidin-1-yl)propanamide |
| 95 | 1-(4-methoxybenzyl)-1-methylcyclopentyl | 2,6-dichloro-N-methylbenzamide |
| 96 | 1-(4-methoxybenzyl)-1-methylcyclopentyl | 2-trifluoromethyl-4-fluoro-N-methylbenzamide |

-continued
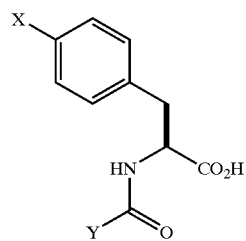
| Example | Y | X |
|---|---|---|
| 97 | 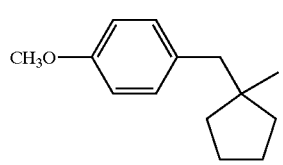 | 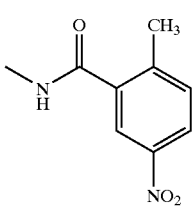 |
| 98 | 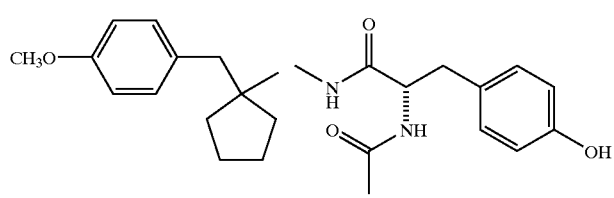 | 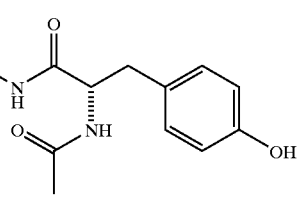 |
| 99 | 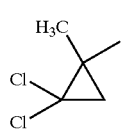 | 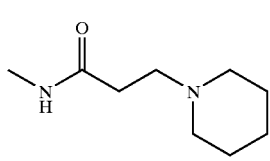 |
| 100 | 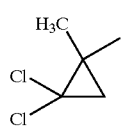 | 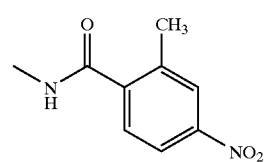 |
| 101 | 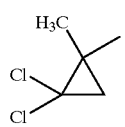 | 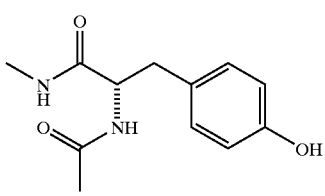 |
| 102 | 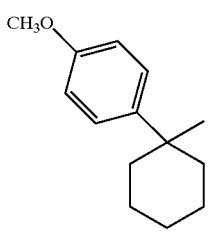 | 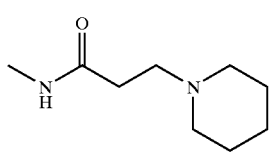 |

-continued
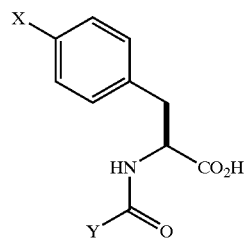
| Example | Y | X |
|---|---|---|
| 103 | 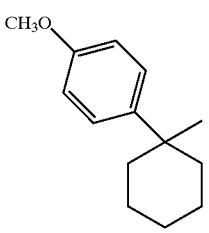 | 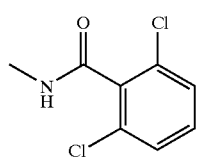 |
| 104 | 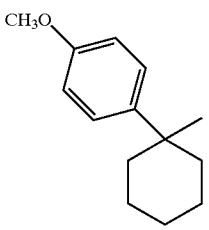 | 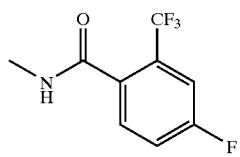 |
| 105 | 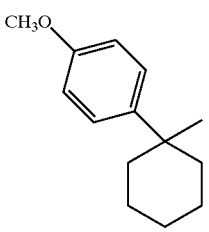 | 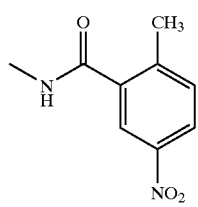 |
| 106 | 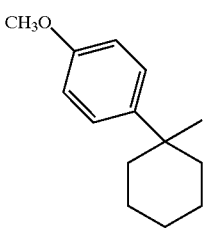 | 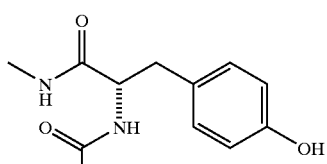 |

Example 107

Synthesis of N-[(1,1-Dimethylethoxy)Carbonyl]-4-[[(9H-fluoren-9-ylmethoxy)Carbonyl]Amino]-L-Phenylalanine Phenylmethyl Ester

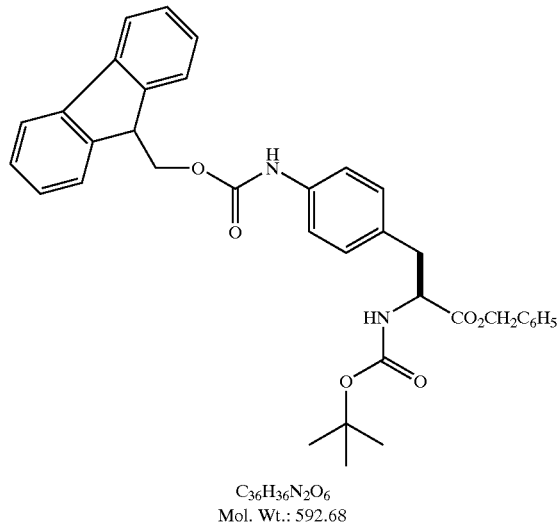

C$_{36}$H$_{36}$N$_2$O$_6$
Mol. Wt.: 592.68

N-[(1,1-Dimethylethoxy)carbonyl]-4-[[(9H-fluoren-9-ylmethoxy)carbonyl]amino]-L-phenylalanine (5.02 g, 10 mmol) and benzyl bromide (3.5 mL, 29 mmol) were stirred in DMF (25 mL) over KHCO3 (1.75 g, 17.5 mmol). After 18 hr, a white precipitate had formed. Most of the DMF was evaporated under reduced pressure, the residue was taken up in 100 mL of dichloromethane and was washed with water (2×50 mL). Most of the dichloromethane was evaporated and ether (100 mL) was added to precipitate the product. Filtration, washing with ether afforded N-[(1,1-dimethylethoxy)carbonyl]-4-[[(9H-fluoren-9-ylmethoxy)carbonyl]amino]-L-phenylalanine phenylmethyl ester (5.3 g), mp 186–187° C.

Example 108

Synthesis of 4-Amino-N-[[1-[(4-Methoxyphenyl)Methyl]Cyclopentyl]Carbonyl]-L-Phenylalanine

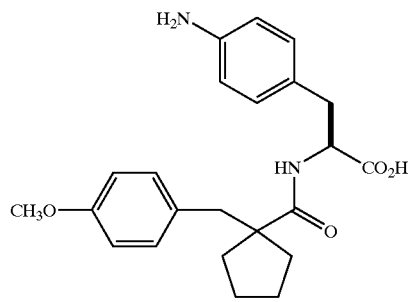

4-Amino-N-[[1-[(4-methoxyphenyl)methyl]cyclopentyl]carbonyl]-L-phenylalanine methyl ester (280 mg, 0.68 mmol) in THF (12 mL) was treated with a solution of lithium hydroxide hydrate (100 mg, 2.4 mmol) in water (2 mL) and the mixture was stirred for 3 hr. The mixture was concentrated and the residue was acidified with 6 H HCl to give a white sticky solid. Trituration with water and drying under high vacuum afforded crude 4-amino-N-[[1-[(4-methoxyphenyl)methyl]cyclopentyl]carbonyl]-L-phenylalanine (200 mg) suitable for use in the next step.

Example 109

Synthesis of 4-(2,3-Dihydro-1,3-Dioxo-1H-pyrrolo[3,4-c]Pyridin-2-yl)-N-[[1-[(4-Methoxyphenyl)Methyl]Cyclopentyl]Carbonyl]-L-Phenylalanine

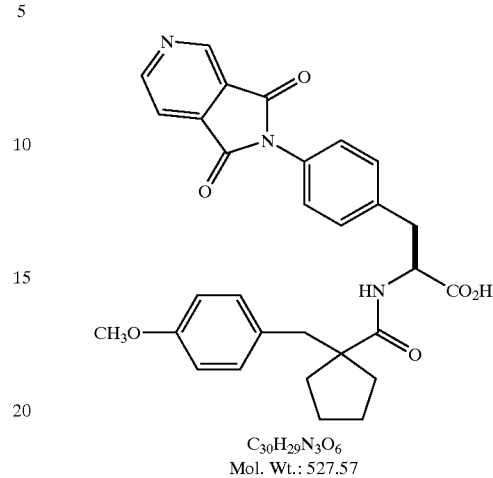

C$_{30}$H$_{29}$N$_3$O$_6$
Mol. Wt.: 527.57

A solution of 4-amino-N-[[1-[(4-methoxyphenyl)methyl]cyclopentyl]carbonyl]-L-phenylalanine (98 mg, 0.23 mmol), DIPEA (30 µL, 0.23 mmol) and 3,4-pyridinedicarboxylic acid anhydride (114 mg, 0.77 mmol) in dichloromethane (10 mL) was stirred 18 hr at room temperature. The mixture was concentrated to remove most of the dichloromethane and the residue was taken up in DMF (3 mL). Carbonyl diimidazole (103 mg, 0.64 mmol) was added to the resulting solution and the reaction was allowed to proceed for 18 hr. The resulting mixture was purified directly by RP-HPLC on a 4×30 cm Rainin C-18 column using a gradient of 5 to 95% acetonitrile:water containing 0.75% trifluoroacetic acid at a flow of 49 mL/min over 35 min. The peak eluting at 45.6% acetonitrile was concentrated and lyophilized to give 4-(2,3-dihydro-1,3-dioxo-1H-pyrrolo[3,4-c]pyridin-2-yl)-N-[[1-[(4-methoxyphenyl)methyl]cyclopentyl]carbonyl]-L-phenylalanine (28 mg) HR FABMS: obs. mass 528.2146. Calcd. mass 528.2134 (M+H).

Example 110

Synthesis of 4-(1,3-Dioxo-2H-isoindol-2-yl)-N-[[1-[(4-Methoxyphenyl)Methyl]Cyclopentyl]Carbonyl]-L-Prolyl]-L-Phenylalanine

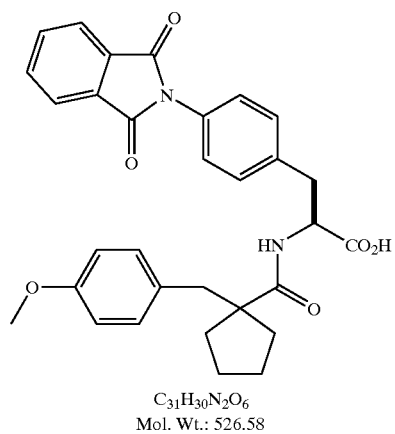

C$_{31}$H$_{30}$N$_2$O$_6$
Mol. Wt.: 526.58

Using the procedure described in example 109, starting with phthalic anhydride, 4-(1,3-dioxo-2H-isoindol-2-yl)-N-

[[1-[(4-methoxyphenyl)methyl]cyclopentyl]carbonyl]-L-prolyl]-L-phenylalanine was obtained, HR FABMS: obs. mass 527.2172. Calcd. mass 527.2182 (M+H).

Example 111

Synthesis of 4-[(RS)-2,3,5,6,7,7a-Hexahydro-1,3-Dioxo-1H-Pyrrolo[3,4-c]Pyridin-2-yl]-N-[[1-[(4-Methoxyphenyl)Methyl]Cyclopentyl]Carbonyl]-L-Phenylalanine and N-[[1-[(4-Methoxyphenyl)Methyl]Cyclopentyl]Carbonyl]-4-[(3aRS,7aRS)-(Octahydro-1,3-Dioxo-1H-Pyrrolo[3,4-c]Pyridin-2-yl)]-L-Phenylalanine

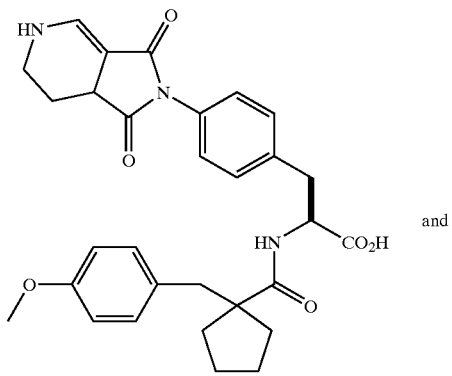

$C_{30}H_{33}N_3O_6$
Mol. Wt.: 531.60 and

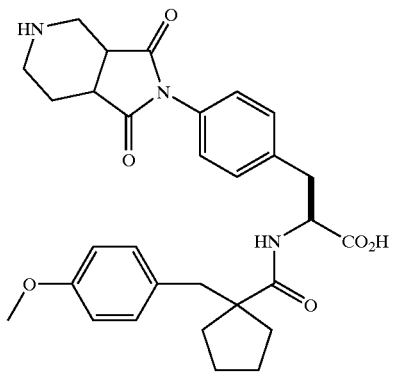

$C_{30}H_{35}N_3O_6$
Mol. Wt.: 533.62

A solution of 4-(2,3-dihydro-1,3-dioxo-1H-pyrrolo[3,4-c]pyridin-2-yl)-N-[[1-[(4-methoxyphenyl)methyl]cyclopentyl]carbonyl]-L-phenylalanine (30 mg, 0.057 mmol) in ethanol (4 mL) containing a few drops of TFA was hydrogenated over 10% Pd(C) (6 mg) for 18 hours. The mixture was filtered and evaporated and the residue was purified by RP-HPLC on a 4×30 cm Rainin C-18 column using a gradient of 5 to 95% acetonitrile:water containing 0.75% trifluoroacetic acid at a flow of 49 mL/min over 35 min. The peak eluting at 59.5% acetonitrile was concentrated and mixture was lyophilized to give N-[[1-[(4-methoxyphenyl)methyl]cyclopentyl]carbonyl]-4-[(3aRS,7aRS)-(octahydro-1,3-dioxo-1H-pyrrolo[3,4-c]pyridin-2-yl)]-L-phenylalanine (4.2 mg), HR FABMS: obs. mass 534.2602. Calcd. mass 534.2604 (M+H). The peak eluting at 62% acetonitrile was concentrated and the mixture lyophilzed to give 4-[(RS)-2,3,5,6,7,7a-hexahydro-1,3-dioxo-1H-pyrrolo[3,4-c]pyridin-2-yl]-N-[[1-[(4-methoxyphenyl) methyl]cyclopentyl]carbonyl]-L-phenylalanine (4.9 mg), HR FABMS:
  obs. mass 532.2452. Calcd. mass 532.2447 (M+H).

Example 112

Synthesis of 4-[[(2,4,6-Trimethylphenyl)Sulfonyl]Amino]-L-Phenylalanine On Wang Resin

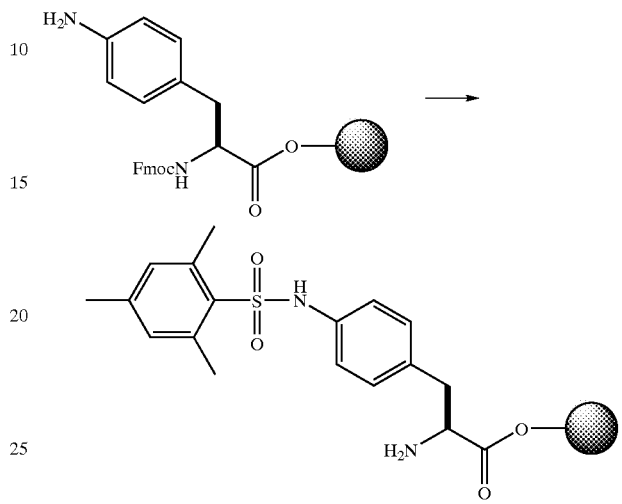

4-Amino-N-[(9H-fluoren-9-ylmethoxy)carbonyl]-L-phenylalanine on Wang resin (3.0 g, 2.28 mmol) obtained from Example 62 was suspended in pyridine (15 mL), the slurry was cooled to 0° C. and 2,4,6-trimethylphenylsulfonyl chloride (2.49 g, 11.4 mmol) was added. The resulting mixture was agitated for 2 hr. The mixture was filtered and washed with dichloromethane and methanol. The coupling procedure was repeated. The resulting resin was treated with 25% piperidine in N-methylpyrrolidinone (2×15 min) and was washed with dichloromethane and methanol to give 4-[[(2,4,6-trimethylphenyl)sulfonyl]amino]-L-phenylalanine on Wang resin.

Example 113

Synthesis of N-[(2,2-Dichloro-1-Methylcyclopropyl)Carbonyl]-4-[[(2,4,6-Trimethylphenyl)Carbonyl]Amino]-L-Phenylalanine

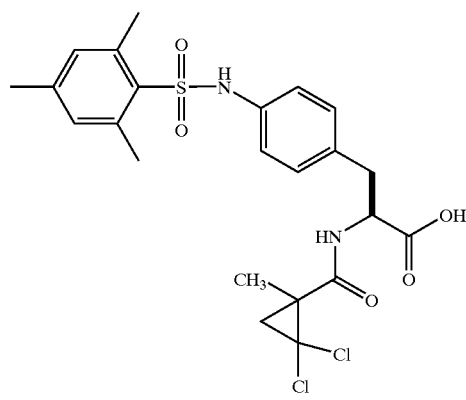

$C_{23}H_{26}Cl_2N_2O_5S$
Mol. Wt.: 513.43

4-[[(2,4,6-Trimethylphenyl)sulfonyl]amino]-L-phenylalanine on Wang resin (0.30 g, 0.23 mmol), 2,2- dichloro-1-methylcyclopropane carboxylic acid (0.19 g, 1.14 mmol), BOP ((0.50 g, 1.14 mmol) and DIPEA (0.26 mL, 1.5 mmol) in N-methylpyrrolidinone (3 mL) was agitated for 3 hr. The mixture was filtered and the resin was washed with dichloromethane and methanol and was air dried. Treatment with 90% TFA in dichloromethane for 3 min effected cleavage from the resin. The mixture was filtered, the filtrate was concentrated and lyophilized from water to give N-[(2,2-dichloro-1-methylcyclopropyl)carbonyl]-4-[[(2,4,6-trimethylphenyl)carbonyl]amino]-L-phenylalanine as a white solid.

Example 114

Synthesis of N-[[1-(4-Methoxyphenyl)Cyclohexyl]Carbonyl]-4-[[(2,4,6-Trimethylphenyl)Sulfonyl]Amino]-L-Phenylalanine

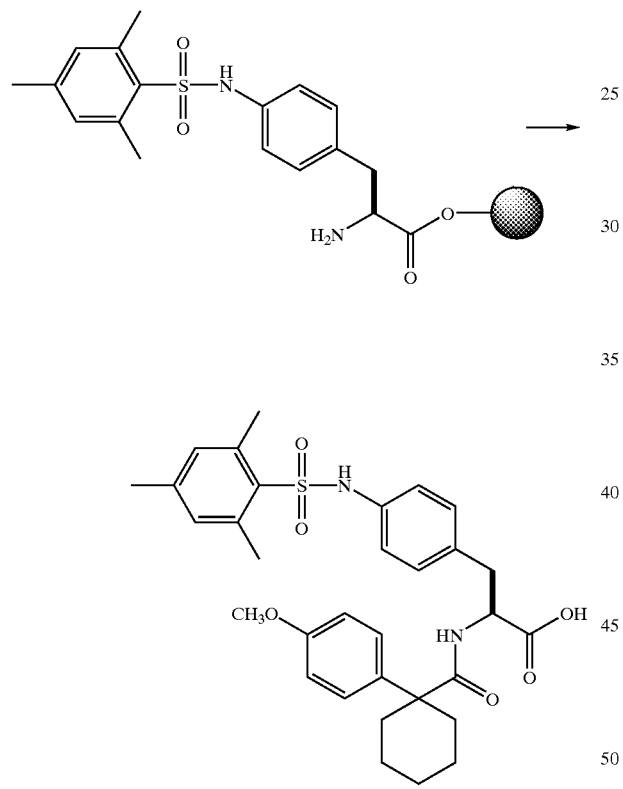

N-[[1-(4-methoxyphenyl)cyclohexyl]carbonyl]-4-[[(2,4,6-trimethylphenyl)sulfonyl]amino]-L-phenylalanine was prepared using the procedure described in Example 113, starting with 1-(4-methoxyphenyl)cyclohexane carboxylic acid.

Example 115

Synthesis of N-[(1-Adamantyl)Carbonyl]-4-[[(2,4,6-Trimethylphenyl)Sulfonyl]Amino]-L-Phenylalanine N-[(1-Adamantyl)carbonyl]-4-[[(2,4,6-trimethylphenyl)sulfonyl]amino]-L-phenylalanine was prepared using the procedure described in Example 113, starting with 1-adamantane carboxylic acid.

Example 116

Synthesis of 4-[[(4-Cyano-4-Phenyl-1-Piperidinyl)Carbonyl]Amino]-L-Phenylalanine on Wang Resin

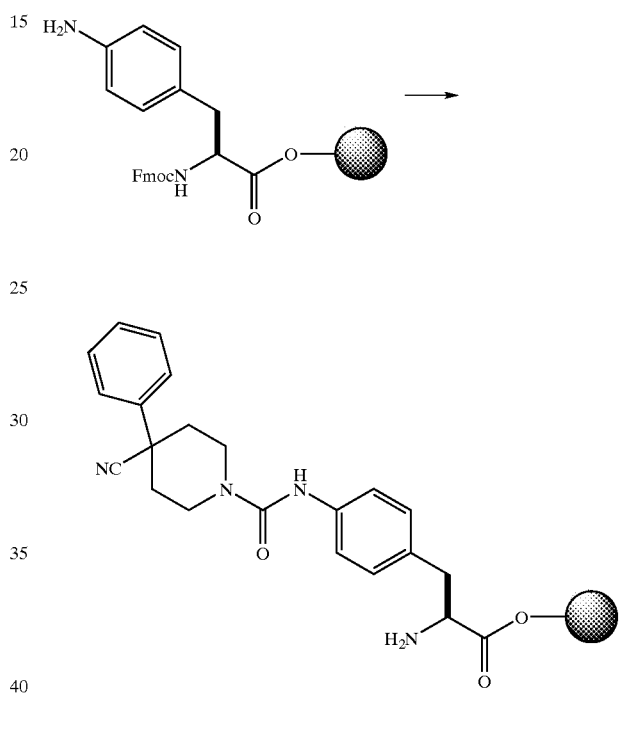

4-Amino-N-[(9H-fluoren-9-ylmethoxy)carbonyl]-L-phenylalanine on Wang resin (300 mg, 0.228 mmol) obtained from Example 62 was placed in a vessel fitted with a glass frit and was washed with dichloromethane (2×10 mL), methanol (2×10 mL) and dichloromethane (2×10 mL). To the resin was added carbonyl diimidazole (0.22 g, 1.4 mmol) and triethylamine (0.38 mL, 2.7 mmol) in 3 mL of dichloromethane. The mixture was agitated over night. The mixture was then filtered and washed with dichloromethane (3×5 mL). To the resin was added 4-cyano-4-phenylpiperidine hydrochloride (0.25 g, 1.14 mmol) and DMAP (0.14 g, 1.14 mmol) in 3 mL of N-methylpyrrolidinone. The resulting mixture was agitated for 3 hours. The reaction mixture was then filtered and washed with dichloromethane (2×10 mL), methanol (2×10 mL), dimethylformamide (2×10 mL) and methanol (2×10 mL). Cleavage of the Fmoc group was effected with 25% piperidine in N-methylpyrrolidinone (2×15 min to give 4-[[(4-cyano-4-phenyl-1-piperidinyl)carbonyl]amino]-L-phenylalanine on Wang resin.

Example 117

Synthesis of 4-[[(4-Cyano-4-Phenyl-1-Piperidinyl)Carbonyl]Amino]-N-[(2,2-Dichloro-1-methylcyclopropyl)carbonyl]-L-phenylalanine

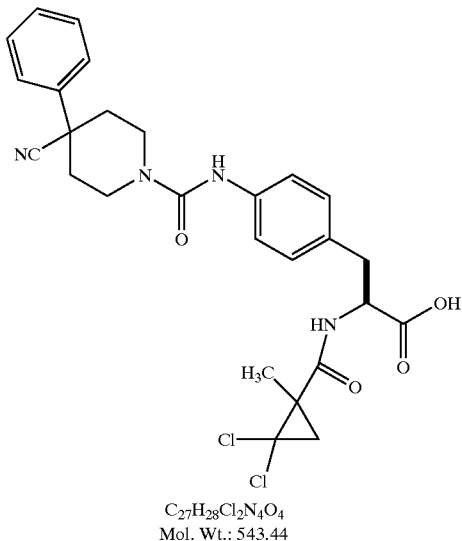

C₂₇H₂₈Cl₂N₄O₄
Mol. Wt.: 543.44

A suspension of 4-[[(4-cyano-4-phenyl-1-piperidinyl)carbonyl]amino]-L-phenylalanine on Wang resin (0.30 g, 0.228 mmol), 2,2-dichloro-1-methylcyclopropane carboxylic acid (0.19 g, 1.14 mmol), BOP (0.50 g, 1.14 mmol) and DIPEA (0.26 mL, 1.5 mmol) in N-methylpyrrolidinone (3 mL) was agitated for 3 hr. The mixture was filtered and washed with dichloromethane and methanol. Cleavage from the resin was effected by treatment with 90% TFA in dichloromethane for 3 min. The mixture was filtered and the filtrate evaporated to give 4-[[(4-cyano-4-phenyl-1-piperidinyl)carbonyl]amino]-N-[(2,2-dichloro-1-methylcyclopropyl)carbonyl]-L-phenylalanine. FAB MS m/z 543 (M+H).

Examples 118–122

Using the procedures described in Examples 116 and 117, the following compounds were prepared:

-continued

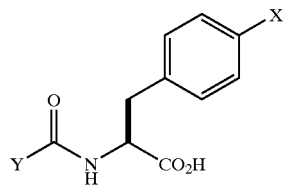

| Example | Y | X |
|---|---|---|
| 121 | (H3C, Cl, Cl cyclopropyl group) | (methyl urea-phenyl-CO2Et group) |
| 122 | (CH3O-phenyl-methyl-cyclohexyl group) | (methyl urea-piperidinyl-phenyl-CN group) |

Example 123

General Procedure for the preparation of ethyl esters from 4-substituted-N-acyl-L-phenylalanine derivatives.

To a suspension of N-(acyl)-4-[(aroyl)amino]-L-phenylalanine (10 mmol) and powdered sodium bicarbonate (4.2 g, 50 mmol) in DMF (75 mL) was added excess iodoethane (7.8 g, 50 mmol) at room temperature. The resulting suspension was stirred until TLC analysis of the mixture indicated the absence of staring material, typically 20 h. The excess iodoethane and some DMF was removed on a rotary evaporator under vaccum. The residue was diluted with 100 mL of ethyl acetate and washed successively with water (2×70 mL), brine solution (70 mL) and dried over MgSO4. Filtration of the drying agent and removal of the solvent afforded a residue which was purified by crystallization or silica gel chromatography.

Example 124

Wang Resin Linked N-[[1-(2-Methoxyethyl) Cyclopentyl]Carbonyl]-4-Nitro-L-Phenylalanine

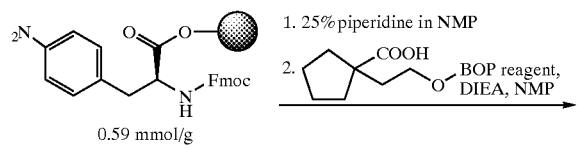

0.59 mmol/g

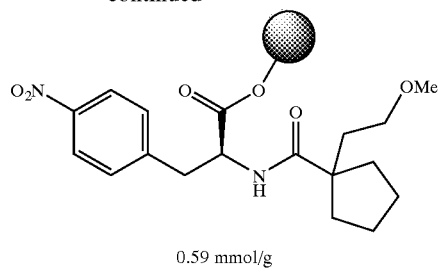

0.59 mmol/g

A mixture of Wang resin linked N-Fmoc-4-nitro-L-phenylalanine (2.30 g, 1.35 mmol) in 27 mL of 25% piperidine in NMP (N-methylpyrrolidinone) was shaken for 30 minutes at room temperature. Solvent was filtered through sintered funnel. With resin still on the funnel, another 27 mL of 25% piperidine in NMP was added and the suspension was allowed to stand at room temperature for 30 minutes. After removal of the solvent by filtration, the resin was then washed with dichloromethane, DMF, isopropyl alcohol, dichloromethane sequentially and was dried under vaccume.

The above resin was placed into a 50 mL round bottom flask containing 13 mL of NMP.

To it was added, 1-(2-methoxyethyl)cyclopentane carboxylic acid (930 mg, 5.4 mmol), diisopropylethylamine (DIEA, 1.3 mL, 7.4 mmol), and BOP reagent (2.4 g, 5.4 mmol). Reaction was shaken overnight. A small aliquot was removed and analyzed by the Kaiser test which showed negative for amine. Resin was collected by filtration and was washed with dichloromethane, DMF, isopropyl alcohol, dichloromethane and dried under reduced pressure to give 1.97 g of Wang resin linked N-[[1-(2-methoxyethyl) cyclopentyl]carbonyl]-4-nitro-L-phenylalanine.

Example 125

Synthesis of Wang Resin Linked 4-Amino-N-[[1-(2-Methoxyethyl)Cyclopentyl]-Carbonyl]-L-Phenylalanine

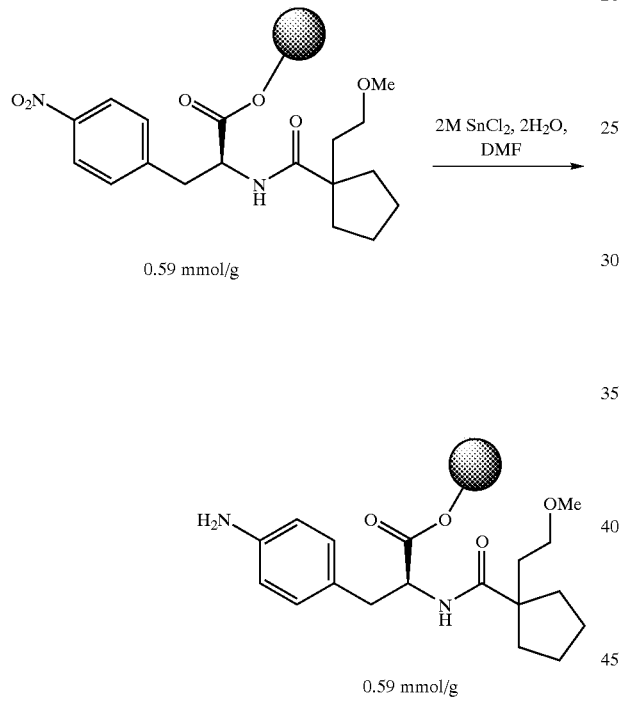

In a 20 mL scintillation vial was placed Wang resin linked N-[[1-(2-methoxyethyl)cyclopentyl]carbonyl]-4-nitro-L-phenylalanine (1.91 g, 1.12 mmol) and a 2 M solution of SnCl2.2H20 in DMF (8 mL). The reaction mixture was shaken overnight at room temperature. The resin was collected by filtration and was washed with DMF, isopropyl alcohol, dichloromethane, and Et2O to give Wang resin linked 4-amino-N-[[1-(2-methoxyethyl)cyclopentyl] carbonyl]-L-phenylalanine (2.21 g). A small sample was cleaved from the resin with 50% TFA/dichloromethane and was analyzed by ESPMS which showed presence of product but no starting material, m/z 335 (M+H).

Example 126

Synthesis of Wang Resin Liked 4-[((2R)-2-Amino-4-Methyl-1-Oxopentyl)Amino]-N-[[1-(2-Methoxyethyl)Cyclopentyl]Carbonyl]-L-Phenylalanine

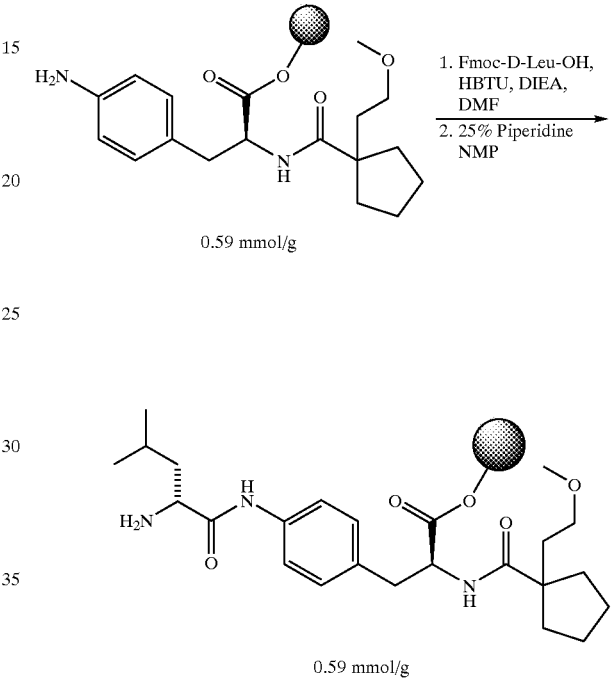

In a 20 mL scintillation vial was placed Wang resin linked 4-amino-N-[[1-(2-methoxyethyl)cyclopentyl]carbonyl]-L-phenylalanine (200 mg, 0.118 mmol), Fmoc-D-Leu-OH (201 mg, 0.571 mmol), DIEA (164 uL, 0.95 mmol), HBTU (360 mg, 0.95 mmol) in DMF (5 mL). The reaction mixture was shaken overnight at room temperature. The resin was filtered and washed with DMF, isopropyl alcohol, dichloromethane. A Kaiser test was negative for amine.

The resin obtained above was treated with 5 mL of 25% piperidine in NMP for 45 minutes at room temperature. After it was filtered through sintered funnel and washed with DMF, the resin was re-suspended in 5 mL of 25% piperidine/NMP in the funnel and was allowed to stand for 15 minutes at room temperature. This process was repeated once more and the resin was then washed with DMF, isopropyl alcohol, dichloromethane. Wang resin linked 4-[((2R)-2-amino-4-methyl-1-oxopentyl)amino]-N-[[1-(2-methoxyethyl) cyclopentyl]carbonyl]-L-phenylalanine (215 mg) was obtained.

Example 127

Synthesis of Wang Resin Linked 4-[(2S,4R)-3-Acetyl-4-(2-Methylpropyl)-5-Oxo-2-Phenyl-1-Imidazolidinyl]-N-[[1-(2-Methoxyethyl)Cyclopentyl]Carbonyl]-L-Phenylalanine and Wang Resin Linked 4-[(2R,4R)-3-Acetyl-4-(2-Methylpropyl)-5-Oxo-2-Phenyl-1-Imidazolidinyl]-N-[[1-(2-Methoxyethyl)Cyclopentyl]Carbonyl]-L-Phenylalanine

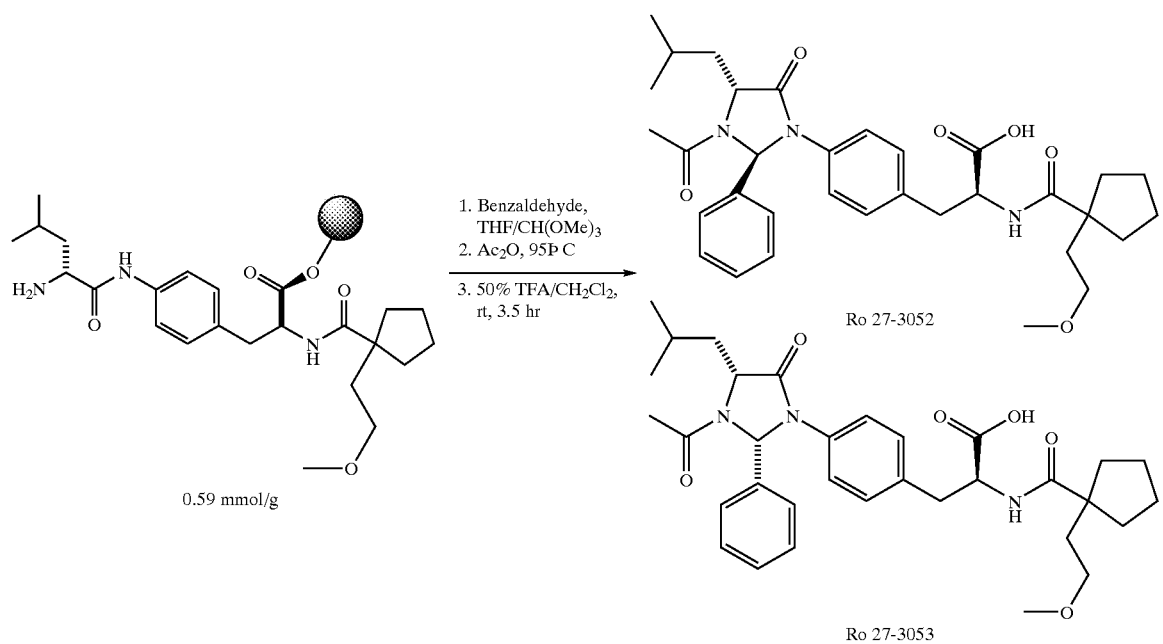

The resin obtained in Example 126 (0.59 mmol/g, 0.202 g, 0.11 mmol) was reacted with benzaldehyde (1.78 mmol, 182 μL) in 4 mL of a mixed solvent THF/trimethylorthoformate (1/1) at room temperature and was shaken for 4 days. To the above suspension was then added 3 mL of acetic anhydride and the mixture was stirred at 95° C. overnight. After the suspension was cooled to room temperature, the solvent was removed by filtration and the resin was washed with dichloromethane, THF and then dichloromethane.

Treatment of resulting resin with 6 mL of TFA/dichloromethane (1/1) at room temperature for 3.5 hr resulted in a crude mixture containing products. The crude products gave the correct mass by ESPMS (M+H)=578. RP-HPLC (41.4 mm×30 mm Dynamax C18 column, 5:95 to 95:5 acetonitrile:water gradient over 30 min monitoring the effluent at 214 Å) separation gave two diastereomeric products tentatively assigned as: 4-[(2S,4R)-3-acetyl-4-(2-methylpropyl)-5-oxo-2-phenyl-1-imidazolidinyl]-N-[[1-(2-methoxyethyl)cyclopentyl]carbonyl]-L-phenylalanine rention time 25.06 min, 25% yield and 4-[(2R,4R)-3-acetyl-4-(2-methylpropyl)-5-oxo-2-phenyl-1-imidazolidinyl]-N-[[1-(2-methoxyethyl)cyclopentyl]carbonyl]-L-phenylalanine, retention time 26.98 min, 33% yield.

Example 128–139

Using procedure described in Example 126–127, the compounds shown below were prepared

| Example | R | HRMS (calcd) | HRMS (obs) |
|---|---|---|---|
| 128 | (Diastereomer 1) | 578.3230 | 578.3222 |

-continued

| Example | R | HRMS (calcd) | HRMS (obs) |
|---|---|---|---|
| 129 | isobutyl-2-phenyl imidazolidinone, Diastereomer 2 | 578.3230 | 578.3233 |
| 130 | isobutyl-2-(4-methoxyphenyl) imidazolidinone, Diastereomer 1 | 608.3336 | 608.3325 |
| 131 | isobutyl-2-(4-methoxyphenyl) imidazolidinone, Diastereomer 2 | 608.3336 | 608.3317 |
| 132 | isobutyl-2-(4-chlorophenyl) imidazolidinone, Diastereomer 1 | 612.2840 | 612.2826 |
| 133 | isobutyl-2-(4-chlorophenyl) imidazolidinone, Diastereomer 2 | 612.2840 | 612.2838 |
| 134 | isobutyl-2-phenyl imidazolidinone, Diastereomer 1 | 578.3230 | 578.3210 |
| 135 | isobutyl-2-phenyl imidazolidinone, Diastereomer 2 | 578.3230 | 578.3225 |

-continued

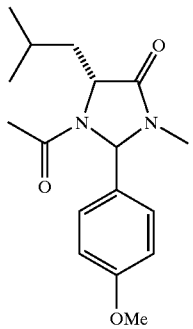

| Example | R | HRMS (calcd) | HRMS (obs) |
|---|---|---|---|
| 136 | (isobutyl-substituted imidazolidinone with 4-methoxyphenyl) Diastereomer 1 | 608.3336 | 608.3320 |
| 137 | (isobutyl-substituted imidazolidinone with 4-methoxyphenyl) Diastereomer 2 | 608.3336 | 608.3331 |
| 138 | (isobutyl-substituted imidazolidinone with 4-chlorophenyl) Diastereomer 1 | 612.2840 | 612.2835 |

-continued

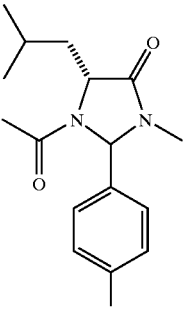

| Example | R | HRMS (calcd) | HRMS (obs) |
|---|---|---|---|
| 139 | (isobutyl-substituted imidazolidinone with 4-chlorophenyl) Diastereomer 2 | 612.2840 | 612.2864 |

Example 140

Synthesis of Wang Resin Linked N-[[1-(4-Methoxyphenyl)Cyclohexyl]Carbonyl]-4-Nitro-L-Phenylalanine

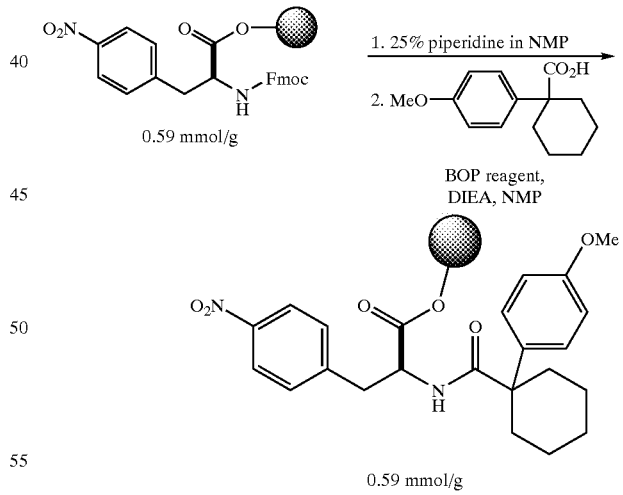

A mixture of Fmoc-4-nitro-L-phenylalanine on Wang resin (581 mg, 0.36 mmol) in 10 mL of 25% piperidine in NMP (N-methylpyrrolidinone) was shaken for 30 minutes at room temperature. Solvent was filtered through a sintered funnel. With the resin still on the funnel, another 27 mL of 25% piperidine in NMP was added and the suspension was allowed to stand at room temperature for 30 minutes. After removal of the solvent by filtration, the resin was then washed with dichloromethane, DMF, isopropyl alcohol, dichloromethane sequentially and was dried under vacuum.

The above resin was placed into a 25 mL round bottom flask containing 4 mL of NMP. To it was added, 1-(4-methoxyphenyl)cyclohexanecarboxylic acid (337 mg, 1.44 mmol), diisopropylethylamine (DIEA, 343 μL, 1.98 mmol), and BOP reagent (637 mg, 1.44 mmol). The reeaction mixture was shaken overnight. A small aliquot was removed and analyzed by the Kaiser test which was negative for amine. The resin was collected by filtration and was washed with dichloromethane, DMF, isopropyl alcohol, dichloromethane and was dried under reduced pressure to give 580 mg (0.59 mmol/g) of Wang resin linked N-[[1-(4-methoxyphenyl)cyclohexyl]carbonyl]-4-nitro-L-phenylalanine.

Example 141

Synthesis of 4-[2-(4-Hydroxyphenyl)-4-Oxo-3-Thiazolidinyl]-N-[[1-(4-Methoxyphenyl)Cyclohexyl]Carbonyl]-L-Phenylalanine

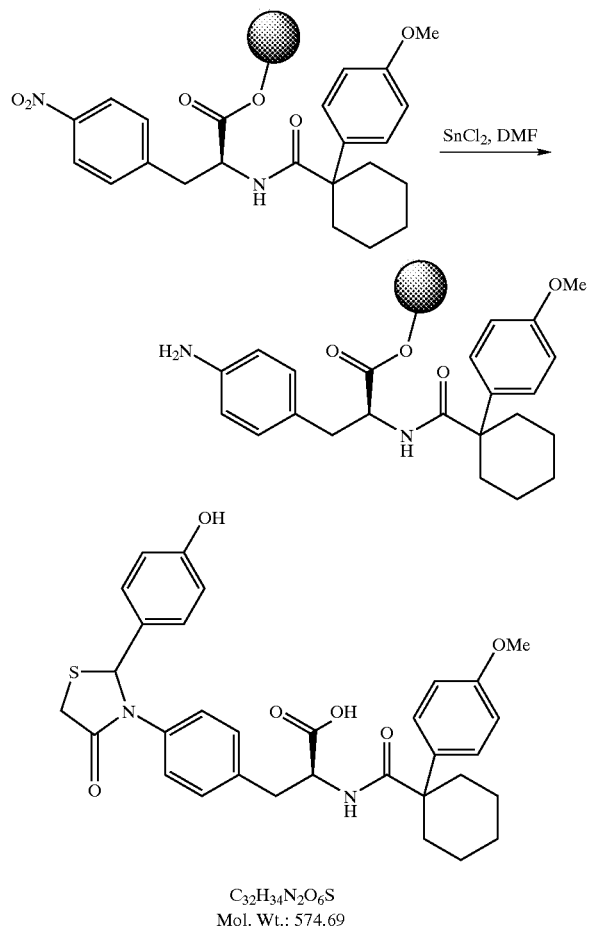

In a 20 mL scintillation vial was added Wang resin linked N-[[1-(4-methoxyphenyl)cyclohexyl]carbonyl]-4-nitro-L-phenylalanine (241 mg, 0.14 mmol) prepared in Example 140 and 2 mL of a solution of 2M SnCl2.2H2O in DMF. The reaction mixture was shaken overnight at room temperature. The resulting resin was collected by filtration and was washed with DMF, isopropyl alcohol, dichloromethane, and ether to yield 243 mg (0.14 mmol) of 4-amino-N-[[(1-(4-methoxyphenyl)cyclohexyl]carbonyl]-L-phenylalanine on Wang resin.

The 4-amino-N-[[(1-(4-methoxyphenyl)cyclohexyl]carbonyl]-L-phenylalanine on Wang resin (243 mg, 0.149 mmol) prepared above was reacted with 4-hydroxybenzaldehyde (153 mg, 1.25 mmol) and mercapto acetic acid (174 μL, 2.5 mmol) in the presence of 3 Å molecular sieves (100 mg) in THF (5 mL) at 90° C. for 4 hr. After it was cooled to room temperature, the reaction mixture was filtered and the resin was washed with THF, dichloromethane, DMF, MeOH and ether (3×30 mL for each solvent). The resin was then treated with 50% of TFA in dichloromethane at room temperature for 1 hr. The suspension was then filtered and the resin was washed with acetonitrile (2×10 mL). The combined filtrates were concentrated to dryness and purified by RP-HPLC to give 4-[2-(4-hydroxyphenyl)-4-oxo-3-thiazolidinyl]-N-[[1-(4-methoxyphenyl)cyclohexyl]carbonyl]-L-phenylalanine (40 mg, 50% yield), HRMS (C32H34N2O6S) obs mass, 575.2199. Calcd mass, 575.2216 (M+H).

Example 142

Using procedure described in Example 141, N-[[1-(4-methoxyphenyl)cyclohexyl]carbonyl]-4-[2-(2-naphthyl)-4-oxo-3-thiazolidinyl]-L-phenylalanine HR MS(C36H36N2O5S) Obs mass, 608.1910. Calcd mass, 608.1904 (M+)was prepared.

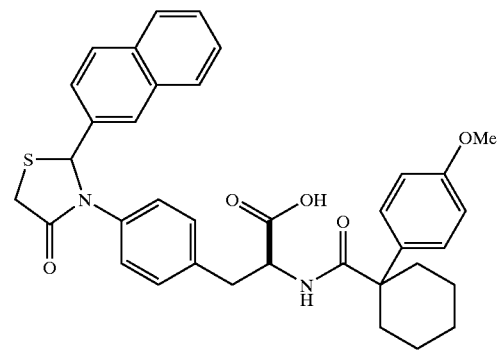

C36H36N2O5S
Mol. Wt.: 608.75

Example 143

Synthesis of (S)-4-(3,4-Dimethyl-2,5-Dioxo-1-Imidazolidinyl)-N-[[1-(4-Methoxyphenyl)Cyclohexyl]Carbonyl]-L-Phenylalanine

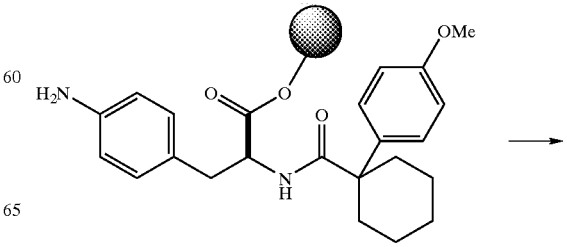

-continued

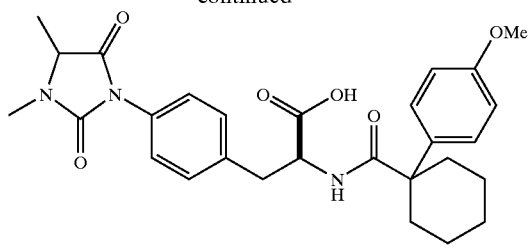

C$_{28}$H$_{33}$N$_3$O$_6$
Mol. Wt.: 507.58

In a 20 mL scintillation vial was added 4-amino-N-[[(1-(4-methoxyphenyl)cyclohexyl]carbonyl]-L-phenylalanine on Wang resin (188 mg, 0.11 mmol, 0.59 mmol/g loading) as prepared in Example 141, Fmoc-N-methyl-L-alanine-OH (114 mg, 0.341 mmol), DIEA (100 uL, 0.58 mmol), HBTU (220 mg, 0.58 mmol) in DMF (2 mL). The reaction mixture was shaken overnight at room temperature. The resin was filtered and rinsed with DMF, isopropyl alcohol, dichloromethane and dried under reduced pressure. A Kaiser test was negative for amine.

The resin obtained above (200 mg) was treated with 5 mL of 25% piperidine in NMP for 45 minutes at room temperature. After it was filtered through a sintered glass funnel and rinsed with DMF, the resin was re-suspended in 5 mL of 25% piperidine/NMP in the funnel and was allowed to stand for 15 minutes at room temperature and filtered. This process was repeated and the resin was then rinsed with DMF, isopropyl alcohol, dichloromethane.

The above resin was placed in a 20 mL scintillation vial with carbonyl diimidazole (CDI, 201 mg, 1.24 mmol) and DIEA (64 µL, 0.374 mmol) in dichloromethane (5 mL). The reaction mixture was shaken overnight at room temperature. Resin was then filtered and washed with dichloromethane, DMF, isopropyl alcohol, dichloromethane.

The resulting resin was transferred to a 50 mL round bottom flask and stirred in 50% TFA/dichloromethane (10 mL) for 3 hours at room temperature. The resin was filtered and rinsed with MeCN. The mother liquor was concentrated. The residue was purified by reversed phase HPLC using a linear gradient of 10:95 to 95:5 (MeCN:H2O) over 40 minutes. (S)-4-(3,4-dimethyl-2,5-dioxo-1-imidazolidinyl)-N-[[1-(4-methoxyphenyl)cyclohexyl]carbonyl]-L-phenylalanine (22 mg, 0.043 mmol) was obtained in 39% overall yield calculated based on the loading of 4-nitro-N-Fmoc-phenyalanine on Wang resin as 0.059 mmol/g. HRMS (C28H33N3O6) Obs mass, 508.2456. Calcd mass, 508.2448 (M+H).

Example 144

Using procedure described in Example 143. N-[[1-(4-methoxyphenyl)cyclohexyl]carbonyl]-4-[(4S)-3-methyl-4-(2-methylpropyl)-2,5-dioxo-1-imidazolidinyl]-L-phenylalanine (46 mg, 0.082 mmol) was synthesized in 52% yield. HRMS (C31H39N3O6): Obs mass, 550.2904. Calcd mass, 550.2917 (M+H).

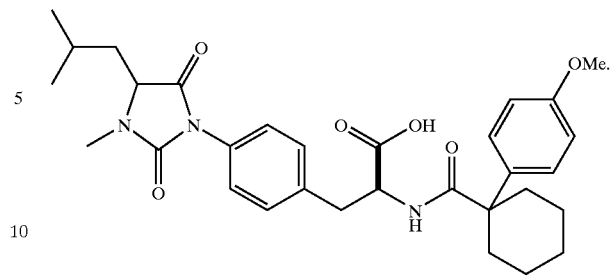

C$_{31}$H$_{39}$N$_3$O$_6$
Mol. Wt.: 549.66

Example 145

2,6-Dimethyl-4-Trifluoromethyl-3-Pyridinecarboxylic Acid

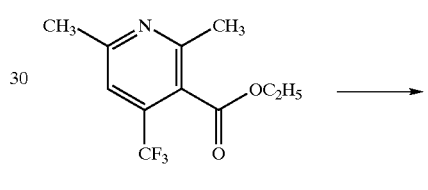

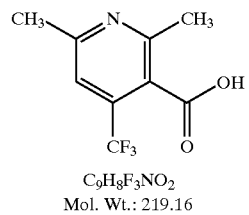

C$_9$H$_8$F$_3$NO$_2$
Mol. Wt.: 219.16

A solution of 2,6-dimethyl-4-trifluoromethyl-3-pyridinecarboxylic acid ethyl ester in 40 mL of THF and 10 mL of 1 N sodium hydroxide solution was heated to reflux for 48 h. TLC of the mixture (3:7 methanol:dichloromethane) indicated that starting material was consumed. The mixture was acidified with acetic acid (5 mL) and evaporated to dryness. The residue was triturated with THF and the solution was concentrated to give 0.7 g of material containing some THF and acetic acid as indicated by NMR. This material was combined with the product of a similar experiment and was chromatographed on 90 g of silica gel, eluting with (3:7) methanol:dichloromethane to give 1.05 g of a solid. This material was diluted with toluene (6 mL) and evaporated several times to remove most of the acetic acid to afford after drying under high vacuum, 0.9 g of a white foam. LR-ES-MS (C9H6F3NO2): 218 (M−H).

Example 146

Preparation of 4-[[(2,6-Dichlorophenyl)Carbonyl]Amino]-N-[[1-(2-Azidoethyl)Cyclopentyl]Carbonyl]-L-Phenylalanine

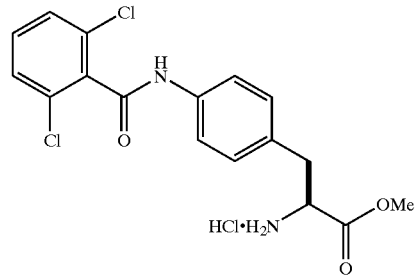

C₁₇H₁₇Cl₃N₂O₃
Mol. Wt.: 403.73

+

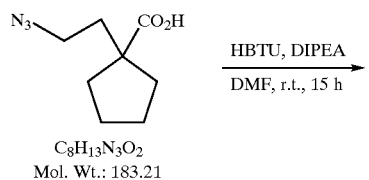

C₈H₁₃N₃O₂
Mol. Wt.: 183.21

HBTU, DIPEA
DMF, r.t., 15 h

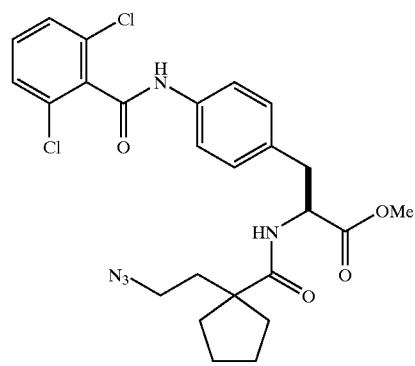

C₂₅H₂₇Cl₂N₅O₄
Mol. Wt.: 532.42

Using the general procedure described in example 46, 4-[[(2,6-dichlorophenyl)carbonyl]amino]-N-[[1-(2-azidoethyl)cyclopentyl]carbonyl]-L-phenylalanine methyl ester was prepared in 78% overall yield. HR MS: (C25H27Cl2N5O4): Obs mass, 532.1519. Calcd mass, 532.1518, (M+H).

Example 147

Preparation of 4-[[(2,6-Dichlorophenyl)Carbonyl]Amino]-N-[[1-(2-Aminoethyl)Cyclopenyl]Carbonyl]-L-Phenylalanine Methyl

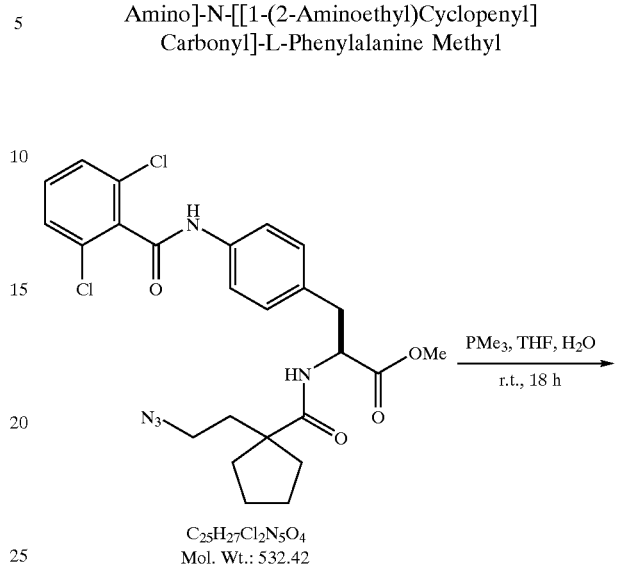

To a suspension of 4-[[(2,6-dichlorophenyl)carbonyl]amino]-N-[[1-(2-azidoethyl)cyclopentyl]carbonyl]-L-phenylalanine methyl ester (15.47 mmol, 8.24 g) in THF (70 mL) was added a solution of 1.0 M trimethylphosphine in toluene (25 mmol, 25 mL) at 0° C. The mixture was stirred 7 h at room temperature, at which time TLC analysis indicated the absence of starting material. Then, 3 equiv. of water (45 mmol, 0.82 mL) were added and the mixture was stirred for 15 h at room temperature. The solvent was removed under vacuum and the residue was azeotrophed two times with toluene to give a pasty material which was dissolved in THF:dichloromethane (~250 mL) and dried over anhydrous sodium sulfate. The solution was filtered through a plug of celite and the celite was washed with THF (100 mL). The combined filtrates were evaporated under vacuum to obtain 5 g (64%) of methyl 4-[[(2,6-dichlorophenyl)carbonyl]amino]-N-[[1-(2-aminoethyl)

cyclopentyl]carbonyl]-L-phenylalanine ester as a pink solid. HR MS: (C25H29Cl2N3O4) Obs mass, 506.1625.

Calcd mass, 506.1613, (M+H).

Example 148

Preparation of 4-[[(2,6-Dichlorophenyl)Carbonyl]Amino]-N-[[1-[2-[(1-Oxoethyl)Amino]Ethyl]Cyclopentyl]Carbonyl]-L-Phenylalanine Methyl Ester

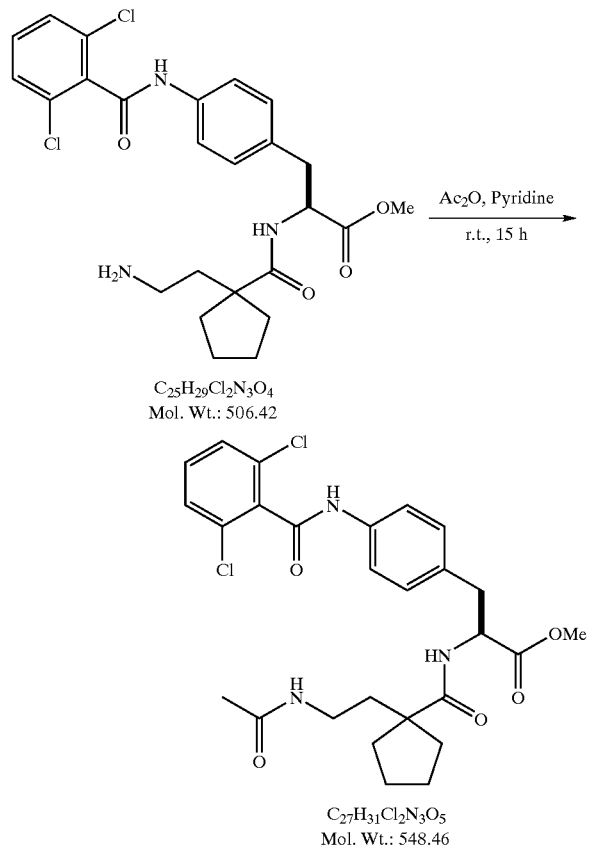

To a solution of methyl 4-[[(2,6-dichlorophenyl)carbonyl]amino]-N-[[1-(2-aminoethyl)cyclopentyl]carbonyl]-L-phenylalanine ester (9.6 mmol, 5 g) in pyridine (70 mL) was added 2 equiv. of acetic anhydride (20 mmol, 2.04 g) at room temperature. The colored solution was stirred for 15 h at room temperature and then diluted with 200 mL of ethyl acetate. The ethyl acetate layer was washed successively with 1N hydrochloric acid (2×100 mL), brine solution (100 mL) and dried over anhydrous magnesium sulfate. Filtration of the drying agent and concentration of the solvent afforded a fluffy solid which was only 85% pure by HPLC. This solid was triturated with ethyl acetate (40 mL) and then hexane (20 mL) was added. The solid was collected by filtration and dried at air to afford 3.38 g (63%) of 4-[[(2,6-dichlorophenyl)carbonyl]amino]-N-[[1-[2-[(1-oxoethyl)amino]ethyl]cyclopentyl]carbonyl]-L-phenylalanine methyl ester as a yellow solid, mp 190–194° C. HR MS (C27H31Cl2N3O5): Obs mass, 548.1696. Calcd mass, 548.1719 (M+H).

Example 149

Preparation of 4-[[(2,6-Dichlorophenyl)Carbonyl]Amino]-L-Phenylalanine Hydrochloride Salt

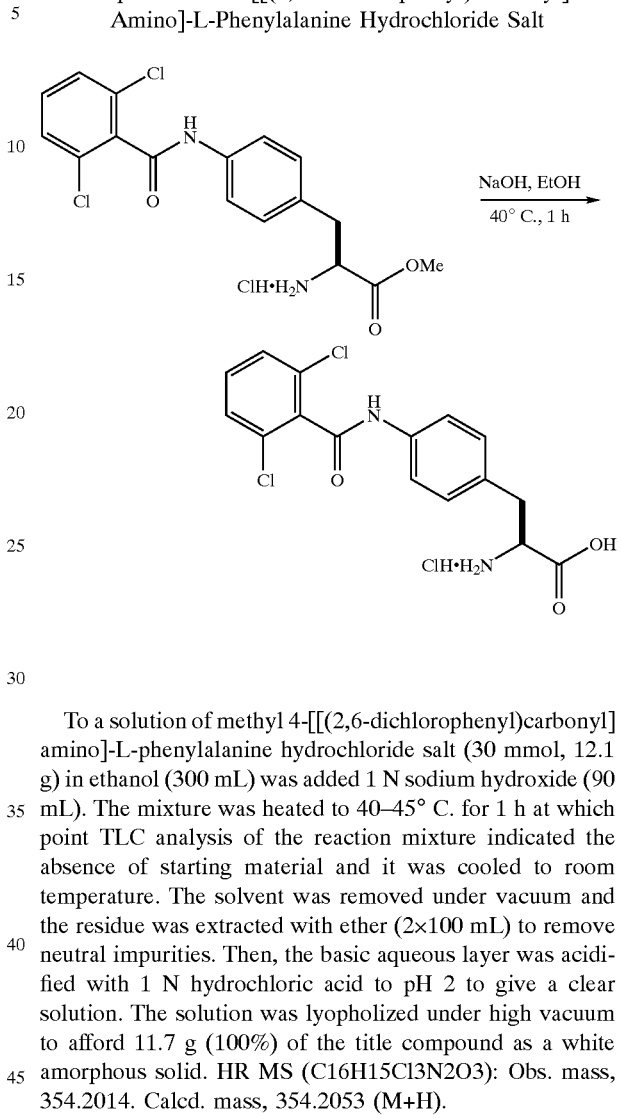

To a solution of methyl 4-[[(2,6-dichlorophenyl)carbonyl]amino]-L-phenylalanine hydrochloride salt (30 mmol, 12.1 g) in ethanol (300 mL) was added 1 N sodium hydroxide (90 mL). The mixture was heated to 40–45° C. for 1 h at which point TLC analysis of the reaction mixture indicated the absence of starting material and it was cooled to room temperature. The solvent was removed under vacuum and the residue was extracted with ether (2×100 mL) to remove neutral impurities. Then, the basic aqueous layer was acidified with 1 N hydrochloric acid to pH 2 to give a clear solution. The solution was lyopholized under high vacuum to afford 11.7 g (100%) of the title compound as a white amorphous solid. HR MS (C16H15Cl3N2O3): Obs. mass, 354.2014. Calcd. mass, 354.2053 (M+H).

Example 150

Preparation of 4-[[(2,6-Dichlorophenyl)Carbonyl]Amino]-N-[(9H-Fluoren-9-ylmethoxy)Carbonyl]-L-phenylalanine

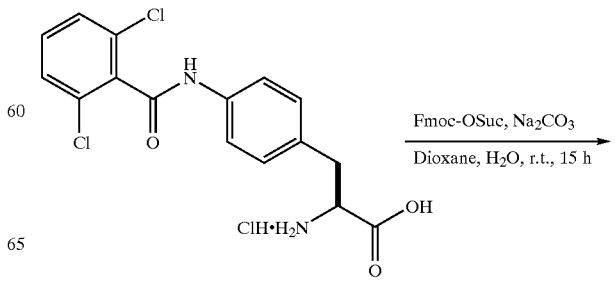

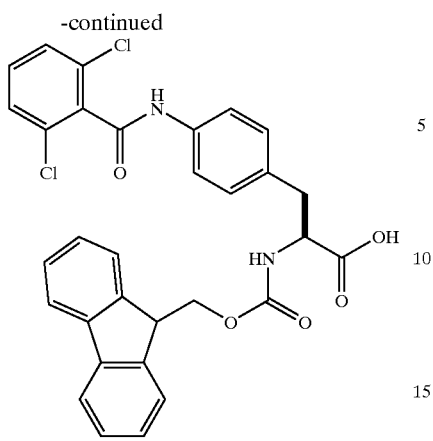

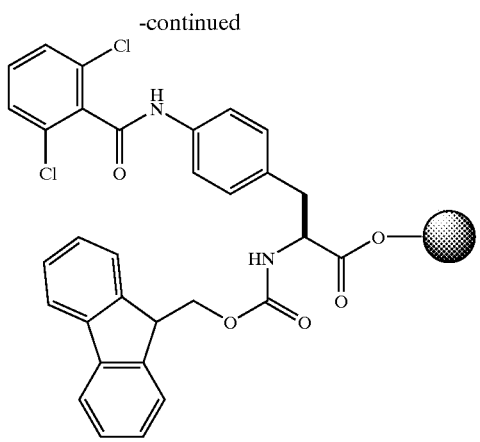

To a mixture of 4-[[(2,6-dichlorophenyl)carbonyl]amino]-L-phenylalanine hydrochloride salt (30 mmol, 10.59 g), N-(9-fluorenylmethoxycarbonyloxy)succinimide (30 mmol, 10.12 g) and sodium carbonate (300 mmol, 31.8 g) were added dioxane (75 mL) and water (25 mL) at room temperature. The suspension was stirred for 15 h at room temperature at which time TLC analysis of the mixture indicated the absence of starting material. The inorganic solids were filtered through celite and washed with ethyl acetate. While washing with ethyl acetate some organic compound was precipitated out from filtrate which was collected and air dried. The filtrate was concentrated under vacuum and the residue was combined with the above organic solid compound and the product was taken up in hot THF and precipatated with ether to obtain 14.1 g (81%), as a white solid, mp 230–234° C. LR MS (C31H24Cl2N2O5): Obs mass, 597. Calcd mass, 597, (M+Na).

Example 151

4-[[(2,6-dichlorophenyl)carbonyl]amino]-N-[(9H-fluoren-9-ylmethoxy)carbonyl]-L-phenylalanine on Wang resin was prepared from the product of example 150 with a loading of 0.765 mmol/g of resin using the general procedure described in example 61.

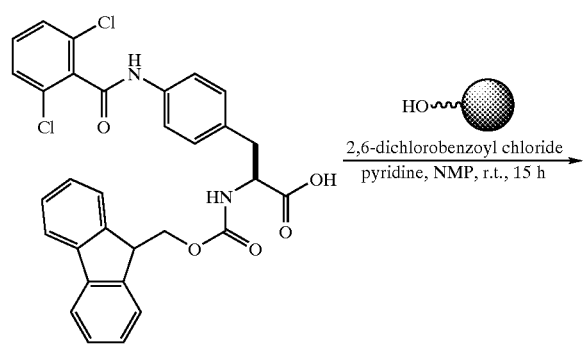

Example 152

Preparation of 4-[[(2,6-Dichlorophenyl)Carbonyl]Amino]-L-Phenylalanine on Wang Resin

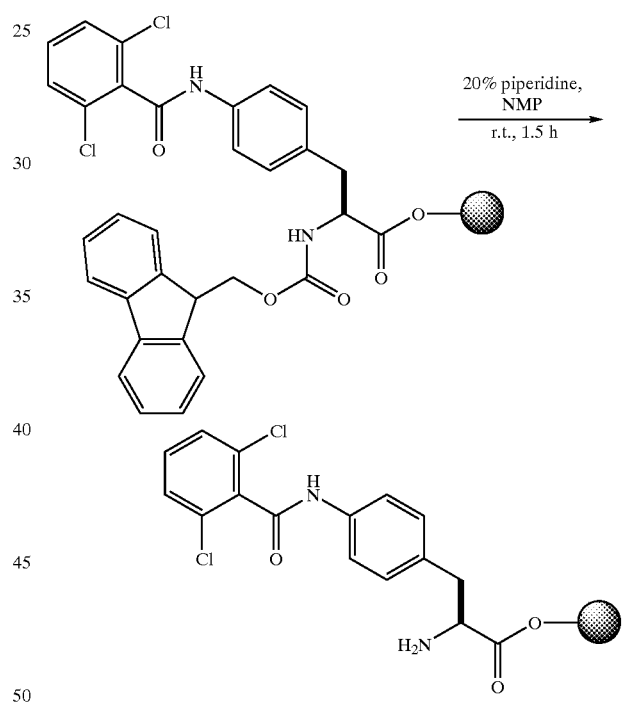

To the 4-[[(2,6-dichlorophenyl)carbonyl]amino]-N-[(9H-fluoren-9-ylmethoxy)carbonyl]-L-phenylalanine on Wang resin prepared above (12.1 mmol, 17.4 g) was added 20% of piperidine in NMP at room temperature. The mixture was shaken for 1.5 h at room temperature and the resin was filtered and washed with DMF (2×20 mL). Then, the resin was suspended in 20% piperidine in NMP (100 mL) and the solvent was decanted. The resin was washed with dichloromethane (2×20 mL) and dried under high vacuum to obtain 13.5 g of 4-[[(2,6-dichlorophenyl)carbonyl]amino]-L-phenylalanine on Wang resin.

Example 153

N-[[1-(2-Azidoethyl)cyclopentyl]carbonyl]-4-[[(2,6-dichlorophenyl)carbonyl]-amion]-L-phenylalanine on Wang resin was prepared from the product of example 152 using the general method described in example 64. The loading was 0.695 mmol/g of resin.

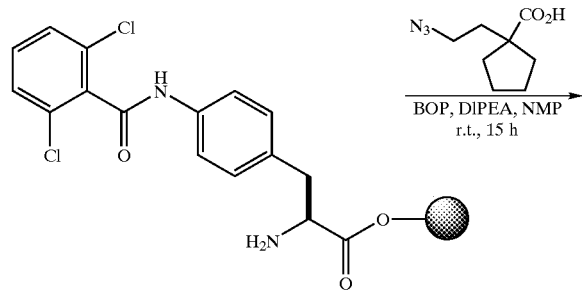

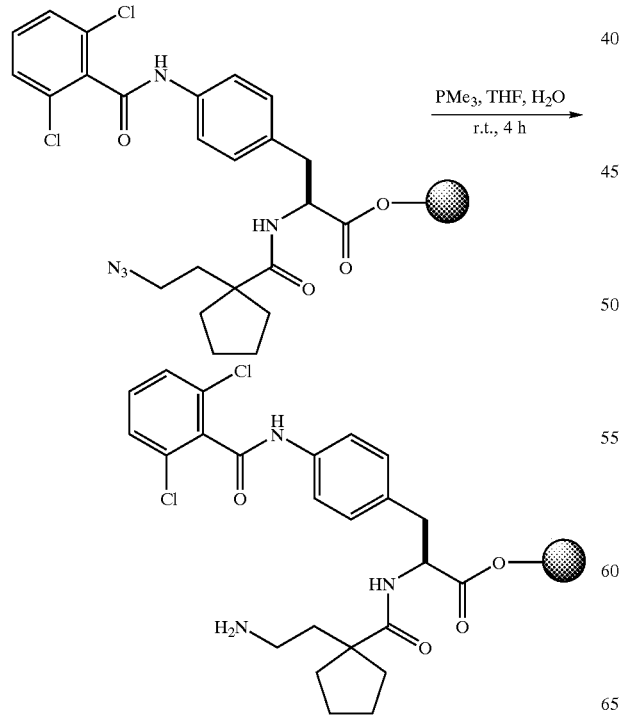

Example 154

Preparation of N-[[1-(2-Aminoethyl)Cyclopentyl] Carbonyl]-4-[[(2,6-Dichlorophenyl)Carbonyl] Amino]-L-Phenylalanine on Wang Resin To a suspension of N-[[1-(2-azidoethyl)cyclopentyl] carbonyl]-4-[[(2,6-dichlorophenyl)carbonyl]amino]-L-phenylalanine on Wang resin (9.33 mmol, 13.43 g, 0.695 mmol per g) in THF (60 mL) was added a solution of 1.0 M trimethylphosphine in THF (37.3 mmol, 37.3 mL) at 0° C. The mixture was allowed to warm to room temperature and stir for 4 h at which time a Kaiser test was possitve for amine. The resin was filtered and was washed with DMF (4×20 mL), dichloromethane (4×10 mL), isopropanol (4×10 mL), DMF (2×20 mL) and dichloromethane (2×20 mL), respectively. After drying under high vacuum, 13.43 g of N-[[1-(2-aminoethyl)cyclopentyl]carbonyl]-4-[[(2,6-dichlorophenyl)carbonyl]amino]-L-phenylalanine on Wang resin was obtained.

Example 155

Preparation of 4-[[(2,6-Dichlorophenyl)Carbonyl] Amino]-N-[[1-[2-[[(1,1-Dimethyl-Ethyl)Carbonyl] Amino]Ethyl]Cyclopentyl]Carbonyl]-L-Phenylalanine on Wang Resin

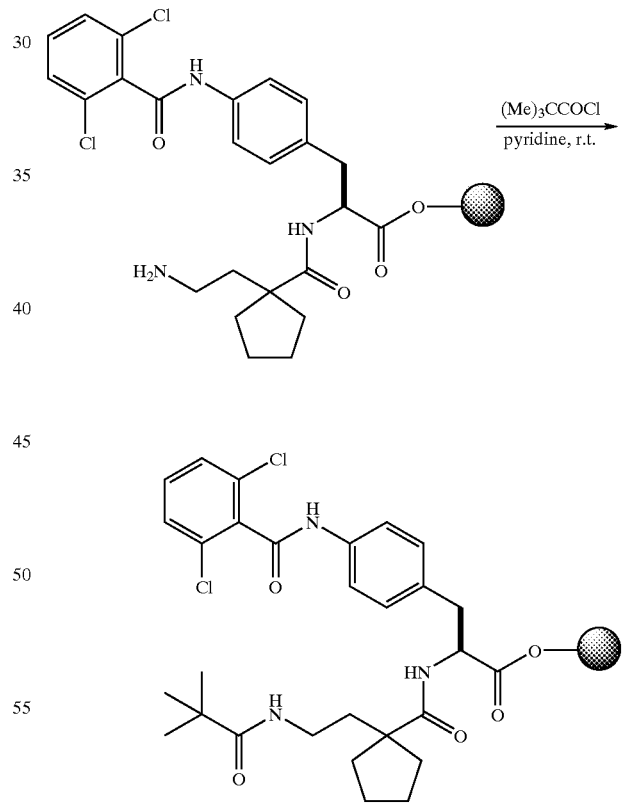

To a mixture of N-[[1-(2-aminoethyl)cyclopentyl] carbonyl]-4-[[(2,6-dichlorophenyl)carbonyl]-amino]-L-phenylalanine on Wang resin (0.069 mmol, 100 mg, 0.695 mmol per gram loading) in pyridine (2 mL) was added excess of 2,2,2-trimethylacetyl chloride (0.28 mmol, 33 mg) at 0° C. The mixture was allowed to warm to room temperature and shaken for 3 h at which time a Kaiser test was negative for amine. The resin was filtered and washed with dichloromethane (2×10 mL) and was dried under high vacuum to afford 4-[[(2,6-dichlorophenyl)carbonyl]amino]-N-[[1-[2-[[N-(1,1-dimethylethyl)carbonyl]amino]-ethyl]cyclopentyl]carbonyl]-L-phenylalanine on Wang resin.

Example 156

4-[[(2,6-dichlorophenyl)carbonyl]amino]-N-[[1-[2-[[N-(1,1-dimethylethyl)-carbonyl]amino]ethyl]cyclopentyl]carbonyl]-L-phenylalanine was prepared by cleavage of the product of example 155 from the resin with TFA using the general procedure described in example 64 to give 25 mg (62%) of a white solid. HR MS (C29H35Cl2N3O5): Obs mass, 576.2019. Calcd mass, 576.2032 (M+H).

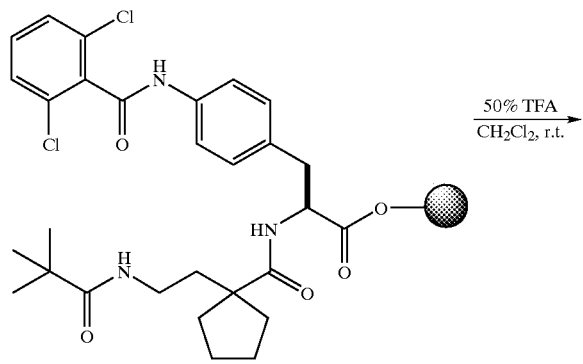

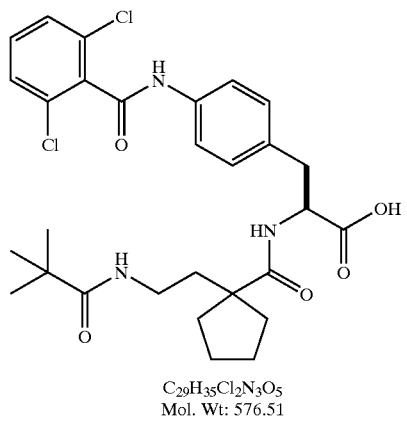

C29H35Cl2N3O5
Mol. Wt: 576.51

Example 157

Preparation of N-[[1-(2-Methoxyethyl)Cyclopentyl]Carbonyl]-N-Methyl-4-Nitro-L-Phenylalanine Methyl Ester

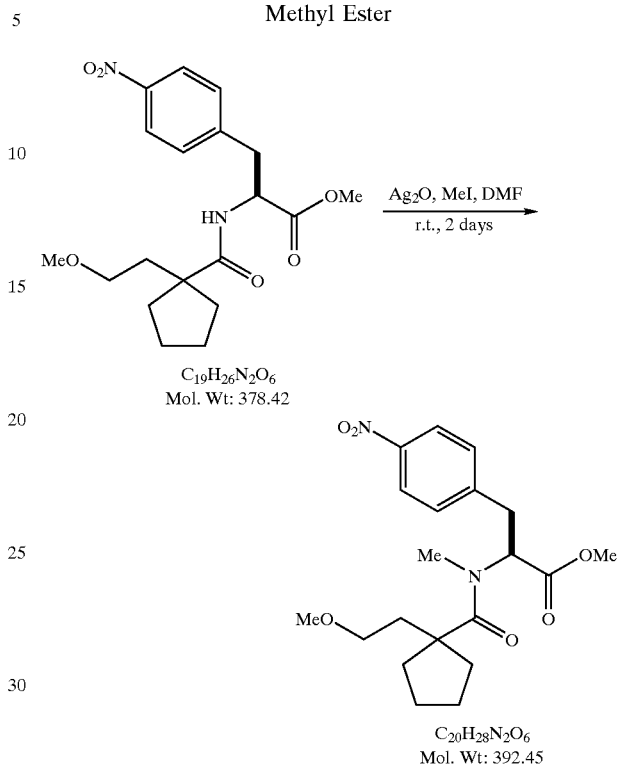

To a suspension of N-[[1-(2-methoxyethyl)cyclopentyl]carbonyl]-4-nitro-L-phenylalanine methyl ester (2.73 mmol, 1.03 g) and silver oxide (10.9 mmol, 2.53 g) in DMF (25 mL) was added methyl iodide (160 mmol, 10 mL) at room temperature. The suspesion was stirred for 2 days at room temperature at which time TLC analysis of the mixture indicated the presence of starting material. An additional 10 mL (160 mmol) of methyl iodide and 2 g (8.6 mmol) of silver oxide were added, respectively. The suspension was stirred for 24 h and the solid was filtered through a pad of celite and was washed with ethyl acetate (30 mL) and methanol (30 mL). The filtrate was concentrated and the residue was extracted with ethyl acetate (3×30 mL). The organic layer was washed with water (20 mL) and brine solution (20 mL) and was dried over anhydrous magnesium sulfate. Filtration of the drying agent and removal of the solvent gave a crude compound which was purified by silica gel column chromatography to obtain 530 mg (50%) as a light brown oil. HR MS (C20H28N2O6): Obs. mass, 392.1940. Calcd. mass, 392.1947 (M+).

Example 158 to 167 using the general procedure described in examples 155 and 156, the analogues shown below were prepared from N-[[1-(2-aminoethyl)cyclopentyl]carbonyl]-4-[[(2,6-dichlorophenyl)carbonyl]amino]-L-phenylalanine on Wang resin.

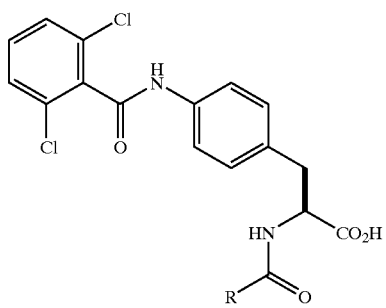

| Example | R | Formula | HRMS[1] Calcd. | Obs. |
|---|---|---|---|---|
| 158 | isoxazole-5-carboxamide-N-ethyl-1-methylcyclopentyl | C28H28Cl2N4O6: | 609.1284 | 609.1275 |
| 159 | N-trifluoroacetyl-prolyl-amide-ethyl-1-methylcyclopentyl | C31H33Cl2F3N4O6 | 685.1807 | 685.1784 |
| 160 | pyridine-4-carboxamide-N-ethyl-1-methylcyclopentyl | C30H30Cl2N4O5: | 597.1691 | 597.1661 |
| 161 | 2-ethylhexanoyl-amide-ethyl-1-methylcyclopentyl | C32H41Cl2N3O5 | 618.2501 | 618.2499 |
| 162 | methoxyacetyl-amide-ethyl-1-methylcyclopentyl | C27H31Cl2N3O6 | 564.1668 | 564.1641 |
| 163 | methyl succinyl-amide-ethyl-1-methylcyclopentyl | C29H33Cl2N3O7 | 606.1774 | 606.1752 |
| 164 | cyclopentylacetyl-amide-ethyl-1-methylcyclopentyl | C31H37Cl2N3O5 | 602.2188 | 602.2165 |

-continued

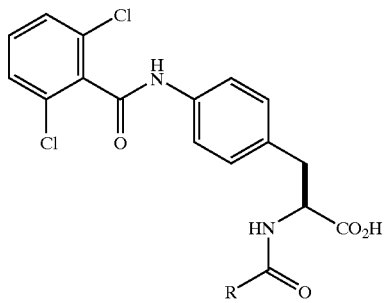

| Example | R | Formula | HRMS[1] Calcd. | Obs. |
|---|---|---|---|---|
| 165 | (1,3-benzodioxole-5-carboxamide with N-ethyl-1-methylcyclopentyl group) | C32H31Cl2N3O7 | 640.1617 | 640.1613 |
| 166 | (phenylacetamide with N-ethyl-1-methylcyclopentyl group) | C32H33Cl2N3O5 | 609.2631 | 609.2558 |
| 167 | (5-tert-butyl-1-methyl-1H-pyrazole-3-carboxamide with N-ethyl-1-methylcyclopentyl group) | C33H39Cl2N5O5 | 656.2406 | 656.2420 |

M + H ion unless otherwise indicated

Example 168

Preparation of 1-(4-Bromobutyl)Cyclopentane Carboxylic Acid Methyl Ester

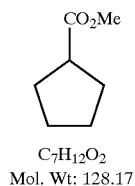

C7H12O2
Mol. Wt: 128.17

1) LDA, THF, -70° C. to -60° C., 1 h
2) 1,4-dibromobutane, -70° C., 1 h then r.t., 15 h

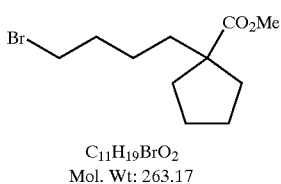

C11H19BrO2
Mol. Wt: 263.17

To a solution of diisopropylamine (150 mmol, 21 mL) in THF (100 mL) was added dropwise a solution of n-butyl lithium (145 mmol, 58 mL, 2.5M) in hexanes at −10° C. while maintaining the temperature below 0° C. After addition, the solution was stirred for 30 min at 0° C. To this, a solution of methyl cyclopentane carboxylate (100 mmol, 13.1 g) in THF (20 mL) was added dropwise at −70° C. maintaining the internal temperature between −60 to −70° C. After addition, the reaction mixture was stirred for 1 h at −50 to −60° C. Then, a solution of 1,4-dibromobutane (100 mmol, 21.59 g) in THF (20 mL) was added dropwise and the light brown suspension was stirred for 1 h at −60 to −70° C. Then, it was allowed to warm to room temperature and stirred overnight. The reaction mixture was poured into a saturated solution of ammonium chloride (200 mL) and the organic compound was extracted into ether (2×100 mL). The combined extracts were washed with a saturated brine solution (150 mL) and dried over anhydrous magnesium sulfate. After filtration of the drying agent, the solution was concentrated under vacuum and the resulting residue was distilled at 120–133° C./2.5 mm Hg to obtain 1-(4-bromobutyl)cyclopentane carboxylic acid methyl ester as a colorless oil (12.8 g, 48%). HR MS (C11H19BrO2): Obs mass, 262.0565. Calcd mass, 262.0568 (M+).

Example 169

Preparation of 1-(4-Cyanobutyl)Cyclopentane Carboxylic Acid Methyl Ester

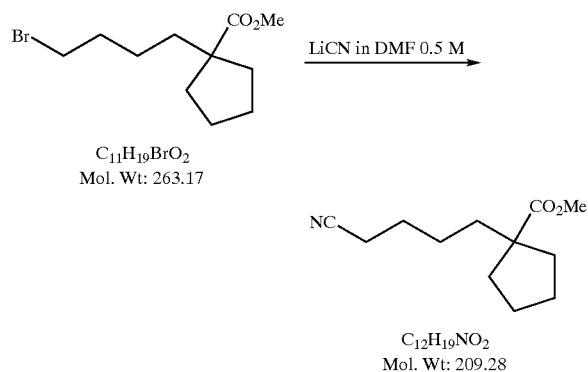

A solution of 1-(4-bromobutyl)cyclopentane carboxlic acid methyl ester was treated with a solution of 0.5 molar lithium cyanide in DMF (5 mmol, 10 mL) and stirred overnight at room temperature followed by heating at 75° C. for two hrs. The reaction mixture was evaporated to dryness, the residue was dissolved in ethyl acetate (30 mL) and washed with sat'd sodium bicarbonate (2×10 mL), and brine (5 mL) and dried over magnesium sulfate to give a yellow oil (860 mg). Silica gel chromtography eluting with 1:3 ethyl acetate:hexane yielded a pale oil (83%, 693 mg). LR MS (C12H19NO2): Obs mass, 227 (M+NH4), 248 (M+K).

Example 170

Preparation of 1-(3-Bromopropyl)Cyclopentane Carboxylic Acid Methyl Ester

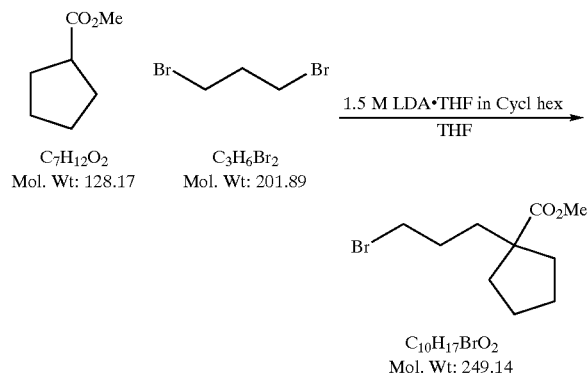

To a solution of 1.5 molar LDA in cyclohexane (60 mmol, 40 mL) cooled to −70° C. was added a solution of cyclopentane carboxylic acid methyl ester (42 mmol, 5.6 g) in THF (15 mL) over 30 min. The mixture was stirred for 1 hr at −70° C. Then a solution of 1,3-dibromopropane (60 mmol, 11.9 g) in THF (30 mL) which had been pre-cooled to −70° C. was added all at once and the reaction mixture was stirred at −70° C. for one hr then at room temperature overnight. The reaction mixture was poured into brine (200 mL), the layers were separated, the aqueous layer was extracted with ether (3×30 mL) and the combined organic layers were washed with brine (20 mL), dried (magnesium sulfate) and concentrated to give a yellow oil (15 g). Distillation through a short path apparatus with a 3' vigreux column gave a yellow oil, 7.96 g (76%), bp 76–80° C. at 0.3 mm.

Example 171

1-(3-Cyanopropyl)cyclopentane carboxylic acid methyl ester was prepared from 1-(3-bromopropyl)cyclopentane carboxylic acid methyl ester using the general method described in example 169 to give a 79% yield of a pale yellow oil. LR MS (C11H17NO2): Calcd mass, 196. Obs mass, 196 (M+H).

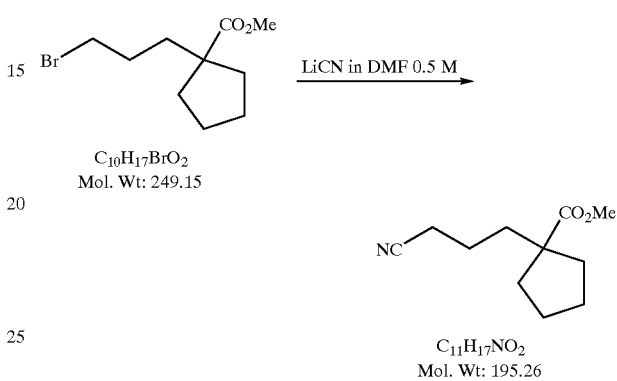

Example 172

Preparation of 1-[4-(Methylthio)Butyl]Cyclopentane Carboxylic Acid Methyl Ester

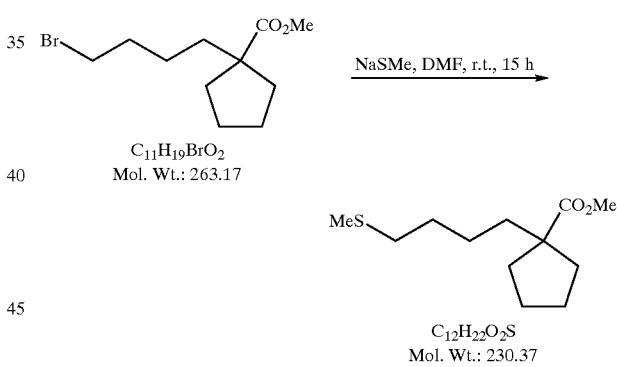

To a solution of 1-(4-bromobutyl)cyclopentane carboxylic acid methyl ester (38 mmol, 10 g) in DMF (100 mL) was added sodium thiomethoxide (72.6 mmol, 5.09 g). After addition of sodium thiomethoxide, the reaction was exothermic and the mixture became a light brown cloudy solution. The mixture was stirred for 15 h at room temperature and was poured into water (200 mL). The organic compound was extracted with ether (2×150 mL). The combined extracts were washed with brine (150 mL) and dried over anhydrous magnesium sulfate. After filtration of the drying agent, the solution was concentrated under vacuum and the resulting residue was purified by silica gel column chromatography to afford 4.43 g (51%) of a colorless oil. LR MS (C12H22O2S): 230 (M+).

Example 173

1-(3-Methylthiopropyl)cyclopentane carboxylic acid methyl ester was prepared from 1-(3-bromopropyl)

cyclopentane carboxylic acid methyl ester using the general procedure described in example 172 to give a 54% yield of a pale yellow oil.

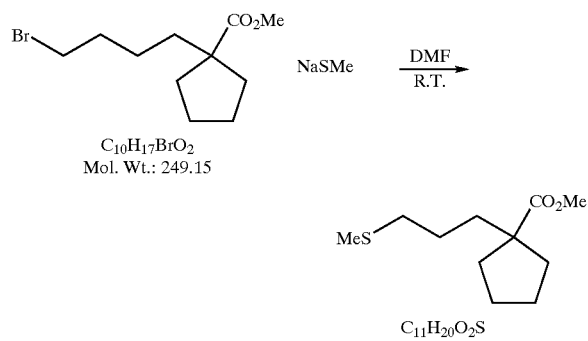

Example 174

Preparation of 1-[(4-(Methylsulfonyl)Butyl] Cyclopentane Carboxylic Acid Methyl Ester

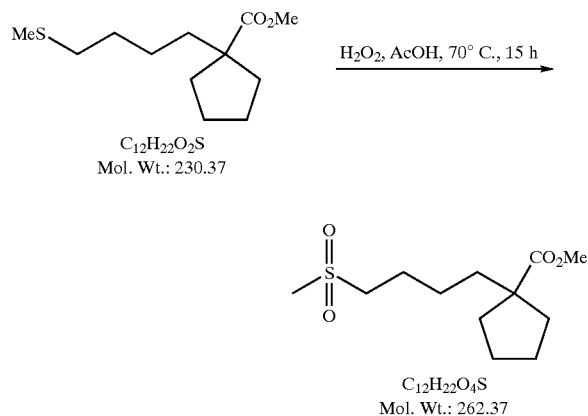

To a solution of 1-[4-(methylthio)butyl]cyclopentane carboxylic acid methyl ester (19.2 mmol, 4.43 g) in AcOH (20 mL) was added 30% hydrogen peroxide (10 mL). The reaction mixture was heated to 70° C. and stirred for 15 h at which time the TLC of the mixture indicated the absence of starting material. The reaction mixture was cooled to room temperature and was concentrated under vacuum. The residue was poured into saturated sodium bicarbonate solution and was extracted with ether (3×100 mL). The combined extracts were washed with a saturated solution of sodium chloride (200 mL) and dried over anhydrous magnesium sulfate. After filtration of the drying agent, the solvent was removed under vacuum and the resulting residue was purified by silica gel column chromatography to afford 4.94 g (98%) as a colorless oil. LR MS (C12H22O4S): 263 (M+H).

Example 175

Preparation of 1-[4-(Methylsulfonyl)Butyl] Cyclopentane Carboxylic Acid

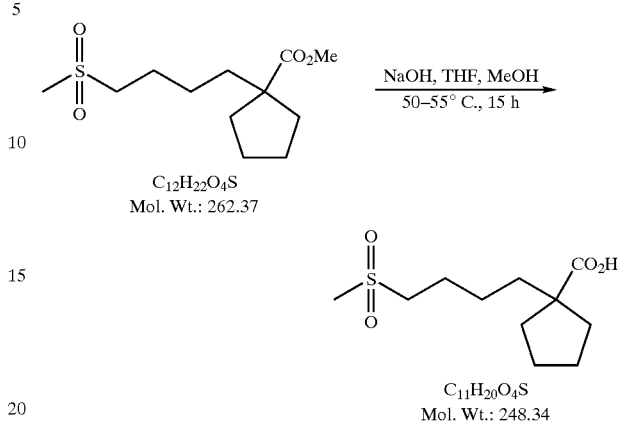

To a solution of 1-[4-(methylsulfonyl)butyl]cyclopentane carboxylic acid methyl ester (18.8 mmol, 4.94 g) in a mixture of THF (38 mL) and methanol (38 mL) was added 1 N sodium hydroxide (38 mL). The mixture was heated to 50–55° C. for 15 h at which point TLC analysis of the reaction mixture indicated the absence of starting material and the mixture was allowed to cool to room temperature. The solvent was removed under vacuum and the residue was diluted with water (100 mL) and extracted with ether (2×50 mL) to remove any neutral impurities. Then, the basic aqueous layer was acidified with 1 N hydrochloric acid and the product was extracted with ethyl acetate (2×75 mL). The combined extracts were washed with brine solution and dried over anhydrous sodium sulfate. After filtration of the drying agent, the solution was concentrated under vacuum and the residue was dried under high vacuum to afford 4.31 g (92%) of the title compound as a low melting white solid. LR MS (C11H20O4S): 249 (M+H).

Example 176

Preparation of 1-(2-Bromoethyl)Cyclopentane Carboxylic Acid Methyl Ester

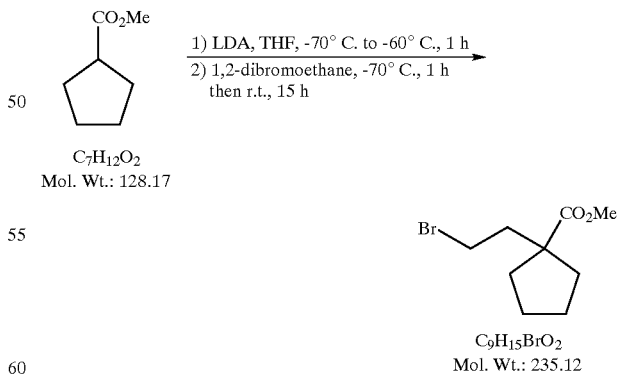

To a solution of diisopropylamine (150 mmol, 21 mL) in THF (100 mL) was added dropwise a solution of n-butyl lithium (145 mmol, 58 mL 2.5M) in hexanes at −10° C. while maintaining the temperature below 0° C. After addition, the solution was stirred for 30 min at 0° C. To this, a solution of cyclopentane carboxylic acid methyl ester (100 mmol, 13.1 g) in THF (20 mL) was added dropwise at −70° C. maintaining the internal temperature between −60 to −70° C. After addition, the reaction mixture was stirred for 1 h at −50 to −60° C. Then, a solution of 1,2-dibromoethane (90 mmol, 16.91 g) in THF (20 mL) was added dropwise and the light brown suspension was stirred for 1 h at −60 to −70° C. Then, it was allowed to warm to room temperature and was stirred overnight. The reaction mixture was poured into a saturated solution of ammonium chloride (200 mL) and the organic compound was extracted into ether (2×100 mL). The combined extracts were washed with a saturated solution of sodium chloride (150 mL) and dried over anhydrous magnesium sulfate. After filtration of the drying agent, the solution was concentrated under vacuum and the resulting residue was distilled at 95–105° C./2.5 mm Hg to obtain 11.5 g (49%) of a colorless oil.

Example 177

Preparation of 1-[2-(4-Morpholino)Ethyl] Cyclopentane Carboxylic Acid Methyl Ester

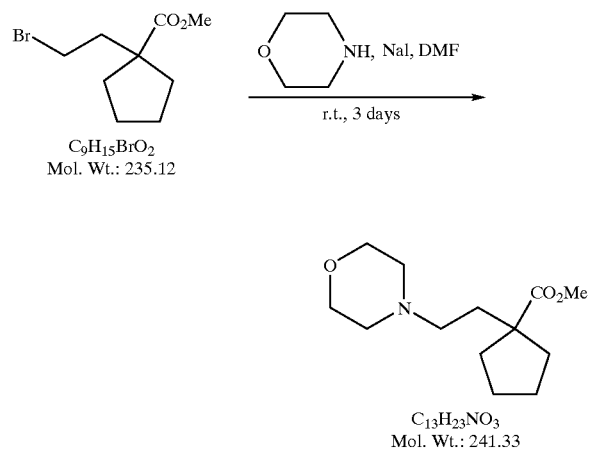

To a solution of 1-(2-bromoethyl)cyclopentane carboxylic acid methyl ester (2 mmol, 0.47 g) in DMF (10 mL) was added sodium iodide (0.3 mmol, 45 mg) and morpholine (10 mmol, 0.87 g). The reaction mixture was stirred for 3 days at room temperature at which time the TLC of the mixture indicated the absence of starting material. The mixture was diluted with ethyl acetate (100 mL) and washed successively with water (2×50 mL) and a saturated solution of sodium chloride (100 mL) and was dried over anhydrous magnesium sulfate. After filtration of the drying agent, the solution was concentrated under vacuum to afford 0.44 g (92%) of a colorless oil. HR MS (C13H23NO3): Obs mass, 241.1675. Calcd mass, 241.1678 (M+).

Example 178

Preparation of 1-[2-(4-Morpholino)Ethyl] Cyclopentane Carboxylic Acid

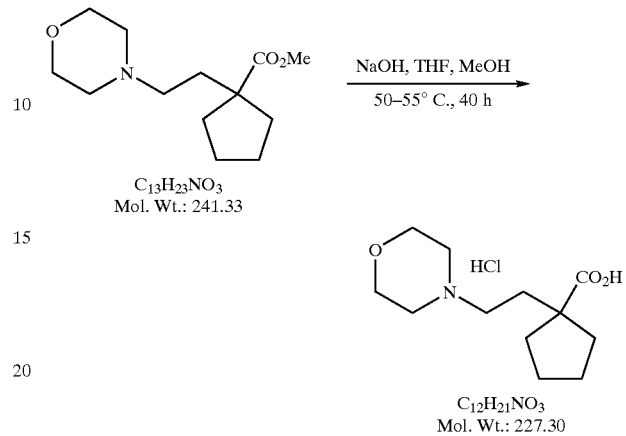

To a solution of 1-[2-(4-morpholino)ethyl]cyclopentane carboxylic acid methyl ester (1.75 mmol, 0.42 g) in a mixture of THF (5 mL) and methanol (5 mL) was added 1 N sodium hydroxide (3.5 mL). The mixture was heated to 50–55° C. for 40 h at which point TLC analysis of the reaction mixture indicated the absence of starting material and the mixture was allowed to cool to room temperature. The solvent was removed under vacuum and the residue was diluted with water (100 mL) and extracted with ether (2×50 mL) to remove any neutral impurities. Then, the basic aqueous layer was neutralized with 1 N hydrochloric acid and extracted with ethyl acetate (2×75 mL). The aqueous layer was neutralized with saturated sodium carbonate solution and extracted with ethyl acetate (3×50 mL). TLC of the aqueous layer indicated the presence of some more product. Thus, all ethyl acetate extracts were combined with aqueous layer and concentrated. The solid residue was triturated with methanol. The undissolved solids were filtered and the filtrate was concentrated under vacuum. The resulting solid was dissolved again in methanol and concentrated HCl was added to form a salt. Then, the methanol was removed to obtain the HCl salt of 1-[2-(morpholino)ethyl]cyclopentane carboxylic acid (1.09 g, may contain some NaCl) as a white solid. LR MS (C12H21NO3): 228 (M+H).

Example 179

Preparation of Methyl 1-(3,3 Difluoro-2-Propylene) Cyclopentane Carboxylate

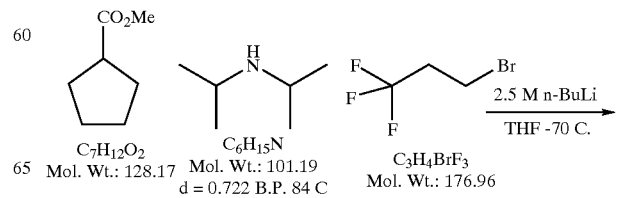

-continued

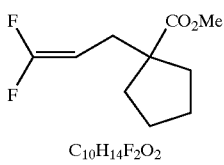

C₁₀H₁₄F₂O₂
Mol. Wt.: 204.21

A solution of 0.89 M LDA (0.24 mmol, 27 mL) was prepared from diisipropylamine (75 mmol, 7.58 g) in THF (50 mL) and 2.5 M n-butyl lithium in hexane (72 mmol, 29 mL). The solution was cooled to −70° C. and cycylopentane carboxylic acid methyl ester (15 mmol, 1.92 g) in THF (10 mL) was added dropwise over 20 min while maintaining the temperature at −70° C. The mixture was stirred an additional 1 h at −70° C. and a solution of trifluoropropyl bromide (15 mmol, 2.65 g) in THF (10 mL) was added over 15 min. The reaction mixture was stirred 1 h at −70° C. and allowed to warm to room temperature overnight. The reaction mixture was poured into brine (150 mL) and the organic layer was separated. The aqueous layer was extracted with ether (30 mL), the combined organic layers were washed with brine (10 mL), dried over anhydrous magnesium sulfate and evaporated to dryness to give a yellow oil ((4.1 g) which gave after chromotography on silica gel (120 g, 10% ethyl acetate in hexane) pale yellow oil (56%, 1.72 g).

Example 180

Preparation of 5-Iodo-2-Pentanone Ethylene Ketal

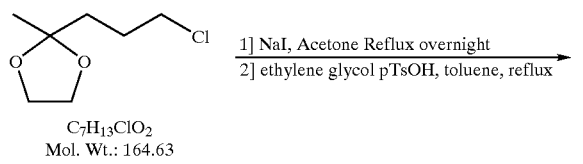

C₇H₁₃ClO₂
Mol. Wt.: 164.63

C₇H₁₃IO₂
Mol. Wt.: 256.08

A solution of 5-chloro-2-pentanone (40 mmol, 6.59 g) in acetone (40 mL) was treated with NaI (60 mmol, 9 g) and refluxed overnight. After cooling to room temperature, the solids were filtered off and the supernatant was concentrated to a dark gummy solid. A 1:1 mixture of ether and pet. ether (20 mL) was added, the mixture was stirred for 30 min., filtered and evaporated to dryness to give 7.2 g of a red oil which upon distillation (34–36° at 0.3 mm) gave 5 g of the ketone. To a solution of this ketone (23.6 mmol, 5 g) in toluene (40 mL) in a 100 mL flask fitted with a Dean-Stark trap was added ethylene glycol (27 mmol, 1.67 g) and 100 mg of para-toluenesulfonic acid and the reaction mixture was refluxed 6 h. After cooling, the toluene solution was washed with 1N NaOH (20 mL), water (5×20 mL), and brine (5 mL) was dried over potassium carbonate, filtered and evaporated to dryness to yield, upon distillation, 4.8 g (47%) of 5-Iodo-2-pentanone ethylene ketal as a colorless oil bp 44–48° C. at 0.3 mm.

Example 181

Preparation of 1-(4-(Ethylenedioxy)Pentyl) Cyclopentane Carboxylic Acid Methyl Ester

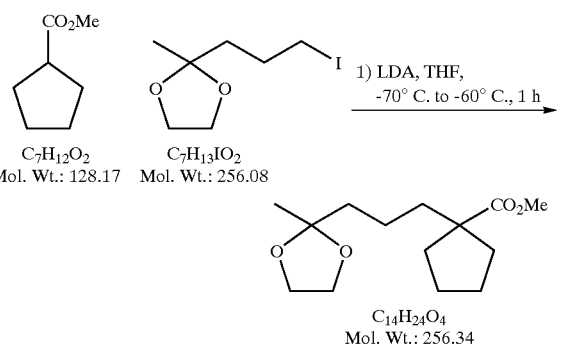

A solution of lithium diisopropylamide-tetrahydrofuran 1.5M solution in cyclohexane (15 mmol, 10 mL) was cooled to −70° C., and a solution of cyclopentane carboxylic acid methyl ester (10 mmol, 1.28 g) in THF (10 mL) was added dropwise over 15 min, maintaining the internal temperature at −60 to −70° C. The yellow solution was stirred 1 h at −70° C. and a solution of 5-iodo-2-pentanone ethylene ketal (10 mmol, 1.28 g) in THF (10 mL) was added over 15 min, while maintaining temperature of −70° C. After srirring for 1 h at −70° C., the reaction mixture was allowed to warm to room temperature overnight. The reaction mixture was poured into brine (150 mL) and the organic layer was separated. The aqueous layer was extracted with ether (20 mL), the combined organic layers were washed with brine (10 mL), dried over anhydrous magnesium sulfate and evaporated to dryness to give 2.5 g (97%) of a pale yellow oil.

Example 182

Preparation of 4-Iodo-2-Butanone Ethylene Ketal

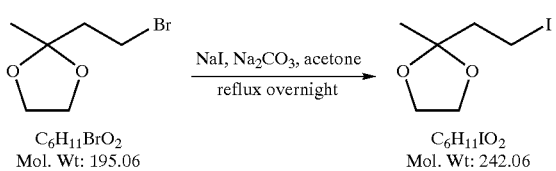

C₆H₁₁BrO₂
Mol. Wt: 195.06

C₆H₁₁IO₂
Mol. Wt: 242.06

A solution of 4 bromo-2-butanone ethylene ketal (16.4 mmol, 3.2 g) in acetone (30 mL) was treated with sodium iodide (24 mmol, 3.7 g) and sodium carbonate (50 mmol, 5.1 g) and was reluxed overnight. The resulting mixture was filtered, washed with acetone (10 mL) and evaporated to dryness to a white solid. The residue was triturated with a mixture of 1:1 ether: pet ether (20 mL), stirred 30 min., filtered and evaporated to give 3.74 g (94%) of a pale yellow oil. LR-ES (C13H22O4): 243 (M+H).

Example 183

1-[3-(Ethylenedioxy)butyl]cyclocarboxylic acid methyl ester was prepared using the general method described in example 181 to give a 25% yield of a colorless oil. LR-ES MS (C13H22O4): 243 (M+H).

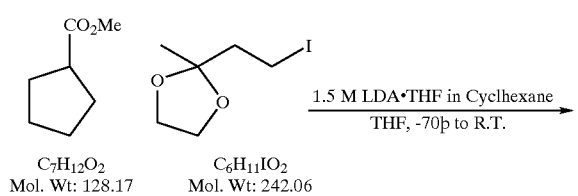

Example 184

Preparation of 4-[[(2,6-Dichlorophenyl)Carbonyl]
Amino]-N-[[1-[3-(Methylsulfonyl)Propyl]
Cyclopentyl]Carbonyl]-L-Phenylalanine Methyl
Ester

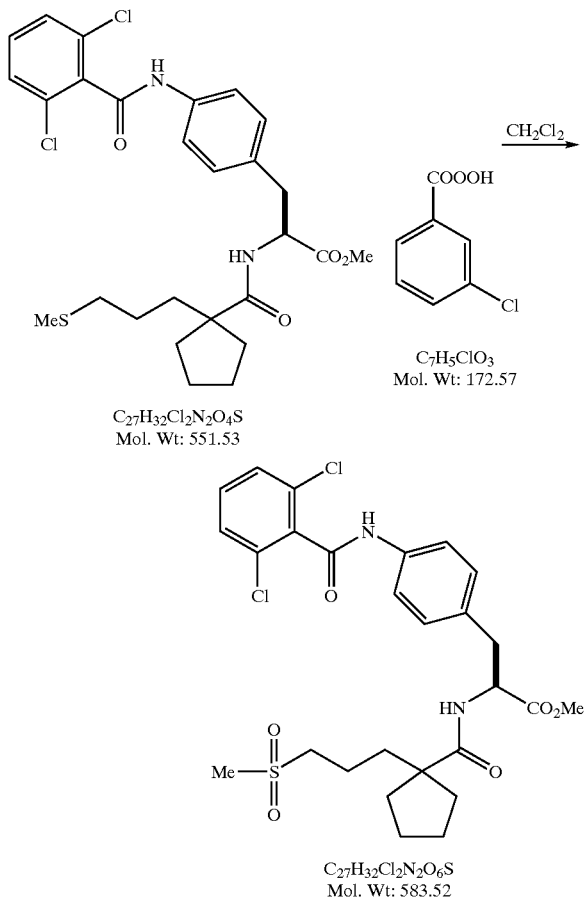

stirring at room temperature for 3 h, the reaction mixture was diluted with dichloromethane (30 mL) and washed with sat'd sodium bicarbonate (10 mL), and brine (5 mL) and dried over magnesium sulfate. Evaporation to a yellow oil and silica gel chromtography eluting with 5% methanol in dichloromethane yielded a white pasty solid (96%, 113 mg). LR-ES MS (C27H32N2O6Cl2S): 583 (M+H).

Example 185

Preparation of 4-[[(2,6-Dichlorophenyl)Carbonyl]
Amino]-N-[[1-[3-[(Methyl-Sulfinyl)Propyl]
Cyclopentyl]Carbonyl]-L-Phenylalanine Methyl
Ester

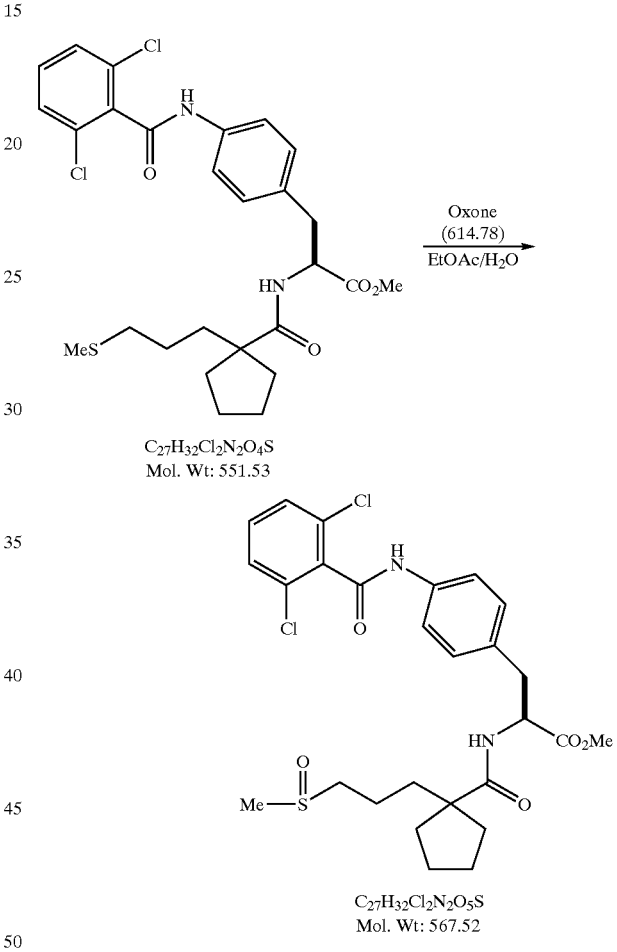

A solution of 4-[[(2,6-dichlorophenyl)carbonyl]amino]-N-[[1-[3-(methylthio)propyl]cyclopentyl]carbonyl]-L-phenylalanine methyl ester (110 mg, 0.2 mmol) in dichloromethane (10 mL) was cooled in ice bath and treated with meta-chloroperbenzoic acid (0.7 mmol, 150 mg). After A solution of 4-[[(2,6-dichlorophenyl)carbonyl]amino]-N-[[1-[3-(methylthio)propyl]cyclopentyl]carbonyl]-L-phenylalanine methyl ester (110 mg, 0.2 mmol) in a mixture of ethyl acetate (8 mL) and THF (3 mL) was treated with a solution of oxone (0.05 mmol, 31 mg) in water (2 mL) and the two phase system was stirred vigorously for 2 h at room temperature followed by further addition of oxone (0.05 mmol, 31 mg) and continued stirring overnight. After separation of the layers, the aqueous phase was extracted with ethyl acetate (5 mL), and the combined organic layers were washed with brine (3 mL), dried over magnesium sulfate and evaporated to dryness to give a white solid. Chromotography on silica gel eluting with methanol (7.5%) in dichloromethane gave a white solid (68%, 78 mg). LR-ES MS (C27H32N2O5Cl2S): 567 (M+H).

Example 187

Preparation of 4-[[(2,6-Dichlorophenyl)Carbonyl]Amino]-N-[[1-[2-[[(Methylamino)Carbonyl]Amino]Ethyl]Cyclopentyl]Carbonyl]-L-Phenylalanine

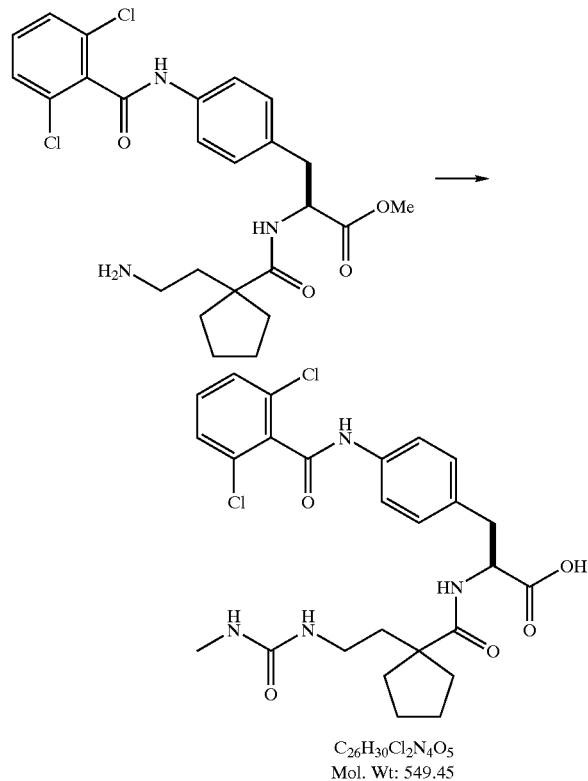

$C_{26}H_{30}Cl_2N_4O_5$
Mol. Wt: 549.45

To a solution of 4-[[(2,6-dichlorophenyl)carbonyl]amino]-N-[[1-(2-aminoethyl)cyclopentyl]carbonyl]-L-phenylalanine methyl ester (40 mg, 0.080 mmol) in dichloromethane (1 mL) was added methyl isocyanate (5 mg, 0.095 mmol). The resultant mixture was stirred for 18 h. The reaction mixture was concentrated in vacuo and the crude urea was used in the next step without purification.

To a solution of the crude methyl ester (50 mg, 0.080 mmol) in MeOH (1 mL) was added a solution of LiOH (8 mg, 0.19 mmol) in water (0.5 mL). The mixture was stirred for 2 h and then it was acidified (pH ~1–2) with 0.5M HCl. The reaction mixture was poured into a round bottom flask and concentrated in vacuo. Purification by reversed-phase HPLC, using a 15–95% acetonitrile-water gradient over 25 min., provided 30 mg (68%). HR MS (C26H30Cl2N4O5): Calcd mass, 549.1671. Obs mass, 549.1677 (M+H).

Examples 188 to 191

Using the general procedure described in example 187, and starting with 4-[[(2,6-dichlorophenyl)carbonyl]amino]-N-[[1-(2-aminoethyl)cyclopentyl]carbonyl]-L-phenylalanine methyl ester, the analogues listed below were prepared:

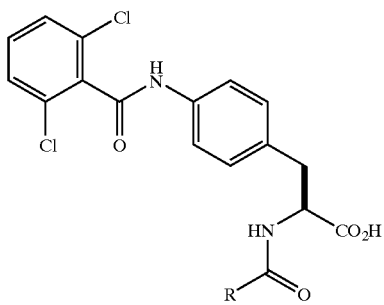

| Example | R | Yield % | Formula | HRMS1 calcd. | found |
|---|---|---|---|---|---|
| 188 | H₂N-C(O)-NH-CH₂CH₂-[1-methylcyclopentyl] | 33[1] | C25H28Cl2N4O5 | 535.1515 | 535.1510 |
| 189 | CH₃O-C(O)-NH-C(O)-NH-CH₂CH₂-[1-methylcyclopentyl] | 60[2] | C27H30Cl2N4O7 | 615.1390 (M + Na) | 613.1372 (M + Na) |

-continued

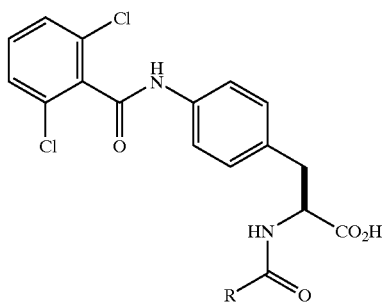

| Example | R | Yield % | Formula | HRMS1 calcd. | found |
|---|---|---|---|---|---|
| 190 | | 65 | C31H31Cl2N5O7 | 678.1499 (M + Na) | 678.1496 (M + Na) |
| 191 | | 62 | C32H34Cl2N4O5 | 647.1804 (M + Na) | 647.1818 (M + Na) |
| 192 | | 50[3] | C26H30N4O4Cl2S | 587.1263 (M + Na) | 587.1251 (M + Na) |

Starting material = trimethylsilylisocyanate
Starting material = methoxycarbonylisocyanate
Starting material = methyl isothiocyanate

Example 193

4-[[(2,6-Dichlorophenyl)Carbonyl]Amino]-N-[[2-[[(Methoxy)Carbonyl]Amino]Ethyl]Cyclopentyl]Carbonyl]-L-Phenylalanine

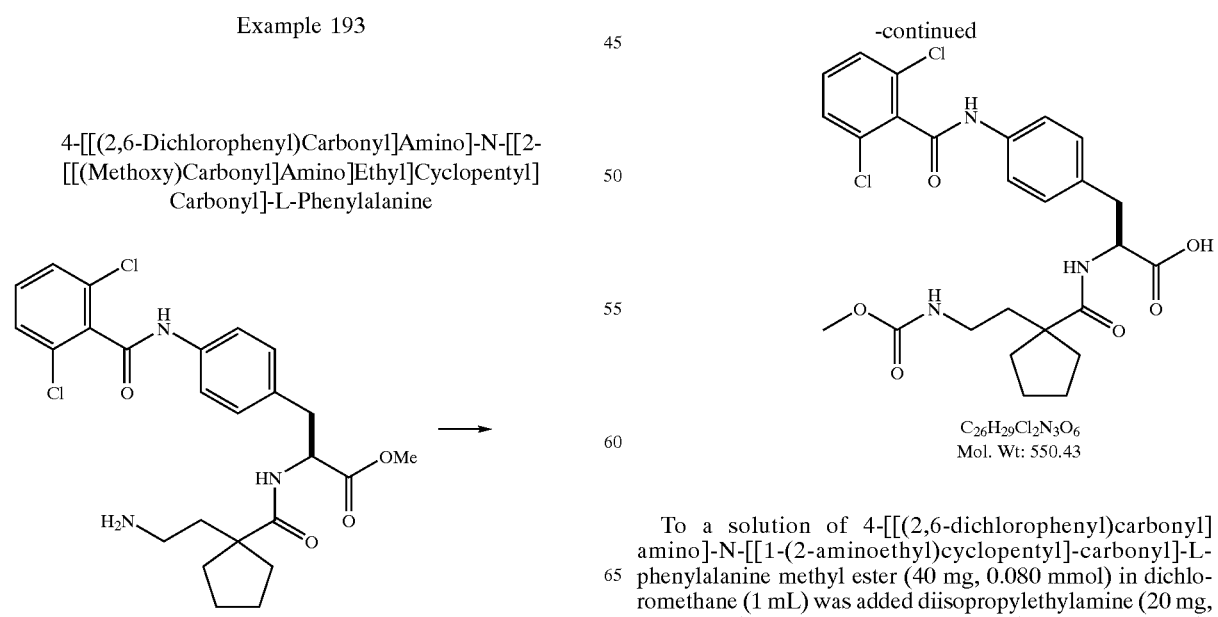

$C_{26}H_{29}Cl_2N_3O_6$
Mol. Wt: 550.43

To a solution of 4-[[(2,6-dichlorophenyl)carbonyl]amino]-N-[[1-(2-aminoethyl)cyclopentyl]-carbonyl]-L-phenylalanine methyl ester (40 mg, 0.080 mmol) in dichloromethane (1 mL) was added diisopropylethylamine (20 mg, 0.16 mmol) and methyl chloroformate (7 mg, 0.080 mmol).

The resultant mixture was stirred for 18 h. The reaction mixture was concentrated in vacuo and the crude carbamate was used in the next step without purification.

To a solution of the crude methyl ester (54 mg, 0.080 mmol) in MeOH (1 mL) was added a solution of LiOH (8 mg, 0.19 mmol) in water (0.5 mL). The mixture was stirred for 2 h and then it was acidified (pH ~1–2) with 0.5M HCl. The reaction mixture was poured into a round bottom flask and concentrated in vacuo. Purification by reversed-phase HPLC, using a 15–95% acetonitrile-water gradient over 25 min., provided 25 mg (57%). HR MS (C26H29N3O6Cl2): Calcd mass, 550.1511. Obs mass, 550.1524 (M+H).

Example 194

Preparation of 4-[[(2,6-Dichlorophenyl)Carbonyl]Amino]-N-[[1-[2-[(Methylsulfonyl)Amino]Ethyl]Cyclopentyl]Carbonyl]-L-Phenylalanine

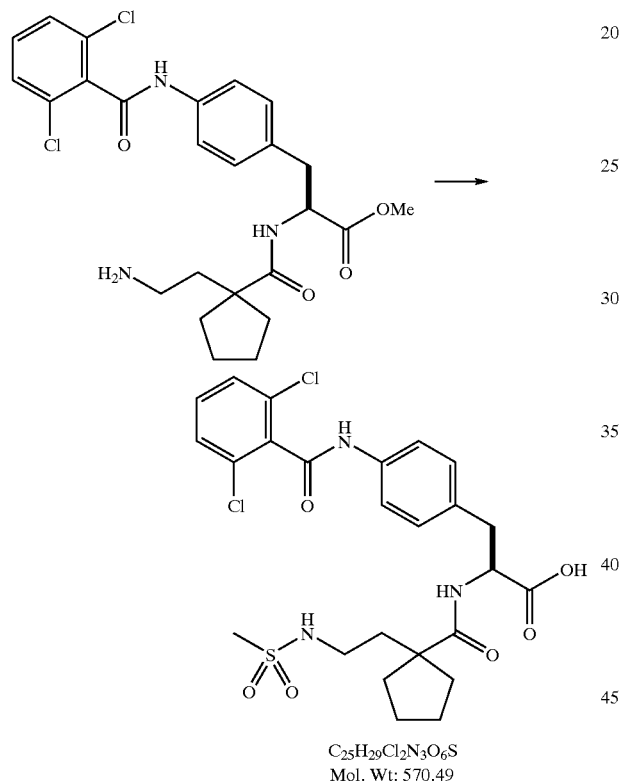

C25H29Cl2N3O6S
Mol. Wt: 570.49

To a solution of 4-[[(2,6-dichlorophenyl)carbonyl]amino]-N-[[1-(2-aminoethyl)cyclopentyl]-carbonyl]-L-phenylalanine methyl ester (40 mg, 0.080 mmol) in dichloromethane (1 mL) was added diisopropylethylamine (12 mg, 0.095 mmol) and methanesulfonyl chloride (9 mg, 0.080 mmol). The resultant mixture was stirred for 18 h. The reaction mixture was concentrated in vacuo and the crude sulfonamide was used in the next step without purification.

To a solution of the crude methyl ester (55 mg, 0.080 mmol) in MeOH (1 mL) was added a solution of LiOH (8 mg, 0.19 mmol) in water (0.5 mL). The mixture was stirred for 2 h and then it was acidified (pH ~1–2) with 0.5M HCl. The reaction mixture was poured into a round bottom flask and concentrated in vacuo. Purification by reversed-phase HPLC, using a 15–95% acetonitrile-water gradient over 25 min., provided 28 mg (61%). HR MS (C25H29N3O6Cl2S): Calcd mass, 592.1052. Obs mass, 592.1068 (M+Na).

Example 195

Preparation of 1-[2-[[(1,1-Dimethylethoxy)Carbonyl]Amino]Ethyl]Cyclopentyl Carboxylic Acid Methyl Ester

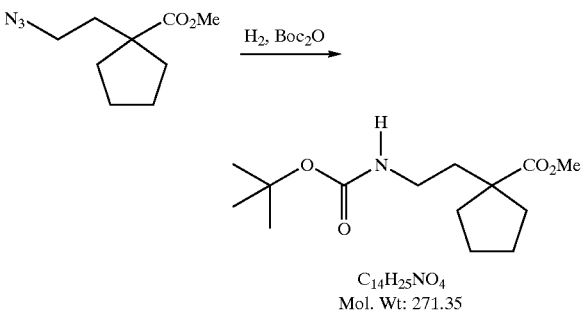

C14H25NO4
Mol. Wt: 271.35

To a solution of 1-(2-azidoethyl)cyclopentane carboxylic acid methyl ester (5.00 g, 25.4 mmol) in ethyl acetate (100 mL) was added di-tert-butyl-dicarbonate (55.4 g, 254 mmol) and 10% Pd on carbon (1.5 g). The reaction mixture was shaken for 3 h under hydrogen gas (50 psi) on a Parr shaker apparatus. The reaction mixture was filtered through a pad of celite and the pad was washed with ethyl acetate (2×150 mL). The combined organic phase was transferred to a round bottom flask and concentrated in vacuo. Purification by flash column chromatography, using hexane-ethyl acetate (9:1), afforded 5.30 g (76%) as a light yellow oil. HR MS (C14H25NO4): Calcd: 272.1862. Obs mass, 272.1856 (M+H).

Example 196

Preparation of 1-[2-[[(1,1-Dimethylethoxy)Carbonyl]Amino]Ethyl]Cyclopentane Carboxylic Acid

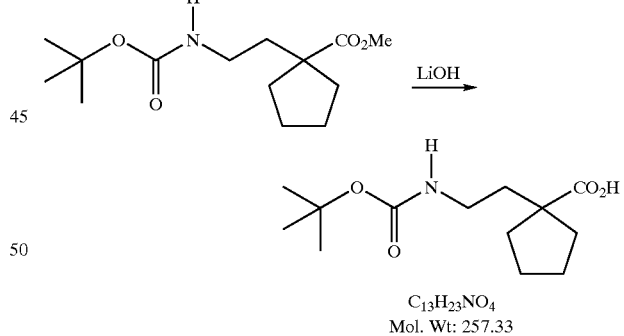

C13H23NO4
Mol. Wt: 257.33

To a solution of the 1-[2-[[(1,1-dimethylethoxy)carbonyl]amino]ethyl]cyclopentane carboxylic acid methyl ester (10.6 g, 39.0 mmol) in THF/MeOH (3:1, 40 mL) was added a solution of LiOH (4.20 g, 98.0 mmol) in water (10 mL). The mixture was stirred for 2.5 h at 50° C. and then cooled to room temperature. The reaction mixture was poured into a round bottom flask and concentrated in vacuo. The mixture was diluted with H2O (60 mL) and acidified with 1M HCl. The aqueous phase was extracted with ethyl acetate (3×200 mL) and the combined organic layer was dried over MgSO4, filtered and concentrated in vacuo. Purification by flash column chromatography, using hexane-ethyl acetate (3:1),

Example 197

Preparation of 1-[2-[[(1,1-Dimethylethoxy)Carbonyl](Methyl)Amino]Ethyl]-Cyclopentane Carboxylic Acid Methyl Ester

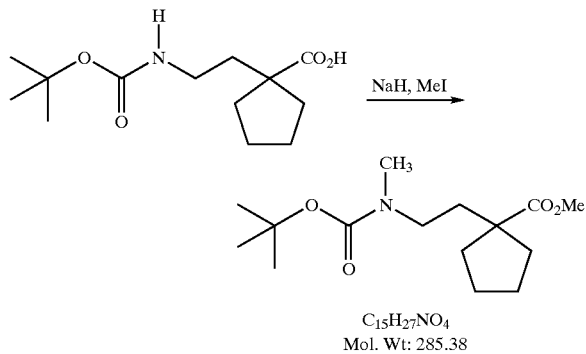

To a slurry of NaH (1.20 g, 47.5 mmol) in DMF (20 Obs mass, mL) at 0° C. was added dropwise a solution of 1-[2-[[(1,1-dimethylethoxy)carbonyl]amino]ethyl]cyclopentane carboxylic acid (5.8 g, 22.6 mmol) in THF (25 mL). The resultant mixture was stirred for 1 h at 0° C. and methyl iodide (3.3 Obs mass, mL, 52.3 mmol) was added dropwise. The reaction mixture was stirred for 1 h at 0° C. and 5 h at room temperature. The reaction was quenched with sat. ammonium chloride (20 Obs mass, mL) solution and transferred to a separatory funnel. The aqueous phase was extracted with ethyl acetate (3×100 mL) and the combined organic layer was dried over MgSO$_4$, filtered and concentrated in vacuo. Purification of the residue by flash column chromatography, using hexane-ethyl acetate (9:1), afforded 5.40 g (84%). HR MS (C15H27NO4): Calcd: 286.2018. Obs mass, 286.2021 (M+H).

Example 198

Preparation of 1-[2-[[(1,1-Dimethylethoxy)Carbonyl](Methyl)Amino]-Ethyl]Cyclopentane Carboxylic Acid

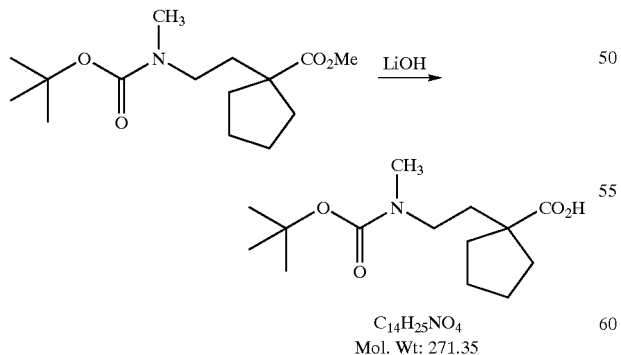

To a solution of 1-[2-[[(1,1-dimethylethoxy)carbonyl](methyl)amino]ethyl]cyclopentane carboxylic acid methyl ester (4.00 g, 14.0 mmol) in THF/MeOH (2:1, 24 mL) was added a solution of LiOH (1.50 g, 35.0 mmol) in water (8 mL). The mixture was stirred overnight at 50° C. and then cooled to room temperature. The reaction mixture was poured into a round bottom flask and concentrated in vacuo. The mixture was diluted with H$_2$O (50 mL) and acidified with 1M HCl. The aqueous phase was extracted with ethyl acetate (3×150 mL) and the combined organic layer was dried over MgSO$_4$, filtered and concentrated in vacuo. Purification by flash column chromatography, using hexane-ethyl acetate (5:1), afforded (3.60 g, 95%) of a white powder. HR MS (C14H25NO4): Calcd mass, 272.1862. Obs mass, 272.1872 (M+H).

Example 199

Preparation of 4-[[(2,6-dichlorophenyl)carbonyl]amino]-N-[[1-[2-(methylamino)-ethyl]cyclopentyl]carbonyl]-L-phenylalanine methyl ester was prepared by coupling of 4-[[(2,6-dichlorophenyl)carbonyl]amino]-L-phenylalanine methyl ester as prepared in example 45 with the product from example 198 using the general procedure described in example 146. The protecting Boc group was removed from the product by treatment with 4 N HCl in dioxane as described in example 45 and the product was used as is in subsequent steps.

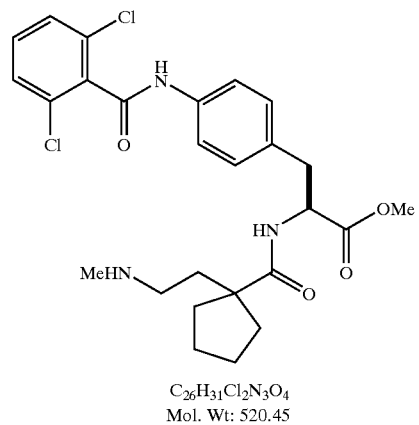

Example 200

Preparation of 4-[[(2,6-Dichlorophenyl)Carbonyl]Amino]-N-[[1-[2-[(Acetyl)(Methyl)-Amino]Ethyl]Cyclopentyl]Carbonyl]-L-Phenylalanine

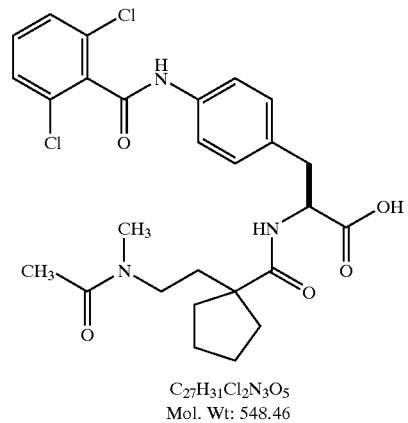

Acetylation of the product of example 199 using the general procedure described in example 148 followed by ester hydrolysis using the general procedure described in example 47 gave the title compound in 75% yield. HR MS (C27H31Cl2N3O5): Calcd mass, 548.1719. Obs mass, 548.1716 (M+H).

Example 201

Preparation of 4-[[(2,6-Dichlorophenyl)Carbonyl]Amino]-N-[[1-[2-[[(Methylamino)Carbonyl](Methyl)Amino]Ethyl]Cyclopentyl]Carbonyl]-L-Phenylalanine

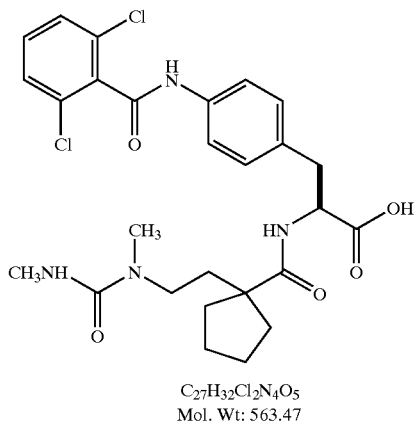

C27H32Cl2N4O5
Mol. Wt: 563.47

Reaction of the product of example 199 with methyl isocyanate using the general procedure described in example 187 followed by ester hydrolysis using the general procedure described in example 47 gave the title compound in 69% yield. HR MS (C27H32Cl2N4O5): Calcd mass, 563.1828. Obs mass, 563.1816 (M+H).

Example 202

Preparation of 4-[[(2,6-Dichlorophenyl)Carbonyl]Amino]-N-[[1-[2-[(Methoxycarbonyl)-(Methyl)Amino]Ethyl]Cyclopentyl]Carbonyl]-L-Phenylalanine

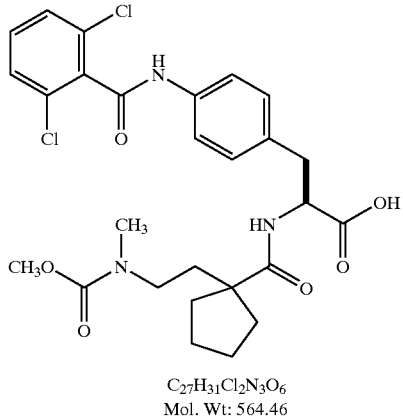

C27H31Cl2N3O6
Mol. Wt: 564.46

Reaction of the product of example 199 with methyl chloroformate using the general procedure described in example 193 followed by ester hydrolysis using the general procedure described in example 47 gave the title compound in 70% yield. HR MS ($C_{27}H_{31}Cl_2N_3O_6$): Calcd mass, 586.1488. Obs mass, 586.1465 (M+Na).

Example 203

4-[[(2,6-Dichlorophenyl)Carbonyl]Amino]-N-[[1-[2-[(Trifluoroacetyl)Amino]Ethyl]Cyclopentyl]Carbonyl]-L-Phenylalanine

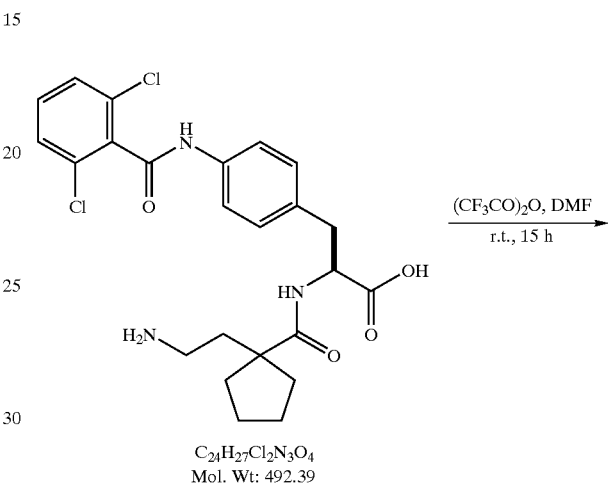

C24H27Cl2N3O4
Mol. Wt: 492.39

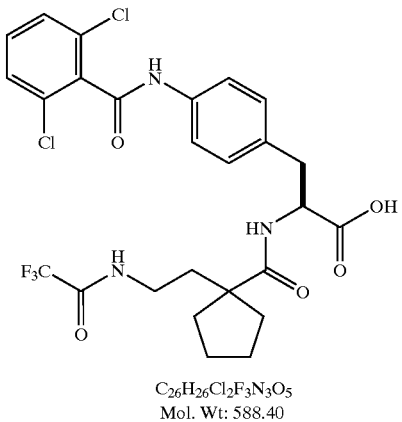

C26H26Cl2F3N3O5
Mol. Wt: 588.40

To a solution of 4-[[(2,6-dichlorophenyl)carbonyl]amino]-N-[[1-(2-aminoethyl)-cyclopentyl]-carbonyl]L-phenylalanine (0.041 mmol, 20 mg) in DMF (2 mL) was added 2 equiv. of trifluoroacetic anhydride (0.082 mmol, 17.2 mg) at room temperature. The mixture was stirred for 15 h at room temperature at which time HPLC analysis of the reaction mixture indicated the absence of staring material. Then, without any work-up, it was purified by reverse phase HPLC to afford 5.7 mg (21%) of a white solid. HR MS: (C26H26Cl2N3O5): Obs. mass, 588.1280. Calcd. mass, 588.1269 (+H).

Example 204

Preparation of 4-[[(2,6-Dichlorophenyl)Carbonyl]Amino]-N-[[1-[2-(Dimethylamino)Ethyl]Cyclopentyl]Carbonyl]-L-Phenylalanine Methyl Ester

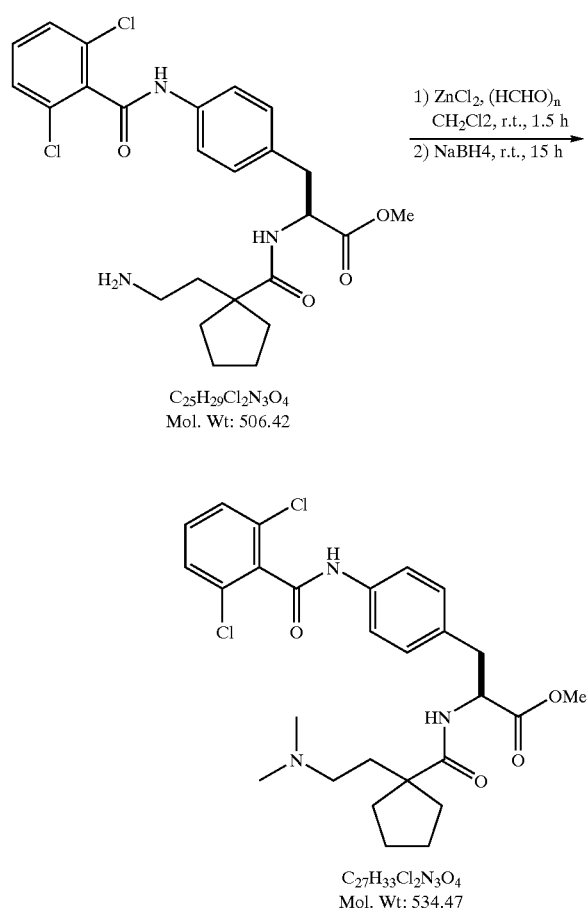

To a mixture of N-[[1-(2-aminoethyl)cyclopentyl]carbonyl]-4-[[(2,6-dichlorophenyl)-carbonyl]amino]-L-phenylalanine methyl ester (0.339 mmol, 0.17 g), zinc chloride (1.36 mmol, 0.185 g) and paraformaldehyde (1.36 mmol, 40.7 mg) was added dichloromethane (2 mL) at room temperature and the mixture was stirred for 1.5 h. Then, sodium borohydride (1.36 mmol, 51.3 mg) was added and the resulting mixture was stirred for 15 h at room temperature. The mixture was poured into $NH_4OH$ (10 mL) and extracted with dichloromethane (2×20 mL). The combined organic layer was washed with brine solution (20 mL) and dried over anhydrous magnesium sulfate. Filtration of the drying agent and removal of the solvent gave a crude product which was purified by HPLC to afford 18 mg (10%) of a light yellow solid. HR MS (C27H33Cl2N3O4): Obs. mass, 534.1927. Calcd. mass, 534.1926 (M+H).

Example 205

Preparation of 4-[[(2,6-Dichlorophenyl)Carbonyl]Amino]-N-[[1-[2-[[(4-Methoxyphenyl)Carbonyl]Amino]Ethyl]Cyclopentyl]Carbonyl]-L-Phenylalanine Methyl Ester

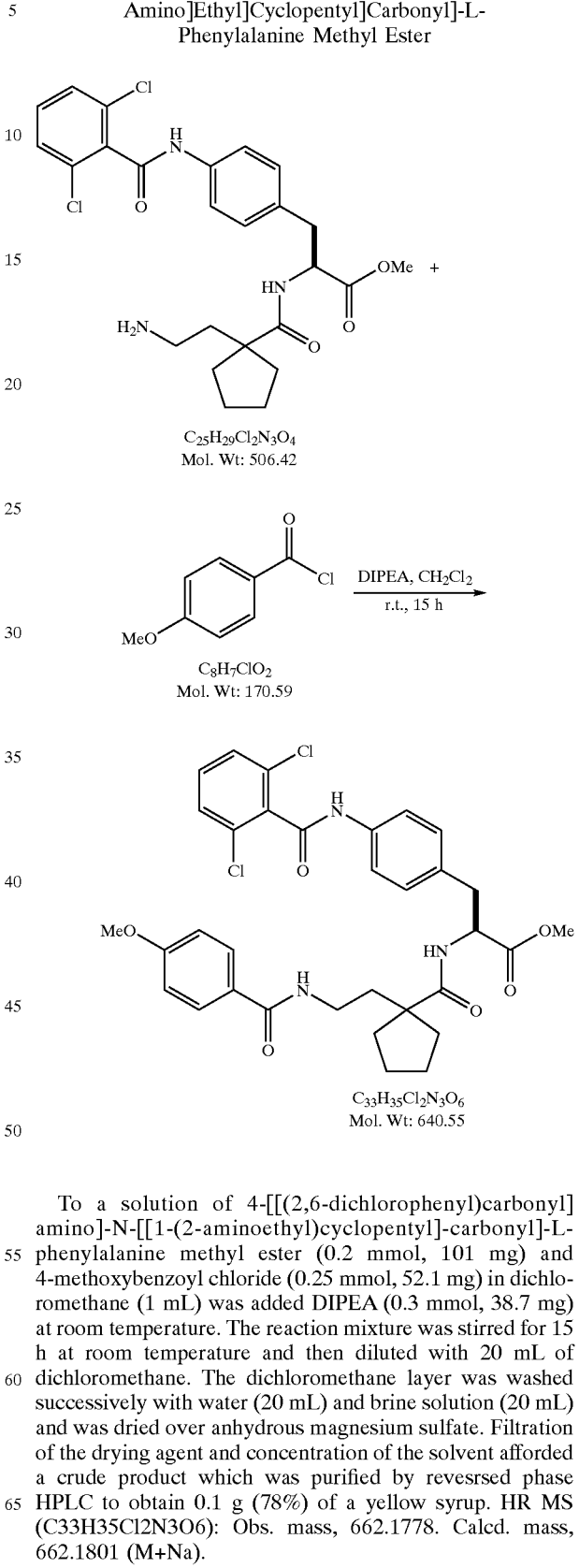

To a solution of 4-[[(2,6-dichlorophenyl)carbonyl]amino]-N-[[1-(2-aminoethyl)cyclopentyl]-carbonyl]-L-phenylalanine methyl ester (0.2 mmol, 101 mg) and 4-methoxybenzoyl chloride (0.25 mmol, 52.1 mg) in dichloromethane (1 mL) was added DIPEA (0.3 mmol, 38.7 mg) at room temperature. The reaction mixture was stirred for 15 h at room temperature and then diluted with 20 mL of dichloromethane. The dichloromethane layer was washed successively with water (20 mL) and brine solution (20 mL) and was dried over anhydrous magnesium sulfate. Filtration of the drying agent and concentration of the solvent afforded a crude product which was purified by revesrsed phase HPLC to obtain 0.1 g (78%) of a yellow syrup. HR MS (C33H35Cl2N3O6): Obs. mass, 662.1778. Calcd. mass, 662.1801 (M+Na).

Example 206

4-[[(2,6-dichlorophenyl)carbonyl]amino]-N-[[1-[2-[[(3-trifluoromethylphenyl)-carbonyl]amino]ethyl]cyclopentyl]carbonyl]-L-phenylalanine methyl ester was prepared from 4-[[(2,6-dichlorophenyl)carbonyl]amino]-N-[[1-(2-aminoethyl)cyclopentyl]carbonyl]-L-phenylalanine methyl ester and 3-trifluoromethylbenzoyl chloride using the general method described in example 205 to give a 99% yield of a white solid. HR MS C33H32Cl2N3O5): Obs. mass, 700.1596. Calcd. mass, 700.1569 (M+Na).

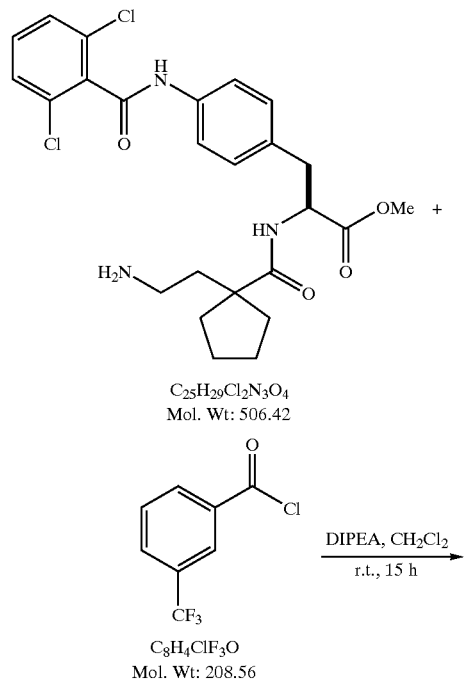

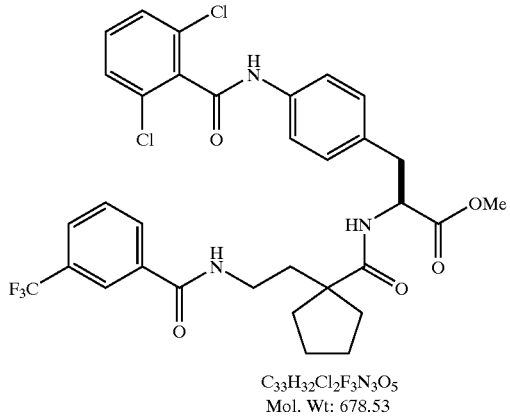

Example 207

1-[4-(Azido)butyl]cyclopentane carboxylic acid methyl ester was prepared from 1-[4-(bromobutyl)]cyclopentane carboxylic acid methyl ester and sodium azide using the general procedure described in example 4 to give a syrup in 87% overall yield. HR MS (C11H19N3O2): Obs mass, 225.1523. Calcd mass, 225.1536 (M+).

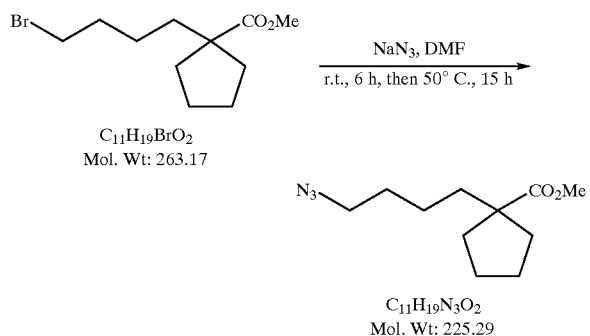

Example 208

1-[4-(Azido)butyl]cyclopentane carboxylic acid was prepared by hydrolysis of the ester prepared in example 207 using the general procedure described in example 15 to give a brown syrup in quantitative yield. HR MS (C10H17N3O2): Obs mass, 211.1285. Calcd mass, 211.1267 (M+).

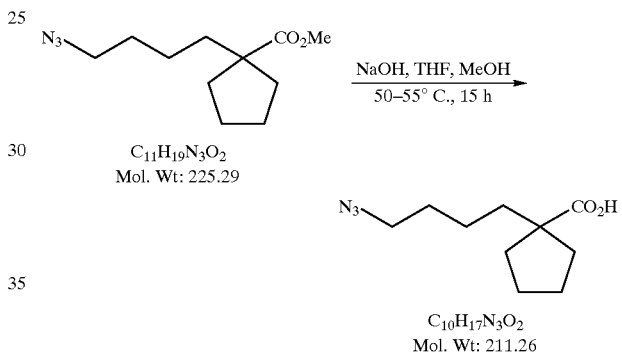

Example 209

1-(3-Azidopropyl)cyclopentane carboxylic acid was prepared from 1-(3-bromopropyl)cyclopentane carboxylic acid methyl ester using the general procedure described in example 4. The acid was isolated as an oil. LR ES MS (C9H15N3O2): 196.1 (M−H).

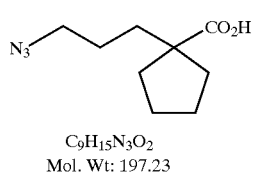

Example 210

4-[[(2,6-dichlorophenyl)carbonyl]amino]-N-[[I-(4-azidobutyl)cyclopentyl]-carbonyl]-L-phenylalanine methyl ester was prepared from 1-[4-(azido)butyl]cyclopentane carboxylic acid and of 4-[[(2,6-dichlorophenyl)carbonyl]amino]-L-phenylalanine methyl ester hydrochloride salt using the procedure described in example 46 to give a 99% yield of a white solid, mp 195–199° C. HR MS (C27H31Cl2N5O4): Obs mass, 560.1833. Calcd mass, 560.1831 (M+H).

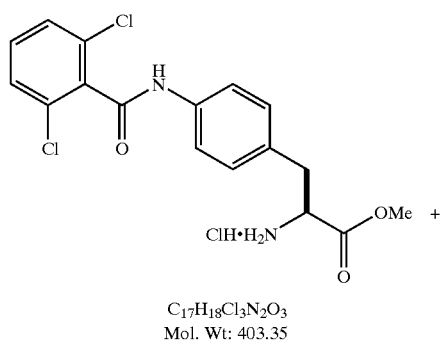

C₁₇H₁₈Cl₃N₂O₃
Mol. Wt: 403.35

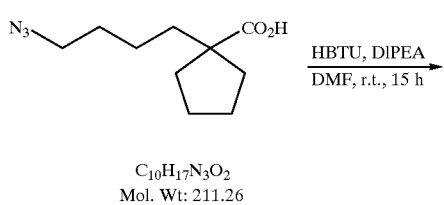

C₁₀H₁₇N₃O₂
Mol. Wt: 211.26

HBTU, DIPEA
DMF, r.t., 15 h

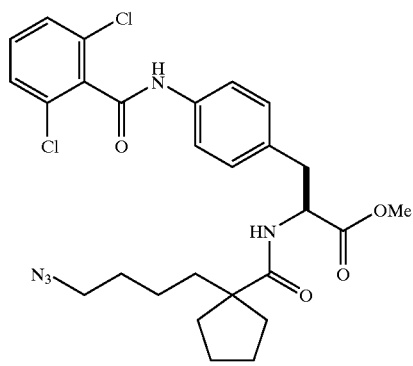

C₂₇H₃₁Cl₂N₅O₄
Mol. Wt: 560.47

Example 211

4-[[(2,6-dichlorophenyl)carbonyl]amino]-N-[[1-(4-aminobutyl)cyclopentyl]-carbonyl]-L-phenylalanine methyl ester was prepared from 4-[[(2,6-dichlorophenyl)-carbonyl]-amino]N-[[1-(4-azidobutyl)cyclopentyl]carbonyl]-L-phenylalanine methyl ester using the general procedure described in example 147 to give a 30% yield of a white solid. HR MS: (C27H33Cl2N3O4): Obs mass, 534.1352. Calcd mass, 534.1368 (M+H).

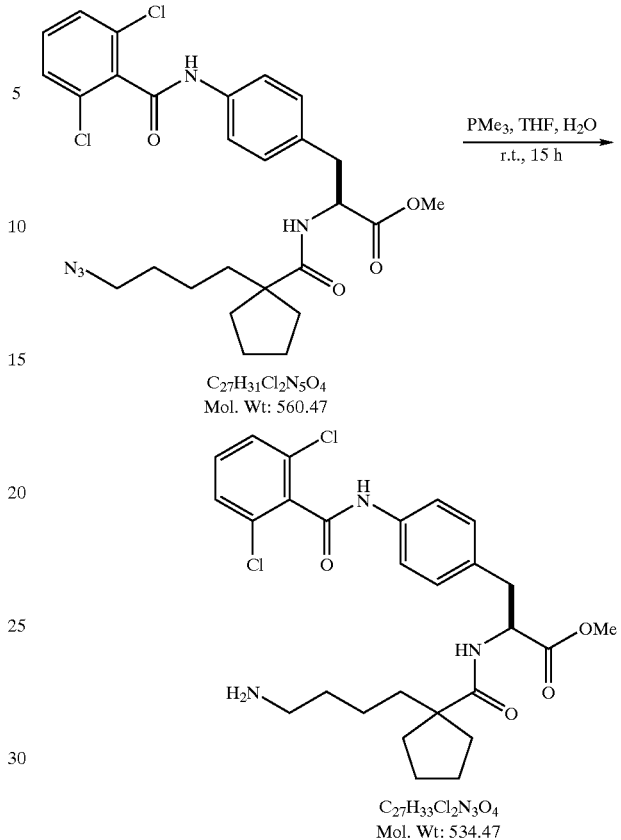

Example 212

4-[[(2,6-dichlorophenyl)carbonyl]amino]-N-[[1-[4-[(acetyl)amino]butyl]-cyclopentyl]carbonyl]-L-phenylalanine methyl ester was prepared from 4-[[(2,6-dichlorophenyl)-carbonyl]amino]-N-[[1-(4-aminobutyl)cyclopentyl]carbonyl]-L-phenylalanine methyl ester using the procedure described in example 148 in 80% overall yield as a white solid. HR MS (C29H35Cl2N3O5): Obs mass, 576.1690. Calcd mass, 576.1714 (M+H).

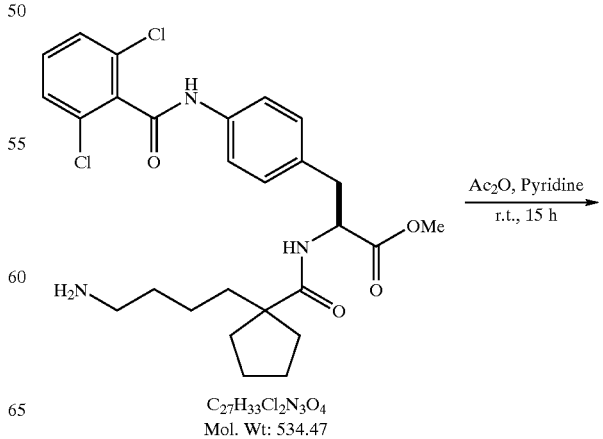

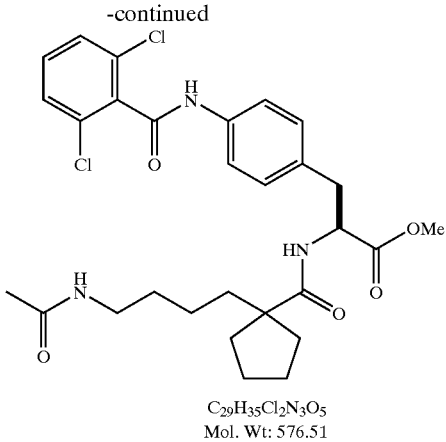

C29H35Cl2N3O5
Mol. Wt: 576.51

Example 213
Preparation of 1-[(5-Tetrazolyl)Methyl] Cyclopentane Methyl Ester

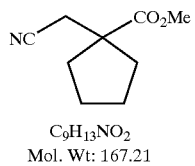

C9H13NO2
Mol. Wt: 167.21

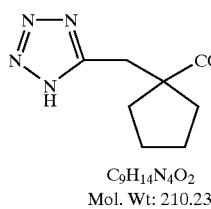

C9H14N4O2
Mol. Wt: 210.23

To a solution of methyl 1-(1-cyanomethyl)cyclopentane carboxylate (5.5 mmol, 0.9 g) in toluene (15 mL) were added trimethylsilyl azide (11 mmol, 1.26 g) and dibutyltin oxide (0.55 mmol, 137 mg) at room temperature. The mixture was heated to 110° C. and stirred for 15 h. Then, the reaction mixture was cooled to room temperature and toluene was removed under vacuum. The brown residue was diluted with ethyl acetate (100 mL) and washed with saturated sodium bicarbonate solution (2×50 mL) and the starting material and some impurities remained in ethyl acetate. The aqueous sodium bicarbonate layer was neutralized with 3N HCl and extracted with ethyl acetate (2×50 mL). The combined extracts were washed with brine solution (50 mL) and dried over anhydrous magnesium sulfate. After filtration of the drying agent, the solution was concentrated under vacuum and the residue was dried under high vacuum to afford 0.31 g (27%) of a low melting white solid. HR MS (C9H14N4O2): Obs mass, 210.0218. Calcd mass, 210.0252 (M+).

Example 214
Preparation of 1-[(1-Tetrazolyl)Methyl] Cyclopentane Carboxylic Acid

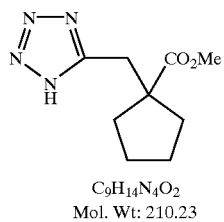

C9H14N4O2
Mol. Wt: 210.23

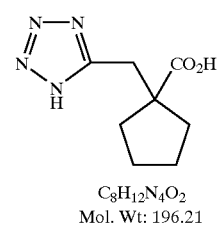

C8H12N4O2
Mol. Wt: 196.21

Using the procedure described in example 15, 1-[(5-tetrazolyl)methyl]cyclopentane carboxylic acid was prepared from the corresponding ester in 67% overall yield as a white solid: mp 192–196° C. HR MS (C8H12N4O2): Obs mass, 196.0329. Calcd mass, 196.0318 (M+).

Example 215
Preparation of 4-[[(2,6-Dichlorophenyl)Carbonyl] Amino]-N-[[1-(Butyl)Cyclopentyl]Carbonyl]-L-Phenylalanine Methyl Ester

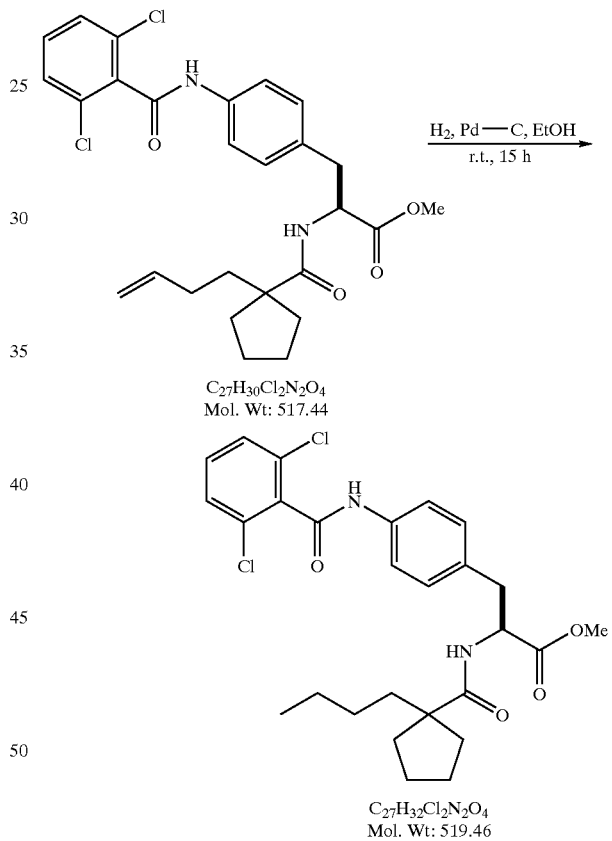

A mixture of 4-[[(2,6-dichlorophenyl)carbonyl]amino]-N-[[1-(3-butenyl)cyclopentyl]carbonyl]-L-phenylalanine methyl ester (0.19 mmol, 100 mg) and 10% palladium on carbon (200 mg) in EtOH (2 mL) was stirred under a hydrogen atmosphere at room temperature for 15 h. Then, the charcoal was filtered and washed with EtOH (10 mL). The filtrate was removed under vacuum to obtain 37.5 mg (37%) of as a white solid: mp 193–196° C. HR MS: Obs. mass, 519.1818. Calcd. mass, 519.1817 (M+H).

Example 216
4-[[(2,6-dichlorophenyl)carbonyl]amino]-N-[[1-[2-[[2-[[(1,1-dimethylethoxy-carbonyl]amino]-1-oxoethyl]amino]

ethyl]cyclopentyl]carbonyl]-L-phenylalanine was prepared by coupling of the product from example 147 with Boc-glycine using the general HBTU protocol described in example 46, followed by treatment with NaOH to effect ester hydrolysis as described in example 47 to give a 75% yield. HR MS (C31H38Cl2N4O7): Calcd mass, 671.2016. Obs mass, 671.2002 (M+Na).

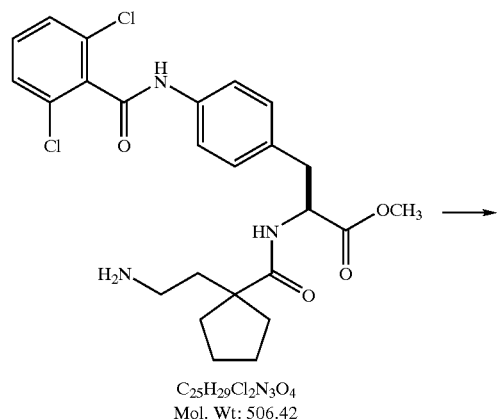

C25H29Cl2N3O4
Mol. Wt: 506.42

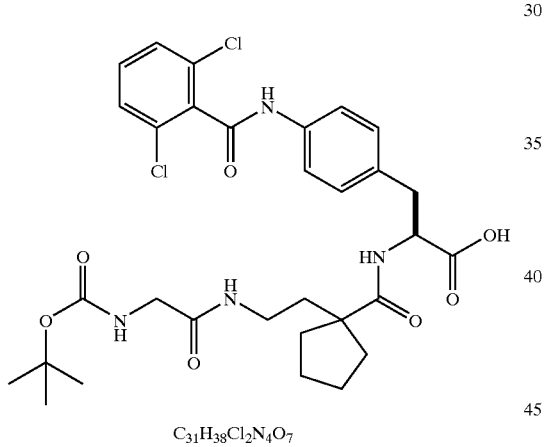

C31H38Cl2N4O7
Mol. Wt: 649.56

Example 217

4-[[(2,6-dichlorophenyl)carbonyl]amino]-N-[[1-[2-[(2-amino-1-oxoethyl)amino]-ethyl]cyclopentyl]carbonyl]-L-phenylalanine was prepared by treatment of the product of example 216 with 4 N HCl in dioxane. HR MS (C26H30Cl2N4O5): Calcd mass, 571.1419. Obs mass, 571.1491 (M+Na).

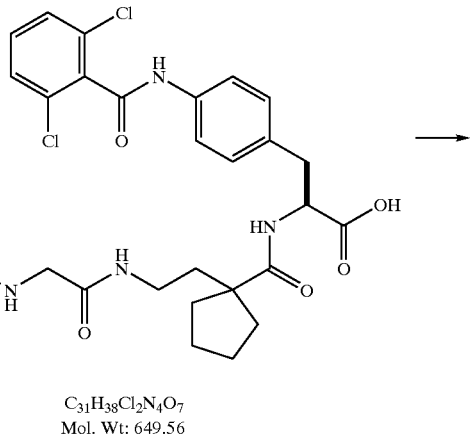

C31H38Cl2N4O7
Mol. Wt: 649.56

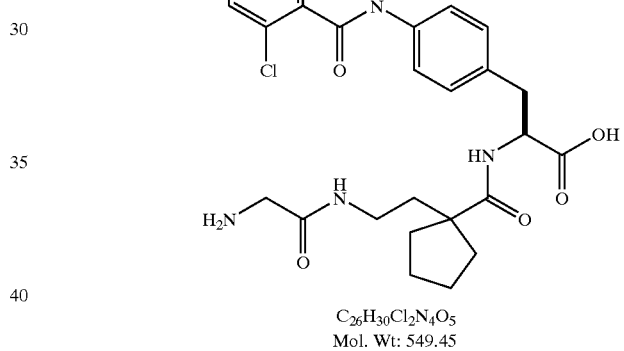

C26H30Cl2N4O5
Mol. Wt: 549.45

Example 218

1-(Cyanomethyl)cyclopentane carboxylic acid methyl ester was prepared from cyclopentane carboxylic acid methyl ester and chloroacetonitrile using the procedure described in example 7 to give a 38% yield. HR MS (C9H13NO2): Obs mass, Calcd mass, 167.0146 (M+).

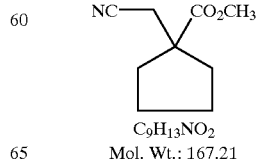

C9H13NO2
Mol. Wt.: 167.21

Examples 219–229

Using the procedure described in example 15, the following cyclopentane carboxylic acids were prepared:

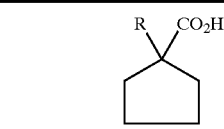

| Example | R | Yield % | Formula | MS |
|---|---|---|---|---|
| 219 | CH₃-S-CH₂CH₂- | 90 | C9H16O2S | HR MS Calcd, 188.0871 Obs, 188.0871 |
| 220 | H₃C-S-(CH₂)₃- | 90 | C11H20O2S | LR-ES MS 214 (M − H) |
| 221 | NC-(CH₂)₃- | 86 | C11H17NO2 | LR-ES MS 196 (M + H) |
| 222 | (2-methyl-1,3-dioxolan-2-yl)-(CH₂)₂- | 73 | C13H22O4 | LR-ES MS 243 (M + H) |
| 223 | CH₃-S-(CH₂)₃- | 90 | C10H18O2S | LR-ES MS 201 (M − H) |
| 224 | F₂C=CH-CH₂- | 90 | C10H14F2O2 | |
| 225 | NC-(CH₂)₂- | 95 | C10H19NO2 | LR-ES 182 |
| 226 | (2-methyl-1,3-dioxolan-2-yl)-CH₂- | 25 | C12H20O4 | LR-ES 229 (M + H) |
| 227 | CH₂=CH-CH₂-CH₂- | 90 | C10H16O2 | HR MS Calcd, 168.2459 Obs, 168.2434 |
| 228 | NC-CH₂- | 98 | C8H11NO2 | HR MS Calcd, 153.0198 Obs, 153.0274 |

Example 229

Preparation of Methyl 1-(4-Chlorobutyl) Cyclopentane Carboxylate

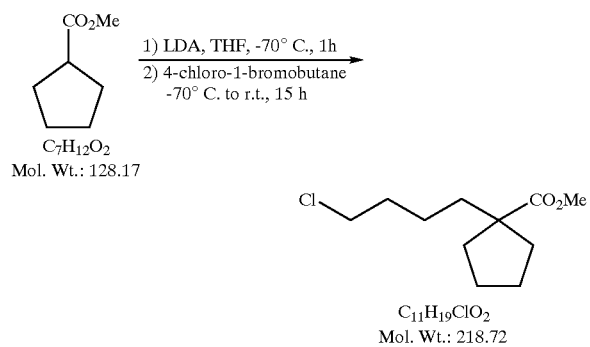

1-(4-Chlorobutyl)cyclopentane carboxylic acid methyl ester was prepared from cyclopentane carboxylic acid methyl ester and 4-chloro-1-bromobutane using the procedure described in example 7 to give a 64% yield. HR MS (C11H19ClO2): Obs. mass, 218.1072. Calcd. mass, 218.1074, (M+).

Example 230

Preparation of 1-(3-Butenyl)Cyclopentane Carboxylic Acid Methyl Ester

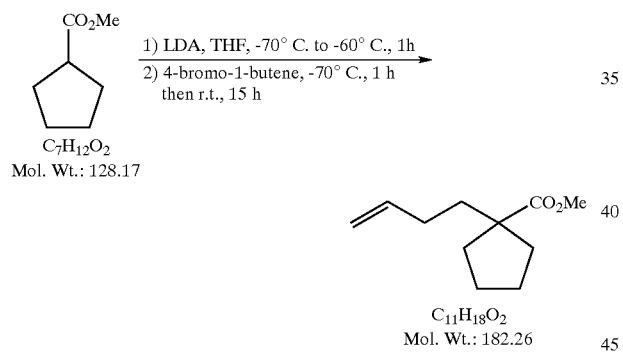

To a solution of diisopropylamine (225 mmol, 31.6 mL) in THF (150 mL) was added dropwise a solution of n-butyl lithium (217.5 mmol, 87 mL, 2.5M) in hexanes at −10° C. while maintaining the temperature below 0° C. After addition, the solution was stirred for 30 min at 0° C. To this, a solution of methyl cyclopentane carboxylate (150 mmol, 19.23 g) in THF (30 mL) was added dropwise at −70° C. maintaining the internal temperature between −60 to −70° C. After addition, the reaction mixture was stirred for 1 h at −50 to −60° C. Then, a solution of 4-bromo-1-butene (142.2 mmol, 19.2 g) in THF (30 mL) was added dropwise and the light brown suspension was stirred for 1 h at −60 to −70° C. Then, it was allowed to warm to room temperature and stirred overnight. The reaction mixture was poured into a saturated solution of ammonium chloride (250 mL) and the mixture was extracted with ether (2×150 mL). The combined extracts were washed with a saturated solution of sodium chloride (150 mL) and dried over anhydrous magnesium sulfate. After filtration of the drying agent, the solution was concentrated under vacuum and the residue was distilled at 63–67° C./2.5 mm Hg to give 13.77 g (53%) of a colorless oil. HR MS (C11H16O2): Obs mass, 182.1311. Calcd mass, 182.1307 (M+).

Example 231

Preparation of 1-[2-(Methylthio)Ethyl]Cyclopentane Carboxylic Acid Methyl Ester

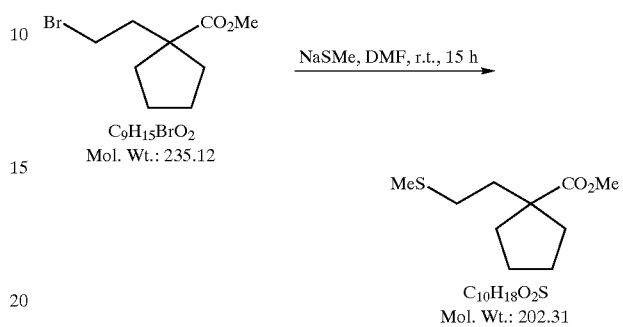

To a solution of 1-(2-bromoethyl)cyclopentane carboxylic acid methyl ester (2.0 mmol, 472 mg) in DMF (5 mL) was added sodium thiomethoxide (2.65 mmol, 186 mg). The reaction mixture was stirred for 15 h at room temperature and was poured into water (30 mL). The organic compound was extracted into diethyl ether (2×20 mL). The combined extracts were washed with a saturated solution of sodium chloride (50 mL) and dried over anhydrous magnesium sulfate. After filtration of the drying agent, the solution was concentrated under vacuum and the resulting residue was purified by silica gel column chromatography to afford 334 mg (82%) of a colorless oil. HR MS C10H18O2S): Obs mass, 202.1024. Calcd mass, 202.1028 (M+).

Example 232

Preparation of 1-[4-(Methoxy)butyl]Cyclopentane Carboxylic Acid

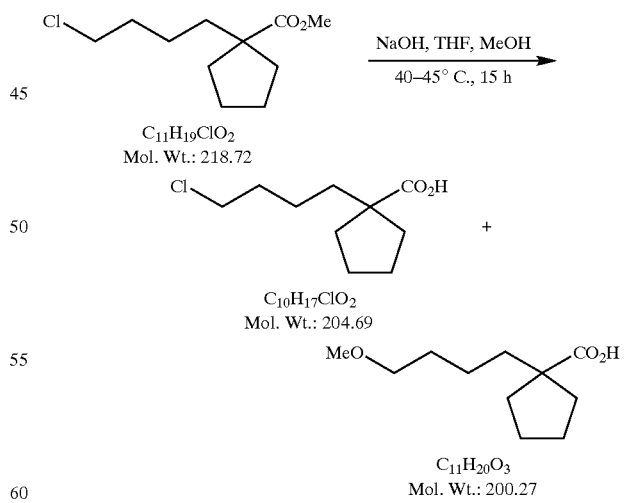

To a solution of 1-(4-chlorobutyl)cyclopentane carboxylic acid methyl ester (30 mmol, 6.56 g) in a mixture of THF (60 mL) and methanol (60 mL) was added 1 N sodium hydroxide (60 mL). The mixture was heated to 40–45° C. for 15 h at which point TLC analysis of the reaction mixture indicated the absence of starting material and it was cooled to room temperature. The solvent was removed under vacuum and the residue was diluted with water (100 mL) and extracted with ether (2×100 mL) to remove any neutral impurities. Then, the basic aqueous layer was acidified with 1 N hydrochloric acid and the product was extracted with ethyl acetate (2×75 mL). The combined extracts were washed with brine solution and were dried over anhydrous sodium sulfate. After filtration of the drying agent, the solution was concentrated under vacuum and the residue was purified by silica gel column chromatography to afford 4.2 g (68%) of 1-(4-chlorobutyl)cyclopentane carboxylic acid as a liquid and 1.3 g (22%) of 1-[4-(methoxy)butyl] cyclopentane carboxylic acid as a viscous oil. HR MS (C11H20O3): Obs mass, 200.0175. Calcd mass, 200.0143 (M+).

Examples 233–248

Using the general coupling procedure described in example 46, the following analogues were prepared:

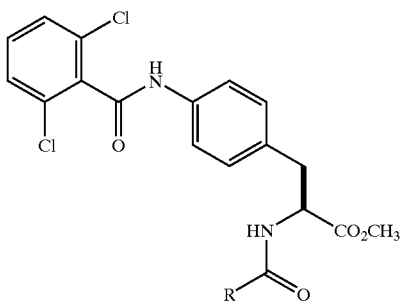

| Example | Starting material from Example | R | Yield % | Formula | HRMS[1] calcd. | found |
|---|---|---|---|---|---|---|
| 233 | 219 | (structure) | 91 | C26H30Cl2N2O4S | 537.1381 | 537.1393 |
| 234 | 232 | (structure) | 67 | C28H34Cl2N2O5 | 549.1923 | 549.1903 |
| 235 | 209 | (structure) |  | C26H29Cl2N5O4 | 568.1 (M + Na) | 568.1 (M + Na) |
| 236 | 220 | (structure) | 81 | C28H34N2O6Cl2S | 619.1413 (M + Na) | 619.1404 (M + Na) |
| 237 | 221 | (structure) | 74 | C28H31N3O4Cl2 | 544.1770 | 544.1765 |
| 238 | 175 | (structure) | 80 | C28H34N2O6Cl2S | 619.1413 (M + Na) | 619.1404 (M + Na) |
| 239 | 222 | (structure) | 67 | C30H36N2O6Cl2 | 591.2028 | 591.2034 |

-continued

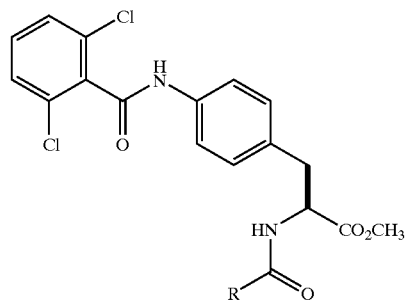

| Example | Starting material from Example | R | Yield % | Formula | HRMS[1] calcd. | found |
|---|---|---|---|---|---|---|
| 240 | 223 | CH₃-S-(CH₂)₃-C(CH₃)(cyclopentyl) | 76 | C27H32N2O4Cl2S | 573.1358 (M + Na) | 573.1343 (M + Na) |
| 241 | 224 | F₂C=CH-CH₂-C(CH₃)(cyclopentyl) | 52 | C26H26N2O4Cl2F2 | | |
| 242 | 225 | NC-(CH₂)₃-C(CH₃)(cyclopentyl) | 76 | C27H29N3O4Cl2 | 530.1613 | 530.1603 |
| 243 | 226 | 1,3-dioxolan-2-yl(CH₃)-CH₂CH₂-C(CH₃)(cyclopentyl) | 73 | C29H34N2O6Cl2 | 577.1852 | 577.1854 |
| 244 | 227 | CH₂=CH-CH₂-C(CH₃)(cyclopentyl) | 99 | C27H30Cl2N2O4 | 517.1661 | 517.1674 |
| 245 | 228 | NC-CH₂-C(CH₃)(cyclopentyl) | 67 | C25H25Cl2N3O4 | 502.1300 | 502.1299 |
| 246 | 214 | tetrazol-5-yl-CH₂-C(CH₃)(cyclopentyl) | 85 | C25H26Cl2N6O4 | 545.1471 | 545.1454 |

M + H ion unless otherwise indicated

Example 247

4-[[(2,6-Dichlorophenyl)carbonyl]amino]-N-[[1-[(2-morpholinyl)ethyl]cyclopentyl]carbonyl]-L-phenylalanine methyl ester was prepared from 4-[[(2,6-Dichlorophenyl)carbonyl]amino]-L-phenylalanine methyl ester and 1-[(2-morpholinyl)ethyl]cyclopentane carboxylic acid using the general coupling procedure described in example 46 to provide a 62% yield. HRMS (C29H35Cl2N3O5): Obs. mass, 576.2531. Calcd. mass, 576.2582, (M+H).

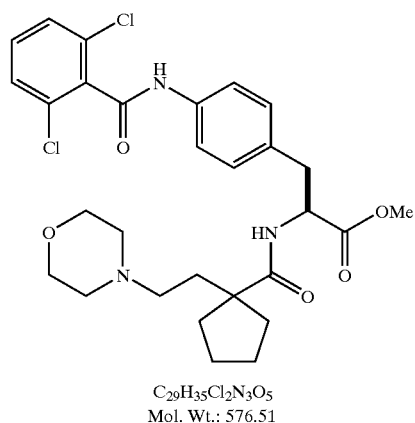

$C_{29}H_{35}Cl_2N_3O_5$
Mol. Wt.: 576.51

Example 248

Preparation of 4-[[(2,6-Dichlorophenyl)Carbonyl]Amino]-N-[[1-(4-Hydroxybutyl)-Cyclopentyl]Carbonyl]-L-Phenylalanine Methyl Ester

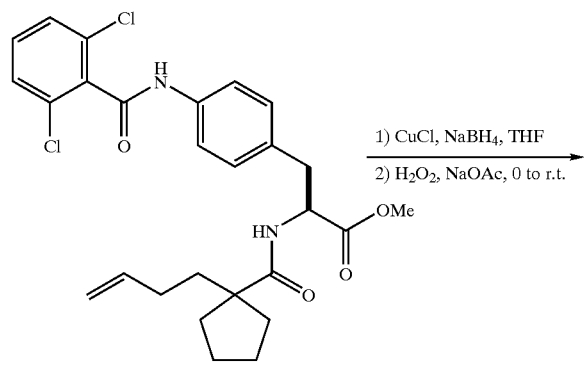

$C_{27}H_{30}Cl_2N_2O_4$
Mol. Wt.: 517.44

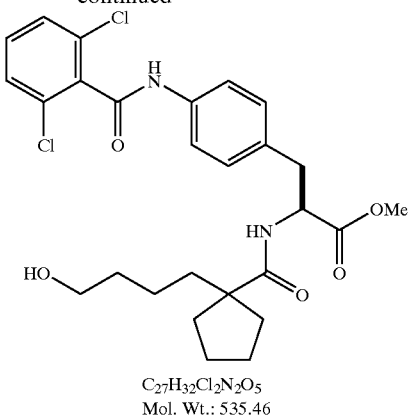

$C_{27}H_{32}Cl_2N_2O_5$
Mol. Wt.: 535.46

To a suspension of 4-[[(2,6-dichlorophenyl)carbonyl]arnino]-N-[[1-(3-butenyl)cyclopentyl]-carbonyl]-L-phenylalanine methyl ester (3.13 mmol, 1.62 g) and anhydrous copper (I) chloride (5.0 mmol, 500 mg) in THF (30 mL) was added solid sodium borohydride (5.0 mmol, 200 mg) at −5° C. over 5 min. After the addition, the reaction mixture was allowed to warm to room temperature and the brown reaction mixture was stirred for 36 h at which time TLC analysis of the mixture indicated the absence of starting material. Then, the excess hydride was quenched by the addition of water (5 mL) and the reaction mixture was cooled to 0° C. To this, a solution of sodium acetate (20 mL, 3.0N) was added dropwise maintaining the temperature below 10° C. this was followed by $H_2O_2$ (25 mL, 30%). After addition of hydrogen peroxide, the reaction mixture was allowed to warm to room temperature and was stirred for 3 h and followed by 1 h at 40–45° C. to complete the hydrolysis. Then, it was poured into a mixture of water (50 mL) and ethyl acetate (50 mL). The two layers were separated and the aqueous layer was extracted with ethyl acetate (2×30 mL). The comined extracts were washed with brine solution and dried over anhydrous magnesium sulfate. Filtration of the drying agent and removal of the solvent gave a crude product which was purified by silica gel column chromatography to afford 1.04 g (62%) of a white amorphous solid. HR MS (C27H32Cl2N2O5): Obs. mass, 535.1758. Calcd. mass, 535.1766, M+H).

Examples 249–274

The compounds shown below were prepared from the corresponding methyl esters according to the procedure given in example 47.

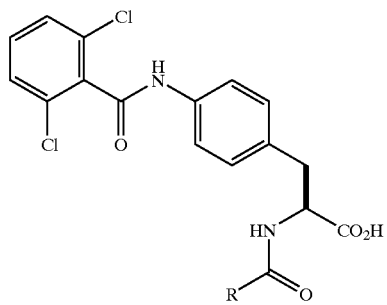

| Example | Starting Material from Example | R | Yield % | Formula | HRMS1 calcd. | found |
|---|---|---|---|---|---|---|
| 249 | 233 | methylthioethyl-(1-methylcyclopentyl) | 84 | C25H28Cl2N2O4S | 523.1225 | 523.1230 |
| 250 | 234 | methoxypropyl-(1-methylcyclopentyl) | 83 | C27H32Cl2N2O5 | 535.1766 | 535.1750 |
| 251 | 148 | acetamidoethyl-(1-methylcyclopentyl) | 66 | C25H29Cl2N3O3 | 534.1562 | 534.1577 |
| 252 | 147 | aminoethyl-(1-methylcyclopentyl) | 30 | C24H27Cl2N3O4 | 492.1458 | 492.1460 |
| 253 | 204 | dimethylaminoethyl-(1-methylcyclopentyl) | 53 | C26H31Cl2N3O4 | 520.1770 | 520.1756 |
| 254 | 252 | Boc-aminoethyl-(1-methylcyclopentyl) | 42 | C29H35Cl2N3O6 | 614.1801 (M + Na) | 614.1786 (M + Na) |
| 255 | 248 | hydroxypropyl-(1-methylcyclopentyl) | 67 | C26H30Cl2N2O5 | 521.1610 | 521.1598 |
| 256 | 247 | morpholinoethyl-(1-methylcyclopentyl) | 9 | C28H33Cl2N3O5 | 562.1875 | 562.1880 |

-continued

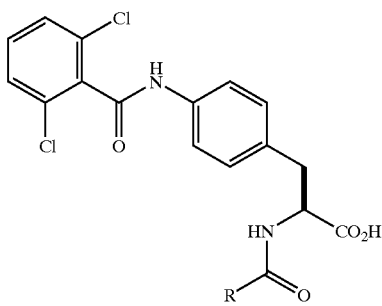

| Example | Starting Material from Example | R | Yield % | Formula | HRMS1 calcd. | found |
|---|---|---|---|---|---|---|
| 257 | 205 | CH3O-C6H4-C(O)NH-CH2CH2-C(CH3)(cyclopentyl) | 60 | C32H33Cl2N3O6 | 648.1644 (M + Na) | 648.1649 (M + Na) |
| 258 | 206 | 3-CF3-C6H4-C(O)NH-CH2CH2-C(CH3)(cyclopentyl) | 55 | C32H30Cl2F3N3O5 | 686.1413 (M + Na) | 686.1441 (M + Na) |
| 259 | 212 | CH3-C(O)NH-(CH2)4-C(CH3)(cyclopentyl) | 52 | C28H33Cl2N3O5 | 562.1875 | 562.1858 |
| 260 | 236 | H3C-S-CH2CH2CH2-C(CH3)(cyclopentyl) | 81 | C27H32N2O4ClS | 551.1538 | 551.1528 |
| 261 | 210 | N3-(CH2)3-C(CH3)(cyclopentyl) | 73 | C26H29Cl2N5O4 | 546.1675 | 546.1678 |
| 262 | 237 | NC-(CH2)3-C(CH3)(cyclopentyl) | 73 | C27H29N3O4Cl2 | 530.1613 | 530.1609 |
| 263 | 238 | H3C-S(O)2-CH2CH2CH2-C(CH3)(cyclopentyl) | 74 | C27H32N2O6Cl2S | 583.1436 | 583.1423 |
| 264 | 239 | CH3-C(O)-CH2CH2-C(CH3)(cyclopentyl) | 50[1] | C27H30N2O5Cl2 | 533.1610 | 533.1590 |

-continued

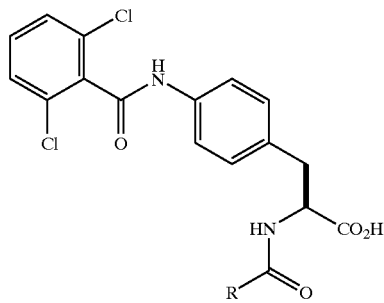

| Example | Starting Material from Example | R | Yield % | Formula | HRMS1 calcd. | found |
|---|---|---|---|---|---|---|
| 265 | 240 | CH3-S-CH2CH2CH2-C(CH3)(cyclopentyl) | 67 | C26H30N2O4Cl2S | 537.1381 | 537.1355 |
| 266 | 241 | F2C=CH-CH2-C(CH3)(cyclopentyl) | 73 | C25H24N2O4Cl2F2 | 547.0984 (M + Na) | 547.0979 (M + Na) |
| 267 | 184 | CH3-SO2-CH2CH2CH2-C(CH3)(cyclopentyl) | 27 | C26H30N2O6Cl2S | 569.1272 | 569.1280 |
| 268 | 242 | NC-CH2CH2CH2-C(CH3)(cyclopentyl) | 45 | C26H27N3O4Cl2 | 538.1277 (M + Na) | 538.1275 (M + Na) |
| 269 | 243 | CH3-C(O)-CH2CH2-C(CH3)(cyclopentyl) | 82 | C26H28N2O5Cl2 | 541.1273 (M + Na) | 541.1277 (M + Na) |
| 270 | 215 | CH3CH2CH2CH2-C(CH3)(cyclopentyl) | 69 | C26H30Cl2N2O4 | 505.1661 | 505.1674 |
| 271 | 244 | CH2=CH-CH2CH2-C(CH3)(cyclopentyl) | 83 | C26H28Cl2N2O4 | 503.1505 | 503.1516 |
| 272 | 245 | NC-CH2-C(CH3)(cyclopentyl) | 51 | C24H23Cl2N3O4 | 488.1144 | 488.1150 |
| 273 | 246 | tetrazolyl-Na-CH2-C(CH3)(cyclopentyl) | 44 | C24H22Cl2N6NaO4 | 575.0954 | 575.0949 |

-continued

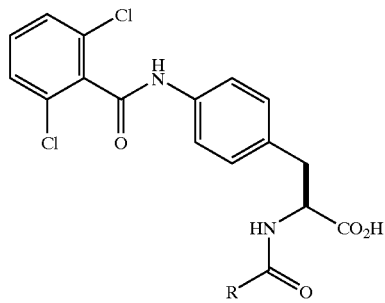

| Example | Starting Material from Example | R | Yield % | Formula | HRMS1 calcd. | found |
|---|---|---|---|---|---|---|
| 274 | 185 | CH₃-S(=O)-CH₂CH₂CH₂-[1-methylcyclopentyl] | 65 | C26H30N2O5Cl2S | 553.1329 | 553.1330 |

M + H ion unless otherwise indicated

Example 275

N-[[1-(3-(Acetylamino)propyl]cyclopenyl]carbonyl]-4-[[(2,6-dichlorophenyl)-carbonyl]amino]-L-phenylalanine methyl ester was prepared in 50% yield from N-[[1-(3-(azidopropyl)cyclopenyl]carbonyl]-4-[[(2,6-dichlorophenyl)carbonyl]amino]-L-phenylalanine methyl ester using the general procedure described in examples 211 and 212.

Example 276

N-[[1-(3-(Acetylamino)propyl]cyclopenyl]carbonyl]-4-[[(2,6-dichlorophenyl)-carbonyl]amino]-L-phenylalanine was prepared from N-[[1-(3-(Acetylamino) propyl]-cyclopenyl]carbonyl]-4-[[(2,6-dichlorophenyl)carbonyl] amino]-L-phenylalanine methyl ester by hydrolysis using the general procedure described in example 47 to give a 70% yield. HR MS (C27H31Cl2N3O5): Obs mass, 570.1533. Calcd mass, 570.1539 (M+Na).

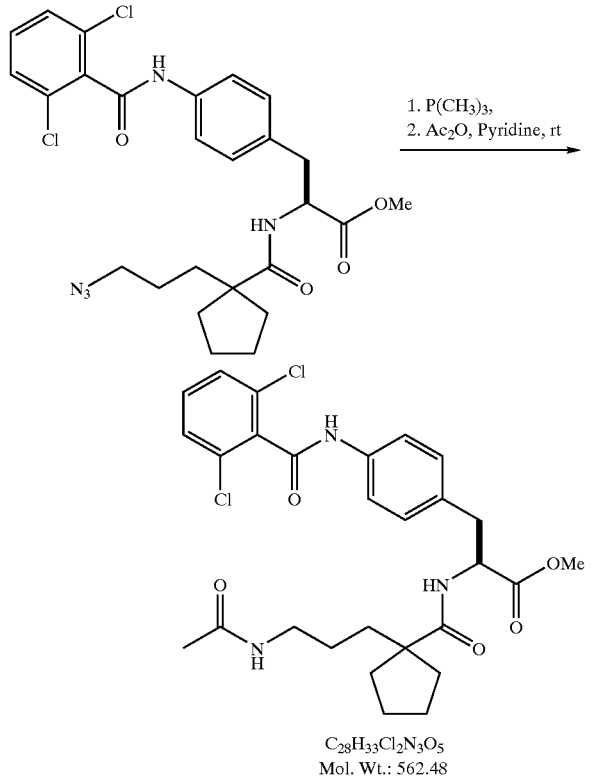

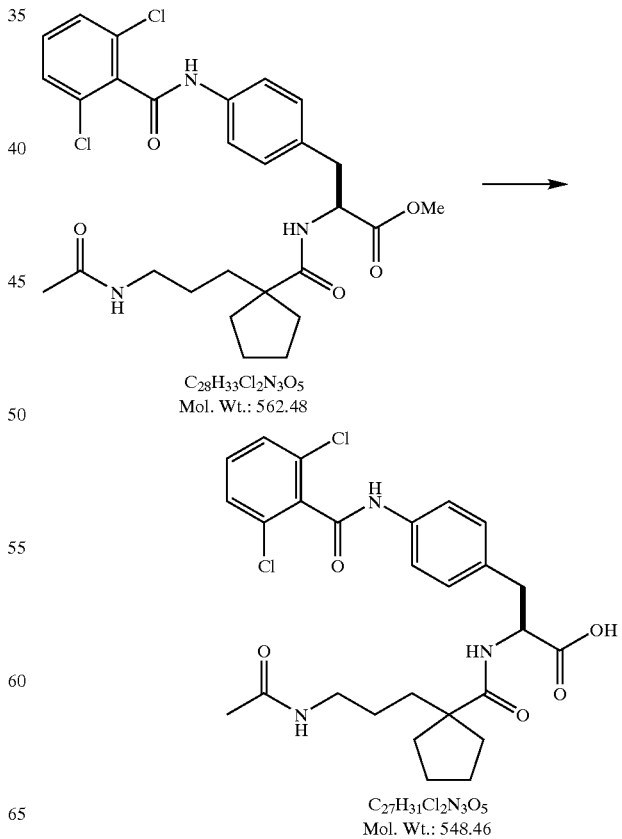

Example 277

General method for the preparation of morpholinoethyl esters from 4-(substituted)-N-acyl-L-phenylalanine derivatives.

To a solution of a 4-(substituted)-N-acyl-L-phenylalanine (0.5 mmol) and 2-morpholinoethanol (0.131 g, 1.0 mmol) in THF (5 mL) was added diisopropylcarbodimide (94.6 mg, 0.75 mmol) and 4-dimethylaminopyridine (30.5 mg, 0.25 mmol) at room temperature. The resulting mixture was stirred at room temperature until time TLC analysis of the reaction mixture indicated the absence of acid, typically 15 h. Then, the mixture was diluted with water (50 mL) and the THF was removed under vaccum and the residue was extracted with dichloromethane (3×25 mL). The combined extracts were washed with water (2×50 mL), brine solution (50 mL) and dried over $MgSO_4$. Filtration of the drying agent and concentration of the solvent gave a white residue which was purified by silica gel column chromatography eluting with dichloromethane-ethyl acetate mixtures to obtain the target product.

Examples 278–356

Procedure for the preparation of 4-[(4R)-3-acyl-5-oxo-2-substituted-4-substituted-1-imidazolidinyl]-N-[[1-[2-(acetylamino)ethyl]cyclopentyl]carbonyl]-L-phenylalanines Step 1.

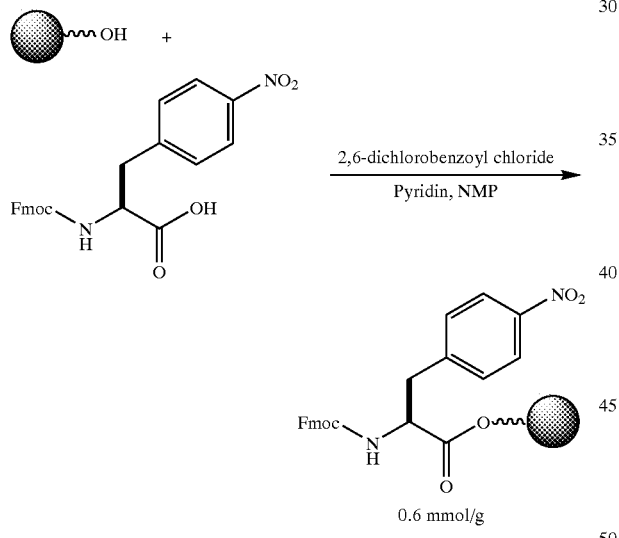

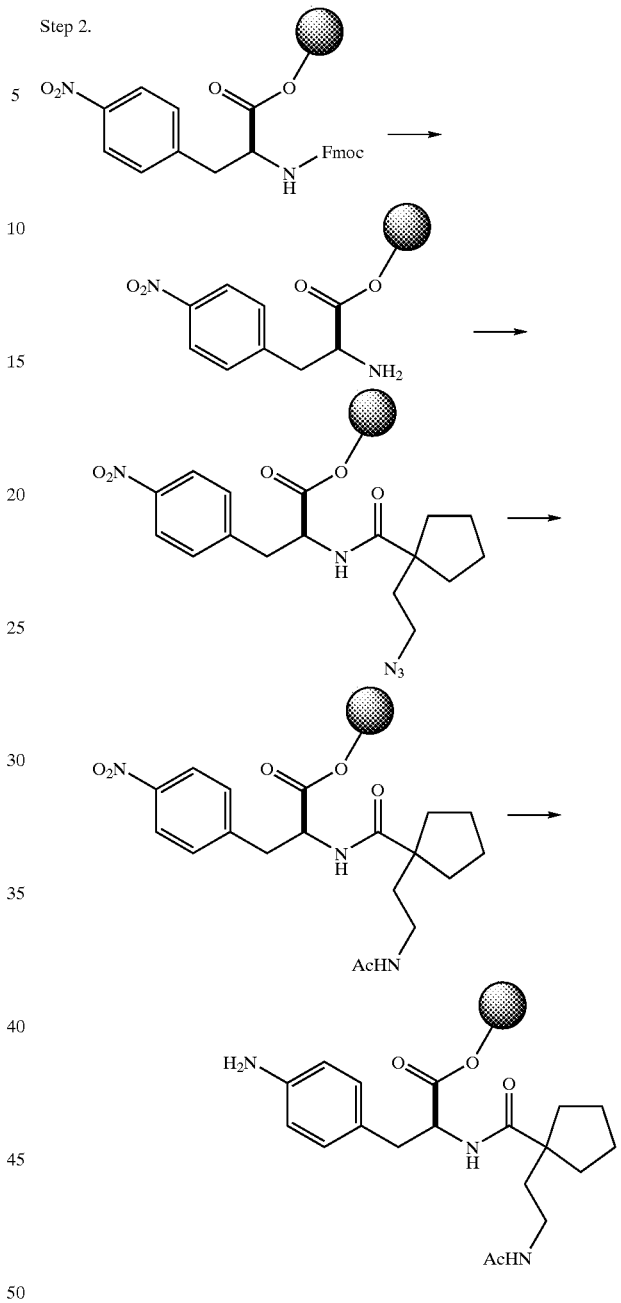

A 250 mL flask was charged with 4-nitro-N-Fmoc-L-phenylalanine (20.7 g, 47.8 mmol) and NMP (30 mL). The mixture was warmed up to accelerate dissolution. After it was cooled to room temperature, the mixture was treated with 2,6-dichlorobenzoyl chloride (20 g, 95.6 mmol) and pyridine (12 mL, 143.4 mmol). This mixture was shaken for 5 min and was added to a suspension of Wang resin (21.7 g, 1.1 mmol/g) in NMP (60 mL). The mixture was then shaken at room temperature overnight. After removal of solvent by filtration, the resin was washed with DMF (4×60 mL), MeOH (4×60 mL), DMF (4×60 mL) and finally dichloromethane (4×60 mL). The resin was then dried under vacuum at room temperature overnight to give 34.27 g of resin with loading of 0.668 mmol/g determined by the UV method (Barry Bunin, *The Combinatorial Index*, p. 219 (Academic Press, 1998)).

The above resin (25.5 g) was treated with 160 mL of 20% piperidine in NMP and shaken for 15 min and was filtered. This process was then repeated 2 times. The resin was then washed with DMF (4×100 mL), MeOH (4×100 mL), DMF (4×100 mL) and finally dichloromethane (4×100 mL). The resin was then dried under vacuum at room temperature overnight to give 22 g of resin.

A portion of this free amine resin (13 g) was suspended in 80 mL of NMP and was treated with 1-1-(2-azidoethyl)cyclopentane carboxylic acid (4.8 g, 26.05 mmol) followed by DIEA (15 mL) and BOP reagent (15.4 g, 34.2 mmol). The reaction was shaken at room temperature overnight. After filtration, the resin was washed with DMF (4×60 mL), MeOH (4×60 mL), DMF (4×60 mL) and finally dichloromethane (4×60 mL). The resin was then dried under vacuum at room temperature overnight to give azide resin. This resin was reduced by treatement with trimethylphosphine (1.0 M in THF, 30 mL) in 20 mL of THF at room temperature for 4 hr and then was treated with water (3 mL) for 30 min. After filtration, the resin was washed with DMF (4×60 mL), MeOH (4×60 mL), DMF (4×60 mL) and finally dichloromethane (4×60 mL). The resin was then dried under vacuum at room temperature overnight to give free aminoethyl resin (13.19 g).

A portion of the above resin (6.3 g) was suspended in dichloromethane (40 mL) and was treated with acetic anhydride (2 mL, 21 mmol) and DIEA (3.6 mL, 21 mmol). The above mixtrue was shaken at room temperature overnight. After filtration, the resin was washed with DMF (4×40 mL), MeOH (4×40 mL), DMF (4×40 mL) and finally dichloromethane (4×40 mL). The resin was then dried under vacuum at room temperature overnight to give acetamide resin (6.27 g). A small sample of resin was collected and treated with 50% TFA in dichloromethane to give the cleavage product, N-[[1-[2-(acetylamino)ethyl]cyclopentyl]carbonyl]-4-nitro-L-phenylalanine. LS MS (M−H, m/z: 391). The remainder of the resin was then treated with SnCl2 (2M in DMF, 40 mL) at room temperature overnight. After filtration, the resin was washed with DMF (4×40 mL), MeOH (4×40 mL), DMF (4×40 mL) and finally dichloromethane (4×40 mL). It was then dried under vacuum at room temperature overnight to give 4-amino-N-[[1-[2-(acetylamino)ethyl]cyclopentyl]carbonyl]-L-phenylalanine on resin (6.1 g).

Step 3. Combinatorial Library Synthesis

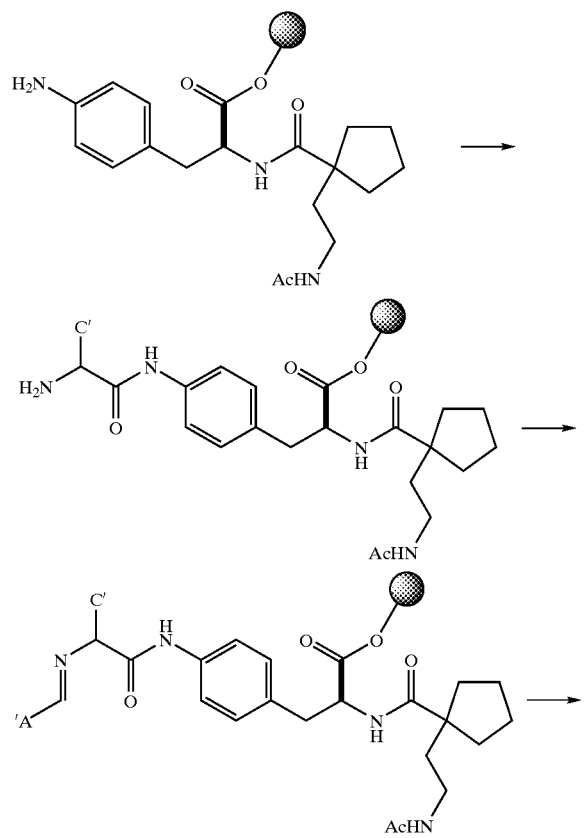

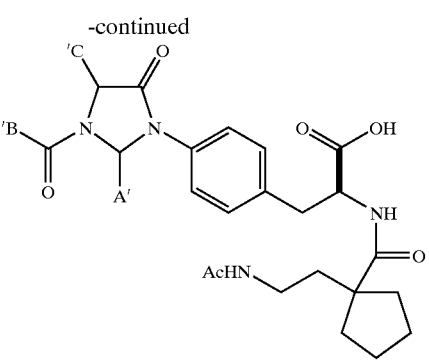

The above free 4-amino-N-[[1-[2-(acetylamino)ethyl]cyclopentyl]carbonyl]-L-phenylalanine on resin was split into 5 reaction vessels. To each vessel was added, in parallel, 8 mL of DMF followed by a Fmoc-D-amino acid (selected from: Fmoc-D-phenylalanine (C1), Fmoc-D-4-chlorophenylalanine (C2), Fmoc-D-3-pyridinylalanine (C3), Fmoc-D-4-methoxyphenylalanine (C4) and Fmoc-D-alanine (C5), 2.25 mmol), HBTU (1.4 g, 3.75 mmol) and DIEA (0.75 mL). The above mixture was shaken at room temperature overnight. The resin from each vessel was filtered, washed with DMF (4×20 mL), MeOH (4×20 mL), DMF (4×20 mL) and finally dichloromethane (4×20 mL). These resins were then individually dried under vacuum at room temperature overnight to give 5 individual Fmoc-D-amino acid containing resins. Each of the five individual batches of resin obtained above was treated in parallel with 10 mL of 20% piperidine in NMP under shaking for 15 min and was filtered. This process was then repeated two times to give the following five derivatives after individual drying: N-[[1-[2-(acetylamino)ethyl]cyclopentyl]carbonyl]-4-[[(2R)-2-amino-1-oxo-3-phenylpropyl]amino]-L-phenylalanine on Wang resin, N-[[1-[2-(acetylamino)ethyl]cyclopentyl]carbonyl]-4-[[(2R)-2-amino-3-(4-chloropheny)-1-oxopropyl]amino]-L-phenylalanine on Wang resin, N-[[1-[2-(acetylamino)ethyl]cyclopentyl]carbonyl]-4-[[(2R)-2-amino-1-oxo-3-(3-pyridinyl)propyl]amino]-L-phenylalanine on Wang resin, N-[[1-[2-(acetylamino)ethyl]-cyclo-pentyl]carbonyl]-4-[[(2R)-2-amino-3-(4-methoxyphenyl)-1-oxopropyl]amino]-L-phenylalanine on Wang resin, and N-[[1-[2-(acetylamino)ethyl]cyclopentyl]carbonyl]-4-[((2R)-2-amino-1-oxopropyl)amino]-L-phenylalanine on Wang resin.

A library of imidazolidin-4-ones was prepared as discrete compounds using the IRORI AccuTag-100 Combinatorial Chemistry System (IRORI AccuTag-100 Combinatorial Chemistry System The technique for labeling a reaction vessel and use of the reaction vessels referred to herein as Microkans is described in the User's Guide, 1996, IRORI, 11025 North Torrey Pines Road, La Jolla, Calif. 92037). IRORI is registered trademark of IRORI. IRORI, AccuTag, Microkan and Synthesis Manager are trademarks of IRORI.

Each of the five resin derivatives was split into 16 Microkans containing radio frequency tags to give a total of 80 Microkan reaction vessels. Using the Synthesis Manager to read the radio frequency tags in each, these were then sorted into 4 groups of 20 so that each group had 4 Microkans containing each of the five resin bound D-aminoacids prepared above. Each group of 20 microkans was individually placed in a reaction vessel containing a mixture of dry solvent (THF/methyl orthoformate=1/1, 80 mL) and one of four aldehydes (benzaldehyde (A1); 4-pyridylaldehyde (A2), 4-chlorobenzaldehyde (A3) or phenylpropionaldehyde (A4) (20×1.33 mmol). The above mixtures were shaken at room temperature for 3 days to form imine intermediates. After removal of the solvent by decantation, the groups of Microkans were individually washed with dry THF (2×20 mL).

The resulting 80 Microkans were then sorted into 4 groups of 20 with each group incorporating one example of each of the D-amino acids (C1to C5) combined with each of the four aldehydes (A1 to A4) according to the table shown below:

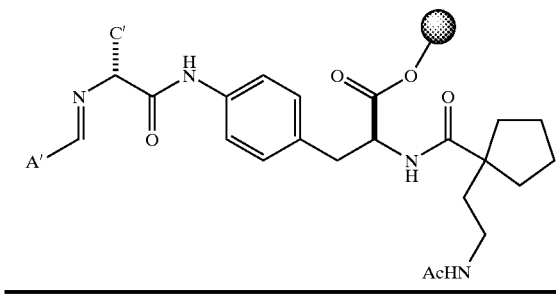

| C'-1/A'-1 | C'-2/A'-1 | C'-3/A'-1 | C'-4/A'-1 | C'-5/A'-1 |
| C'-1/A'-2 | C'-2/A'-2 | C'-3/A'-2 | C'-4/A'-2 | C'-5/A'-2 |
| C'-1/A'-3 | C'-2/A'-3 | C'-3/A'-3 | C'-4/A'-3 | C'-5/A'-3 |
| C'-1/A'-4 | C'-2/A'-4 | C'-3/A'-4 | C'-4/A'-4 | C'-5/A'-4 |

A'-1 = phenyl
A'-2 = 4-pyridyl
A'-3 = 4-chlorophenyl
A'-4 = 2-phenylethyl
C'-5 = methyl
C'-1 = benzyl
C'-2 = 4-chlorobenzyl
C'-3 = 3-pyridinylmethyl
C'-4 = 4-methoxybenzyl Each group of 20 Microkans was individually placed in a reaction vessel containing dry solvent (THF/methyl orthoformate=1/1, 10 mL). To the first reaction vessel was then added acetic anhydride (B1) (5.5 mmol) and the resulting mixture was shaken at 90° C. for 4 hr. The remaining three reaction vessels were individually treated with an anhydride: butryric anhydride (B2), succinic anhdride (B3) and phenoxyacetic anhyride (B4) and subjected to the same reaction conditions in parallel. After filtration, each of the four groups of Microkans was individually washed with DMF (4×40 mL), MeOH (4×40 mL), DMF (4×40 mL) and finally dichloromethane (4×40 mL). The Microkans were then sorted into separate vials using the Synthesis Manager to identify each by means of the individual radio freqency tags. Each vial was treated with cleavaging reagent 50% TFA/dichloromethane (2.5 mL). The vials were shaken for 2 hr at room temperature and the resulting mixtures were filtered. The filtrate from each reaction was concentrated to dryness to give the crude product which was then treated with ether under shaking at room temperature for 20 min. The suspension was allowed to stand at room temperature for 15–30 min and the ether was removed. The ether wash was repeated and residues were dissolved in MeCN/H2O (2/1). A portion of this solution was set aside for analysis and the balance was freeze-dried to give crude products. The analytical samples were analyzed by LCMS using a Micromass platform II with a 5 min linear gradent (5% MeCN in water to 95% MeCN in water contain 0.01% of TFA) to determine purity while recording the MS spectra to verify the identity of the major peak. The subset of this library derived from 4-pyridylaldehide (A-2) was removed from the collection because of low purity scores. The remaining 60 members were purified by reversed-phase HPLC to give a library of imidazolidinones with purity greater than 90%. During the separation, some of the diastereomers could be separated to give the diastereomers at the 2-position of the imidazolidine ring designated diastereomers 1 and 2(based upon the order of elution) while others were assayed as mixtures of diastereomers. The molecular weights of these purified products were comfirmed by ESMS (M–H, M, or M+H) as shown in table below.

| Example # | MOLSTRUCTURE | MS | MW | LOT # |
|---|---|---|---|---|
| 278 | | 667.0 (M – H) | 668.79 | 30073-72A |

-continued
| Example # | MOLSTRUCTURE | MS | MW | LOT # |
|---|---|---|---|---|
| | Diastereomer 1 | | | |
| 279 | 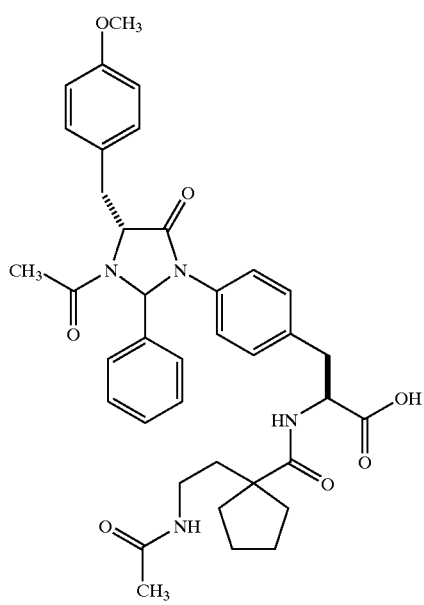 | 667.0 (M − H) | 668.79 | 30073-72B |
| | Diastereomer 2 | | | |
| 280 | 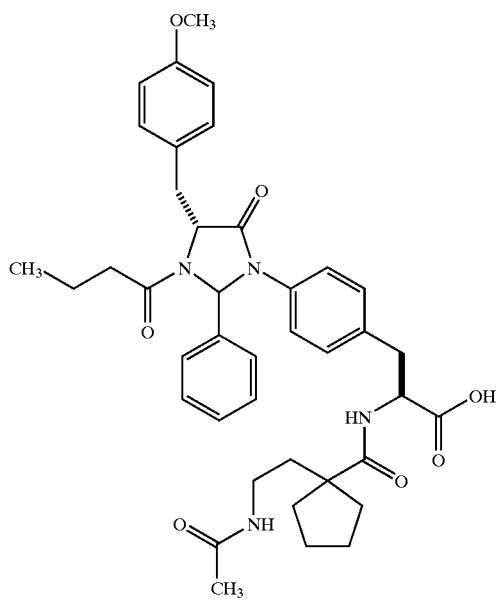 | 695.0 (M − H) | 696.85 | 30073-73A |

-continued
| Example # | MOLSTRUCTURE | MS | MW | LOT # |
|---|---|---|---|---|
| | Diastereomer 1 | | | |
| 281 | 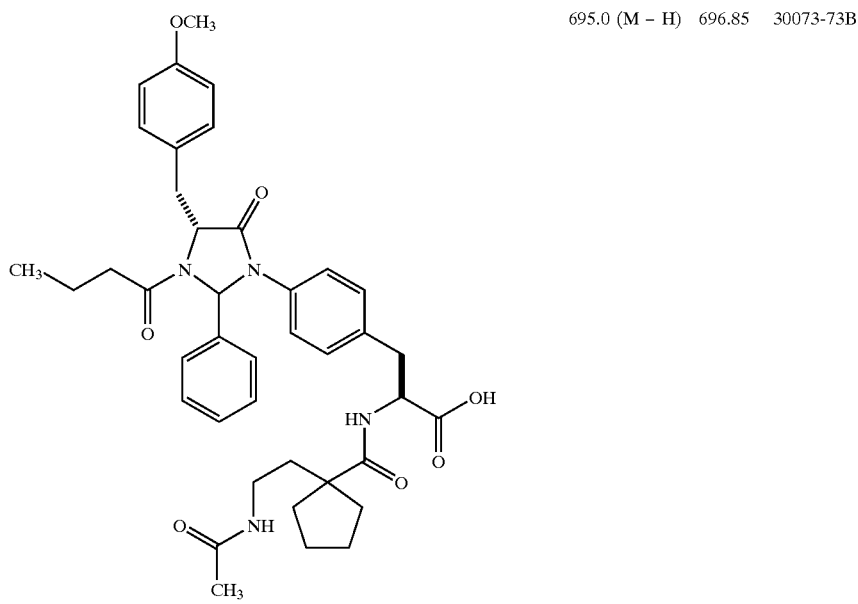 | 695.0 (M − H) | 696.85 | 30073-73B |
| | Diastereomer 2 | | | |
| 282 | 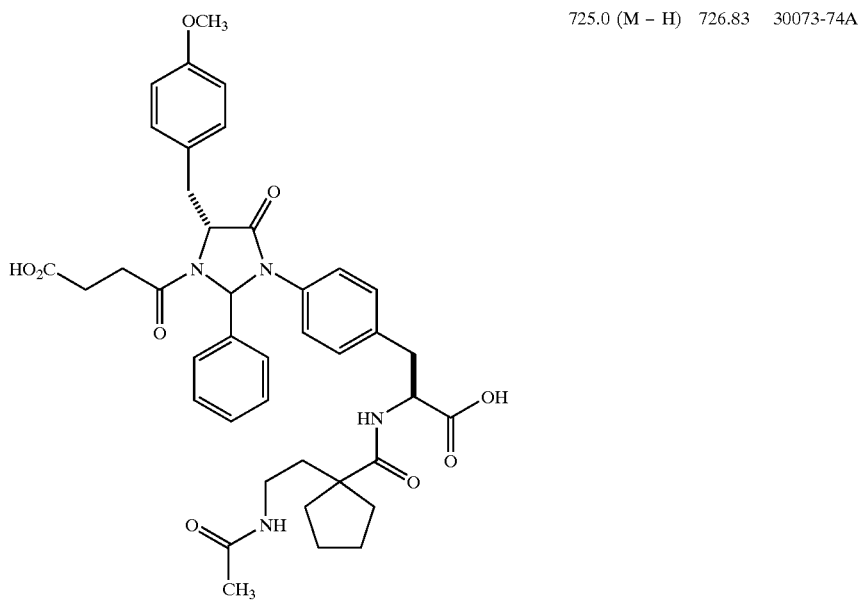 | 725.0 (M − H) | 726.83 | 30073-74A |

| Example # | MOLSTRUCTURE | MS | MW | LOT # |
|---|---|---|---|---|
Diastereomer 1
283 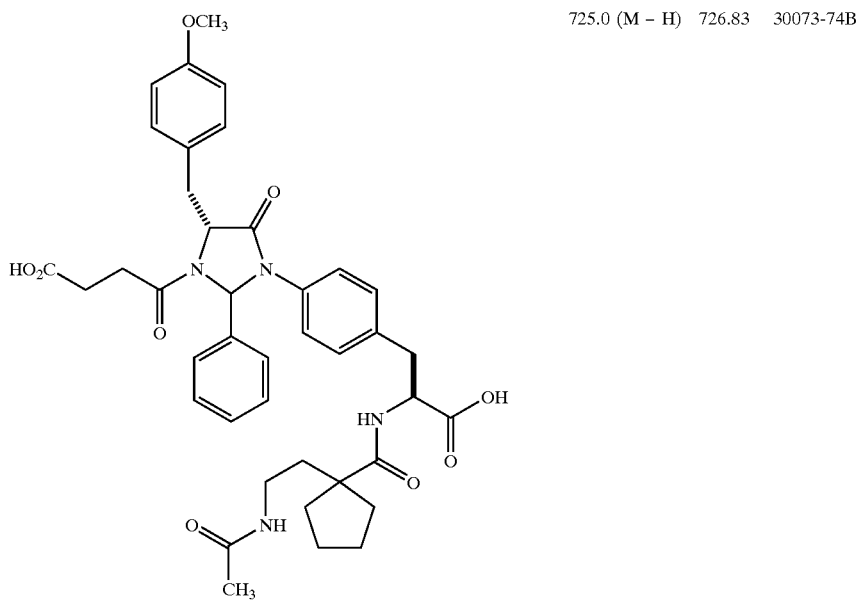 725.0 (M − H) 726.83 30073-74B
Diastereomer 2
284 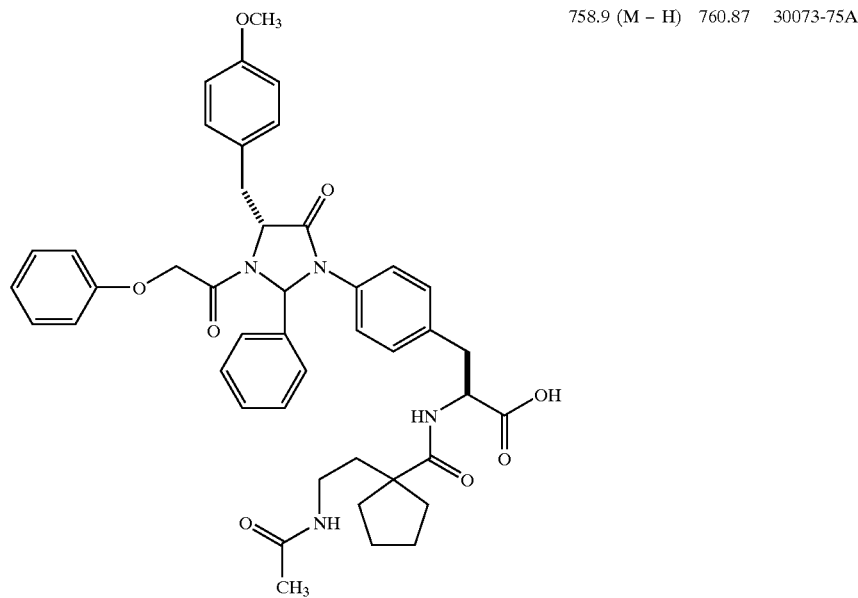 758.9 (M − H) 760.87 30073-75A

| Example # | MOLSTRUCTURE | MS | MW | LOT # |
|---|---|---|---|---|
| | Diastereomer 1 | | | |
| 285 | 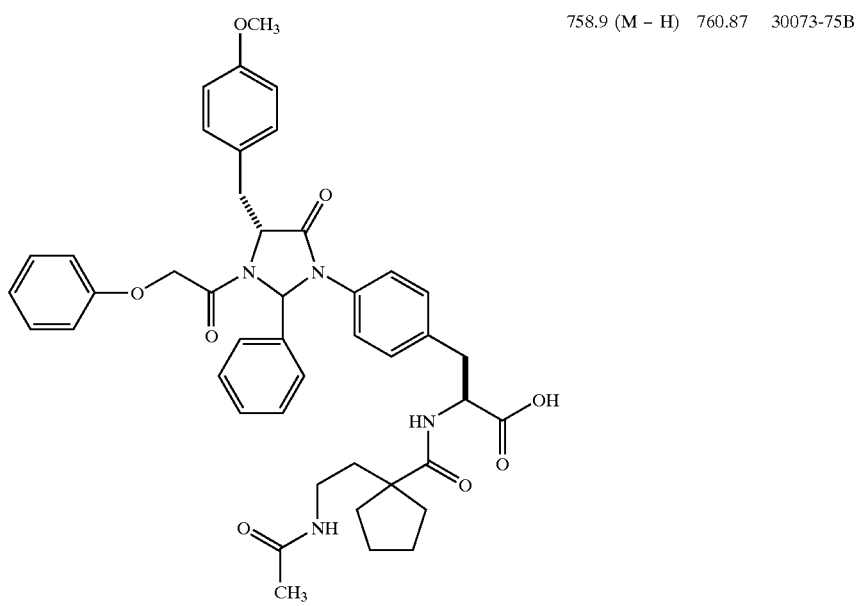 | 758.9 (M − H) | 760.87 | 30073-75B |
| | Diastereomer 2 | | | |
| 286 | 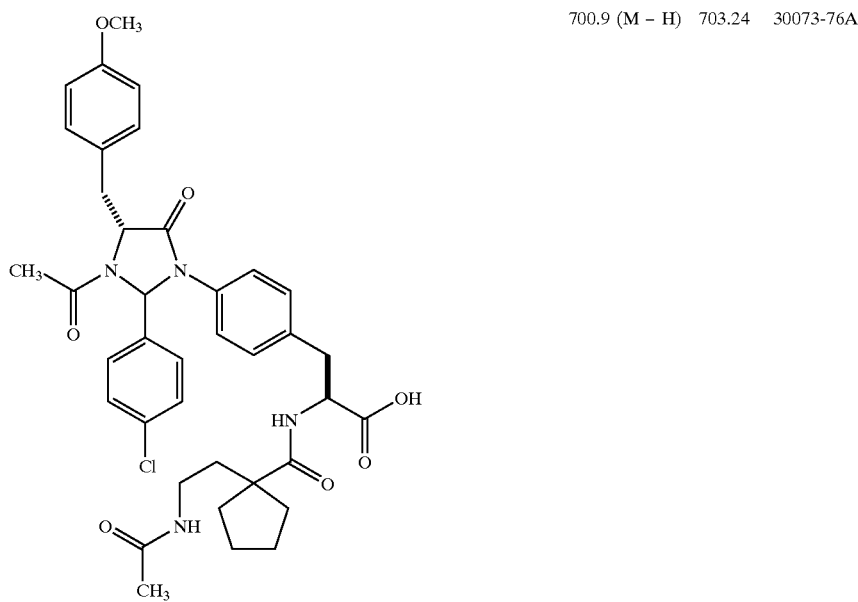 | 700.9 (M − H) | 703.24 | 30073-76A |

| Example # | MOLSTRUCTURE | MS | MW | LOT # |
|---|---|---|---|---|
| | Diastereomer 1 | | | |
| 287 | 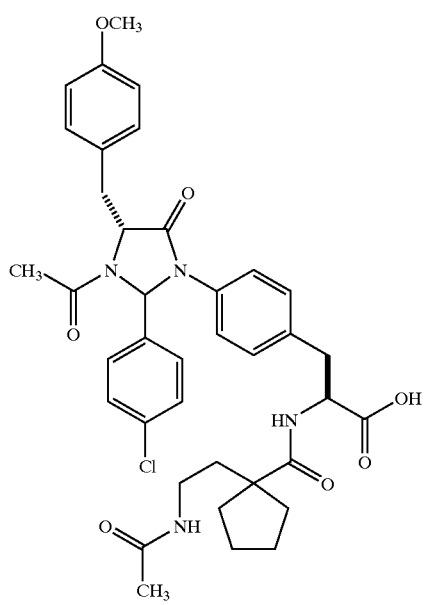 | 700.9 (M − H) | 703.24 | 30073-76B |
| | Diastereomer 2 | | | |
| 288 | 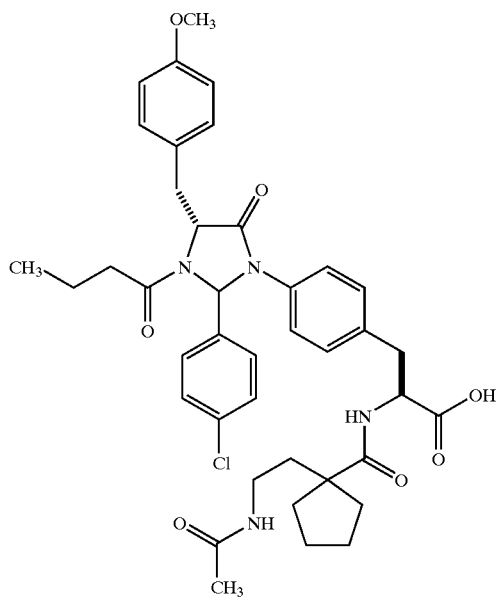 | 729.0 (M − H) | 731.30 | 30073-77A |

| Example # | MOLSTRUCTURE | MS | MW | LOT # |
|---|---|---|---|---|
| | Diastereomer 1 | | | |
| 289 | 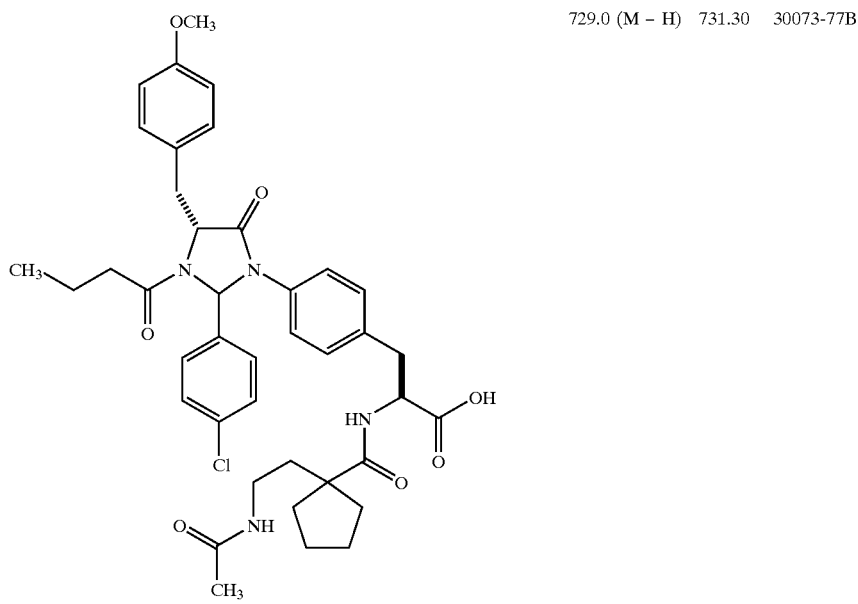 | 729.0 (M − H) | 731.30 | 30073-77B |
| | Diastereomer 2 | | | |
| 290 | 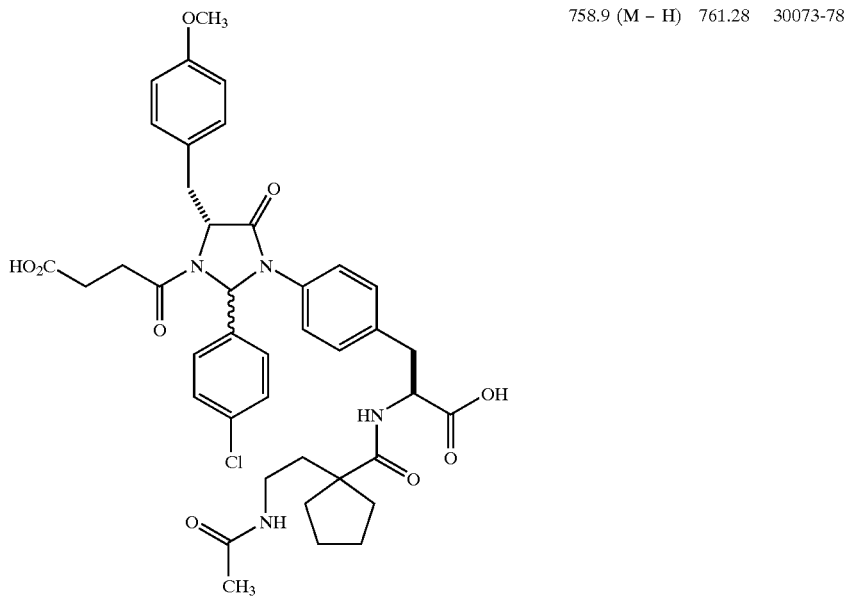 | 758.9 (M − H) | 761.28 | 30073-78 |

-continued
| Example # | MOLSTRUCTURE | MS | MW | LOT # |
|---|---|---|---|---|
| | Diastereomeric Mixture | | | |
| 291 | 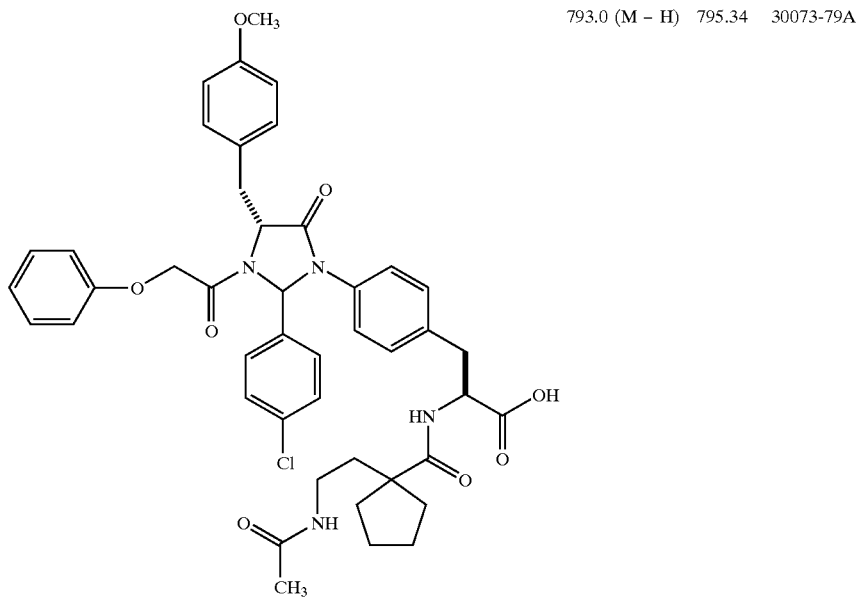 | 793.0 (M − H) | 795.34 | 30073-79A |
| | Diastereomer 1 | | | |
| 292 | 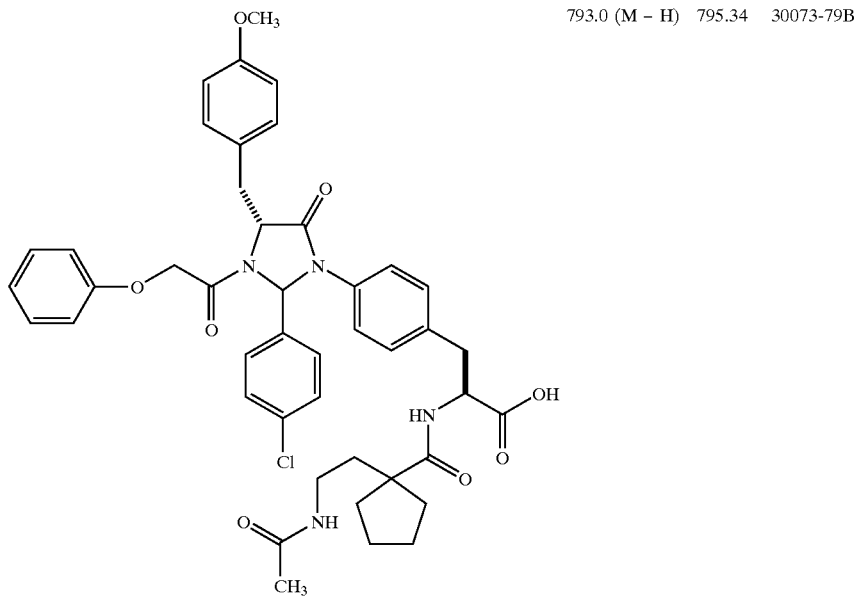 | 793.0 (M − H) | 795.34 | 30073-79B |

| Example # | MOLSTRUCTURE | MS | MW | LOT # |
|---|---|---|---|---|
| | Diastereomer 2 | | | |
| 293 | 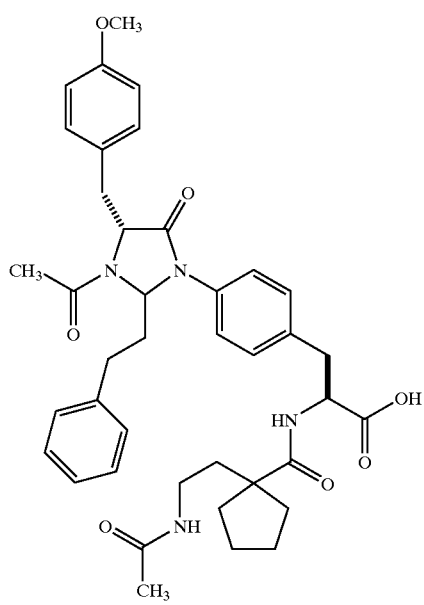 | 695.0 (M − H) | 696.85 | 30073-80A |
| | Diastereomer 1 | | | |
| 294 | 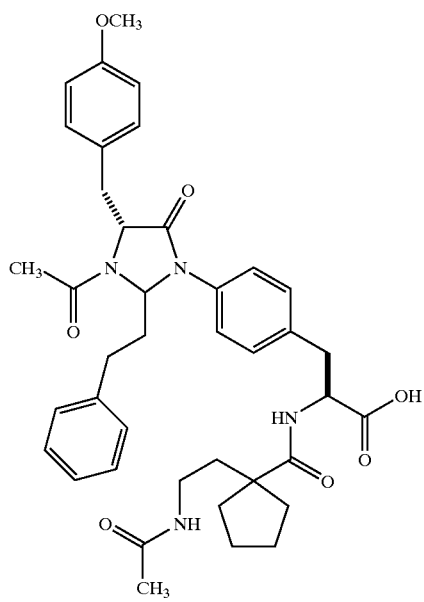 | 695.0 (M − H) | 696.85 | 30073-80B |

| Example # | MOLSTRUCTURE | MS | MW | LOT # |
|---|---|---|---|---|
| | Diastereomer 2 | | | |
| 295 | 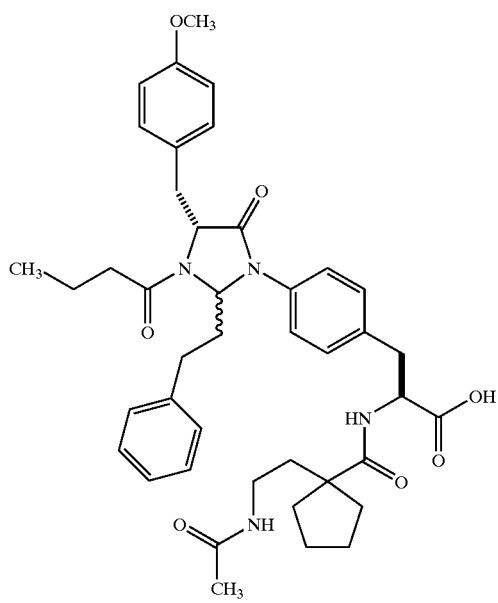 | 723.0 (M − H) | 724.91 | 30073-81 |
| | Diastereomeric Mixture | | | |
| 296 | 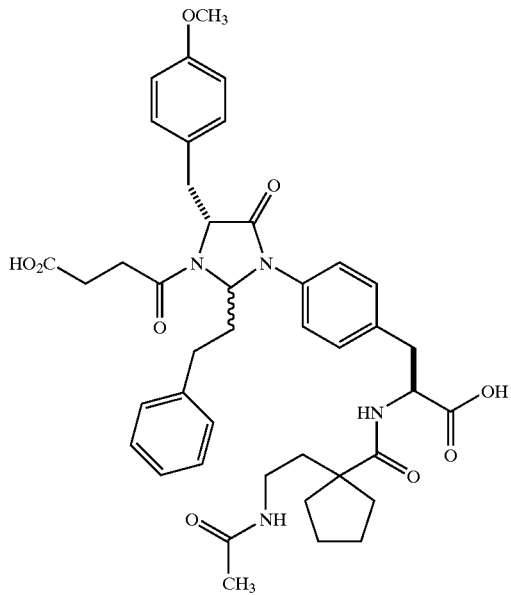 | 753.2 (M − H) | 754.89 | 30073-82 |

| Example # | MOLSTRUCTURE | MS | MW | LOT # |
|---|---|---|---|---|
Diastereomeric Mixture
297 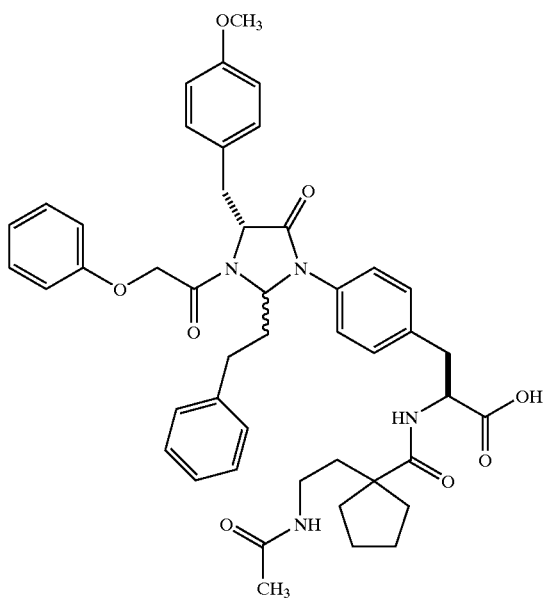 786.9 (M − H)  788.95  30073-83
Diastereomeric Mixture
298 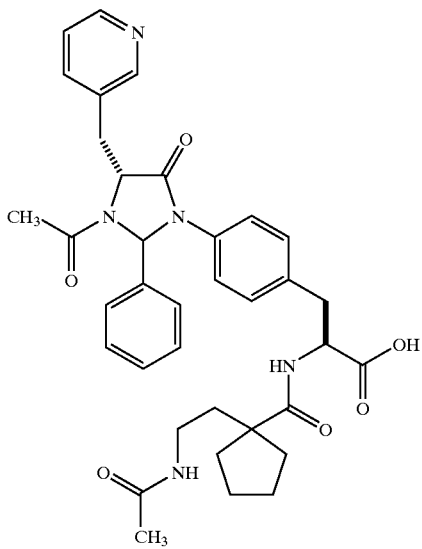 640.0 (M + H)  639.76  30073-84A

| Example # | MOLSTRUCTURE | MS | MW | LOT # |
|---|---|---|---|---|
| | Diastereomer 1 | | | |
| 299 | 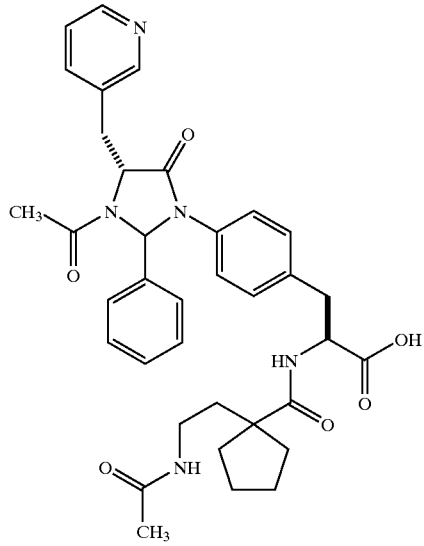 | 640.0 (M + H) | 639.76 | 30073-84B |
| | Diastereomer 2 | | | |
| 300 | 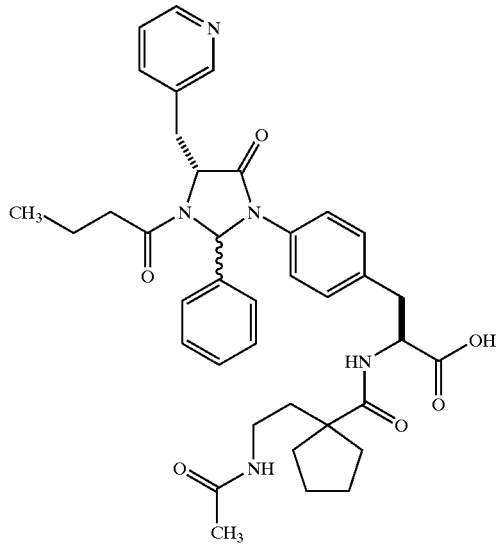 | 666.1 (M − H) | 667.81 | 30073-85 |

| Example # | MOLSTRUCTURE | MS | MW | LOT # |
|---|---|---|---|---|
| | Diastereomeric Mixture | | | |
| 301 | 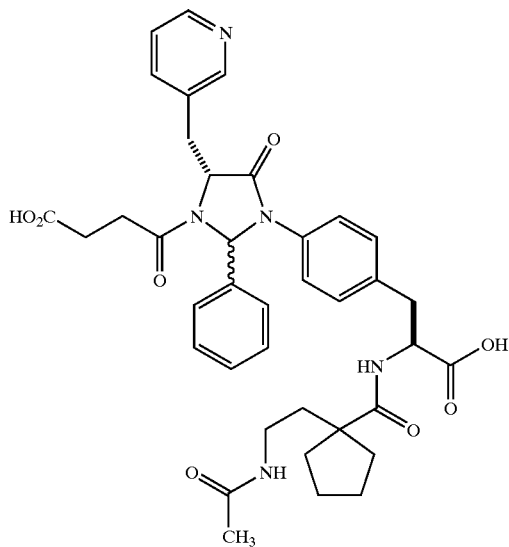 | 696.1 (M − H) | 697.80 | 30073-86 |
| | Diastereomeric Mixture | | | |
| 302 | 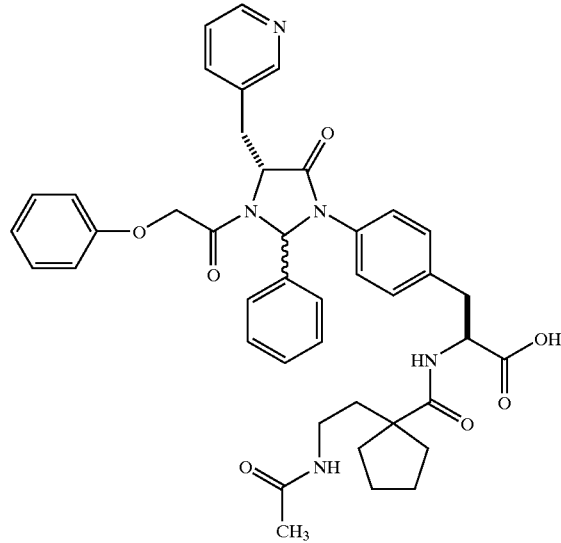 | 729.9 (M − H) | 731.86 | 30073-87 |

| Example # | MOLSTRUCTURE | MS | MW | LOT # |
|---|---|---|---|---|
| | Diastereomeric Mixture | | | |
| 303 | 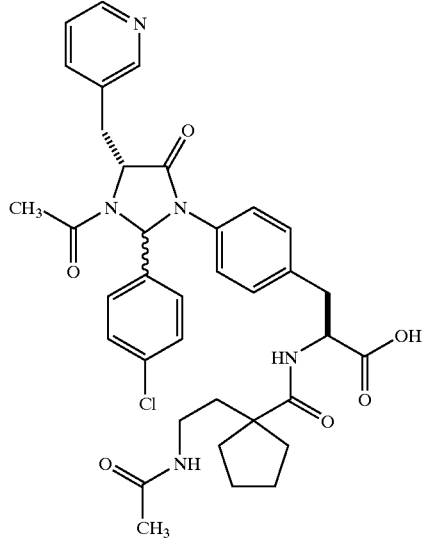 | 671.9 (M − H) | 674.20 | 30073-88 |
| | Diastereomeric Mixture | | | |
| 304 | 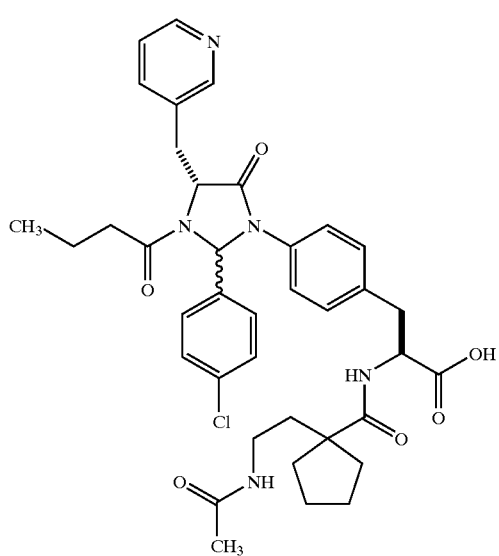 | (M) | 702.26 | 30073-89 |

| Example # | MOLSTRUCTURE | MS | MW | LOT # |
|---|---|---|---|---|
| | Diastereomeric Mixture | | | |
| 305 | 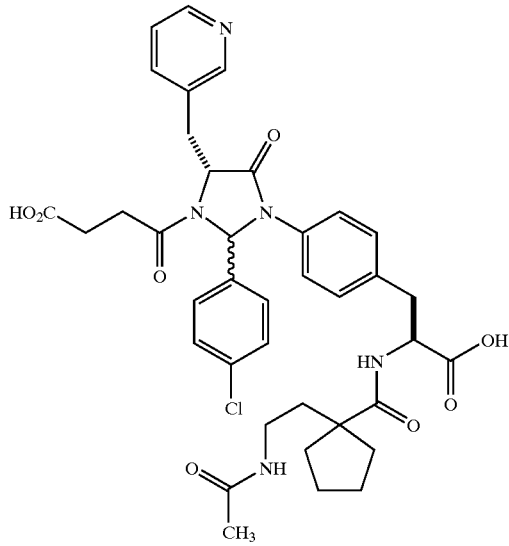 | 731.9 (M) | 732.24 | 30073-90 |
| | Diastereomeric Mixture | | | |
| 306 | 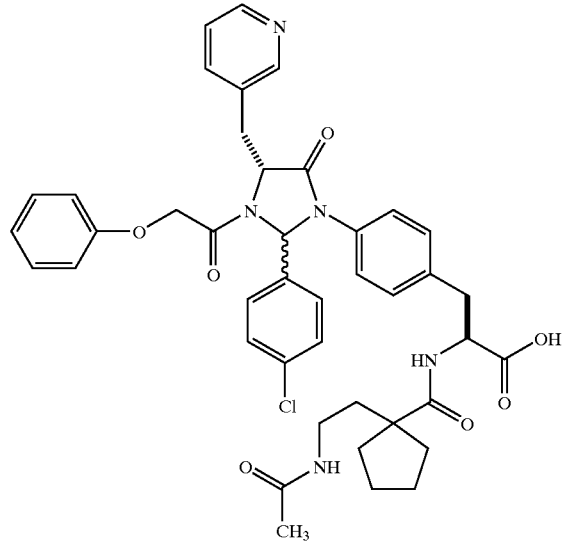 | 764.0 (M − H) | 766.30 | 30073-91 |

| Example # | MOLSTRUCTURE | MS | MW | LOT # |
|---|---|---|---|---|
| | Diastereomeric Mixture | | | |
| 307 | 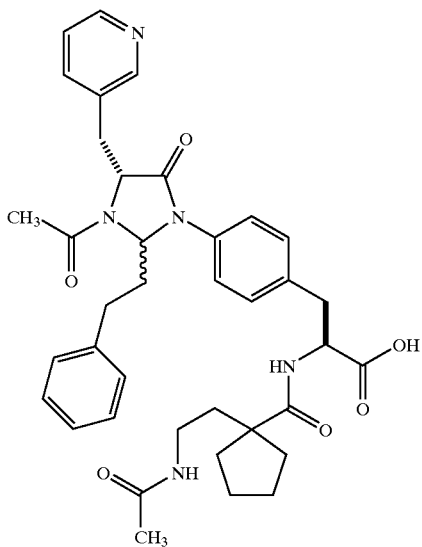 | 668.0 (M + H) | 667.81 | 30073-92 |
| | Diastereomeric Mixture | | | |
| 308 | 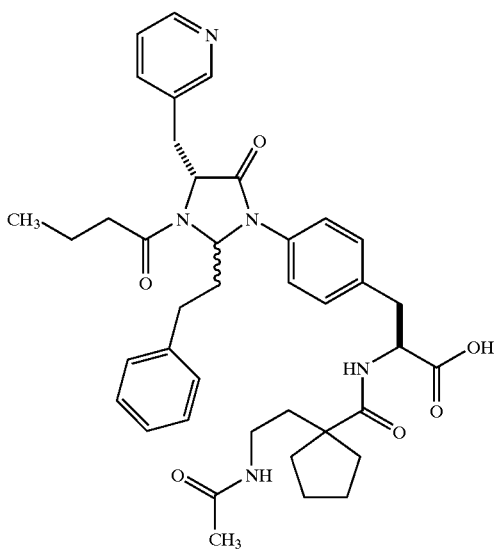 | 696.1 (M + H) | 695.87 | 30073-93 |

| Example # | MOLSTRUCTURE | MS | MW | LOT # |
|---|---|---|---|---|
| | Diastereomeric Mixture | | | |
| 309 | 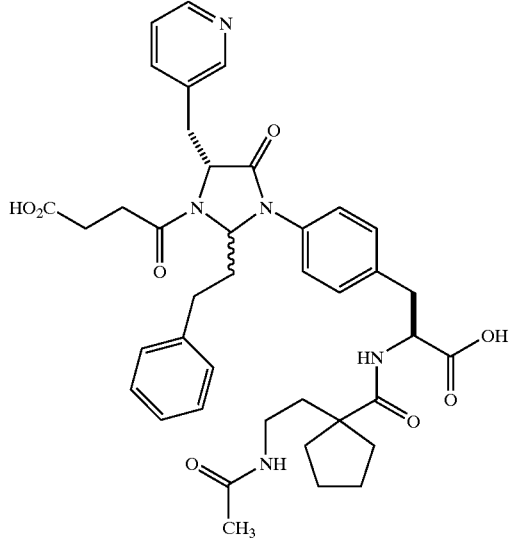 | 726.1 (M + H) | 725.85 | 30073-94 |
| | Diastereomeric Mixture | | | |
| 310 | 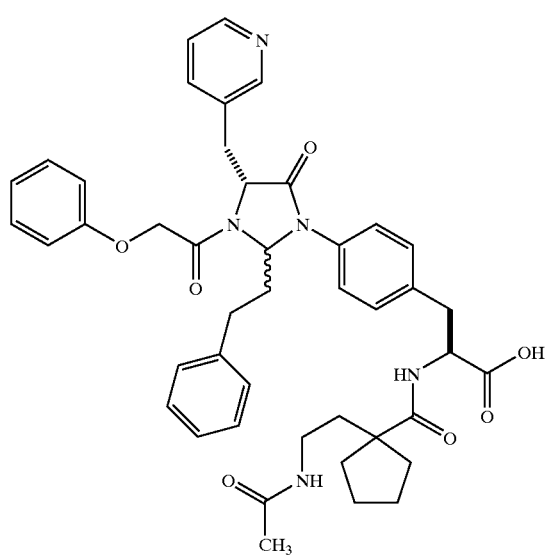 | 760.1 (M + H) | 759.91 | 30073-95 |

-continued
| Example # | MOLSTRUCTURE | MS | MW | LOT # |
|---|---|---|---|---|
| | Diastereomeric Mixture | | | |
| 311 | 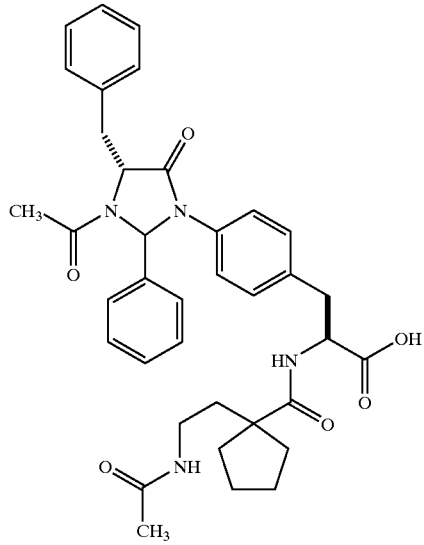 | 639.0 (M + H) | 638.77 | 30073-96A |
| | Diastereomer 1 | | | |
| 312 | 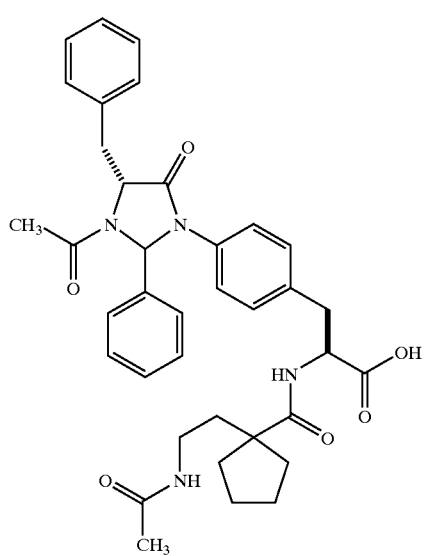 | 639.0 (M + H) | 638.77 | 30073-96B |

| Example # | MOLSTRUCTURE | MS | MW | LOT # |
|---|---|---|---|---|
| | Diastereomer 2 | | | |
| 313 | 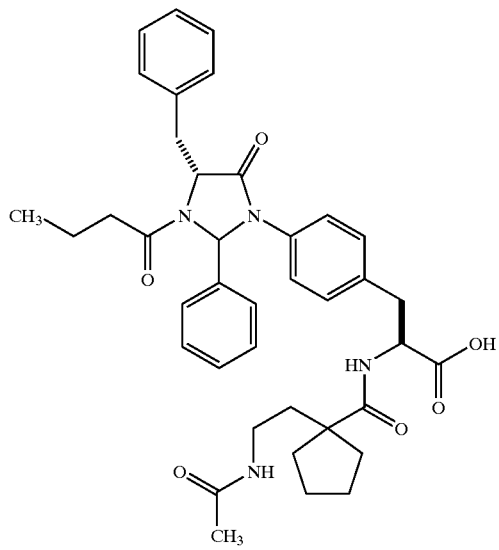 | 665.0 (M − H) | 666.82 | 30073-97A |
| | Diastereomer 1 | | | |
| 314 | 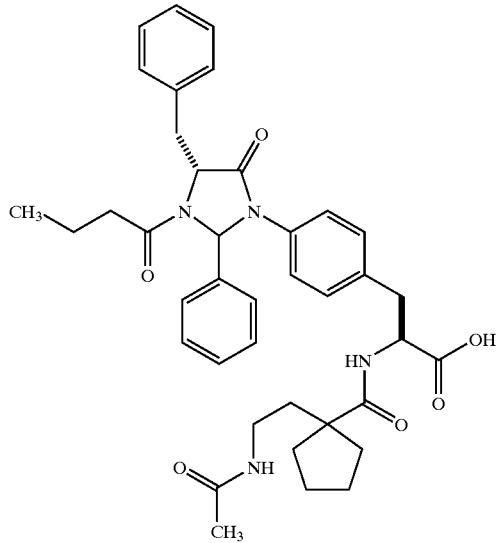 | 667.0 (M + H) | 666.825 | 30073-97B |

| Example # | MOLSTRUCTURE | MS | MW | LOT # |
|---|---|---|---|---|
| | Diastereomer 2 | | | |
| 315 | 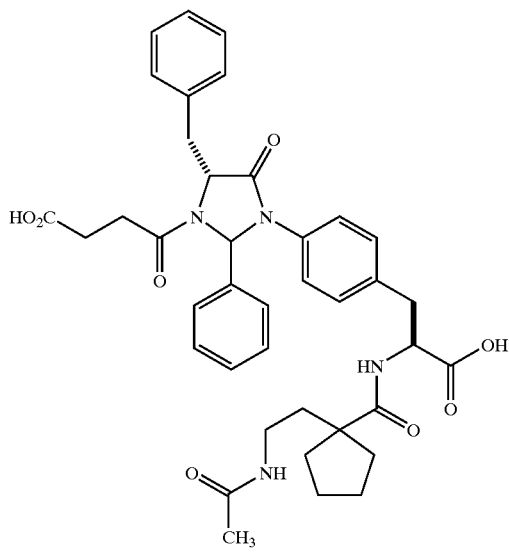 | 695.0 (M − H) | 696.81 | 30073-98A |
| | Diastereomer 1 | | | |
| 316 | 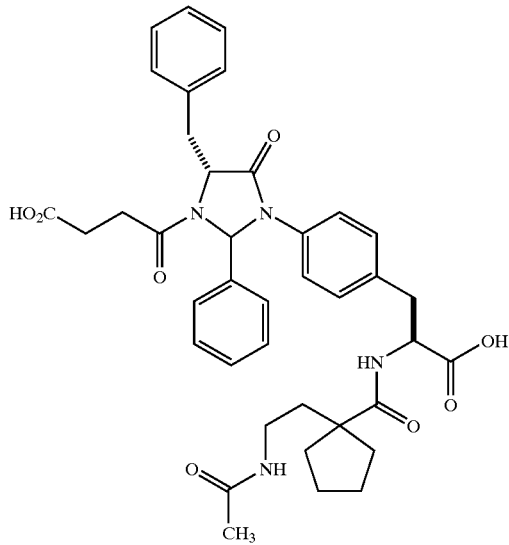 | 695.0 (M − H) | 696.81 | 30073-97B |

| Example # | MOLSTRUCTURE | MS | MW | LOT # |
|---|---|---|---|---|
| | Diastereomer 2 | | | |
| 317 | 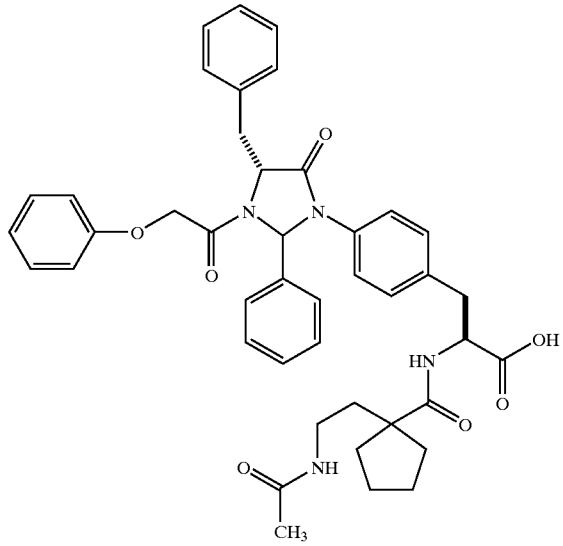 | 729.0 (M − H) | 730.87 | 30073-99A |
| | Diastereomer 1 | | | |
| 318 | 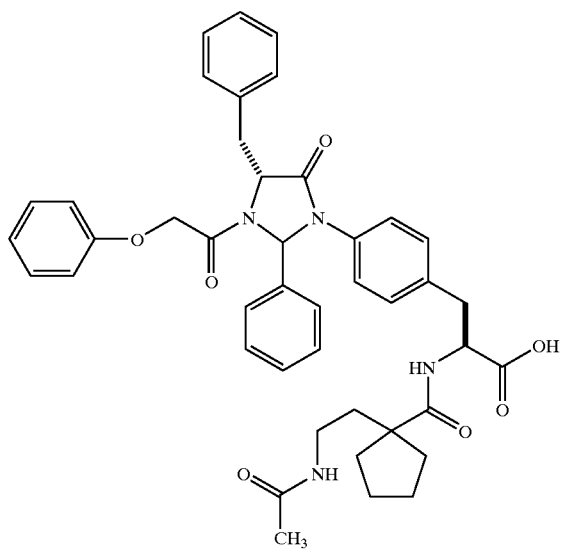 | 729.0 (M − H) | 730.87 | 30073-99B |

-continued
| Example # | MOLSTRUCTURE | MS | MW | LOT # |
|---|---|---|---|---|
| | Diastereomer 2 | | | |
| 319 | 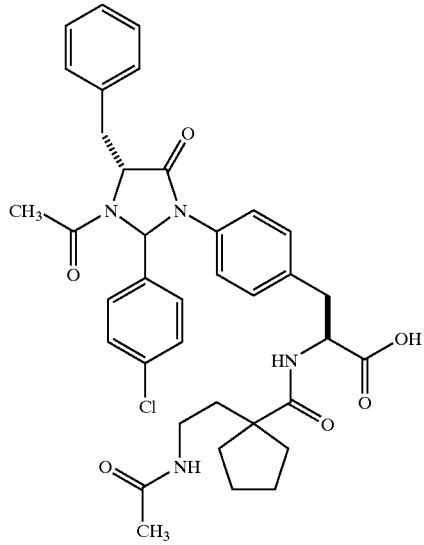 | 670.9 (M − H) | 673.22 | 30073-100A |
| | Diastereomer 1 | | | |
| 320 | 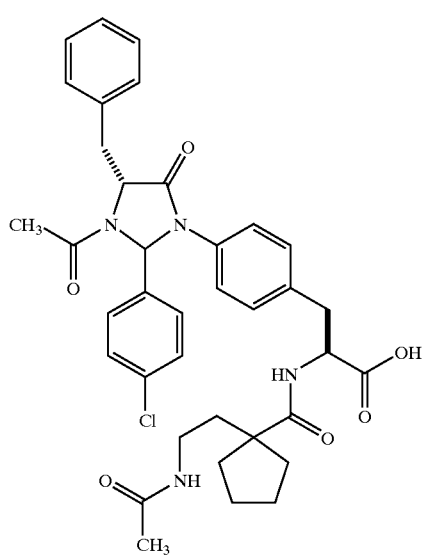 | 670.9 (M − H) | 673.22 | 30073-100B |

-continued
| Example # | MOLSTRUCTURE | MS | MW | LOT # |
|---|---|---|---|---|
| | Diastereomer 2 | | | |
| 321 | 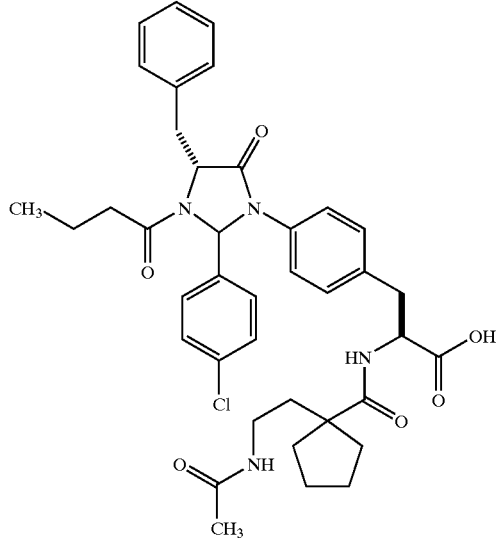 | 698.9 (M − H) | 701.27 | 30073-101A |
| | Diastereomer 1 | | | |
| 322 | 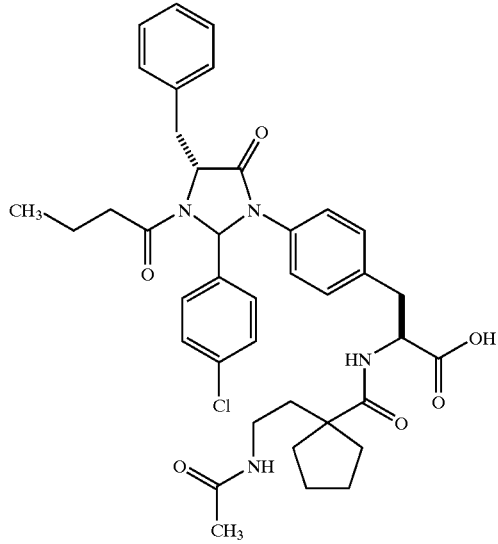 | 699.0 (M − H) | 701.27 | 30073-101B |

-continued
| Example # | MOLSTRUCTURE | MS | MW | LOT # |
|---|---|---|---|---|
| | Diastereomer 2 | | | |
| 323 | 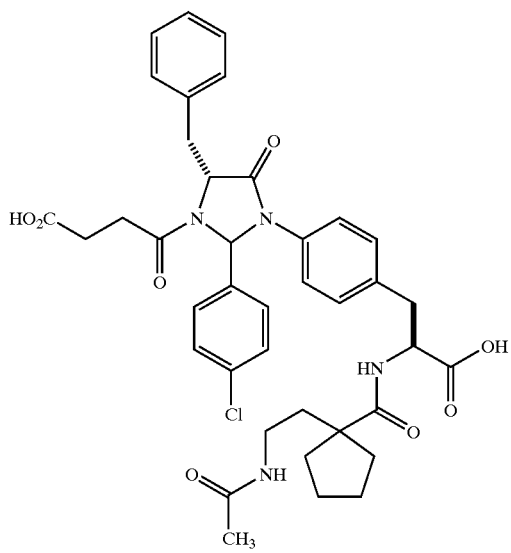 | 728.9 (M − H) | 731.25 | 30073-102A |
| | Diastereomer 1 | | | |
| 324 | 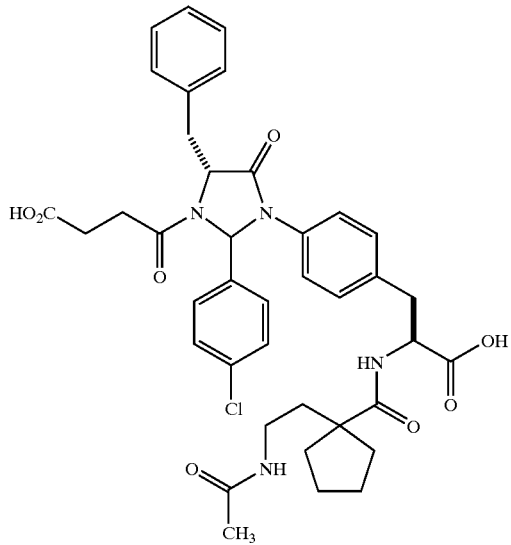 | 728.8 (M − H) | 731.256 | 30073-102B |

| Example # | MOLSTRUCTURE | MS | MW | LOT # |
|---|---|---|---|---|
| | Diastereomer 2 | | | |
| 325 | 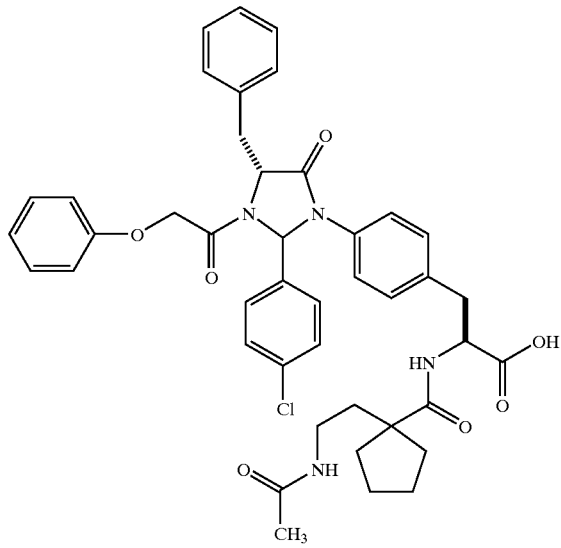 | | 765.31 | 30073-103A |
| | Diastereomer 1 | | | |
| 326 | 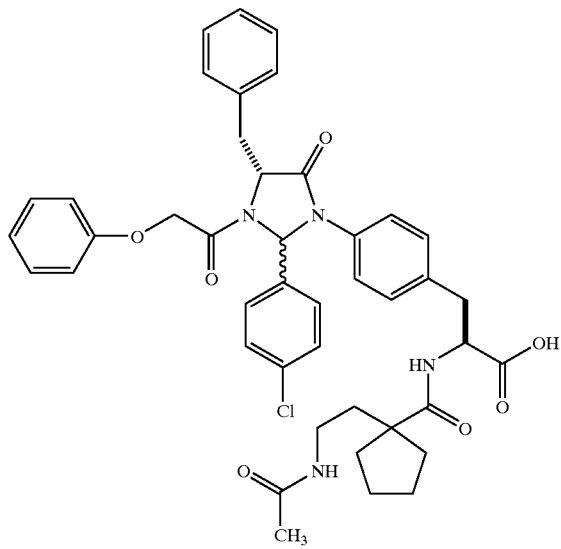 | 762.9 (M − H) | 765.31 | 30073-103B |

-continued
| Example # | MOLSTRUCTURE | MS | MW | LOT # |
|---|---|---|---|---|
| | Mixture of Diastereomer | | | |
| 327 | 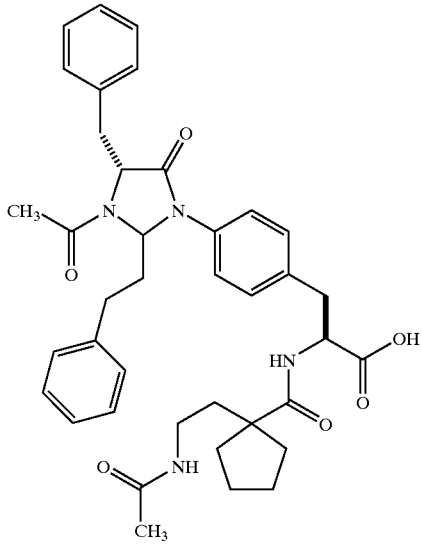 | 665.1 (M − H) | 666.82 | 30073-104A |
| | Diastereomer 1 | | | |
| 328 | 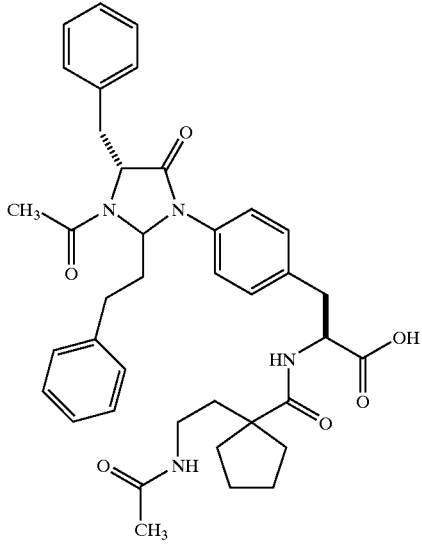 | 665.0 (M − H) | 666.82 | 30073-104B |

| Example # | MOLSTRUCTURE | MS | MW | LOT # |
|---|---|---|---|---|
| | Diastereomer 2 | | | |
| 329 | 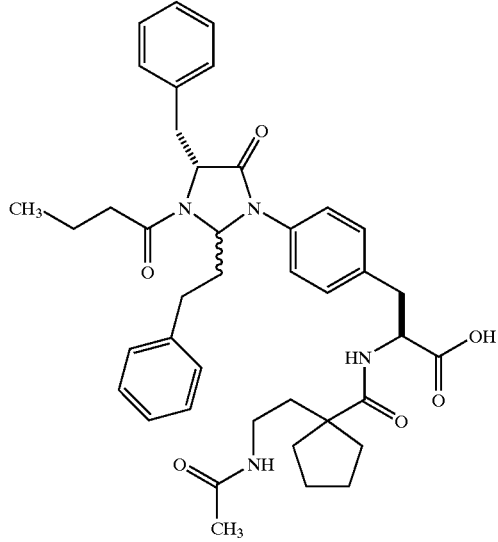 | 693.0 (M − H) | 694.88 | 30073-105 |
| | Diastereomeric Mixture | | | |
| 330 | 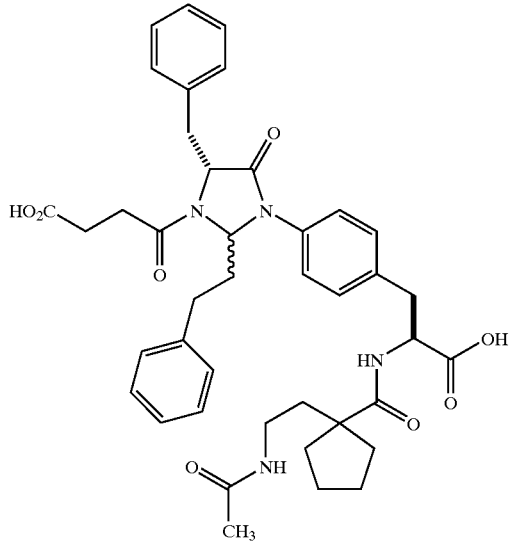 | 723.1 (M − H) | 724.86 | 30073-144 |

-continued
| Example # | MOLSTRUCTURE | MS | MW | LOT # |
|---|---|---|---|---|
| | Diastereomeric Mixture | | | |
| 331 | 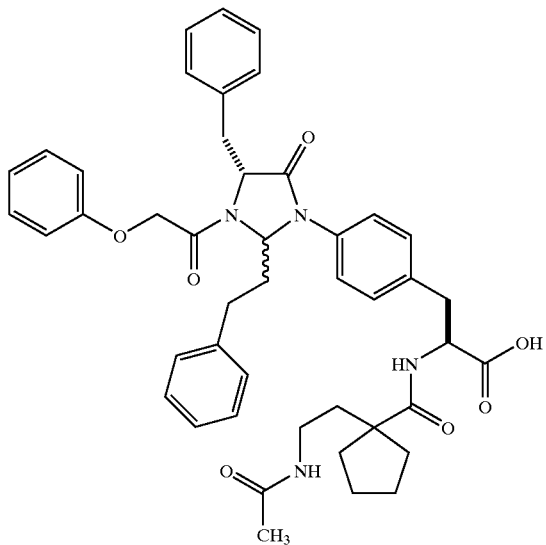 | 757.0 (M − H) | 758.92 | 30073-145 |
| | Diastereomeric Mixture | | | |
| 332 | 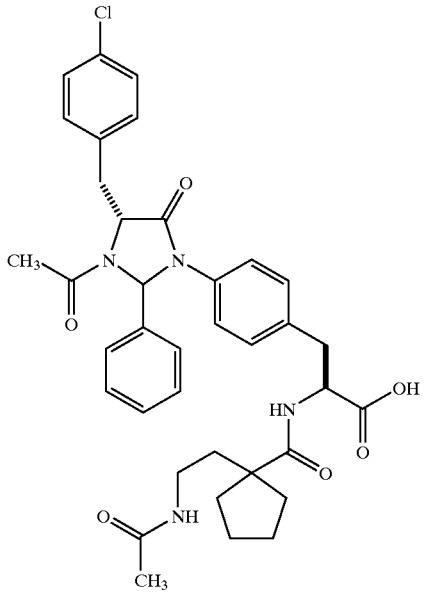 | 670.9 (M − H) | 673.22 | 30073-146A |

| Example # | MOLSTRUCTURE | MS | MW | LOT # |
|---|---|---|---|---|
| | Diastereomer 1 | | | |
| 333 | 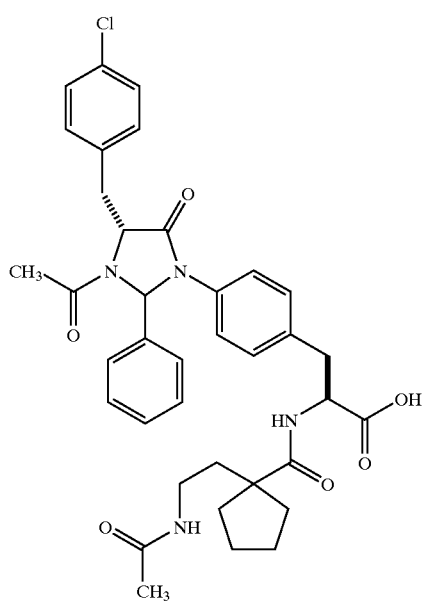 | 670.9 (M − H) | 673.22 | 30073-146B |
| | Diastereomer 2 | | | |
| 334 | 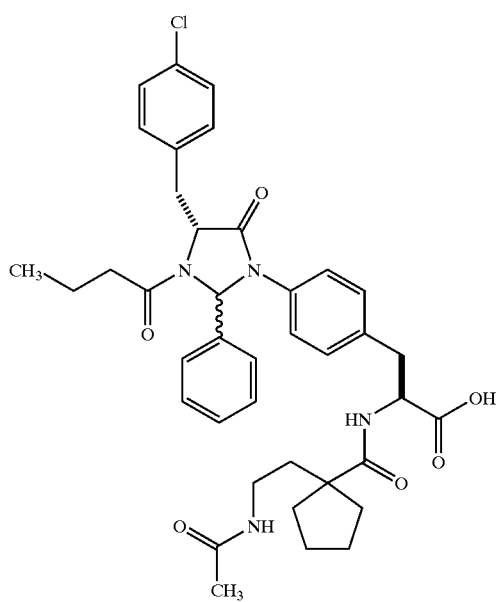 | 669.0 (M − H) | 701.27 | 30073-147 |

| Example # | MOLSTRUCTURE | MS | MW | LOT # |
|---|---|---|---|---|
| | Diastereomeric Mixture | | | |
| 335 | 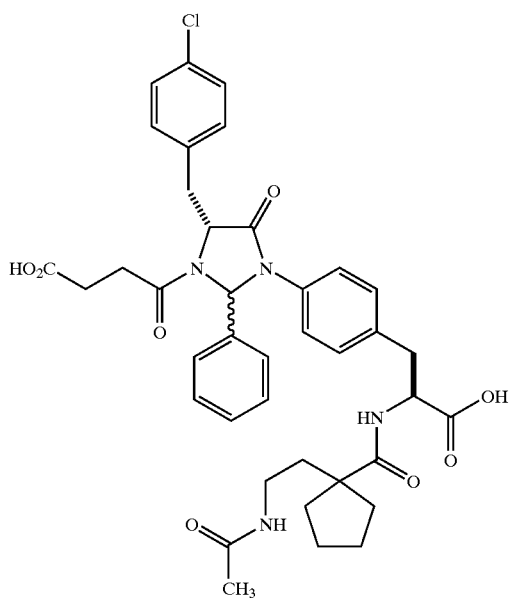 | 729.0 (M − H) | 731.25 | 30073-148 |
| | Diastereomeric Mixture | | | |
| 336 | 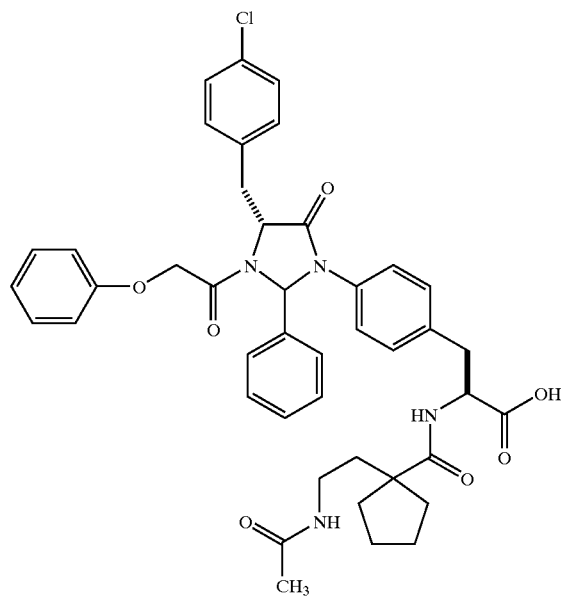 | 762.7 (M − H) | 765.31 | 30073-149A |

-continued
| Example # | MOLSTRUCTURE | MS | MW | LOT # |
|---|---|---|---|---|
| | Diastereomer 1 | | | |
| 337 | 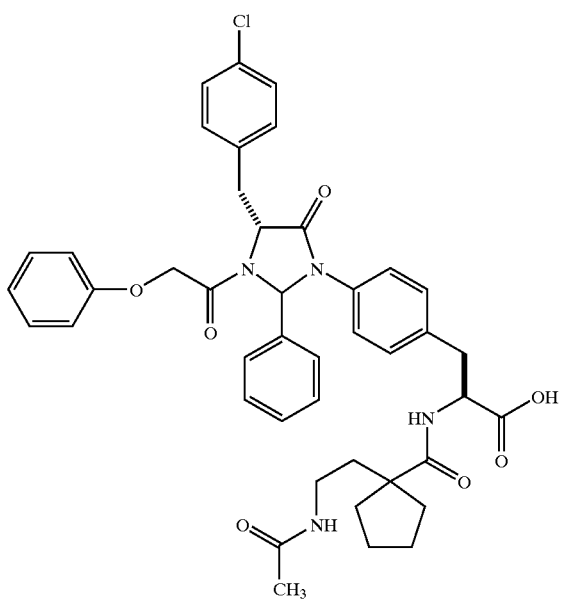 | 762.7 (M − H) | 765.31 | 30073-149B |
| | Diastereomer 2 | | | |
| 338 | 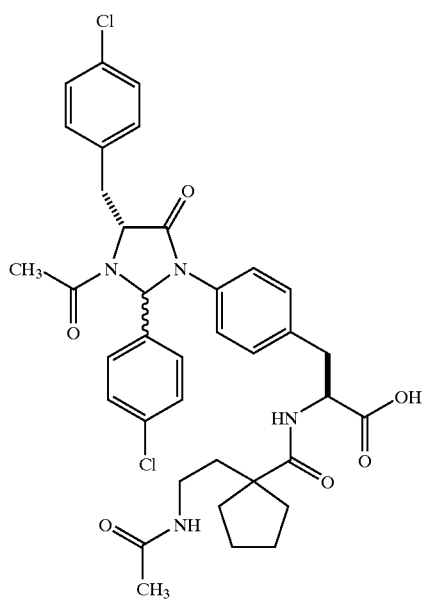 | 704.8 (M − H) | 707.66 | 30073-150 |

-continued
| Example # | MOLSTRUCTURE | MS | MW | LOT # |
|---|---|---|---|---|
| | Diastereomeric Mixture | | | |
| 339 | 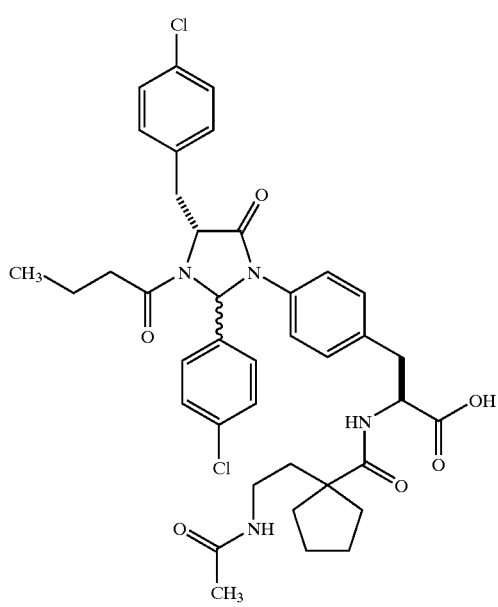 | 732.9 (M − H) | 735.71 | 30073-151 |
| | Diastereomeric Mixture | | | |
| 340 | 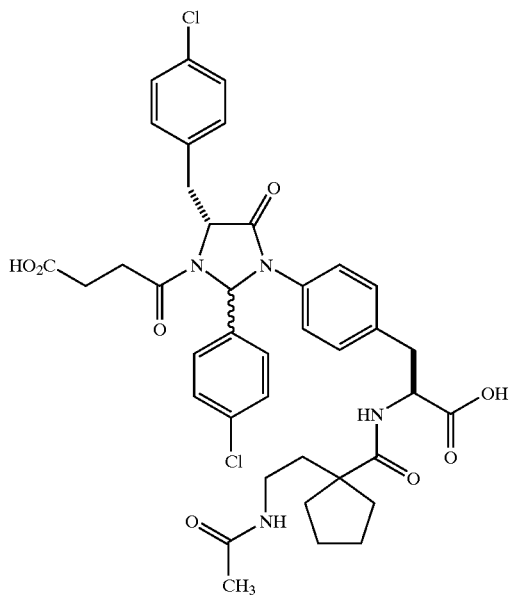 | 764.3 (M − H) | 765.70 | 30073-152 |

-continued
| Example # | MOLSTRUCTURE | MS | MW | LOT # |
|---|---|---|---|---|
| 341 | Diastereomeric Mixture 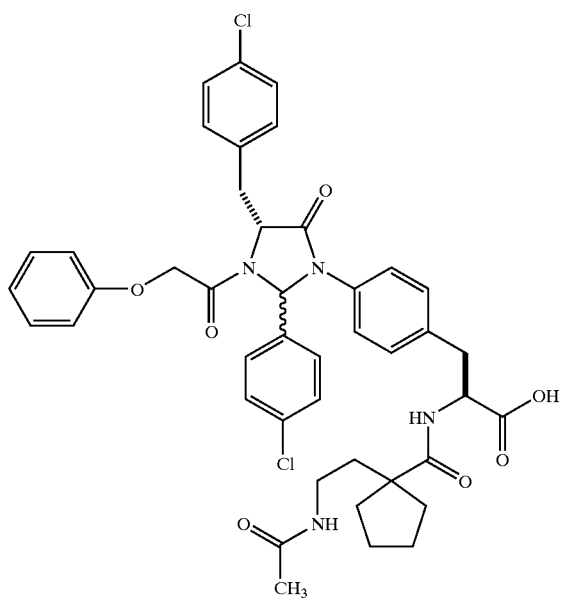 Diastereomeric Mixture | 796.9 (M − H) | 799.76 | 30073-153 |
| 342 | 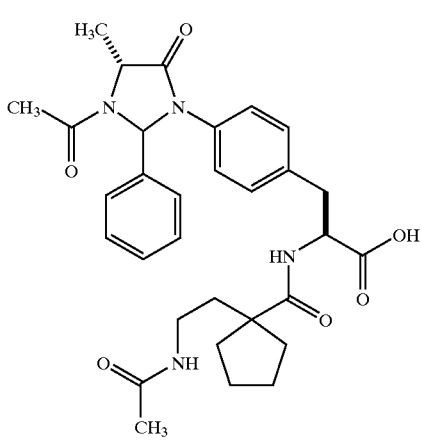 Diastereomer 1 | 560.9 (M − H) | 562.67 | 30073-154A |
| 343 | 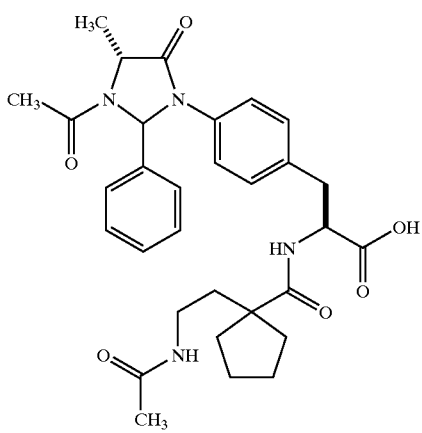 | 561.0 (M − H) | 562.67 | 30073-154B |

| Example # | MOLSTRUCTURE | MS | MW | LOT # |
|---|---|---|---|---|
| | Diastereomer 2 | | | |
| 344 | 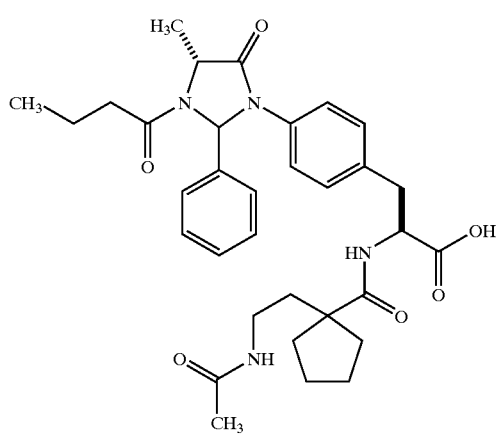 | 589.0 (M − H) | 590.73 | 30073-155A |
| | Diastereomer 1 | | | |
| 345 | 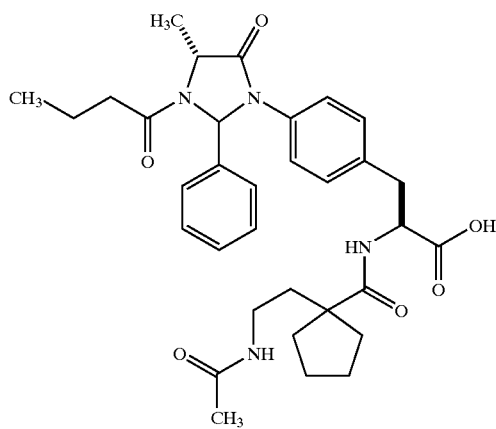 | 589.0 (M − H) | 590.73 | 30073-155B |
| | Diastereomer 2 | | | |
| 346 | 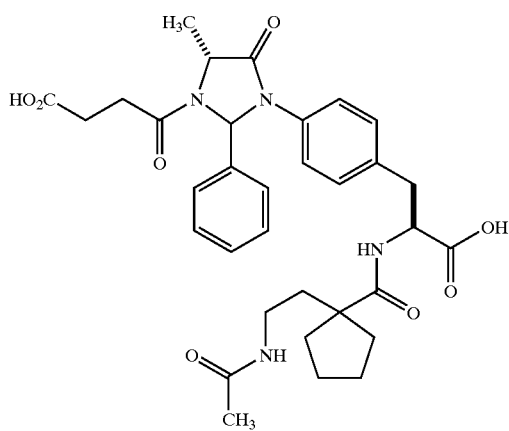 | 619.2 (M − H) | 620.71 | 30073-156A |

| Example # | MOLSTRUCTURE | MS | MW | LOT # |
|---|---|---|---|---|
| | Diastereomer 1 | | | |
| 347 | 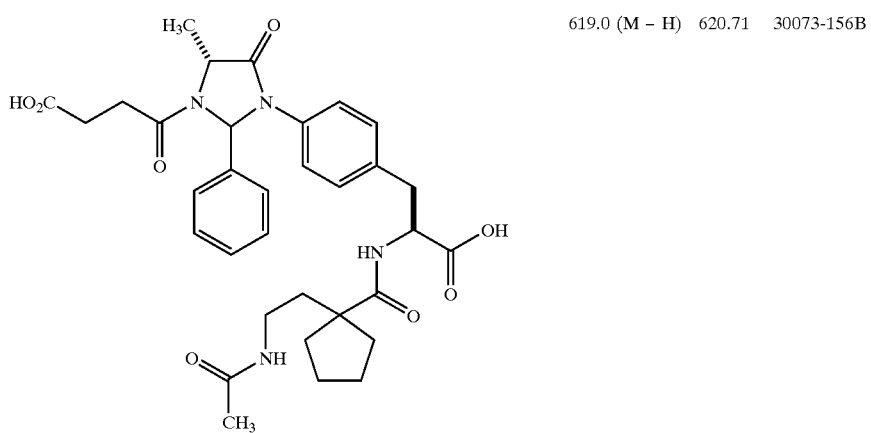 | 619.0 (M − H) | 620.71 | 30073-156B |
| | Diastereomer 2 | | | |
| 348 | 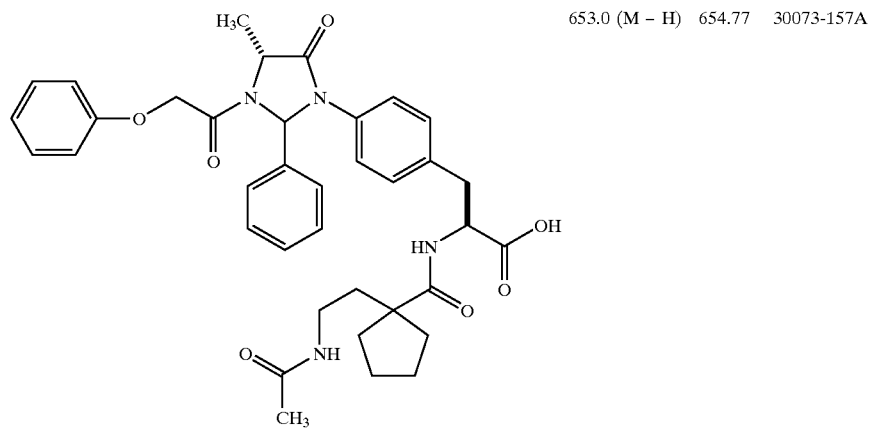 | 653.0 (M − H) | 654.77 | 30073-157A |
| | Diastereomer 1 | | | |
| 349 | 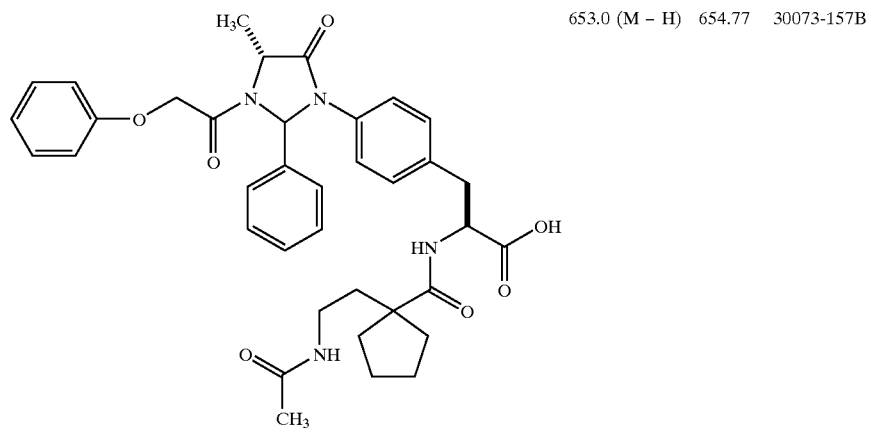 | 653.0 (M − H) | 654.77 | 30073-157B |

| Example # | MOLSTRUCTURE | MS | MW | LOT # |
|---|---|---|---|---|
| | Diastereomer 2 | | | |
| 350 | 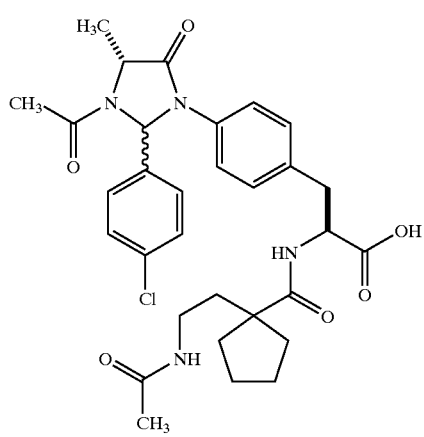 | 594.9 (M − H) | 597.1 | 30073-144 |
| | Diastereomic Mixture | | | |
| 351 | 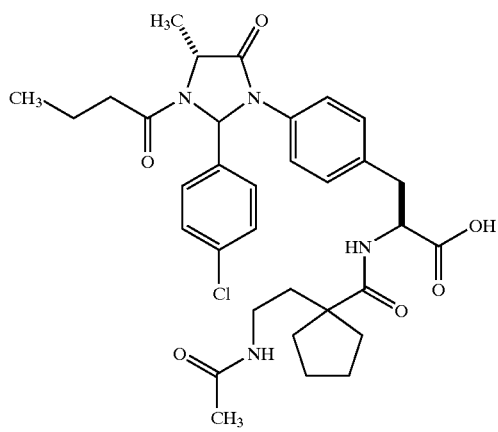 | 622.9 (M − H) | 625.17 | 30073-159A |
| | Diastereomer 1 | | | |
| 352 | 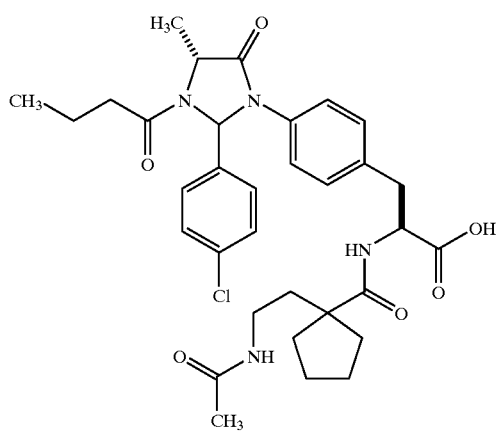 | 623.0 (M − H) | 625.17 | 30073-159B |

-continued
| Example # | MOLSTRUCTURE | | MS | MW | LOT # |
|---|---|---|---|---|---|
| | Diastereomer 2 | | | | |
| 353 | 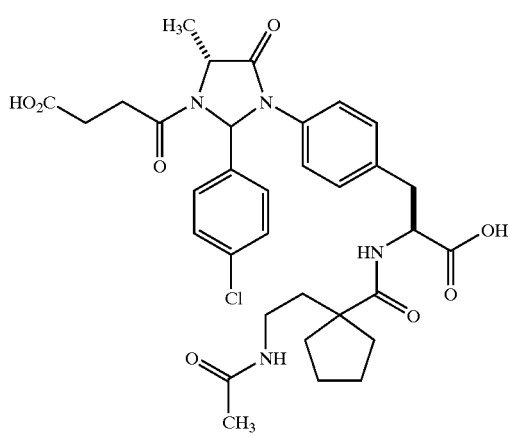 | | 652.9 (M − H) | 655.15 | 30073-160A |
| | Diastereomer 1 | | | | |
| 354 | 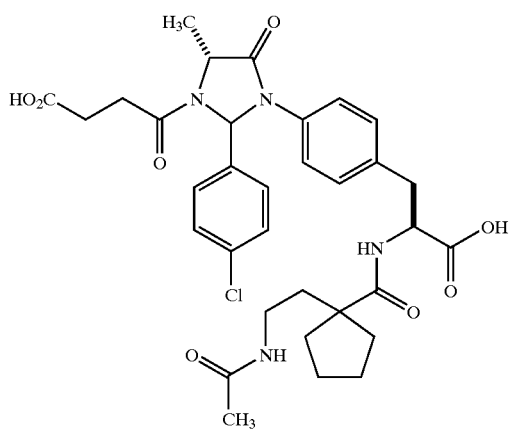 | | 653.0 (M − H) | 655.15 | 30073-160B |
| | Diastereomer 2 | | | | |
| 355 | 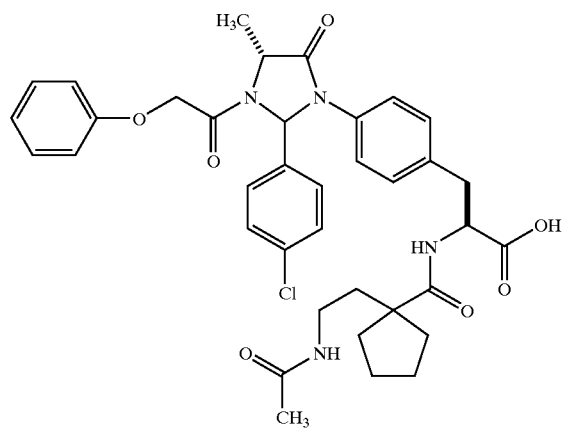 | | 687 (M − H) | 689.21 | 30073-161A |

| Example # | MOLSTRUCTURE | MS | MW | LOT # |
|---|---|---|---|---|
| | Diastereomer 1 | | | |
| 356 | 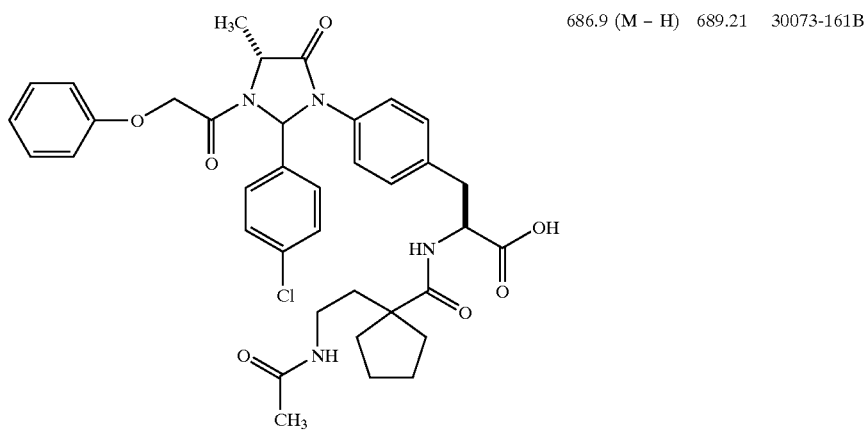 | 686.9 (M − H) | 689.21 | 30073-161B |
| | Diastereomer 2 | | | |

Example 357

Preparation of 4-[[(2,6-Dichlorophenyl)Carbonyl] Amino]-N-[[1-[(2-(Methylsulfinyl)Ethyl] Cyclopentyl]Carbonyl]-L-Phenylalanine

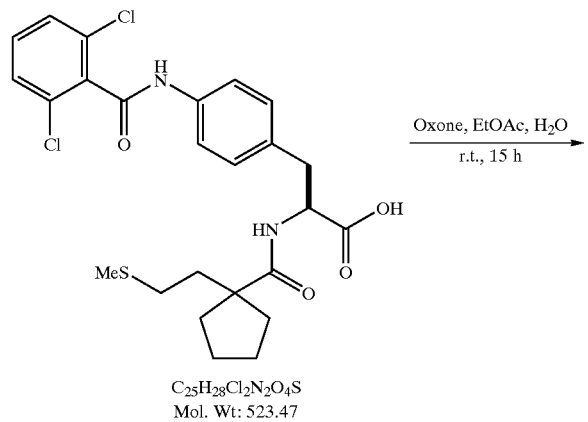

To a suspension of 4-[[(2,6-dichlorophenyl)carbonyl] amino]-N-[[1-[(2-(methylthio)ethyl]cyclopentyl]carbonyl]-L-phenylalanine (0.095 mmol, 50 mg) in ethyl acetate (4 mL) was added THF (1.5 mL) to afford a clear solution. Then, water (3 mL) and oxone (0.048 mmol, 30 mg) was added at room temperature. The mixture was stirred for 15 h at which time TLC analysis of the mixture indicated the absence of starting material. The solid was collected by filtration and washed with water. This material was purified by reverse phase HPLC to afford 26.3 mg (51%) of a white solid: mp 255–258° C. HR MS (C25H28Cl2N2O5S): Obs mass, 539.1187. Calcd mass, 539.1174 (M+H).

Example 358

Preparation of 4-[[(2,6-Dichlorophenyl)Carbonyl] Amino]-N-[[1-[(2-[(Methylsulfonyl)Ethyl] Cyclopentyl]Carbonyl]-L-Phenylalanine

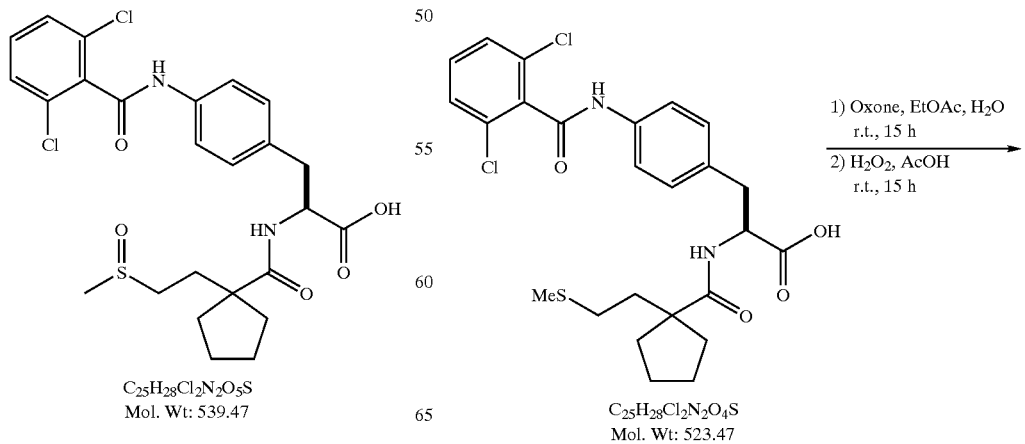

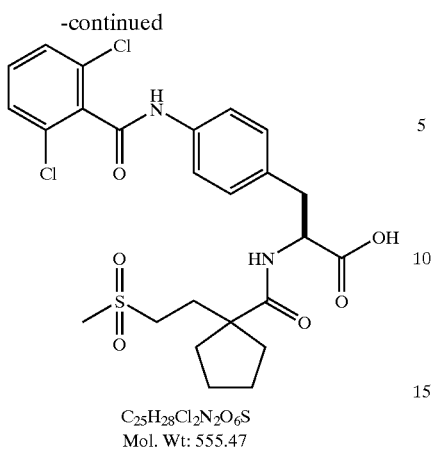

C25H28Cl2N2O6S
Mol. Wt: 555.47

To a suspension of 4-[[(2,6-dichlorophenyl)carbonyl]amino]-N-[[1-[(2-(methylthio)ethyl]cyclopentyl]carbonyl]-L-phenylalanine (0.095 mmol, 50 mg) in ethyl acetate (4 mL) was added THF (1 mL) to afford a clear solution. Then, water (2 mL) and oxone (0.019 mmol, 12 mg) was added at room temperature. The mixture was stirred for 15 h and the precipitated sulfoxide was collected by filtration and washed with water. Then, the solid was redissolved in acetic acid (2 mL) and treated with 30% hydrogen peroxide (0.7 mL). The mixture was stirred for 15 h at room temperature at which time the TLC analysis indicated the absence of sulfoxide. This mixture was directly purified by reverse phase HPLC to afford 14 mg (66%) of a white solid, mp 184–187° C. HR MS (C25H28Cl2O6S): Obs mass, 577.0928. Calcd mass, 577.0944 (M+Na).

Example 359

Preparation of 4-[(2-Chloro-5-Bromophenylcarbonyl)Amino]-N-[(1,1-Dimethylethyoxy)carbonyl]-L-Phenylalanine Methyl Ester

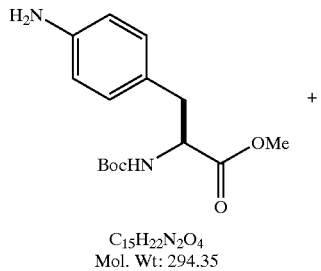

C15H22N2O4
Mol. Wt: 294.35

+

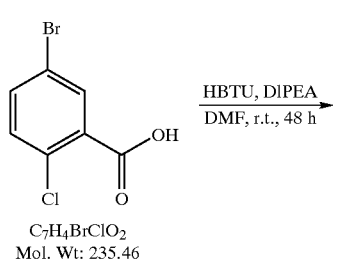

C7H4BrClO2
Mol. Wt: 235.46

HBTU, DIPEA
DMF, r.t., 48 h
→

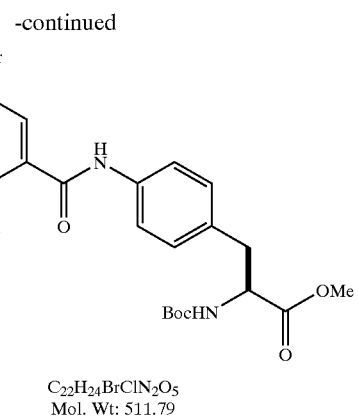

C22H24BrClN2O5
Mol. Wt: 511.79

To a mixture of 4-amino-N-[(1,1-dimethylethoxy)carbonyl)-L-phenylalanine methyl ester (20 mmol, 5.88 g), 2-chloro-5-bromobenzoic acid (22 mmol, 5.18 g) and HBTU (22 mmol, 8.34 g) in DMF (70 mL) was added diisopropylethylamine (50 mmol, 8.7 mL) at room temperature. The suspension was stirred for 48 h at which time TLC analysis of the mixture indicated the absence of starting material. Then, the mixture was diluted with water (100 mL) and the solids were collected by filtration and washed with water (150 mL). After air drying, the crude product was purified by silica gel column chromatography to obtain 1.02 g (10%) of a white solid: mp 158–161° C. HR MS (C22H24BrClN2O5): Ob, 533.0442. Calcd mass, 533.0455 (M+Na).

Example 360

Preparation of 4-[(2-Chloro-5-Cyanophenylcarbonyl)Amino]-N-[(1,1-Dimethylethoxy)Carbonyl]-L-Phenylalanine Methyl Ester

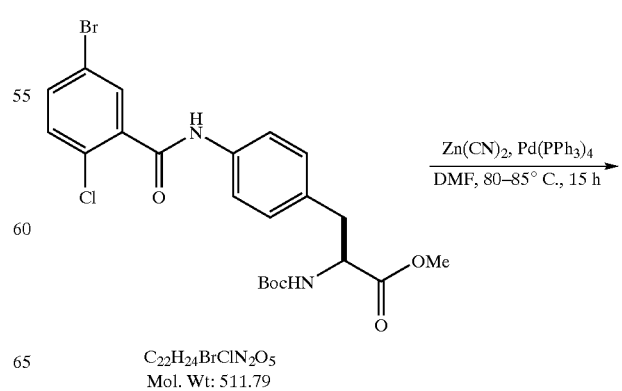

C22H24BrClN2O5
Mol. Wt: 511.79

Zn(CN)2, Pd(PPh3)4
DMF, 80–85° C., 15 h
→

-continued

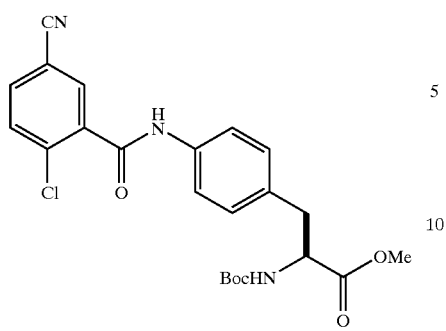

C₂₃H₂₄ClN₃O₅
Mol. Wt: 457.91

-continued

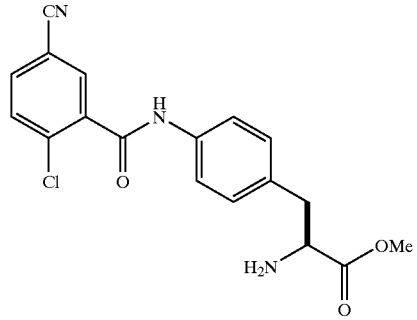

C₁₈H₁₆ClN₃O₃
Mol. Wt: 357.79

To a mixture of 4-[(2-chloro-5-bromophenylcarbonyl)amino]-N-[(1,1-dimethylethoxy)carbonyl]-L-phenylalanine methyl ester (2 mmol, 1.02 g), zinc cyanide (1.3 mmol, 152 mg) and Pd(PPh₃)₄ (0.2 mmol, 231 mg) was added distilled and deoxygenated DMF (8 mL) at room temperature. The suspension was heated to 80–85° C and stirred for 15 h at which time TLC analysis of the mixture indicated the absence of starting material. Then, the reaction mixture was cooled to room temperature and diluted with ethyl acetate (70 mL) and washed with 20% aqueous ammonium hydroxide (50 mL), brine solution (50 mL) and was dried over anhydrous magnesium sulfate. Filtration of the drying agent and concentration of the solvent gave a crude product which was purified by silica gel column chromatography to obtain 555 mg (61%) of a white solid, mp 185–187° C. HR MS (C23H24ClN3O5): Obs mass, 480.1301. Calcd mass, 480.1302 (M+Na).

To a solution of 4-[(2-chloro-5-cyanophenylcarbonyl)amino]-N-[(1,1-dimethylethoxy)carbonyl]-L-phenylalanine methyl ester (1.2 mmol, 0.55 g) in dichloromethane (12 mL) was added trifluoroacetic acid (3 mL) at room temperature. The reaction mixture was stirred for 15 h at room temperature at which time TLC analysis of the mixture indicated the absence of starting material. Then, the solvent was removed under vacuum and the residue was azeotroped with toluene (2×10 mL) and dried under high vacuum to afford 0.43 g (100%) of a yellow solid. HR MS (C18H16ClN3O3): Obs mass, 358.0963. Calcd mass, 358.0959 (M+H).

Example 362

Preparation of 4-[(2-Chloro-5-Cyanophenylcarbonyl)Amino]-N-[[1-(2-Methoxy-Ethyl)Cyclopentyl]Carbonyl]-L-Phenylalanine Methyl Ester Example 361

Preparation of 4-[(2-Chloro-5-Cyanophenylcarbonyl)Amino]-L-Phenylalanine Methyl Ester TFA Salt

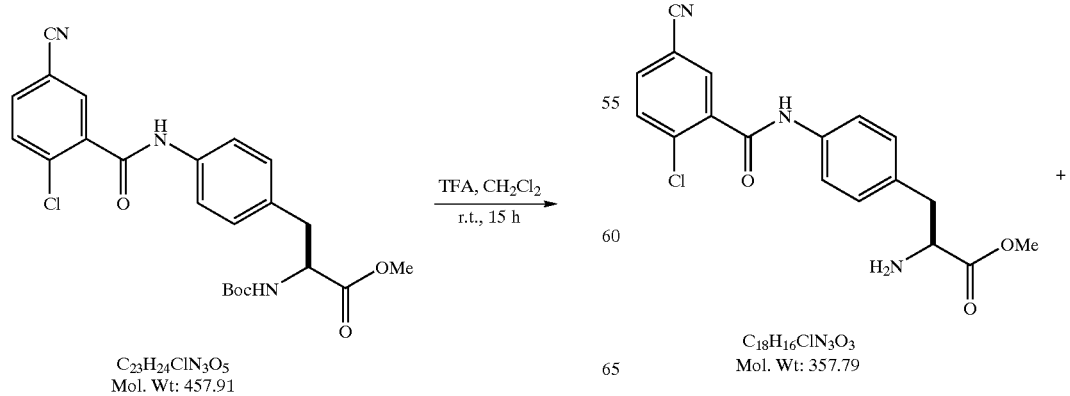

C₂₃H₂₄ClN₃O₅
Mol. Wt: 457.91

C₁₈H₁₆ClN₃O₃
Mol. Wt: 357.79

Example 363

Preparation of 4-[(2-Chloro-5-Cyanophenylcarbonyl)Amino]-N-[[1-(2-Methoxyethyl)Cyclopentyl]Carbonyl]-L-Phenylalanine

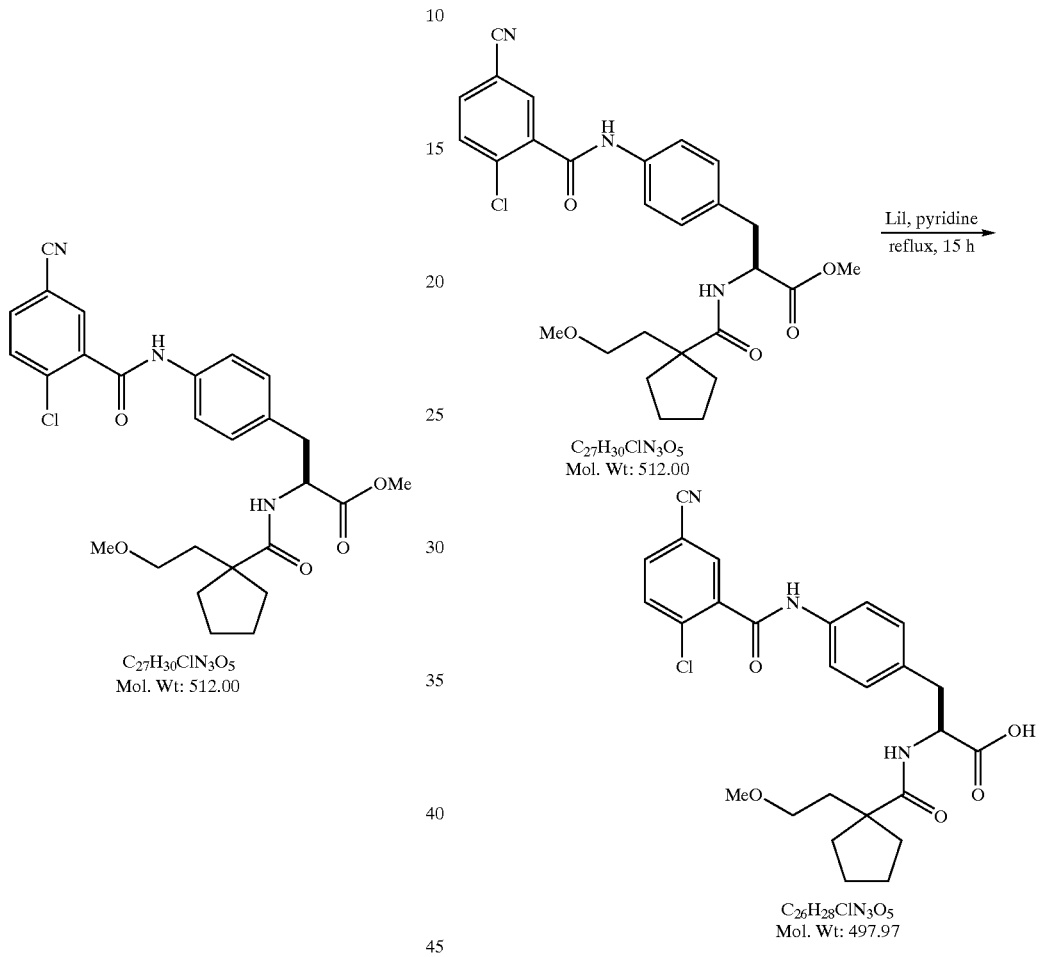

To a solution of 4-[(2-chloro-5-cyanophenylcarbonyl)amino]-L-phenylalanine methyl ester TFA salt (0.55 mmol, 0.35 g), HBTU (0.65 mmol, 0.24 g) and 1-(2-methoxyethyl)cyclopentane carboxylic acid (0.65 mmol, 0.11 g) in DMF (3 mL) was added diisopropylethylamine (1.65 mmol, 0.29 mL) at room temperature. The clear solution was stirred for 15 h at room temperature and diluted with 50 mL of ethyl acetate. Then, the ethyl acetate layer was washed successively with 0.5N hydrochloric acid (2×20 mL), saturated sodium bicarbonate solution (2×20 mL) and brine solution and was dried over anhydrous magnesium sulfate. Filtration of the drying agent and concentration of the solvent gave a crude product which was purified by silica gel column chromatography to afford 0.25 g (87%) of a white solid: mp 172–175° C. HR MS (C27H30ClN3O5): Obs mass, 512.1949. Calcd mass, 512.1953 (M+H).

To a mixture of 4-[(2-chloro-5-cyanophenylcarbonyl)amino]-N-[[1-(2-methoxy-ethyl)cyclopentyl]carbonyl]-L-phenylalanine methyl ester (0.1 mmol, 51 mg) and lithium iodide (1.0 mmol, 133 mg) was added pyridine (2 mL) at room temperature. The solution was refluxed for 15 h at which time TLC analysis of the mixutre indicated the absence of starting material. Then, the mixture was cooled to room temperature and diluted with water (15 mL) and the bulk of the pyridine was removed under reduced pressure. Then it was extracted with ether (2×15 mL) to remove any neutral impurities. The aqueous layer was acidified with 1N HCl and the precipitated white solid was collected by filtration and washed with 20 mL of water and 20 mL of hexane. After air-drying, the crude product was crystallized from acetonitrile to afford 20 mg (40%) of a white solid: mp 169–172° C. HR MS (C26H26ClN3O5): Obs mass, 498.1802. Calcd mass, 498.1795, M+H).

Example 364

Preparation of 4-[[(2,4-Dimethylpyridin-3-yl)Carbonyl]Amino]-N-[[1-[4-(methylsulfonyl)Butyl]Cyclopentyl]Carbonyl]-L-Phenylalanine

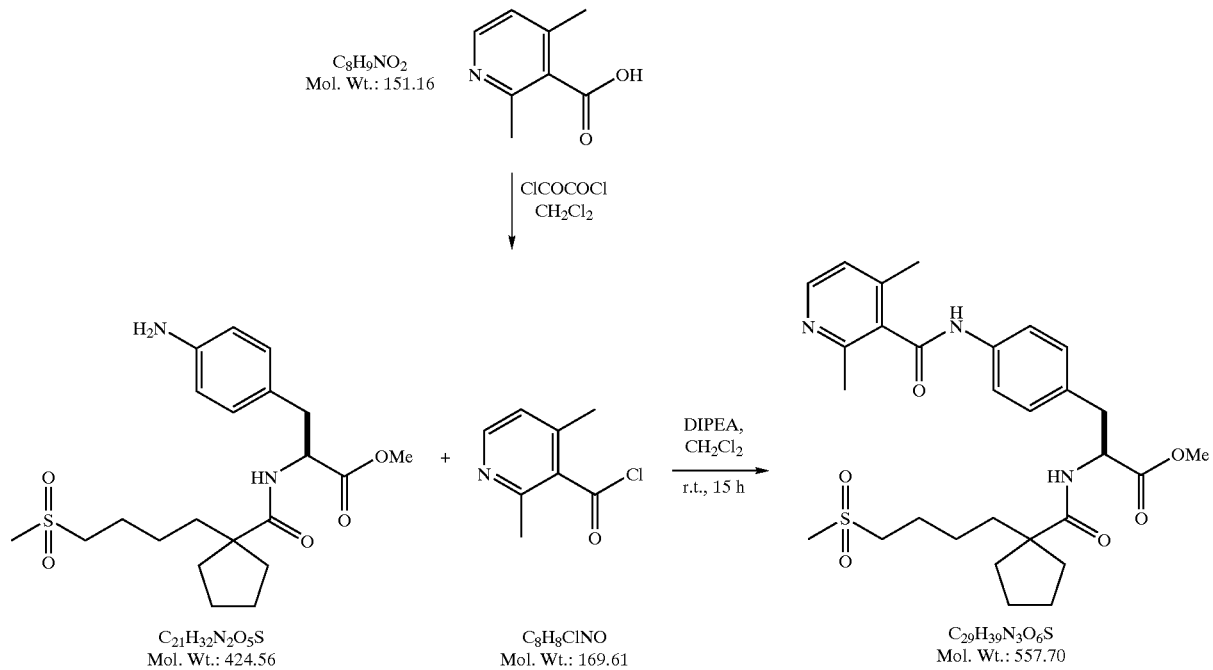

To a solution of 2,4-dimethylpyridinecarboxylic acid (0.6 mmol, 102 mg) in dichloromethane (3 mL) was added a drop of DMF and oxalyl chloride (0.78 mmol, 99 mg) at 0° C. (ice bath). The solution was stirred at this temperature for 30 min, warmed to room temperature and stirred for an additional 1 h. Then, the solvent and excess oxalyl chloride was removed under vacuum and the residue was dried under high vacuum. To this 4-amino-N-[[1-[4-(methylsulfonyl)butyl]cyclopentyl]carbonyl]-L-phenylalanine methyl ester (0.5 mmol, 212 mg) was added and the mixture was dissolved in dichloromethane (5 mL). To this clear solution was added DIPEA (2.0 mmol, 0.258 g) at room temperature. The mixture was stirred for 15 h at which time TLC analysis of the mixture indicated the absence of starting material. Then, the mixture was diluted with dichloromethane (20 mL) and water (100 mL). The two layers were separated and the organic layer was washed with saturated sodium bicarbonate solution (20 mL), brine solution (30 mL) and dried over anhydrous magnesium sulfate. Filtration of the drying agent and removal of the solvent gave a crude product which was purified by silica gel column chromatography to afford 0.232 g (80%) of a white solid. HR MS ($C_{29}H_{39}N_3O_6S$): Obs. mass, 558.2629. Calcd. mass, 558.2638, M+H).

Preparation of 4-[[(2,4-dimethyl-3-pyridinyl)carbonyl]amino]-N-[[1-[4-(methylsulfonyl)-butyl]cyclopentyl]carbonyl]-L-phenylalanine.

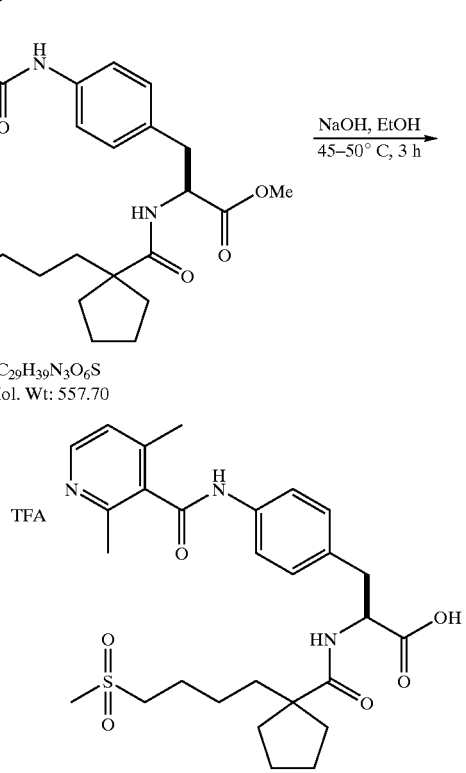

Using the procedure described in example 47, 4-[[(2,4-dimethyl-3-pyridyl)carbonyl]amino]-N-[[1-[4-(methylsulfonyl)butyl]cyclopentyl]carbonyl]-L-phenylalanine methyl ester prepared above was hydrolyzed in 88% yield to give a white solid. HR MS (C28H37N3O6S): Obs. mass, 544.2471. Calcd. mass, 544.2481 (M+H).

Example 365

4-[(4R)-3-Acetyl-5-Oxo-2-Phenyl-4-(Phenylmethyl)-1-Imidazolidinyl]-N-[[1-4-(Methylsulfonyl)Butyl]Cyclopentyl]Carbonyl]-L-Phenylalanine Synthesis of N-[(1,1-dimethylethoxy)carbonyl]-4-[[(2R)-2-amino-1-oxo-3-phenylpropyl]amino]-L-phenylalanine methyl ester

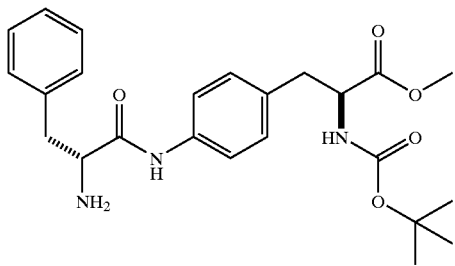

C24H31N3O5
Mol. Wt: 441.52

To the solution of 4-amino-N-[(1,1-dimethylethoxy)carbonyl]-L-phenylalanine methyl ester (5.09 g, 17 mmol) in DMF (60 mL) was added Fmoc-D-Phenylalanine (8.70 g, 22.5 mmol), DIPEA (12 mL, 69 mmol) and HBTU (8.50 g, 22.5 mmol). The mixture was then stirred at room temperature for 4 h. The reaction mixture was diluted with water (150 mL) and the light yellow solid which precipitated was collected by filtration. This solid was then redissolved in 60 mL of acetone and the solution was treated with 100 mL of water. The solid was collected by filtration and was washed with 1N HCl, H2O. After drying at 60° C. under vaccum overnight, a light yellow solid was obtained (13.2 g). A portion of this solid (2.51 g, 3.78 mmol) was dissolved in 15 mL of DMF and to the solution was added 1.5 mL of piperidine. The above solution was stirred at room temperature for 45 min. After removal of the solvent, the residue was recrystillized from ethyl acetate-hexane to give N-[(1,1-dimethylethoxy)carbonyl]-4-[[(2R)-2-amino-1-oxo-3-phenylpropyl]amino]-L-phenylalanine methyl ester (1.36 g, 3.0 mmol) in 81.5% yield. LR MS 442 (M+H).

Synthesis of 4-(3-acetyl-5-oxo-2-phenyl-4-phenylmethyl-1-imidazolidinyl)-N-[(1,1-dimethylethoxy)carbonyl]-L-phenylalanine methyl ester

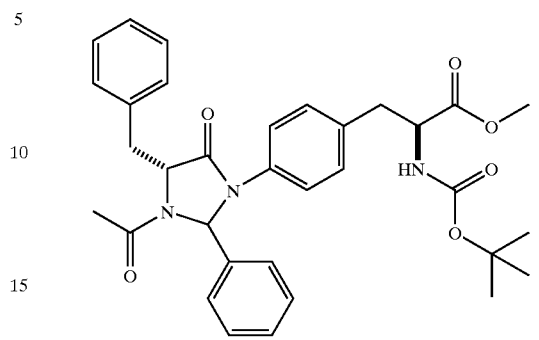

A solution of above amine (1.48, 3.35 mmol) and benzaldehyde (376 µl, 3.7 mmol) in dichloromethane (10 mL) and methyl orthoformate (10 mL) was stirred at room temperature for 3 days. The reaction flask was then warmed to 90° C. and acetic anhydride (neat, 1.8 mL) was added. The resulting mixture was stirred at 110° C. for 4 hr. The solvent was then evaporated and crude product was purified by silica gel chromatography (ethyl acetate:hexane=1:1) to give 4-(3-acetyl-5-oxo-2-phenyl-4-phenylmethyl-1-imidazolidinyl)-N-[(1,1-dimethylethoxy)carbonyl]-L-phenylalanine methyl ester diatereomer 1 (417 mg) and diastereomer 2 (1.25 g) These compounds are diastereomeric at the 2-position of the imidazolidinone ring. Both diastereomers gave LR MS (C33H37N3O6): 572 (M+H).

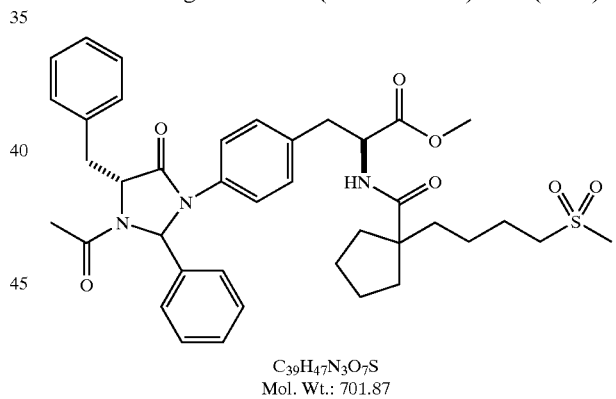

C39H47N3O7S
Mol. Wt.: 701.87

4-(3-acetyl-5-oxo-2-phenyl-4-phenylmethyl-1-imidazolidinyl)-N-[(1,1,-dimethylethoxy)carbonyl]-L-phenylalanine methyl ester (Diastereomer 1) (415 mg, 0.7 mmol) was treated with 10 mL of 4N HCl in dioxane at room temperature for 2 hr. After removal of solvent, the residue was dried overnight under vacuum. The residue (241 mg, 0.471 mmol) was dissolved in DMF (4 mL) and was treated with 1-(4-methylsulfonyl)butyl)cyclopentane carboxylic acid (153 mg, 0.617 mmol), HBTU (234 mg, 0.617 mmol) and DIEA (246 µL, 1.42 mmol) at room temperature for 4 hr. The mixture was diluted with 30 mL of ethyl acetate, the mixture was washed with 1N HCl, water and brine (8 mL each), After it was dried over MgSO4, the solvent was removed and the residue was filtered through silica gel eluting with ethyl acetate:hexane=4:1 to give 4-(3-acetyl-5- oxo-2-phenyl-4-phenylmethyl-1-imidazolidinyl)-N-[[1-[4-(methylsulfonyl)butyl]cyclopentyl]carbonyl]-L-phenylalanine methyl ester diastereomer 1 (147 mg, 0.2 mmol) in 44% yield. LR MS: 702 (M+H).

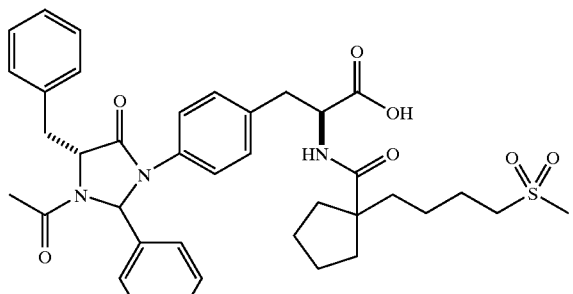

C38H45N3O7S
Mol. Wt.: 687.85

4-(3-acetyl-5-oxo-2-phenyl-4-phenylmethyl-1-imidazolidinyl)-N-[[1-[4-(methylsulfonyl)butyl]cyclopentyl]carbonyl]-L-phenylalanine methyl ester diastereomer 1 (90 mg, 0.128 mmol) in EtOH (3 mL) was treated with NaOH (1N, 0.3 mL) at room temperature for 30 min. The resulting solution was acidified with 1 drop of HOAc and was purified by HPLC (C-18, linear gradent from 5% acetonitrile to 95% in water over 30 min) to give 84 mg (95%, 0.122 mmol) of 4-(3-acetyl-5-oxo-2-phenyl-4-phenylmethyl-1-imidazolidinyl)-N-[[1-[4-(methyl-sulfonyl)butyl]cyclopentyl]carbonyl]-L-phenylalanine diastereomer 1. LR MS: 688 (M+H).

Example 366

4-[(4R)-3-Acetyl-5-oxo-2-phenyl-4-(3-pyridinylmethyl)-1-imidazolidinyl]-N-[(1-phenylcyclopenyl)carbonyl]-L-phenylalanine was prepared from Fmoc-D-3-pyridinylalanine, benzaldehyde and 4-amino-N-[(1,1-dimethylethoxy)carbonyl]-L-phenylalanine methyl ester using the general procedure described in example 365. MS: 631 (M+H)

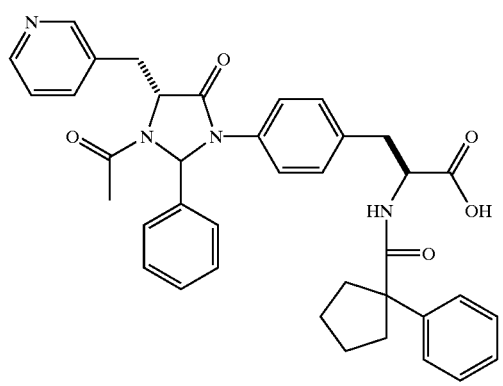

C38H38N4O5
Mol. Wt.: 630.73

Example 367

Preparation of 4-(5-Bromo-1,3-Dioxo-2H-Isoindol-2-yl)-N-[(1,1-dimethylethoxy)carbonyl]-L-phenylalanine methyl ester

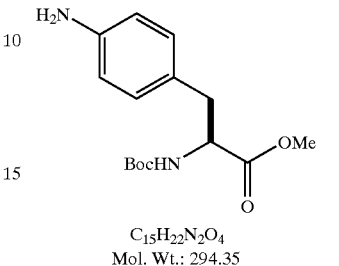

C15H22N2O4
Mol. Wt.: 294.35

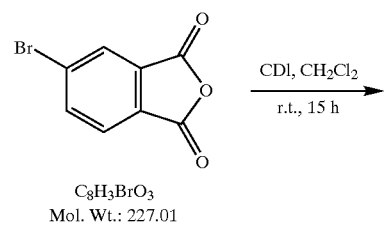

C8H3BrO3
Mol. Wt.: 227.01

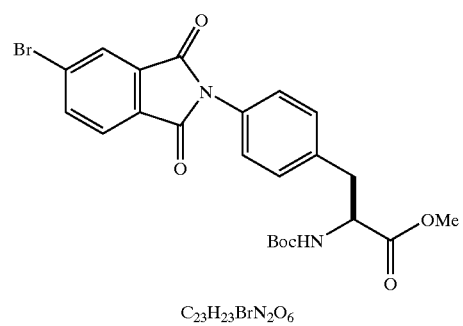

C23H23BrN2O6
Mol. Wt.: 503.34

To a suspension of 4-amino-N-[(1,1-dimethylethoxy)carbonyl]-L-phenylalanine methyl ester (6.78 mmol, 1.99 g) in dichloromethane (90 mL) was added a solution of 4-bromophthalic anhydride (6.78 mmol, 1.54 g) in dichloromethane (30 mL) and 1,1'-carbonyldiimidazole (6.78 mmol, 1.1 g) at room temperature. The resulting solution was stirred for 15 h at which time TLC analysis of the mixture indicated the absence of starting material. The mixture was diluted with water (100 mL) and layers were separated. The aqueous layer was extracted with dichloromethane (2×100 mL) and the combined extracts were washed with brine solution and dried over anhydrous magnesium sulfate. Filtration of the drying agent and concentration of the solvent under vacuum gave a crude product which was purified by silica gel column chromatography to obtaine 2.4 g (70%) of a white solid: mp 168–170° C. HR MS C23H23BrN2O6): Obs mass, 525.0656. Calcd mass, 525.0637 (M+Na).

Example 368

Preparation of 4-(5-Cyano-1,3-Dioxo-2H-Isoindol-2-yl)-N-[(1,1-dimethylethoxy)Carbonyl]-L-phenylalanine methyl ester

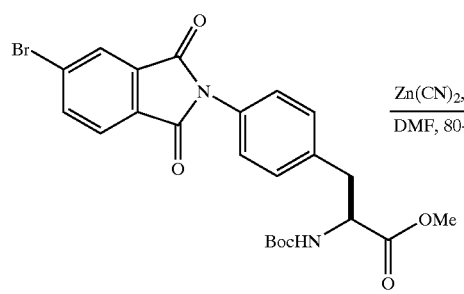

C23H23BrN2O6
Mol. Wt.: 503.34

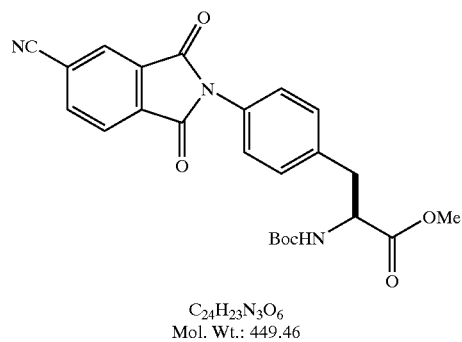

C24H23N3O6
Mol. Wt.: 449.46

To a mixture of 4-(5-bromo)1,3-dioxo-2H-isoindol-2-yl)-N-[(1,1-dimethylethoxy)carbonyl]-L-phenylalanine methyl ester (0.5 mmol, 0.25 g), zinc cyanide (0.3 mmol, 35 mg) and Pd(PPh3)4 (0.05 mmol, 57.7 mg) was added distilled and deoxygenated DMF (2 mL) at room temperature. The suspension was heated to 80–85° C. and was stirred for 15 h under argon an atmosphere. At this time TLC analysis of the mixture indicated the absence of starting material. The reaction mixture was cooled to room temperature and was diluted with ethyl acetate (50 mL) and was washed with 20% aqueous ammonium hydroxide (50 mL) and brine solution (50 mL) and was dried over anhydrous magnesium sulfate. Filtration of the drying agent and concentration afforded a crude product which was purified by silica gel column chromatography to afford 170 mg (75%) of a white solid. HR MS (C24H23N3O6): Obs mass, 472.1472. Calcd mass, 472.1485 (M+Na).

Example 369

Preparation of 4-(5-Cyano-1,3-Dioxo-2H-Isoindol-2-yl)-L-Phenylalanine Methyl Ester TFA Salt

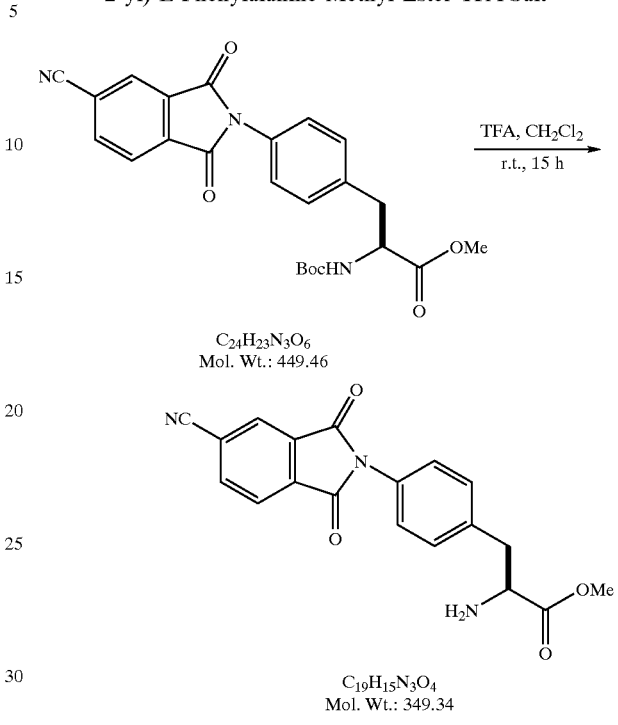

To a solution of 4-(5-cyano-1,3-dioxo-2H-isoindol-2-yl)-N-[(1,1-dimethylethoxy)carbonyl]-L-phenylalanine methyl ester (1.33 mmol, 0.6 g) in dichloromethane (12 mL) was added trifluoroacetic acid (3 mL) at room temperature. The reaction mixture was stirred for 15 h at room temperature at which time TLC analysis of the mixture indicated the absence of starting material. The solvent was removed under vacuum and the residue was azeotrophed with toluene (2×10 mL) and dried under high vacuum to afford 0.46 g (100%) of a yellow solid. HR MS (C19H15N3O4): Obs mass, 350.0156. Calcd mass, 350.0183 (M+H).

Example 370

Preparation of 4-[(4-Cyano)1,3-Dioxo-2H-Isoindol-2-yl]-N-[[1-(2-Methoxyethyl-Cyclopenyl]Carbonyl]-L-Phenylalanine Methyl Ester

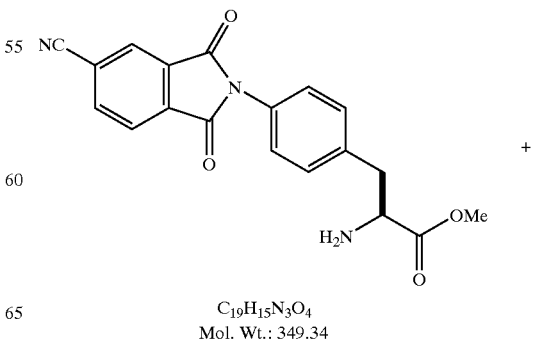

C19H15N3O4
Mol. Wt.: 349.34

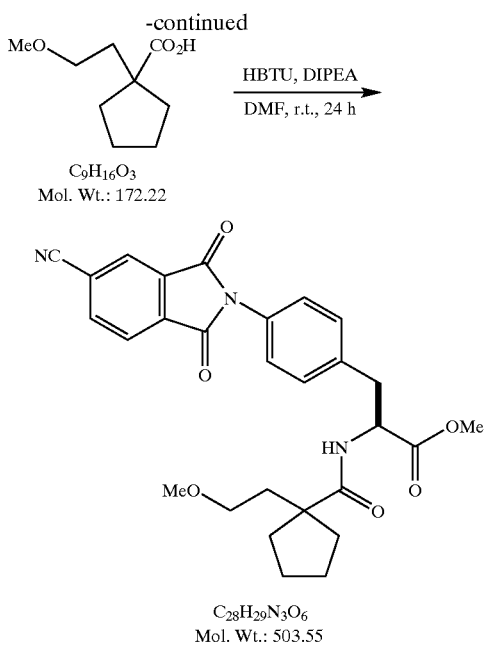

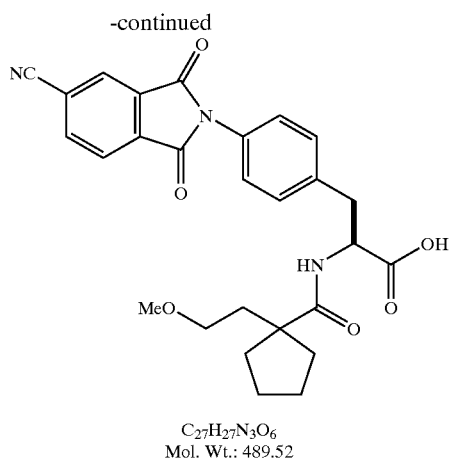

To a solution of 4-(5-cyano-1,3-dioxo-2H-isoindol-2-yl)-N-[(1,1-dimethylethoxy)carbonyl]-L-phenylalanine methyl ester TFA salt (0.65 mmol, 0.22 g), HBTU (0.7 mmol, 0.26 g) and 1-(2-methoxyethyl)cyclopentane carboxylic acid (0.7 mmol, 0.12 g) in DMF (3 mL) was added diisopropylethylamine (2.0 mmol, 0.35 mL) at room temperature. The clear solution was stirred 24 h at room temperature and was diluted with 50 mL of ethyl acetate. The ethyl acetate layer was washed successively with 0.5N hydrochloric acid (2×20 mL), saturated sodium bicarbonate solution (2×20 mL), brine solution and was dried over anhydrous magnesium sulfate. Filtration of the drying agent and concentration of the solvent gave a crude product which was purified by silica gel column chromatography to obtain 0.25 g (77%) of a white solid: mp 122–126° C. HR MS (C26H29N3O6): Obs mass, 504.2135. Calcd mass, 504.2134 (M+H).

Example 371

Preparation of 4-(5-Cyano-1,3-Dioxo-2H-Isoindol-2-yl)-N-[[1-(2-Methoxyethyl)Cyclopentyl]Carbonyl]-L-Phenylalanine

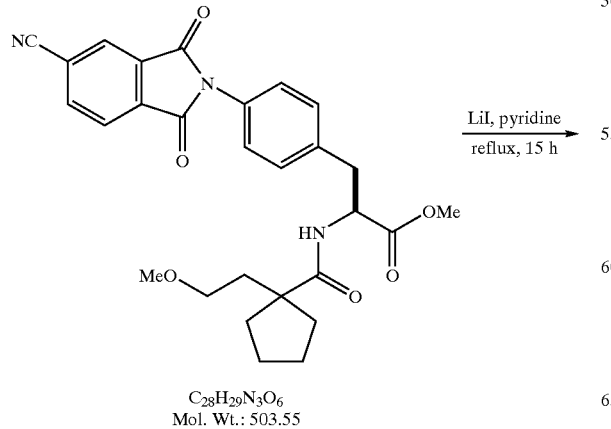

To a mixture of 4-(5-cyano-1,3-dioxo-2H-isoindol-2-yl)-N-[[1-(2-methoxyethyl)cyclopentyl]carbonyl]-L-phenylalanine methyl ester (0.3 mmol, 151 mg) and lithium iodide (3.0 mmol, 397 mg) was added pyridine (6 mL) at room temperature. The solution was refluxed for 15 h at which time TLC analysis of the mixutre indicated the absence of starting material. Then, it was cooled to room temperature and diluted with water (15 mL) and the bulk of the pyridine was removed by concentration under reduced pressure. The residue was extracted with ether (2×15 mL) to remove any neutral impurities. The aqueous layer was acidified with 1N HCl and the precipitated white solid was collected by filtration and washed with 20 mL of water and 20 mL of hexane. After air-drying, the crude product was purified by reverse phase HPLC to afford 50 mg (34%) of a white solid, mp 143–146° C. HR MS (C27H27N3O6): Obs mass, 490.1990. Calcd mass, 490.1978 (M+H).

Example 372

4-[[(2,4-Dimethyl-3-pyridinyl)carbonyl]amino]-N-[[1-[4-(methylsulfonyl)-butyl]cyclopentyl]carbonyl]-L-phenylalanine ethyl ester was prepared using the general method described in example 123 starting with 4-[[(2,4-dimethylpyridin-3-yl)carbonyl]amino]-N-[[1-[4-(methylsulfonyl)butyl]cyclopentyl]carbonyl]-L-phenylalanine.

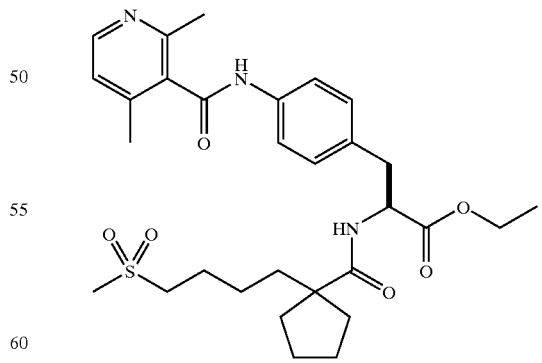

Example 373

4-[[(2,6-Dichlorophenyl)carbonyl]amino]-N-[[1-(2-methoxyethyl)cyclopentyl]-carbonyl]-L-phenylalanine ethyl ester was prepared using the general method described in example 123 starting with 4-[[(2,6-dichlorophenyl)carbonyl]amino]-N-[[1-(2-methoxyethyl)cyclopernyl]carbonyl]-L-phenylalanine.

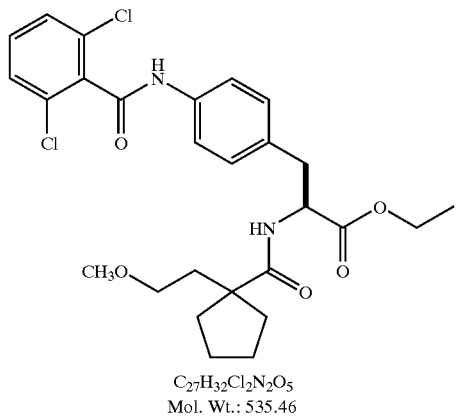

C₂₇H₃₂Cl₂N₂O₅
Mol. Wt.: 535.46

Example 374

4-[[(2,6-Dichlorophenyl)carbonyl]amino]-N-[[-1-[4-(methylsulfonyl)butyl]-cyclopentyl]carbonyl]-L-phenylalanine ethyl ester was prepared using the general method described in example 123 starting with 4-[[(2,6-dichlorophenyl)carbonyl]amino]-N-[[-1-[4-(methylsulfonyl)butyl]cyclopentyl]carbonyl]-L-phenylalanine.

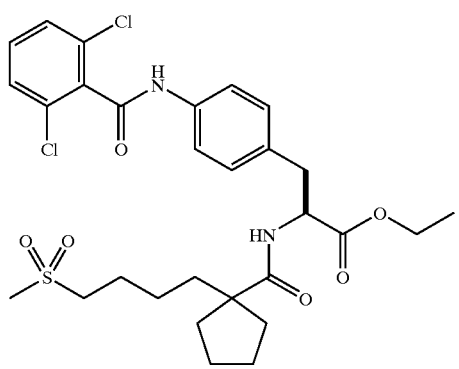

Example 375

4-[(4R)-3-acetyl-4-(phenylmethyl)-5-oxo-2-phenyl-1-imidazolidinyl]-N-[[1-[4-(methylsulfonyl)butyl]cyclopentyl]carbonyl]-L-phenylalanine ethyl ester was prepared using the method described in example 123 from 4-[(4R)-3-acetyl-4-(phenylmethyl)-5-oxo-2-phenyl-1-imidazolidinyl]-N-[[1-[4-(methylsulfonyl)butyl]cyclopentyl]carbonyl]-L-phenylalanine.

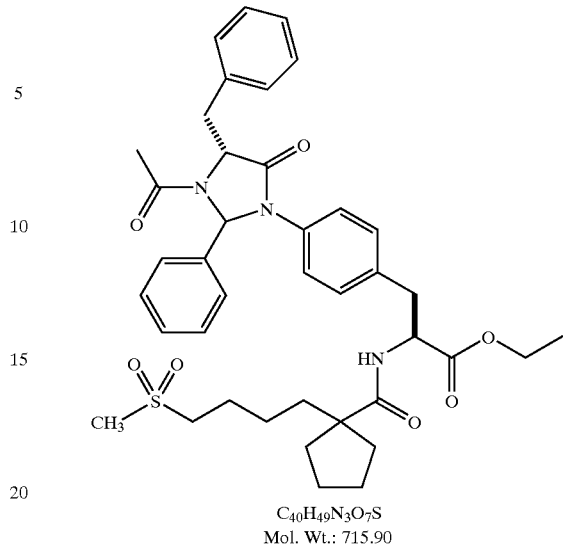

C₄₀H₄₉N₃O₇S
Mol. Wt.: 715.90

Example 377

4-[[(2,6-Dichlorophenyl)carbonyl]amino]-N-[[1-(2-methoxyethyl)cyclopentyl]-carbonyl]-L-phenylalanine 2-(4-morpholino)ethyl ester was prepared using the general method described in example 277 starting with 4-[[(2,6-dichlorophenyl)carbonyl]amino]-N-[[1-(2-methoxyethyl)cyclopentyl]carbonyl]-L-phenylalanine.

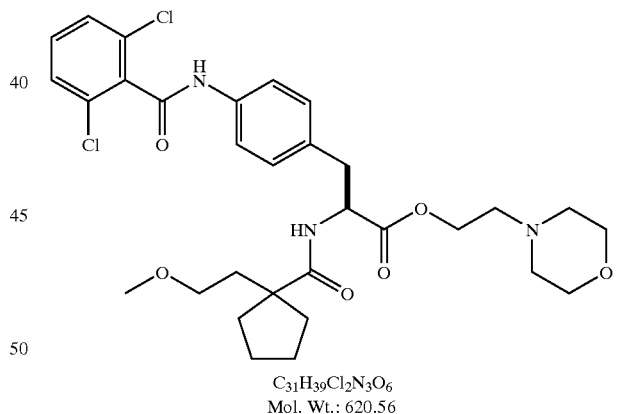

C₃₁H₃₉Cl₂N₃O₆
Mol. Wt.: 620.56

Example 378

4-[(2,4-Dimethyl-3-pyridinyl)carbonyl]amino]-N-1-[(4-methylsulfonyl)butyl]-cyclopentyl]carbonyl-L-phenylalanine 2-(4-morpholino)ethyl ester was prepared from 4-[(2,4-dimethyl-3-pyridinyl)carbonyl]amnino]-N-1-[(4-methylsulfonyl)butyl]cyclopentyl]carbonyl-L-phenylalanine using the procedure described in example 277.

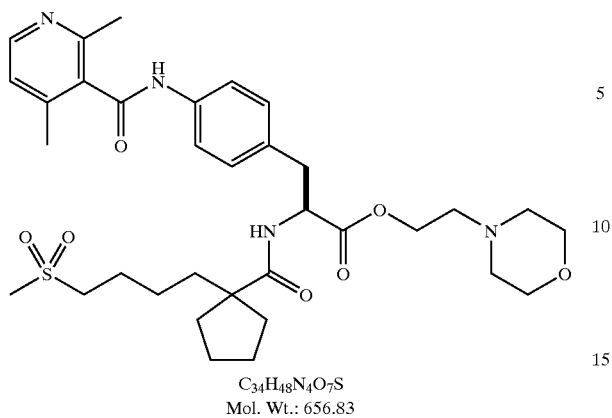

Example 379

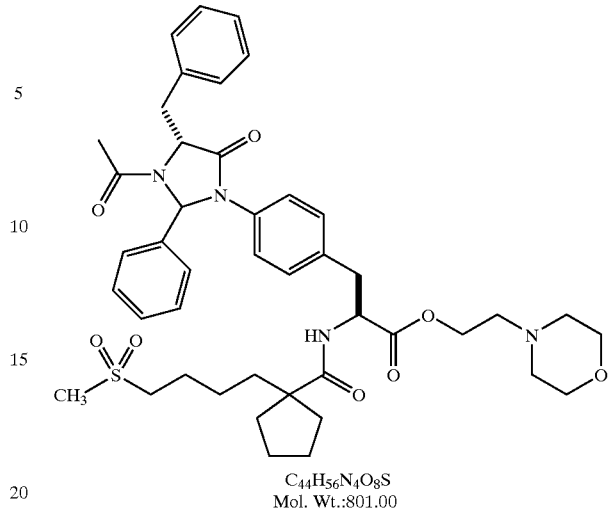

Example 380a

4-[[(2,6-dichlorophenyl)carbonyl]amino]-N-[[1-[4-(methylsulfonyl)butyl]-cyclopentyl]carbonyl]-L-phenylalanine 2-(4-morpholino)ethyl ester was prepared from 4-[[(2,6-dichlorophenyl)carbonyl]amino]-N-[[1-[4-(methylsulfonyl)butyl]cyclopentyl]carbonyl]-L-phenylalanine using the procedure described in example 277.

4-[[(2,6-Dichlorophenyl)carbonyl]amino]-N-[[1-(2-methoxyethyl)cyclopentyl-]carbonyl]-L-phenylalanine 2-(N,N-diethylamino)ethyl ester was prepared using the general method described in example 277 starting with 4-[[(2,6-dichlorophenyl)carbonyl]amino]-N-[[1-(2-methoxyethyl)cyclopentyl]carbonyl]-L-phenylalanine.

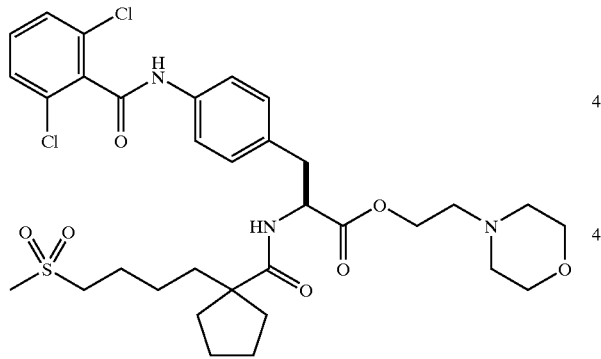

Example 380

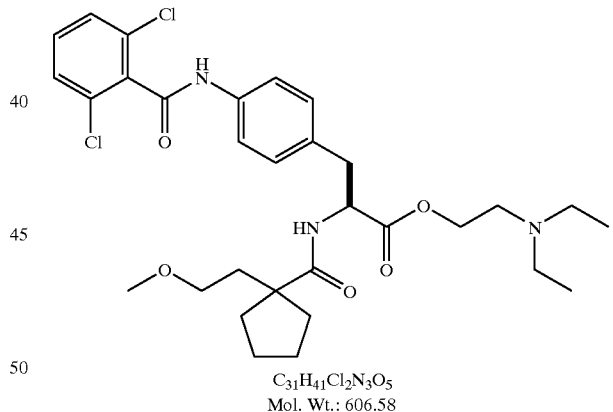

Example 381

4-[(4R)-3-acetyl-4-(phenylmethyl)-5-oxo-2-phenyl-1-imidazolidinyl]-N-[[1-[4-(methylsulfonyl)butyl] cyclopentyl]carbonyl]-L-phenylalanine 2-(4-morpholino) ethyl ester was prepared from 4-[(4R)-3-acetyl-4-(phenylmethyl)-5-oxo-2-phenyl-1-imidazolidinyl]-N-[[1-[4-(methylsulfonyl)butyl]cyclopentyl]carbonyl]-L-phenylalanine using the procedure described in example 277.

4-[(2,6-Dimethyl-4-trifluoromethyl-3-pyridinyl) carbonyl]amino]-N-[[1-[4-(methylsulfonyl)butyl] cyclopentyl]carbonyl]-L-phenylalanine was prepared from 4-amino-N-[[1-[4-(methylsulfonyl)butyl]cyclopentyl] carbonyl]-L-phenylalanine methyl ester and 2,6-dimethyl-4-trifluoromethyl-3-pyridine carboxylic acid using the general procedure described in example 364.

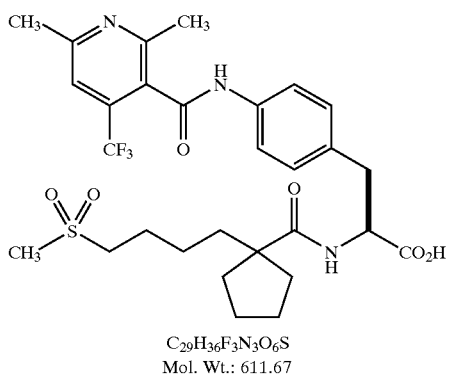

C29H36F3N3O6S
Mol. Wt.: 611.67

Example 382

Preparation of 4-Trifluoromethyl-5-Pyrimidine Carboxylic Acid

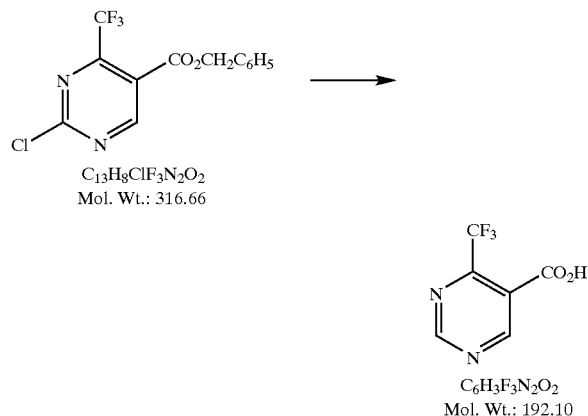

A solution of 2-chloro-4-trifluoromethyl-5-pyrimidine carboxylic acid benzyl ester in cyclohexene (3 mL, 30 mmole) and ethanol (9 mL) was treated with 10% palladium on carbon and the resulting mixture was heated to reflux for 1 h. The mixture was cooled to room temperature and filtered through a pad of Celite and concentrated to give a quantitative yield of a gummy, off-white solid. LR ES MS (C6H3F3N2O2): 191 (M–H).

Examples 383–387

The 4-[[(heteroaryl)carbonyl]amino]-N-[[1-[4-(methylsulfonyl)butyl]-cyclopentyl]carbonyl]-L-phenylalanine derivatives shown in the table below were prepared from 4-amino-N-[[1-[4-(methylsulfonyl)butyl]cyclopentyl]carbonyl]-L-phenylalanine methyl ester and the appropriate heteroaromatic carboxylic acids using the general procedure described in example 34

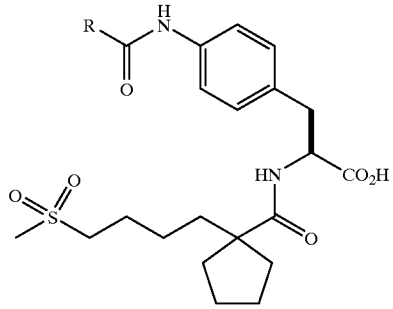

| Example | R | Yield % | HRMS1 Formula | calcd. | found | IC50 nM |
|---|---|---|---|---|---|---|
| 383 | ![CF3-pyrimidine] | | | | | |
| 384 | ![isopropyl-dimethylthiazole] | | | | | |
| 385 | ![trimethylisoxazole] | | | | | |
| 386 | ![phenyl-dimethyltriazole] | | | | | |
| 387 | ![dimethylpyrazolopyrimidine] | | | | | |

Example 388

Preparation of 4-Amino-N-Methyl-N-[[1-(2-Methoxyethyl)Cyclopentyl]Carbonyl]-L-Phenylalanine Methyl Ester

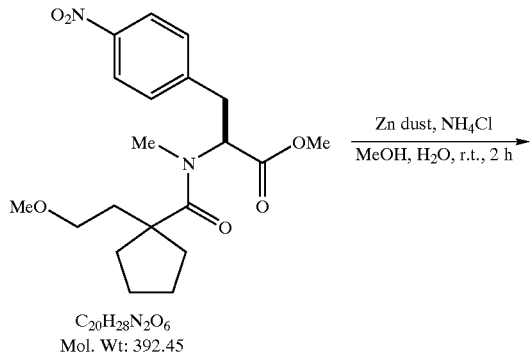

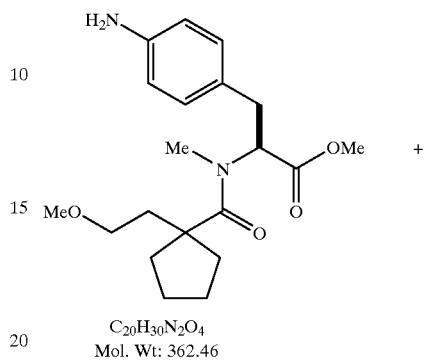

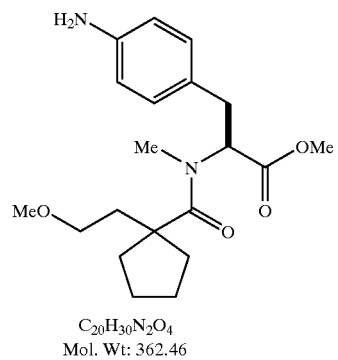

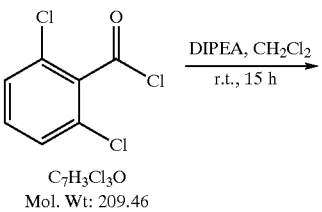

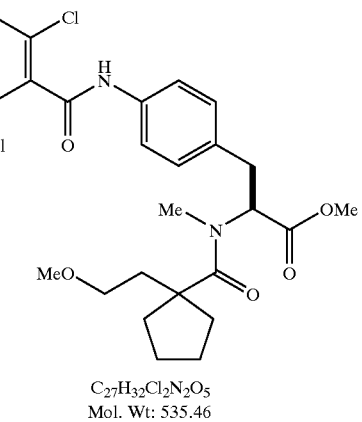

To a mixture of N-[[1-(2-methoxyethyl)cyclopentyl]carbonyl]-N-methyl-4-nitro-L-phenylalanine methyl ester (1.35 mmol, 530 mg), zinc dust (~325 mesh, 13.5 mmol, 0.88 g, 10 equiv.) and ammonium chloride (20.2 mmol, 1.08 g, 15 equiv.) was added methanol (10 mL) and water (5 mL) at room temperature. After addition of water, the reaction was exothermic. The suspension was stirred for 2 h at room temperature at which time TLC analysis of the mixture indicated the absence of starting material, the reaction mixture was filtered through a pad of celite and the filter cake was washed with methanol (50 mL) and water (40 mL). The mixture was concentrated and extracted with ethyl acetate (3×30 mL). The combined extracts were washed with brine solution (30 mL) and dried over anhydrous magnesium sulfate. Filtration of the drying agent and concentration of the solvent afforded 490 mg (100%) of a yellow oil. HR MS ($C_{20}H_{30}N_2O_4$): Obs. mass, 362.2202. Calcd. mass, 362.2206 (M+).

Example 389

4-[[(2,6-Dichlorophenyl)carbonyl]amino]-N-methyl-N-[[1-(2-methoxyethyl)-cyclopenyl]carbonyl]-L-phenylalanine methyl ester was prepared from of 4-amino-N-methyl-N-[[1-(2-methoxyethyl)cyclopentyl]carbonyl]-L-phenylalanine methyl ester and 1-(2-methoxyethyl)cyclopentane carboxylic acid using the general procedure described in example 44 to afford a 64% yield of a white solid. HR MS ($C_{27}H_{32}Cl_2N_2O_5$): Obs. mass, 535.1742. Calcd. mass, 535.1766 (M+H).

Example 390

4-[[(2,6-dichlorophenyl)carbonyl]amino]-N-methyl-N-[[1-(2-methoxyethyl)-cyclopentyl]carbonyl]-L-phenylalanine was prepared from 4-[[(2,6-dichlorophenyl)carbonyl-amino]-N-[[1-(2-methoxyethyl)cyclopentyl]carbonyl]-N-methyl-L-phenylalanine methyl ester using the general procedure described in example 47 to give a 43% yield of a white solid. HR MS ($C_{26}H_{30}Cl_2N_2O_5$): Obs. mass, 519.1453. Calcd mass, 519.1454 (M–H).

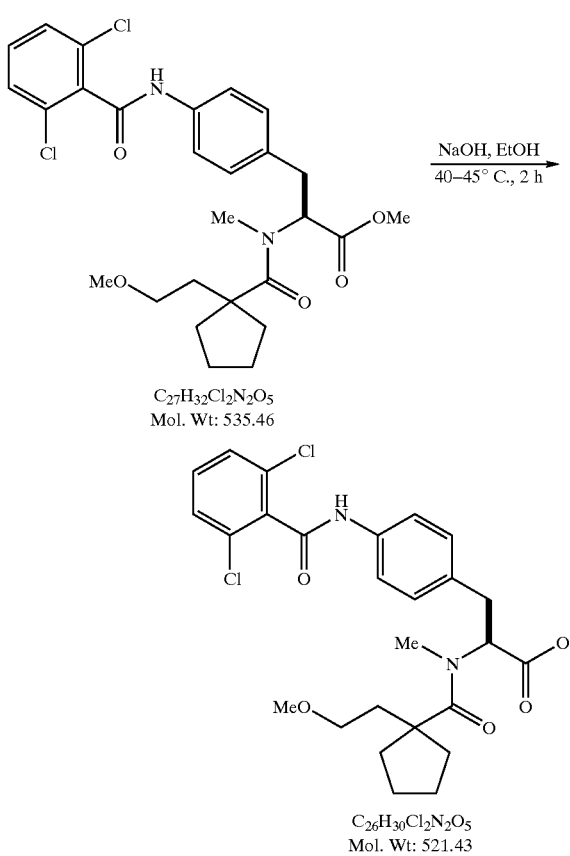

Example 391

Preparation of 1-(2-Methoxyethyl)Cyclopentane Carboxylate Methyl Ester

To a solution of diisopropylamine (21 mL, 150 mmol) in THF (100 mL) was added dropwise a solution of n-butyl lithium (58 mL, 145 mmol) in hexanes at −10° C. while maintaining the temperature below 0° C. After addition, the solution was stirred for 30 min at 0° C. To this, a solution of methyl cyclopentane carboxylate (12.8 g, 100 mmol) in THF (20 mL) was added dropwise at −70° C. maintaining the internal temperature between −60 to −70° C. After addition, the reaction mixture was stirred for 30 min at −50 to −60° C. Then, a solution of 2-methoxy ethyl bromide (12.5 g, 90 mmol) in THF (20 mL) was added dropwise and the light brown suspension was stirred for 30 min at −60 to −70° C. Then, it was allowed to warm to room temperature and stirred overnight. The reaction mixture was poured into a saturated solution of ammonium chloride (250 mL) and was extracted with ether (2×100 mL). The combined extracts were washed with a saturated solution of sodium chloride (100 mL) and dried over anhydrous magnesium sulfate. After filtration of the drying agent, the solution was concentrated under vacuum to afford 16.55 g of crude product as a black liquid. Distillation at 70–75° C./1.5 mm Hg afforded 7.98 g of a colorless oil and a further 2.76 g as a light yellow oil for a total yield of 10.74 g (64%). HR MS (C10H18O3): Obs. mass, 186.1257. Calcd. mass, 186.1256 (M+).

Example 392

Preparation of 1-(2-Methoxyethyl)Cyclopentane Carboxylic Acid

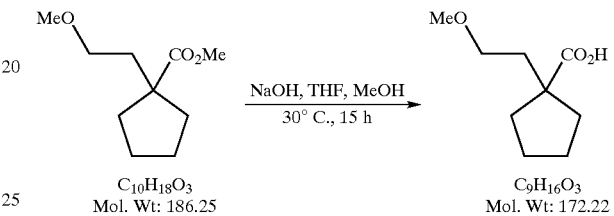

To a solution of 1-(2-methoxyethyl)cyclopentane carboxylate methyl ester (7.987 g, 42.9 mmol) in a mixture of THF (170 mL) and methanol (170 mL) was added 1 N sodium hydroxide (170 mL). The mixture was heated to 40° C. for 2 h at which point TLC (ether:hexane 1:1, iodine chamber) analysis indicated the absence of starting material and the mixture was cooled to room temperature. The solvent was removed under vacuum and the residue was diluted with water (100 mL) and was extracted with ether (2×200 mL) to remove any neutral impurities. The basic aqueous layer was acidified with 1 N hydrochloric acid and the product was extracted with ethyl acetate (2×100 mL). The combined extracts were washed with brine solution and dried over sodium sulfate. After filtration of the drying agent, the solution was concentrated under vacuum and the residue was dried under high vacuum to afford 6.183 g (82%) of a light brown oil. HR MS (C9H16O3): Obs. mass, 172.0154. Calcd. mass, 172.0126 (M+).

Example 393

Preparation of N-[(1,1-Dimethylethoxy)Carbonyl]-4-Nitro-L-Phenylalanine Methyl Ester

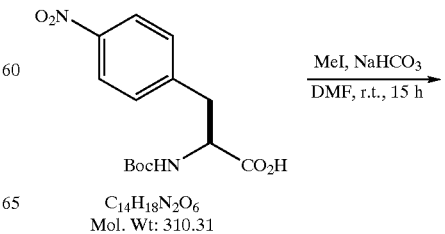

-continued

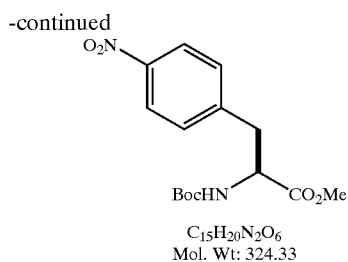

C₁₅H₂₀N₂O₆
Mol. Wt: 324.33

To suspesion of of 4-nitro-N-[(1,1-dimethylethoxy) carbonyl]-L-phenylalanine (226.2 mmol, 70.2 g) and sodium carbonate (1.13 mol, 95 g) in DMF (500 mL) was added methyl iodide (1.13 mol, 70.4 InL) at room temperature. The suspesion was stirred for 15 h at room temperature at this time TLC analysis of the mixture indicated the absence of starting acid and the excess methyl iodide and some DMF were removed under high vacuum. The residue was poured into water (2 L) and stirred at room temperature as a precipitate formed slowly over 72 h. The precipitated solids were collected by filtration and washed with water (2 L). After air and vacuum drying, 72 g (98%) of a light yellow solid, mp 95–96° C. were obtained. $^1$H-NMR, (DMSO-d₆) (400 MHz) δ 8.16 (d, 2H, J=20 Hz), 7.53 (d, 2H, J=20 Hz), 7.39 (d, 1H, J=22 Hz), 4.26–4.28 (m, 1H), 3.6 (s, 3H), 2.96–3.19 (m, 2H), 1.25 (s, 9H). $^{13}$C NMR, CDCl₃ (100 Mhz) δ 172.04, 155.29, 146.27, 145.96, 130.48, 123.18, 78.36, 54.44, 51.9, 36.1, 27.99. HR MS: Obs. mass, 325.1404. Calcd. mass, 325.1400 (M+H).

Example 394

Preparation of of 4-Amino-N-[(1,1-Dimethylethoxy)Carbonyl]-L-Phenylalanine Methyl Ester

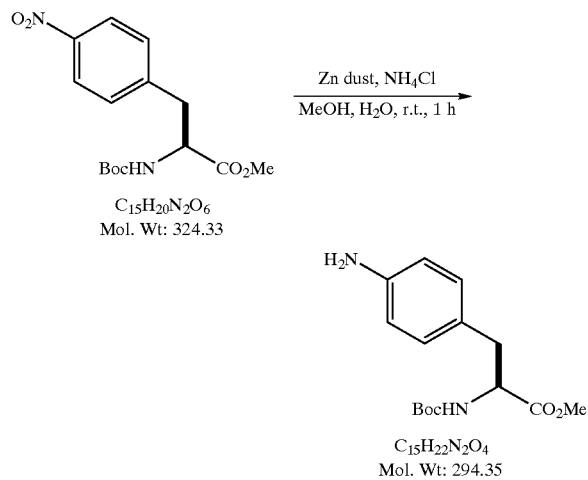

To a mixture of of N-[(1,1-dimethylethoxy)carbonyl]-4-nitro-L-phenylalanine methyl ester (222 mmol, 72 g), zinc dust (~325 mesh, 2.2 mol, 145.2 g, 10 equiv) and ammonium chloride (3.3 mol, 178.1 g, 15 equiv) was added methanol (1 L) and water (500 mL) at room temperature. After addition of water, an exothermic reaction ensued and the internal temperature rose to 45 to 50° C. The suspension was stirred for 30 min to 1 h at room temperature, at which time TLC analysis of the mixture indicated the absence of starting material, and the reaction mixture was filtered through a pad of celite and the filtered cake was washed with methanol (1 L) and water (500 mL). Concentration to remove most of the methanol afforded white solid which was collected by filtration and washed with water. After air drying, 65.5 g of a white solid, mp 86–89° C. was obtained. $^1$H-NMR (DMSO-d₆) (400 MHz) δ 6.9 (d, 2H, J=20 Hz), 6.62 (d, 2H, J=20 Hz), 7.39 (d, 1H, J=22 Hz), 4.26–4.28 (m, 1H), 3.68 (s, 3H), 2.96–3.19 (m, 2H), 1.25 (s, 9H). HR MS: Obs. mass, 294.1614. Calcd. mass, 294.1621 (M+).

Example 395

Preparation 4-[[(2,6-Dichlorophenyl)Carbonyl] Amino]-N-[(1,1-Dimethylethoxy)Carbonyl]-L-Phenylalanine Methyl Ester

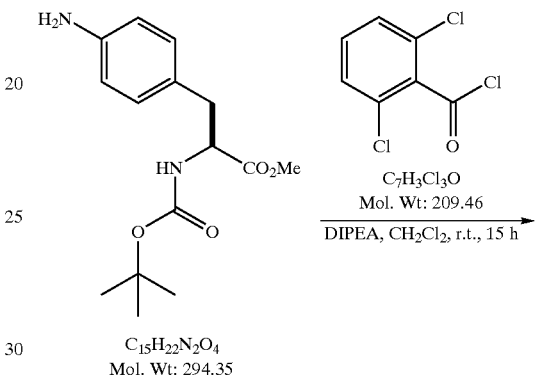

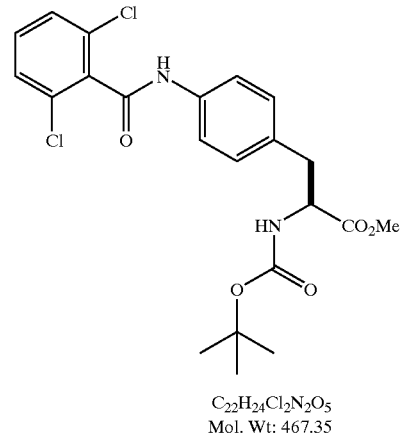

C₂₂H₂₄Cl₂N₂O₅
Mol. Wt: 467.35

To a solution of 4-amino-N-[(1,1-dimethylethoxy) carbonyl]-L-phenylalanine methyl ester (127.6 mmol, 37.57 g) and 2,6-dichlorobenzoyl chloride (140.6 mmol, 29.45 g) in dichloromethane (350 mL) was added diisopropylethylamine (192 mmol, 33.4 mL) at room temperature. The brown solution was stirred for 15 h at room temperature to afford a white suspension. At this time, TLC analysis of the mixture indicated the absence of starting material. The solids were collected by filtration and were washed with dichloromethane (150 mL) and air dried to obtain 52.75 g (88.4%) of a white solid: mp 192–194° C. $^1$H NMR (DMSO-d₆) (400 MHz) δ 10.68 (s, 1H), 7.47–7.6 (m, 5H), 7.2–7.29 (m, 3H), 4.12–4.17 (m, 1H), 3.62 (s, 3H), 2.79–2.99 (m, 2H), 1.33 (s, 9H), $^{13}$C NMR, CDCl₃ (100 Mhz) d 172.49, 161.82, 155.37, 136.99, 136.36, 131.28, 131.16, 129.48, 128.19, 119.31, 78.27, 55.3, 51.76, 35.9, 27.77. HR MS: Obs. mass, 466.1069. Calcd. mass, 466.1062).

Example 396

Preparation of 4-[[(2,6-Dichlorophenyl)Carbonyl]Amino]-L-Phenylalanine Methyl Ester Hydrochloride Salt

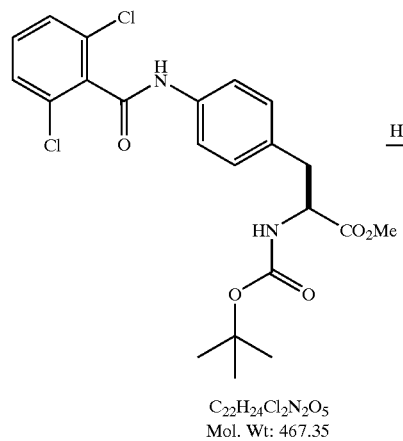

C22H24Cl2N2O5
Mol. Wt: 467.35

HCl in dioxane, r.t., 2 h

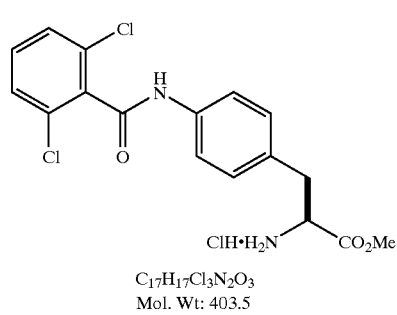

C17H17Cl3N2O3
Mol. Wt: 403.5

Solid 4-[[(2,6-dichlorophenyl)carbonyl]amino]-N-[(1,1-dimethylethoxy)carbonyl]-L-phenyl-alanine methyl ester (92.97 mmol, 43.45 g) in dioxane (90 mL) was treated with 166 mL of 4.0 N hydrochloric acid in dioxane at room temperature. After 5 minutes, the solids went into solution and the mixture was stirred for 2 h. The reaction mixture was concentrated a yellow syrup and 250 mL of ethyl ether was added. A gum was formed which was dissolved in THF (100 mL) and methanol (100 mL). The solvent was removed under vacuum to obtain 43.7 (100%) of a white solid: mp 180–195° C. $^1$H NMR (DMSO-$d_6$) (400 MHz) δ 10.81 (s, 1H), 7.76 (d, 2H, J=22 Hz), 7.58 (d, 2H, J=18 Hz), 7.51 (t, 1H, J=15 Hz), 7.24 (d, 2H, J=22 Hz), 4.23–4.26 (m, 1H), 3.56 (s, 3H), 3.14–3.17 (m, 2H). $^{13}$C NMR, CDCl$_3$ (100 Mhz) d 169.03, 161.72, 137.56, 136.11, 131.19, 130.95, 129.93, 129.79, 128.06, 119.46, 53.17, 52.6, 35.13. HR MS (C17H16Cl2N2O3•HCl): Obs. mass, 367.0611. Calcd. mass, 367.0616 (M+H).

Example 397

Preparation of 4-[[(2,6-Dichlorophenyl)Carbonyl]Amino]-N-[[1-(2-Methoxyethyl)-Cyclopentyl]Carbonyl]-L-Phenylalanine Methyl Ester

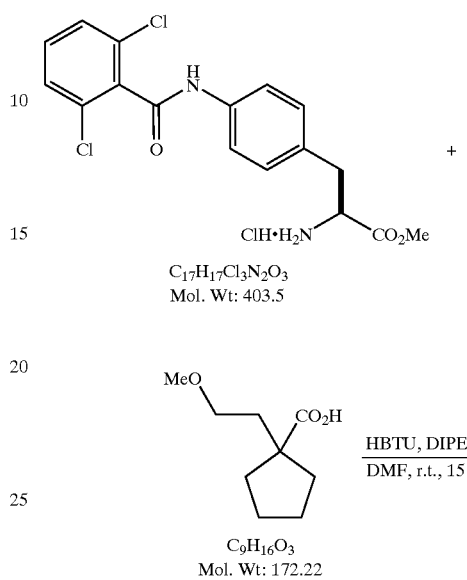

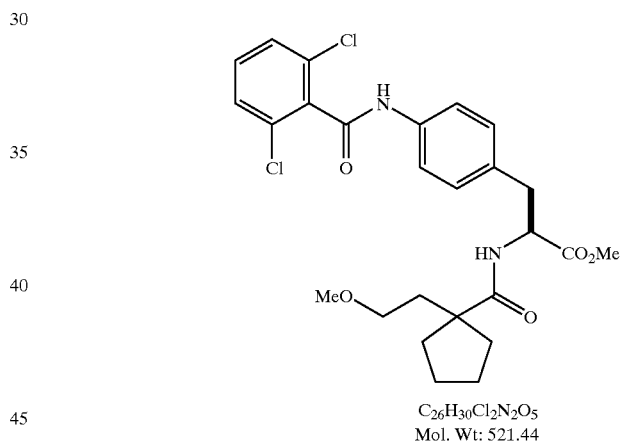

To a solution of 4-[[(2,6-dichlorophenyl)carbonyl]amino]-L-phenylalanine methyl ester hydrochloride salt (43.03 mmol, 11.75 g) and 1-(2-methoxyethyl)cyclopentane carboxylic acid (43.5 mmol, 7.5 g) in DMF (130 mL) was added HBTU (43.5 mmol, 16.5 g) and diisopropylethylamine (108.8 mmol, 19.02 mL) at room temperature. The clear solution was stirred 23 h at room temperature and was diluted with 200 mL of ethyl acetate. The ethyl acetate layer was washed successively with 0.5 N hydrochloric acid (2×100 mL), saturated sodium bicarbonate solution (2×100 mL), brine solution and was dried over anhydrous magnesium sulfate. Filtration of the drying agent and concentration of the solvent gave 18.86 g (84%) of a white solid, mp 85–87° C. $^1$H NMR (DMSO-$d_6$) (400 MHz) δ 10.65 (s, 1H), 7.88 (d, 1H, J=19 Hz), 7.47–7.59 (m, 5H), 7.21 (d, 2H, J=19 Hz), 4.47–4.53 (m, 1H), 3.64 (s, 3H), 2.88–3.1 (m, 7H), 1.76–1.98 (m, 4H), 1.23–1.47 (m, 6H). HR MS C26H30Cl2N2O5): Obs. mass, 521.1586. Calcd. mass, 521.1610 (M+H).

Example 398

Preparation of 4-[[(2,6-Dichlorophenyl)Carbonyl]Amino]-N-[[1-(2-Methoxyethyl)Cyclopentyl]Carbonyl]-L-Phenylalanine

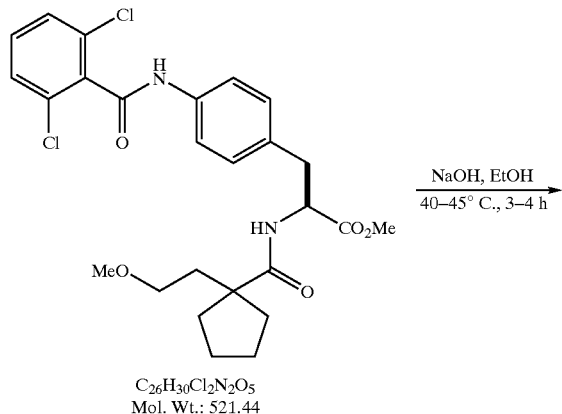

To a suspension of 4-[[(2,6-dichlorophenyl)carbonyl]amino]-N-[[1-(2-methoxyethyl)-cyclopentyl]carbonyl]-L-phenylalanine methyl ester (20.17 mmol, 10.52 g) in ethanol (80 mL) and tetrahydrofuran (10 mL) was added aqueous 1.0 N sodium hydroxide (80 mL) at room temperature. The mixture was heated to 50° C. and the resulting clear solution was stirred overnight. Then, the ethanol solution was concentrated and diluted with 50 mL of water and was extracted with 200 mL of ether to remove neutral impurities. The aqueous layer was acidified with 1N HCl and the precipitated white solid was collected by filtration and washed with 200 mL of water and 200 mL of hexane. After air-drying, 8.4 g (82%) of as a white solid: mp 136–140° C. was obtained. $^1$H NMR, DMSO-d$_6$ (400 MHz) δ 10.64 (s, 1H), 7.73 (d, 1H, J=22 Hz), 7.46–7.59 (m, 5H), 7.22 (d, 2H, J=22 Hz), 4.43–4.48 (m, 1H), 2.87–3.11 (m, 7H), 1.76–2.01 (m, 4H), 1.23–1.47 (m, 6H). HR MS (C25H28Cl2N2O5): Obs. mass, 507.1464. Calcd. mass, 507.1454 (M+H).

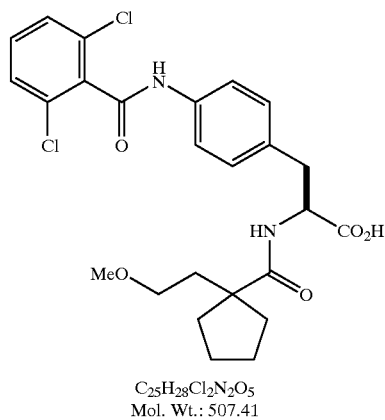

Example 399

Preparation of 3-(1-Methyltetrazol-5-yl)Benzyl Chloride

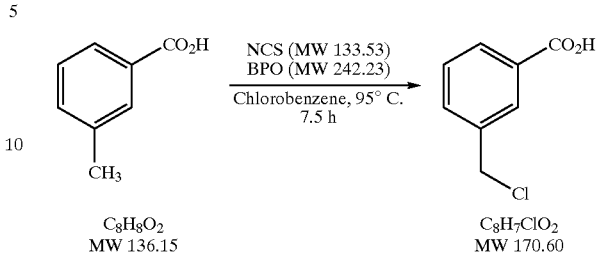

Preparation of 3-chloromethylbenzoic Acid.

A 2 L, three-necked, round bottom flask equipped with a mechanical stirrer, thermometer and condenser with an open end (no nitrogen inlet tube was connected to avoid pressure build-up in the apparatus) was charged with 109 g (800 mmol) of m-toluic acid and 320 mL of chlorobenzene. The mixture was heated to ca. 90° C. with a steam bath to give a homogeneous solution and 53.4 g (400 mmol, 0.5 equiv) of N-chlorosuccinimide (NCS) and 800 mg (3.3 mmol) of benzoyl peroxide (BPO) were added. The yellow solution was stirred at ca. 95° C. for 2.5 h. Then, 26.7 g (200 mmol, 0.25 equiv) of NCS and 400 mg (1.65 mmol) of BPO were added and the mixture was stirred at 95° C. for 2.5 h. Then, a further 26.7 g (200 mmol, 0.25 equiv) of NCS and 400 mg (1.65 mmol) of BPO were added and the mixture was stirred at 95° C. for 2.5 h. To the reaction mixture was added 480 mL of water and the resulting suspension was allowed to cool to room temperature with stirring overnight. To the yellow slurry was added 480 mL of hexane. The resulting suspension was stirred at room temperature for 30 min, then filtered through a coarse sintered glass filter. The collected solid was washed thoroughly with 2×130 mL of water and then with 2×130 mL of hexane, and dried by suction for 2.5 h. The solid was then suspended in 800 mL of water and the mixture was heated on a steam bath for 30 min. After standing at room temperature overnight, the white solid was collected by filtration and dried by suction for 1.5 h. Further drying at 55° C. under high vacuum overnight yielded 73.7 g (54.0%) of 3-chloromethylbenzoic acid; mp 134–136° C.

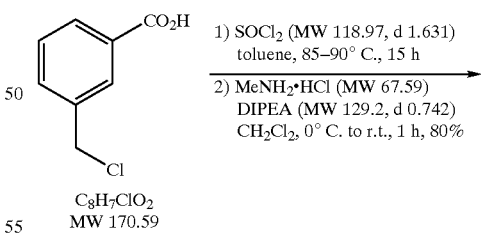

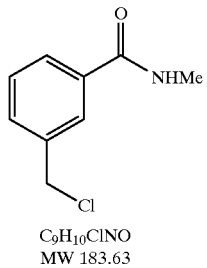

Preparation of 3-(chloromethyl)-N-methylbenzamide.

A 250 mL, round bottom flask equipped with a magnetic stirrer, reflux condenser and calcium chloride drying tube was charged with 34.1 g (200 mmol) of 3-chloromethylbenzoic acid and 125 mL of toluene (dried over molecular sieves 4A). To this suspension was added 21.9 mL (300 mmol) of thoinyl chloride and the mixture was heated to 85–90° C. for 15 h. While heating, evolution of gas, presumably hydrogen chloride and sulfur dioxide, was observed. The reaction mixture was cooled to room temperature and excess thionyl chloride and toluene were removed under vacuum. The resulting oily residue was azeotroped with 100 mL of toluene, then dried under high vacuum for 1 h to give the crude acid chloride.

A 1 L, three necked, round bottom flask equipped with a magnetic stirrer, addition funnel, thermometer and argon bubbler was charged with the crude acid chloride obtained above, and 400 mL of dichloromethane (dried over molecular sieves 4A). After the solution was cooled to −5 to 0° C. (using an ice-sodium chloride bath), 14.9 g (220 mmol) of methylamine hydrochloride was added in one portion. To this mixture was added 69.6 mL (400 mmol) of diisopropylethylamine (DIPEA) dropwise over 15–20 min, while maintaining the temperature of the reaction mixture below 2° C. After completion of the addition, the mixture was stirred for 45 min at 0 to 5° C., then allowed to warm to room temperature. After stirring for 15 min at room temperature, TLC analysis indicated complete reaction. The reaction mixture was diluted with 250 mL of water, and stirred for 5 minutes. The two layers were separated and the aqueous phase was extracted with 2×100 mL of dichloromethane. The combined organic layers were washed successively with 300 mL of water, and 300 mL of saturated sodium chloride solution. After drying over anhydrous magnesium sulfate, the solution was concentrated by rotary evaporation under house vacuum. The residue was further dried in vacuo to give a light yellow solid. This solid was dissolved in 110 mL of toluene at ~60–70° C. The resulting solution was allowed to cool to room temperature and seeded with crystals of product, then stored in a refrigerator overnight. The resulting precipitate was collected by filtration and washed with 30 mL of hexane. After drying under high vacuum, 29.4 g (80.0% yield) of 3-(chloromethyl)-N-methylbenzamide was obtained as a light yellow solid; mp 59–61° C.

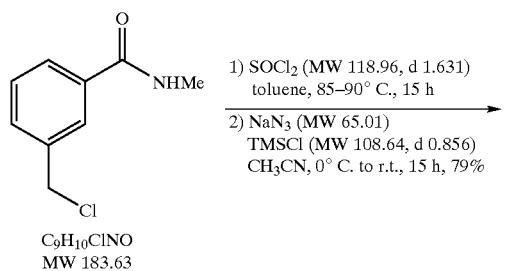

was charged with 27.2 g (148 mmol) of 3-(chloromethyl)-N-methylbenzamide, 100 mL of toluene (dried over molecular sieves 4A). To this solution was added 16.2 mL (222 mmol) of thionyl chloride and the mixture was heated to 85–90° C. for 15 h (Note 6). While heating, evolution of gas, presumably hydrogen chloride and sulfur dioxide, was observed. After cooling to room temperature, excess thionyl chloride and toluene were removed under vacuum. The resulting residue was azeotroped with 100 mL of toluene, then dried under high vacuum for 1 h to give the crude imidoyl chloride. A 500 mL, three necked, round bottom flask equipped with a magnetic stirrer, thermometer and argon bubbler was charged with 11.6 g (178 mmol) of sodium azide and 140 mL of acetonitrile (freshly opened bottle). To this suspension was added 23.7 mL (187 mmol) of chlorotrimethylsilane and the mixture was stirred for 1.5 h at room temperature. After cooling to 0° C., a solution of the crude imidoyl chloride, prepared above, in 40 mL of acetonitrile was added. This heterogeneous mixture was stirred for 1–2 h at 0° C., then allowed to warm to room temperature and stirred for 15 h. TLC analysis indicated complete reaction. The reaction mixture was quenched by the addition of 150 mL of water, then diluted with 150 mL of ethyl acetate. The two layers were separated and the aqueous phase was extracted with 2×100 mL of ethyl acetate. The combined organic layers were washed successively with 200 mL of water, and 200 mL of saturated sodium chloride solution. After drying over anhydrous magnesium sulfate, the solution was concentrated. The residue was further dried in vacuo to give a light yellow solid (29.7 g). This solid was dissolved in 220 mL of 5.5:4.5 hexane-:ethyl acetate at ~60–70° C. The resultant solution was allowed to cool to room temperature and was seeded with crystals of product, then stored in a refrigerator overnight. The resulting precipitate was collected by filtration and washed with 50 mL of hexane. After drying by suction, 24.5 g (79.5% yield) of 3-(1-methyltetrazol-5-yl)benzyl chloride was obtained as a white amorphous solid; mp 63–65° C.

Example 400

1-[[3-(1-Methyltetrazol-5-yl)phenyl]methyl]cyclobutane carboxylic acid methyl ester was prepared from 3-(1-methyltetrazol-5-yl)benzyl chloride using the general method described in example 7 to give a 77% yield of a viscous oil. HR MS: obs. mass, 287.1514. Calcd. masss, 287.1508 (M+H).

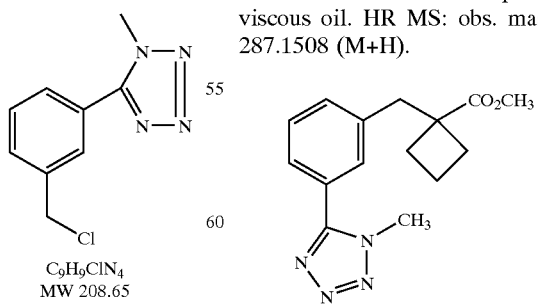

Preparation of 3-(1-methyltetrazol-5-yl)benzyl Chloride.

A 250 mL round bottom flask equipped with a magnetic stirrer, reflux condenser and calcium chloride drying tube

Example 401

1-[[3-(1-Methyltetrazol-5-yl)phenyl]methyl]cyclobutane carboxylic acid was prepared from 1-[[3-(1-methyltetrazol-5-yl)phenyl]methyl]cyclobutane carboxylic acid methyl ester using the general procedure described in example 15 to give an 83% yield of a viscous oil. HR MS: obs. mass, 273.1226. Calcd. mass, 273.1238 (M+H)

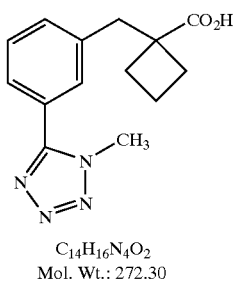

$C_{14}H_{16}N_4O_2$
Mol. Wt.: 272.30

Example 402

4-Amino-N-[[1-[4-(methylsulfonyl)butyl]cyclopentyl]carbonyl]-L-phenylalanine methyl ester was prepared from 4-nitro-L-phenylalanine methyl ester and 4-(methylsulfonyl)butyl]cyclopentane carboxylic acid using the general procedure described in example 26. HR MS (C21H32N2O5S): Obs mass, 425.2121. Calcd mass, 425.2110 (M+H).

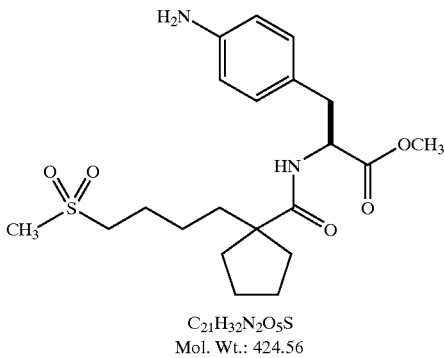

$C_{21}H_{32}N_2O_5S$
Mol. Wt.: 424.56

Example 403

1-(4-Bromobutyl)cyclobutane carboxylic acid methyl ester was prepared from 1,4-dibromobutane and cyclobutane carboxylic acid methyl ester using the general procedure described in example 168.

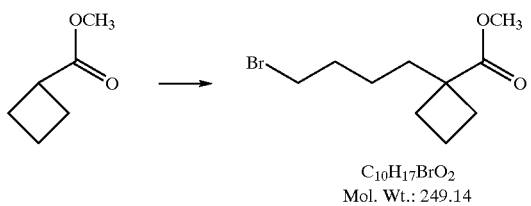

$C_{10}H_{17}BrO_2$
Mol. Wt.: 249.14

Example 404

1-[4-(Methylthio)butyl]cyclobutane carboxylic acid methyl ester was prepared from 1-(4-bromobutyl)cyclobutane carboxylic acid methyl ester and sodium methylmercaptan using the procedure described in example 172.

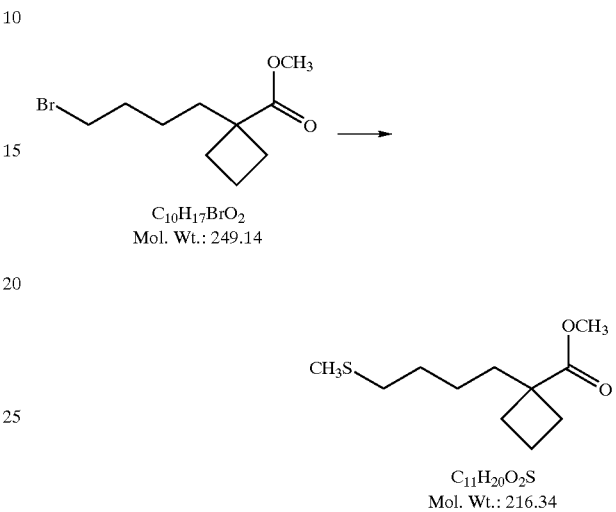

$C_{10}H_{17}BrO_2$
Mol. Wt.: 249.14

$C_{11}H_{20}O_2S$
Mol. Wt.: 216.34

Example 405

1-[4-(methylsulfonyl)butyl]cyclobutane carboxylic acid was prepared from 1-[4-(methylthio)butyl]cyclobutane carboxylic acid methyl ester using the general procedures described in examples 174 and 175.

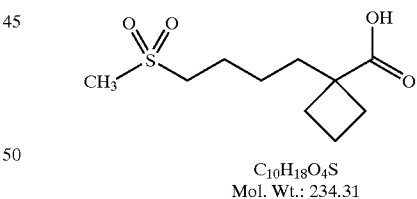

$C_{10}H_{18}O_4S$
Mol. Wt.: 234.31

Example 406

4-[[(2,6-dichlorophenyl)carbonyl]amino]-N-[[1-[4-(methylsulfonyl)butyl]-cylcobutane]carbonyl]-L-phenylalanine was prepared from 4-[[(2,6-dichlorophenyl)-carbonyl]amino]-L-phenylalanine methyl ester and 1-[4-(methylsulfonyl)butyl]cyclobutane carboxylic acid using the procedure described in examples 46 and 47.

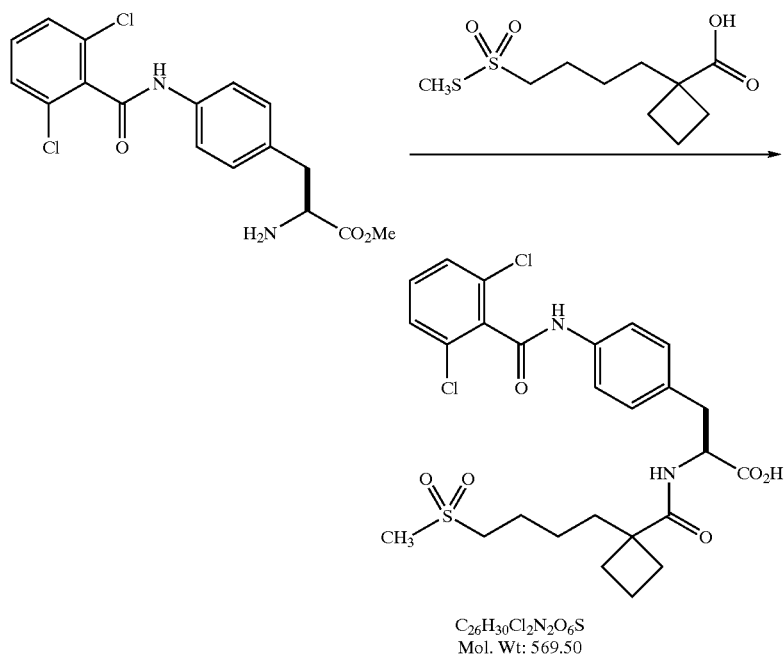

C<sub>26</sub>H<sub>30</sub>Cl<sub>2</sub>N<sub>2</sub>O<sub>6</sub>S
Mol. Wt: 569.50

Example 407

4-[(4R)-3-Acetyl-4-(phenylmethyl)-5-oxo-2-phenyl-1-imidazolidinyl]-N-[(1-phenylcyclopentyl)carbonyl]-L-phenylalanine was prepared from Fmoc-D-phenylalanine, benzaldehyde and 4-amino-N-[(1,1-dimethylethoxy) carbonyl]-L-phenylalanine methyl ester using the general procedure described in example 365.

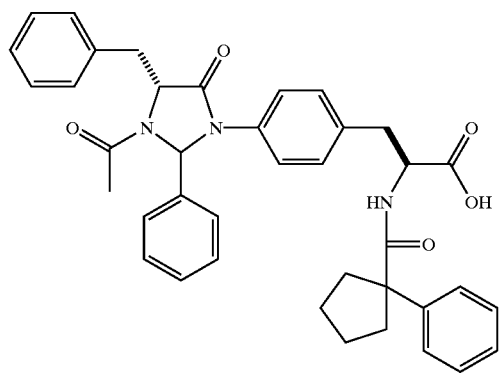

$C_{39}H_{39}N_3O_5$
Mol. Wt: 629.74

Example 408

4-[3-Acetyl-5-oxo-2-[(3-pyridinyl)methyl]-4-phenylmethyl-1-imidazolidinyl]-N-[[1-[4-(methylsulfonyl) butyl]cyclopentyl]carbonyl]-L-phenylalanine methyl ester was prepared from 4-amino-N-[(1,1-dimethylethoxy) carbonyl]-L-phenylalanine methyl ester and Fmoc-D-pyridinylalanine using the general method described in example 365.

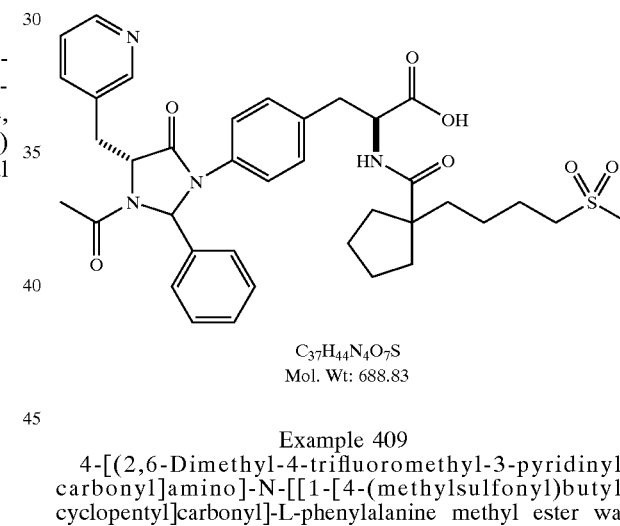

$C_{37}H_{44}N_4O_7S$
Mol. Wt: 688.83

Example 409

4-[(2,6-Dimethyl-4-trifluoromethyl-3-pyridinyl) carbonyl]amino]-N-[[1-[4-(methylsulfonyl)butyl] cyclopentyl]carbonyl]-L-phenylalanine methyl ester was prepared from 4-amino-N-[[1-[4-(methylsulfonyl)butyl] cyclopentyl]carbonyl]-L-phenylalanine methyl ester.

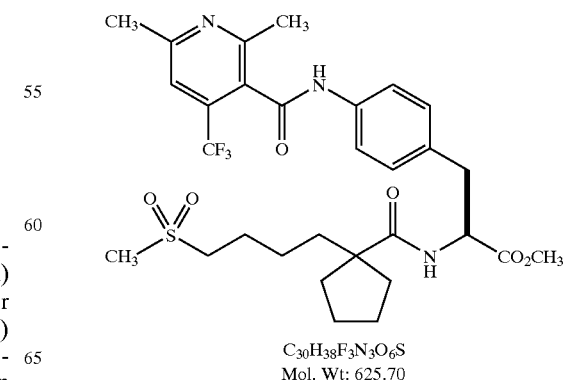

$C_{30}H_{38}F_3N_3O_6S$
Mol. Wt: 625.70

To a solution of 2,6-dimethyl-4-trifluoromethyl-5-pyridinecarboxylic acid (0.42 mmol, 92 mg) in dichloromethane (5 mL) was added 3 drops of DMF and oxalyl chloride (0.57 mmol, 73 mg) at 0° C. (ice bath). The solution was stirred at this temperature for 30 min, warmed to room temperature and stirred for an additional 30 min. Then, the solvent and excess oxalyl chloride was removed under vacuum and the residue was dried under high vacuum and dissoved in 3 mL of ethyl acetate (dried over 4A sieves). The acid chloride solution was then added to a solution of 4-amino-N-[[1-[4-(methylsulfonyl)butyl]cyclopentyl]carbonyl]-L-phenylalanine methyl ester (0.35 mmol, 148 mg) in ethyl acetate (dried over 4A sieves) (5 mL) containing Amberlyst A-21 ion exchange resin (2 meq, 450 mg). The mixture was then sonicated with a Ace High Intensity Ultrasonic Processor, 600 watts at 40% power with a mini-probe for total of 9 hrs. Then the mixture was diluted with ethyl acetate (20 mL) and washed with saturated sodium bicarbonate solution (10 mL), brine solution (5 mL) and dried over anhydrous magnesium sulfate. Filtration of the drying agent and removal of the solvent gave a crude product which was purified by silica gel column chromatography to afford 0.152 g (70%) of a yellow solid.

Example 410

VLA-4/VCAM-1 Screening Assay

VLA-4 antagonist activity, defined as ability to compete for binding to immobilized VCAM-1, was quantitated using a solid-phase, dual antibody ELISA. VLA-4 ($\alpha 4 \beta 1$ integrin) bound to VCAM-1 was detected by a complex of anti-integrin $\beta 1$ antibody: HRP-conjugated anti-mouse IgG: chromogenic substrate (K-Blue). Initially, this entailed coating 96 well plates (Nunc Maxisorp) with recombinant human VCAM-1 (0.4 $\mu$g in 100 $\mu$l PBS), sealing each plate and then allowing the plates to stand at 4° C. for ~18 hr. The VCAM-coated plates were subsequently blocked with 250 $\mu$l of 1% BSA/0.02% NaN$_3$ to reduce non-specific binding. On the day of assay, all plates were washed twice with VCAM Assay Buffer (200 $\mu$l/well of 50 mM Tris-HCl, 100 mM NaCl, 1 mM MnCl$_2$, 0.05% Tween 20; pH 7.4). Test compounds were dissolved in 100% DMSO and then diluted 1:20 in VCAM Assay Buffer supplemented with 1 mg/mL BSA (i.e., final DMSO=5%). A series of 1:4 dilutions were performed to achieve a concentration range of 0.005 nM–1.563 $\mu$M for each test compound. 100 $\mu$l per well of each dilution was added to the VCAM-coated plates, followed by 10 $\mu$l of Ramos cell-derived VLA-4. These plates were sequentially mixed on a platform shaker for 1 min, incubated for 2 hr at 37° C, and then washed four times with 200 $\mu$l/well VCAM Assay Buffer. 100 $\mu$l of mouse anti-human integrin $\beta 1$ antibody was added to each well (0.6 $\mu$g/mL in VCAM Assay Buffer + 1 mg/mL BSA) and allowed to incubate for 1 hr at 37° C. At the conclusion of this incubation period, all plates were washed four times with VCAM Assay Buffer (200 $\mu$l/well). A corresponding second antibody, HRP-conjugated goat anti-mouse IgG (100 $\mu$l per well @ 1:800 dilution in VCAM Assay Buffer + 1 mg/mL BSA), was then added to each well, followed by a 1 hr incubation at room temperature and concluded by three washes (200 $\mu$l/well) with VCAM Assay Buffer. Color development was initiated by addition of 100 $\mu$l K-Blue per well (15 min incubation, room temp) and terminated by addition of 100 $\mu$l Red Stop Buffer per well. All plates were then read in a UV/Vis spectrophotometer at 650 nM. Results were calculated as % inhibition of total binding (i.e., VLA-4 +VCAM-1 in the absence of test compound) The results are provided in the following table:

TABLE 2

| Example | conc. nM | % Inh. @ conc. | IC$_{50}$ nM |
|---|---|---|---|
| 27 | | | 2.7 |
| 28 | | | 22.6 |
| 29 | | | 3.6 |
| 30 | | | 6.1 |
| 31 | | | 9.8 |
| 35 | | | 5.0 |
| 36 | | | 4.6 |
| 37 | | | 5.0 |
| 40 | | | 2.1 |
| 41 | | | 1.7 |
| 42 | | | 0.61 |
| 43 | | | 0.63 |
| 47 | | | 2.5 |
| 48 | | | 0.44 |
| 49 | | | 4.7 |
| 50 | | | 1.3 |
| 51 | | | 1.6 |
| 52 | | | 1.1 |
| 53 | | | 0.5 |
| 54 | | | 0.82 |
| 55 | | | 0.47 |
| 56 | | | 0.94 |
| 57 | | | 0.42 |
| 58 | | | 0.58 |
| 59 | | | 0.26 |
| 60 | | | 1.05 |
| 64 | | | 3.0 |
| 65 | 100 | 92" | 2.4 |
|  | 10 | 72 | |
| 66 | 100 | 85" | |
|  | 10 | 47 | |
| 67 | 100 | 81 | |
|  | 10 | 41 | |
| 68 | 100 | 86 | 8.2 |
|  | 10 | 49 | |
| 69 | 100 | 87 | 5.8 |
|  | 10 | 49 | |
| 70 | 100 | 86 | 7.0 |
|  | 10 | 49 | |
| 71 | 100 | 86 | 2.5 |
|  | 10 | 51 | |
| 72 | 100 | 80 | |
|  | 10 | 39 | |
| 73 | 100 | 90 | |
|  | 10 | 64 | |
| 74 | 100 | 86 | 13.6 |
|  | 10 | 50 | |
| 75 | 100 | 92 | 3.8 |
|  | 10 | 68 | |
| 76 | 100 | 93 | 4.6 |
|  | 10 | 73 | |
| 77 | 100 | 93 | 5.6 |
|  | 10 | 67 | |
| 78 | 100 | 93 | 9.0 |
|  | 10 | 63 | |
| 79 | 100 | 95 | 1.2 |
|  | 10 | 77 | |
| 80 | 100 | 89 | 6.4 |
|  | 10 | 53 | |
| 81 | 100 | 93 | 1.4 |
|  | 10 | 73 | |
| 82 | | | 7.3 |
| 83 | | | 1.1 |
| 84 | | | 4.4 |
| 85 | | | 0.43 |
| 86 | | | 6.8 |
| 87 | | | 1.5 |
| 88 | | | 3.9 |
| 89 | | | 81 |
| 90 | | | 1.04 |
| 91 | | | 40 |
| 92 | | | 3.0 |
| 93 | | | 1.9 |

TABLE 2-continued

| Example | conc. nM | % Inh. @ conc. | IC$_{50}$ nM |
|---|---|---|---|
| 94 | | | 0.96 |
| 95 | | | 0.69 |
| 96 | | | 17.4 |
| 97 | | | 0.50 |
| 98 | | | 11.7 |
| 99 | | | 2.1 |
| 100 | | | 0.26 |
| 101 | | | 18.3 |
| 102 | | | 0.95 |
| 103 | | | 0.70 |
| 104 | | | 10.4 |
| 105 | | | 0.83 |
| 106 | | | 13.5 |
| 109 | | | 62 |
| 110 | | | 8.2 |
| 111* | | | 9.4 |
| 113 | | | 43 |
| 114 | | | 155 |
| 115 | | | 22.7 |
| 116 | | | 0.88 |
| 118 | | | 0.35 |
| 119 | | | 5.0 |
| 120 | | | 2.9 |
| 121 | | | 66 |
| 122 | | | 2.1 |
| 128 | | | 5.0 |
| 129 | | | 153 |
| 130 | | | 6.6 |
| 131 | | | 63 |
| 132 | | | 2.8 |
| 133 | | | 60 |
| 134 | | | 0.19 |
| 135 | | | 17 |
| 136 | | | 0.73 |
| 137 | | | 19 |
| 138 | | | 0.42 |
| 139 | | | 38 |
| 141 | | | 3.9 |
| 142 | | | 1.7 |
| 143 | | | 0.85 |
| 144 | | | 0.75 |
| 156 | | | 1.15 |
| 158 | | | 5 |
| 159 | | | 6.4 |
| 160 | | | 5.8 |
| 161 | | | 9.4 |
| 162 | | | 1.2 |
| 163 | | | 2.4 |
| 164 | | | 6.2 |
| 165 | | | 11 |
| 166 | | | 2.5 |
| 167 | | | 9.2 |
| 187 | | | 0.26 |
| 192 | | | 0.14 |
| 193 | | | 0.55 |
| 194 | | | 0.33 |
| 200 | | | 0.81 |
| 201 | | | 1.2 |
| 202 | | | 1.0 |
| 203 | | | 0.64 |
| 216 | | | 2.9 |
| 217 | | | 2.0 |
| 249 | | | 0.29 |
| 250 | | | 0.32 |
| 251 | | | 0.37 |
| 252 | | | 5.1 |
| 253 | | | 3.4 |
| 254 | | | 2.0 |
| 255 | | | 0.5 |
| 256 | | | 2.4 |
| 257 | | | 40 |
| 258 | | | 14 |
| 259 | | | 3.6 |
| 270 | | | 1.1 |
| 271 | | | 0.55 |
| 272 | | | 1.0 |
| 273 | | | 1.5 |
| 363 | | | 0.64 |
| 371 | | | 1.65 |

4-[(RS)-2,3,5,6,7,7a-hexahydro-1,3-dioxo-1H-pyrrolo[3,4-c]pyridin-2-yl]-N-[[1-[(4-methoxyphenyl)methyl]cyclopentyl]carbonyl]-L-phenylalanine Example 411

Ramos (VLA-4)/VCAM-1 Cell-Based Screening Assay Protocol Materials:

Soluble recombinant human VCAM-1 (mixture of 5- and 7-Ig domain) was purified from CHO cell culture media by immunoaffinity chromatography and maintained in a solution containing 0.1 M Tris-glycine (pH 7.5), 0.1 M NaCl, 5 mM EDTA, 1 mM PMSF, 0.02% 0.02% NaN$_3$ and 10 μg/mL leupeptin. Calcein-AM was purchased from Molecular Probes Inc.

Methods:

VLA-4 (α4β1 integrin) antagonist activity, defined as ability to compete with cell-surface VLA-4 for binding to immobilized VCAM-1, was quantitated using a Ramos-VCAM-1 cell adhesion assay. Ramos cells bearing cell-surface VLA-4, were labeled with a fluorescent dye (Calcein-AM) and allowed to bind VCAM-1 in the presence or absence of test compounds. A reduction in fluorescence intensity associated with adherent cells (% inhibition) reflected competitive inhibition of VLA-4 mediated cell adhesion by the test compound.

Initially, this entailed coating 96 well plates (Nunc Maxisorp) with recombinant human VCAM-1 (100 ng in 100 μl PBS), sealing each plate and allowing the plates to stand at 4° C. for ~18 hr. The VCAM-coated plates were subsequently washed twice with 0.05% Tween-20 in PBS, and then blocked for 1 hr (room temperature) with 200 μl of Blocking Buffer (1% BSA/0.02% thimerosal) to reduce non-specific binding. Following the incubation with Blocking Buffer, plates were inverted, blotted and the remaining buffer aspirated. Each plate was then washed with 300 μl PBS, inverted and the remaining PBS aspirated.

Test compounds were dissolved in 100% DMSO and then diluted 1:25 in VCAM Cell Adhesion Assay Buffer (4 mM CaCl$_2$, 4 mM MgCl$_2$ in 50 mM TRIS-HCl, pH 7.5) (final DMSO=4%). A series of eight 1:4 dilutions were performed for each compound (general concentration range of 1 nM–12,500 nM). 100 μl/well of each dilution was added to the VCAM-coated plates, followed by 100 μl of Ramos cells (200,000 cells/well in 1% BSA/PBS). Plates containing test compounds and Ramos cells were allowed to incubate for 45 min at room temperature, after which 165 μl/well PBS was added. Plates were inverted to remove non-adherent cells, blotted and 300 μl/well PBS added. Plates were again inverted, blotted and the remaining buffer gently aspirated. 100 μl Lysis Buffer (0.1% SDS in 50 mM TRIS-HCl, pH 8.5) was added to each well and agitated for 2 min on a rotary shaking platform. The plates were then read for fluorescence intensity on a Cytofluor 2300 (Millipore) fluorecence measurement system (excitation=485 nm, emission=530 nm). The results are shown in the following table:

TABLE 3

| Example | Conc. (nM) | % Inh @ Conc. | $IC_{50}$ in Ramos Cell Based Assay (nM) |
|---|---|---|---|
| 43 | | | 36.5 |
| 53 | | | 37.5 |
| 55 | | | 18.5 |
| 95 | | | 34.5 |
| 100 | | | 54.5 |
| 56 | | | 31.5 |
| 57 | | | 27 |
| 58 | | | 47 |
| 59 | | | 13.5 |
| 156 | | | 28 |
| 158 | | | 124 |
| 159 | | | 313 |
| 160 | | | 328 |
| 162 | | | 23 |
| 163 | | | 85 |
| 187 | | | 5.7 |
| 188 | | | 36 |
| 189 | | | 130 |
| 190 | | | 650 |
| 191 | | | 322 |
| 192 | | | 22 |
| 193 | | | 40 |
| 194 | | | 27 |
| 200 | | | 19 |
| 201 | | | 19 |
| 202 | | | 31 |
| 203 | | | 47 |
| 216 | | | 356 |
| 217 | | | 211 |
| 249 | | | 62 |
| 250 | | | 28 |
| 251 | | | 9 |
| 252 | | | 228 |
| 253 | | | 89 |
| 254 | | | 360 |
| 255 | | | 27 |
| 256 | | | 151 |
| 257 | | | 635 |
| 258 | | | 1,034 |
| 259 | | | 129 |
| 260 | | | 130 |
| 276 | | | 22 |
| 260 | | | 94 |
| 261 | | | 184 |
| 262 | | | 39 |
| 263 | | | 5 |
| 270 | | | 150 |
| 271 | | | 67 |
| 272 | | | 96 |
| 273 | | | 104 |
| 278 | | | 2 |
| 280 | | | 4.2 |
| 282 | | | 1.8 |
| 283 | 10 | 32 | |
| 284 | | | 2.9 |
| 286 | | | 24 |
| 288 | 10 | 92 | |
| 291 | 10 | 48 | |
| 293 | | | 40 |
| 299 | | | 1.7 |
| 300 | 10 | 32 | |
| 303 | 10 | 70 | |
| 304 | 10 | 35 | |
| 305 | 10 | 37 | |
| 311 | | | 3 |
| 313 | 10 | 68 | |
| 315 | 10 | 71 | |
| 316 | 10 | 22 | |
| 317 | 10 | 17 | |
| 319 | 10 | 68 | |
| 321 | 10 | 59 | |
| 323 | 10 | 76 | |
| 324 | 10 | 20 | |
| 322 | | | 5 |

TABLE 3-continued

| Example | Conc. (nM) | % Inh @ Conc. | $IC_{50}$ in Ramos Cell Based Assay (nM) |
|---|---|---|---|
| 342 | 10 | 24 | |
| 344 | | | 19 |
| 346 | 10 | 23 | |
| 349 | 10 | 58 | |
| 350 | | | 13 |
| 351 | | | 13 |
| 357 | | | 25 |
| 358 | | | 75 |
| 363 | | | 11 |

Example 412

Oral Dosage Form

| Item | Ingredients | mg/tablet | | | |
|---|---|---|---|---|---|
| 1 | Compound of invention | 25 | 100 | 250 | 500 |
| 2 | Anhydrous lactose | 83 | 35 | 19 | 38 |
| 3 | Croscarmellose sodium | 6 | 8 | 16 | 32 |
| 4 | Povidone K30 | 5 | 6 | 12 | 24 |
| 5 | Magnesium stearate | 1 | 1 | 3 | 6 |
| | Total weight (mg) | 120 | 150 | 300 | 600 |

Manufacturing procedure:

1. Mix items 1, 2, 3 in a suitable mixer for 15 minutes.
2. Granulate the powder mix from step 1 with 20% PVP K30 solution.
3. Dry the granulation in step 2 at 50° C.
4. Pass the granulation from step 3 through a suitable milling equipment.
5. Add the item 5 to the milled granulation from Step 4 and mix for 3 minutes.
6. Compress the granulation from Step 5 on a suitable press.

Example 413

Aerosol Administration Formulation

| Ingrdients | Qty/mL |
|---|---|
| Compound of invention | 3–150 mg* |
| Sodium chloride | 8.0 mg |
| Phophate buffer (20 mM)pH 7.0* q.s. | 1.0 mL |

Depending upon activity of the compound pH can be adjusted with Sodium hydroxide solution (1 N) or HCl solution (10% w/v)

Procedure:

Dissolve the drug substance in the buffer.

Filter the solution through a 0.22 micron filter.

The particle size distribution after nebulizing the above solution (as measured using Malvern Mastersizer X) is in the range of 1–6 microns.

What is claimed is:

1. A compound of the formula:

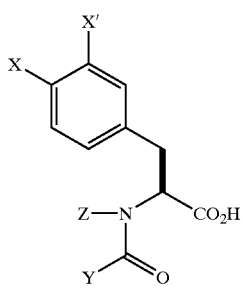

I wherein:
one of X and X' is H, halogen, or lower alkyl, and the other is a group of the formula:

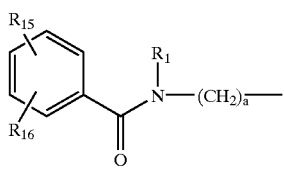

X-6 wherein:
$R_1$ is hydrogen or lower alkyl,
$R_{15}$ is halogen, nitro, lower alkyl sulfonyl, cyano, lower alkyl, lower alkoxy, lower alkoxycarbonyl, carboxy, lower alkyl aminosulfonyl, perfluorolower alkyl, lower alkylthio, hydroxy lower alkyl, alkoxy lower alkyl, alkylthio lower alkyl, alkylsulfinyl lower alkyl, alkylsufonyl lower alkyl, lower alkylsulfinyl, lower alkanoyl, aryl, aryloxy, aroyl or a group of the formula $R_{17}$—C≡C—,
$R_{16}$ is H, halogen, nitro, cyano, lower alkyl, OH, perfluorolower alkyl, or lower alkylthio, and
$R_{17}$ is hydrogen, aryl, heteroaryl, or lower alkyl which is unsubstituted or substituted by OH, aryl, or heteroaryl, and
a is 0 or 1;
Y is a group of the formula:

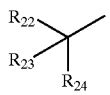

Y-1 wherein:
$R_{22}$ and $R_{23}$ are independently aryl, heteroaryl or lower alkyl which is unsubstituted or substituted by one or more chloro, bromo, nitro, hydroxy, lower alkoxy, aryl, lower alkanoyl, aroyl or cyano,
$R_{24}$ is aryl, cyano, alkylsulfonyl or lower alkyl or alkenyl unsubstituted or substituted by an aryl or heteroaryl ring, and when $R_{22}$ is aryl and $R_{23}$ is aryl or lower alkyl, H, and the total number of carbon atoms in $R_{22}$, $R_{23}$ and $R_{24}$ is from 6 to 14; or Y is a 3–7 membered ring of the formula:

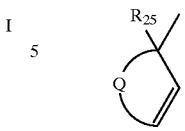

Y-2 wherein:
$R_{25}$ is lower alkyl, unsubstituted or fluorine substituted lower alkenyl, or a group of formula $R_{26}$—$(CH_2)_e$—,
$R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula —$NR_{28}R_{29}$, wherein:
$R_{28}$ H or lower alkyl,
$R_{29}$ is hydrogen, lower alkyl, lower alkoxycarbonyl, lower alkoxycarbonylaminocarbonyl, lower alkanoyl, aroyl, heteroaroyl, perfluoro lower alkanoyl, lower alkyl sulfonyl, lower alkylaminocarbonyl, arylaminocarbonyl, heterocycloalkyl carbonyl, lower alkylaminothiocarbonyl, or
$R_{28}$ and $R_{29}$ taken together with the nitrogen atom to which they are attached form a 4, 5 or 6-membered saturated heterocyclic ring containing one or two heteroatoms with the second heteroatom being O, S, or N—$R_{27}$;
Q is —$(CH_2)_fO$—, —$(CH_2)_fS$—, —$(CH_2)_f$—, or when f=0, a bond,
$R_{27}$ is hydrogen, lower alkyl, aryl, lower alkanoyl, aroyl, or lower alkoxycarbony;
the carbon atoms in said ring are unsubstituted or substituted by lower alkyl or halogen,
e is an integer from 0 to 4, and
f is an integer from 0 to 3; and
Z is hydrogen or lower alkyl;
and the pharmaceutically acceptable salts and esters thereof.

2. The compound of claim 1 wherein X' is hydrogen.
3. The compound of claim 2 having the formula:

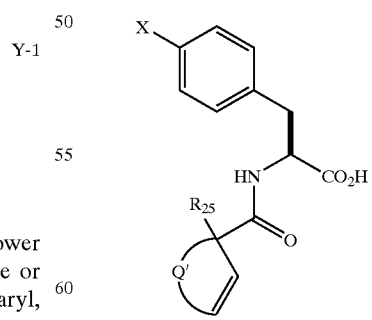

Ia wherein Q' is unsubstituted or lower alkyl substituted —$(CH_2)_f$—, f is 1, 2 or 3, and X and $R_{25}$ are as in claim 1.

4. The compound of claim 3 wherein f is 2 whereby said compound is of the formula:

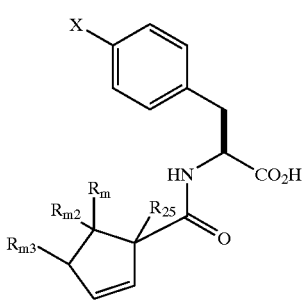

wherein $R_{m1}$, $R_{m2}$ and $R_{m3}$ are independently hydrogen or lower alkyl, and $R_{25}$ is lower alkyl, lower alkenyl which is unsubstituted or substituted by fluorine, or a group of the formula $R_{26}$—$(CH_2)_e$— wherein $R_{26}$ and e are as in claim 1.

5. The compound of claim 4 wherein said compound is of the formula:

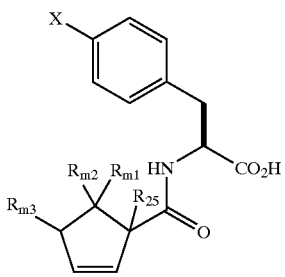

wherein $R_{m1}$, $R_{m2}$ and $R_{m3}$ and $R_{25}$ are as in claim 4.

6. The compound of claim 4 wherein said compound is of the formula:

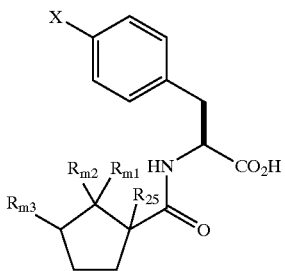

wherein $R_{m1}$, $R_{m2}$ and $R_{m3}$ and $R_{25}$ are as in claim 4.

7. The compound of claim 6 wherein said compound is of the formula:

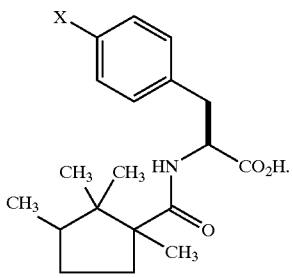

8. The compound of claim 6 wherein $R_{m1}$, $R_{m2}$ and $R_{m3}$ are all hydrogen, and $R_{25}$ is lower alkyl or lower alkenyl which is unsubstituted or substituted by fluorine.

9. The compound of claim 1 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

10. The compound of claim 9 wherein $R_{15}$ and $R_{16}$ are chloro.

11. The compound of claim 10 wherein $R_{15}$ and $R_{16}$ are o-chloro.

12. The compound of claim 11 wherein a is 0.

13. The compound of claim 12 having the formula:

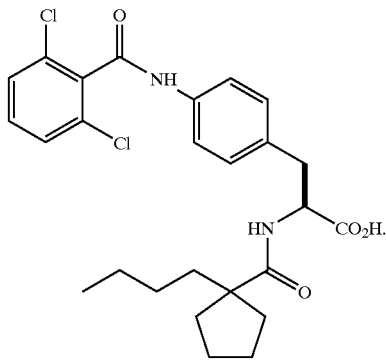

14. The compound of claim 12 having the formula:

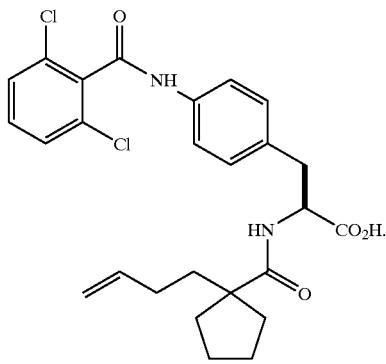

15. The compound of claim 12 having the formula:

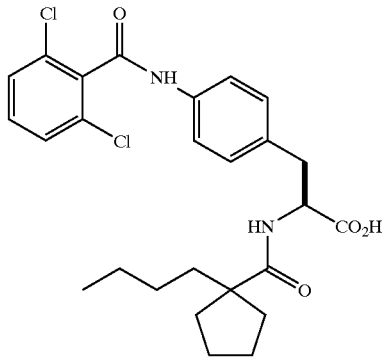

-continued

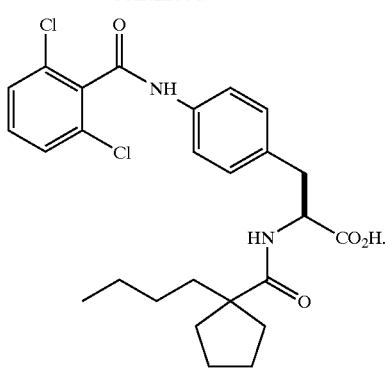

16. The compound of claim 4 having the formula:

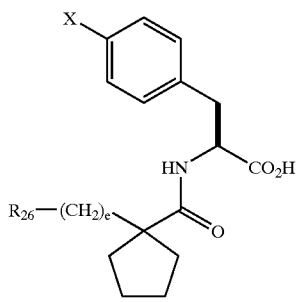

where in X, $R_{26}$ and e are as in claim 1.

17. The compound of claim 16 wherein e is 0 whereby said compound is of the formula:

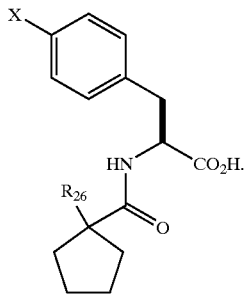

18. The compound of claim 17 wherein $R_{26}$ is cyano or aryl.

19. The compound of claim 18 wherein $R_{26}$ is cyano or phenyl which is unsubstituted or mono-substituted by halogen, lower alkyl or lower alkoxy.

20. The compound of claim 19 wherein said compound is of the formula:

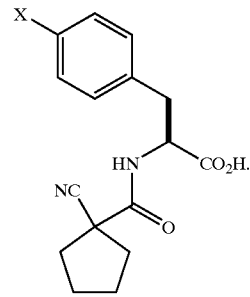

21. The compound of claim 19 wherein $R_{26}$ is phenyl which is unsubstituted or mono-substituted by halogen, lower alkyl or lower alkoxy.

22. The compound of claim 21 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

23. The compound of claim 22 wherein $R_{15}$ and $R_{16}$ are hydrogen.

24. The compound of claim 23 wherein a is 0.

25. The compound of claim 24 having the formula:

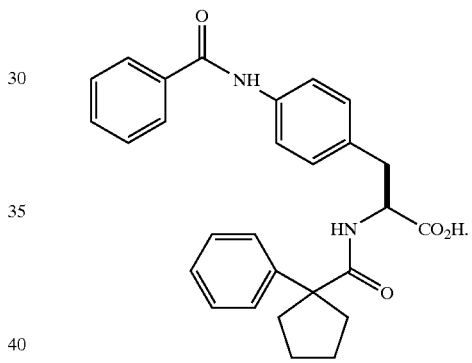

26. The compound of claim 22 where $R_{15}$ is aroyl and $R_{16}$ is hydrogen.

27. The compound of claim 26 wherein $R_{15}$ is o-aroyl.

28. The compound of claim 27 wherein a is 0.

29. The compound of claim 28 having the formula:

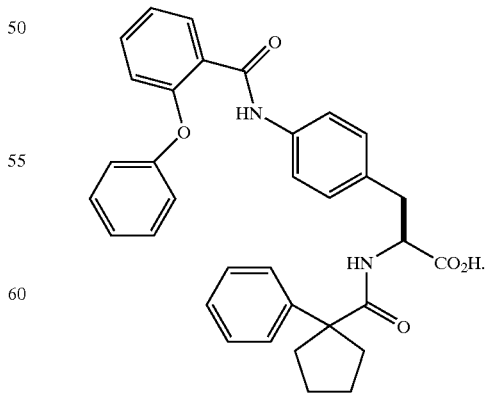

30. The compound of claim 16 wherein e is 1 whereby said compound is of the formula:

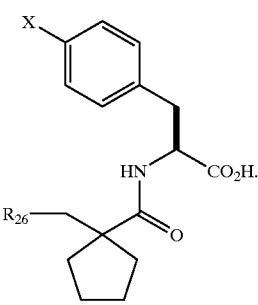

31. The compound of claim 30 wherein $R_{26}$ is lower alkoxy or aryl.

32. The compound of claim 31 wherein $R_{26}$ is methoxy, or is phenyl which is unsubstituted, mono-substituted by halogen, lower alkoxy, cyano or tetrazolyl which tetrazolyl is unsubstituted or monosubstituted by methyl, or disubstituted by lower alkoxy.

33. The compound of claim 32 wherein $R_{26}$ is methoxy.

34. The compound of claim 33 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

35. The compound of claim 34 wherein $R_{15}$ and $R_{16}$ are chloro.

36. The compound of claim 35 wherein $R_{15}$ and $R_{16}$ are o-chloro.

37. The compound of claim 36 wherein a is 0.

38. The compound of claim 37 having the formula:

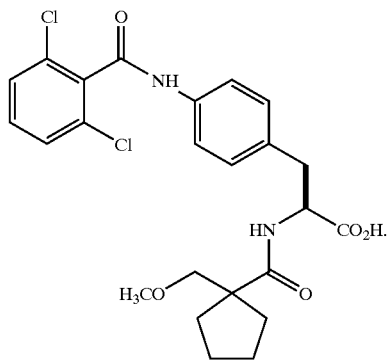

39. The compound of claim 32 wherein $R_{26}$ is phenyl which is mono- or di-substituted by lower alkoxy.

40. The compound of claim 39 wherein $R_{26}$ is phenyl which is mono-substituted by lower alkoxy.

41. The compound of claim 40 wherein $R_{26}$ is a group of the formula:

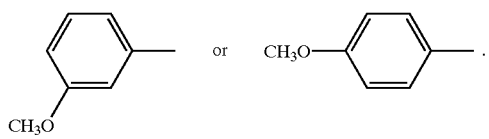

42. The compound of claim 41 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

43. The compound of claim 42 wherein $R_{15}$ and $R_{16}$ are halogen.

44. The compound of claim 43 wherein $R_{15}$ and $R_{16}$ are chloro.

45. The compound of claim 44 wherein $R_{15}$ and $R_{16}$ are o-chloro.

46. The compound of claim 45 wherein a is 0.

47. The compound of claim 46 having the formula:

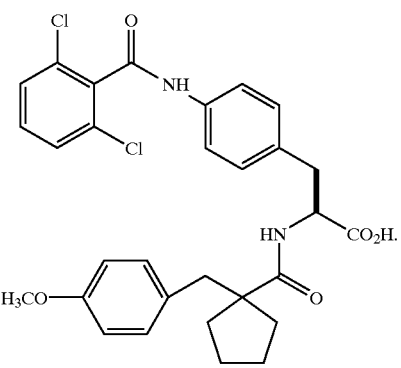

48. The compound of claim 46 having the formula:

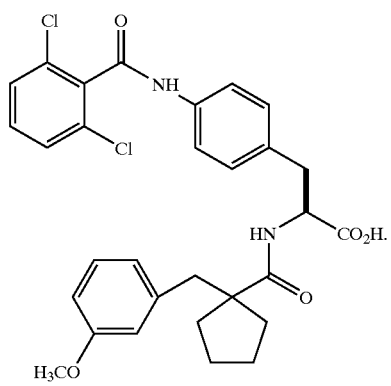

49. The compound of claim 42 wherein $R_{15}$ is hydrogen, halogen, nitro, perfluoro lower alkyl, or lower alkyl and $R_{16}$ is hydrogen, nitro, perfluoro lower alkyl, or lower alkyl.

50. The compound of claim 49 wherein $R_{15}$ and $R_{16}$ are both hydrogen, or $R_{15}$ is o-methyl and $R_{16}$ is p-nitro, or $R_{15}$ is o-methyl and $R_{16}$ is m-nitro, or $R_{15}$ is o-perfluoromethyl and $R_{16}$ is p-fluoro, or $R_{15}$ is hydrogen and $R_{16}$ is o-nitro.

51. The compound of claim 50 wherein a is 0.

52. The compound of claim 51 having the formula:

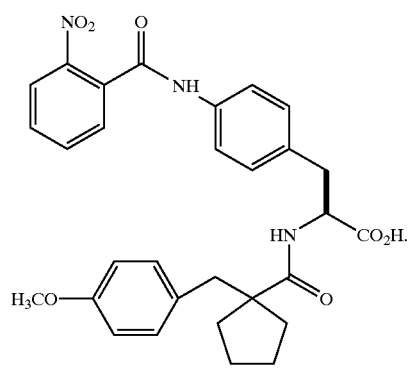

53. The compound of claim 51 having the formula:

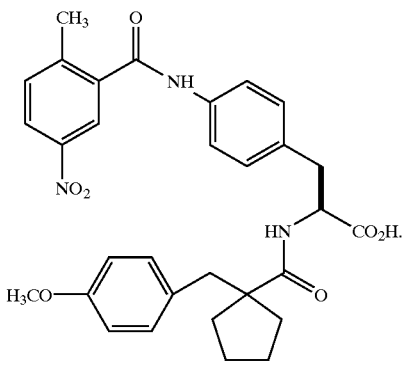

54. The compound of claim 51 having the formula:

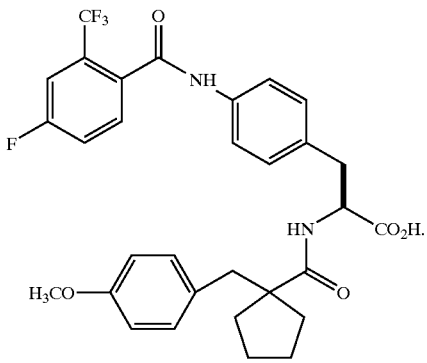

55. The compound of claim 51 having the formula:

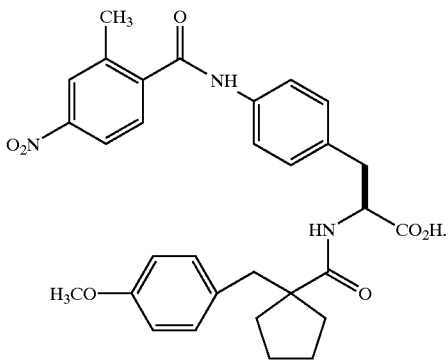

56. The compound of claim 32 wherein $R_{26}$ is unsubstituted phenyl.

57. The compound of claim 56 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

58. The compound of claim 57 wherein $R_{15}$ and $R_{16}$ are halogen.

59. The compound of claim 58 wherein $R_{15}$ and $R_{16}$ are chloro.

60. The compound of claim 59 wherein $R_{15}$ and $R_{16}$ are o-chloro.

61. The compound of claim 60 wherein a is 0.

62. The compound of claim 61 having the formula:

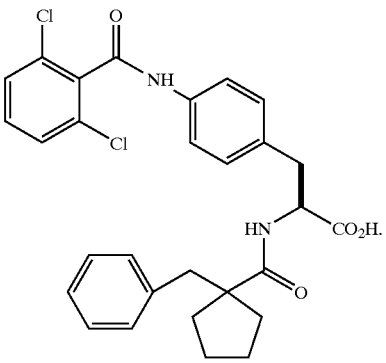

63. The compound of claim 57 wherein $R_{15}$ is hydrogen, halogen, nitro, perfluoro lower alkyl, or lower alkyl and $R_{16}$ is hydrogen, nitro, perfluoro lower alkyl, or lower alkyl.

64. The compound of claim 63 wherein $R_{15}$ is hydrogen or lower alkyl and $R_{16}$ is nitro.

65. The compound of claim 64 wherein $R_{15}$ is o-methyl and $R_{16}$ is p-nitro, or $R_{15}$ is o-methyl and $R_{16}$ is m-nitro, or $R_{15}$ is hydrogen and $R_{16}$ is o-nitro.

66. The compound of claim 65 wherein a is 0.

67. The compound of claim 66 having the formula:

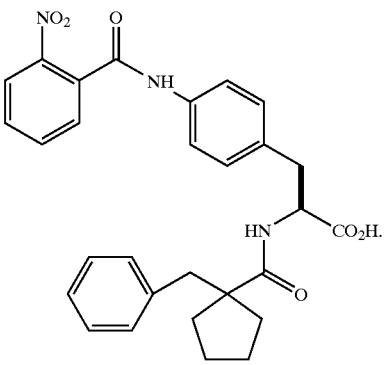

68. The compound of claim 66 having the formula:

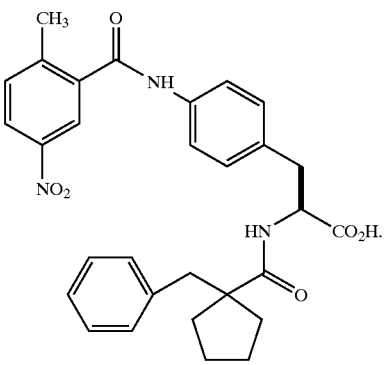

69. The compound of claim 39 wherein $R_{26}$ is phenyl which is di-substituted by lower alkoxy.

70. The compound of claim 69 wherein $R_{26}$ is a group of the formula:

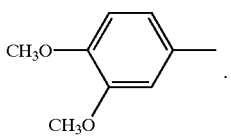

71. The compound of claim 70 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

72. The compound of claim 71 wherein $R_{15}$ and $R_{16}$ are halogen.

73. The compound of claim 72 wherein $R_{15}$ and $R_{16}$ are chloro.

74. The compound of claim 73 wherein $R_{15}$ and $R_{16}$ are o-chloro.

75. The compound of claim 74 wherein a is 0.

76. The compound of claim 75 having the formula:

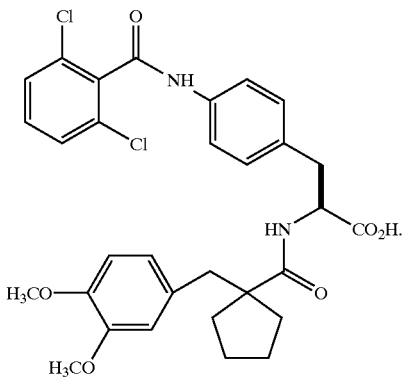

77. The compound of claim 32 wherein $R_{26}$ is phenyl monosubstituted by chloro, tetrazolyl, which is unsubstituted or mono-subsituted by methyl, or cyano.

78. The compound of claim 77 wherein $R_{26}$ is a group of the formula:

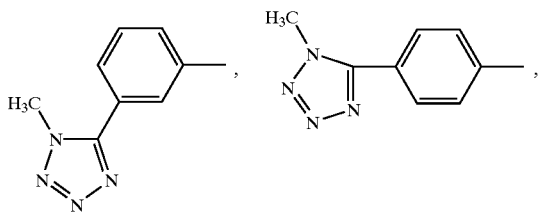

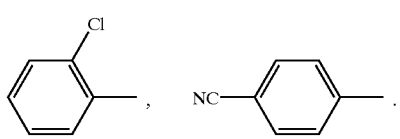

79. The compound of claim 78 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

80. The compound of claim 79 wherein $R_{15}$ and $R_{16}$ are halogen.

81. The compound of claim 80 wherein $R_{15}$ and $R_{16}$ are chloro.

82. The compound of claim 81 wherein $R_{15}$ and $R_{16}$ are o-chloro.

83. The compound of claim 82 wherein a is 0.

84. The compound of claim 83 having the formula:

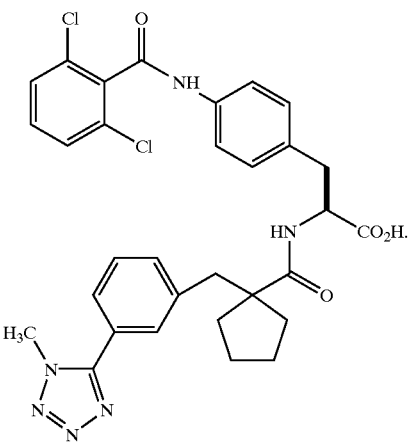

85. The compound of claim 83 having the formula:

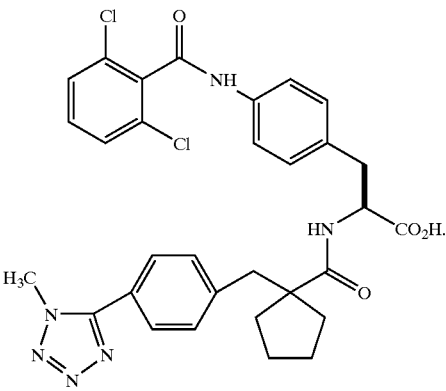

86. The compound of claim 83 having the formula:

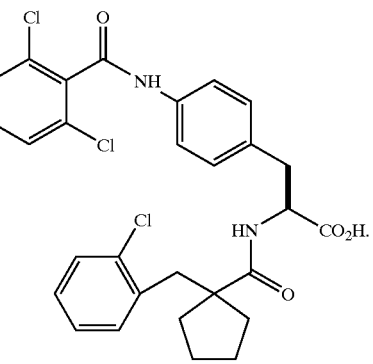

87. The compound of claim 83 having the formula:

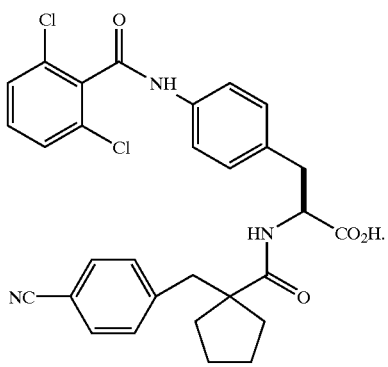

88. The compound of claim 30 wherein $R_{26}$ is tetrazolyl or cyano.

89. The compound of claim 88 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

90. The compound of claim 89 wherein $R_{15}$ and $R_{16}$ are halogen.

91. The compound of claim 90 wherein $R_{15}$ and $R_{16}$ are chloro.

92. The compound of claim 91 wherein $R_{15}$ and $R_{16}$ are o-chloro.

93. The compound of claim 92 wherein a is 0.

94. The compound of claim 93 having the formula:

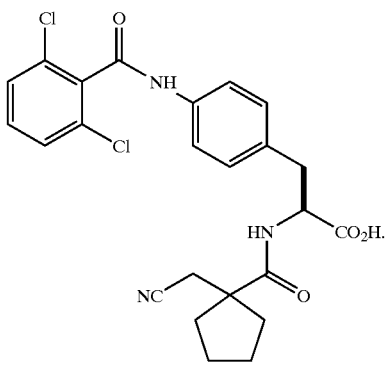

95. The compound of claim 93 having the formula:

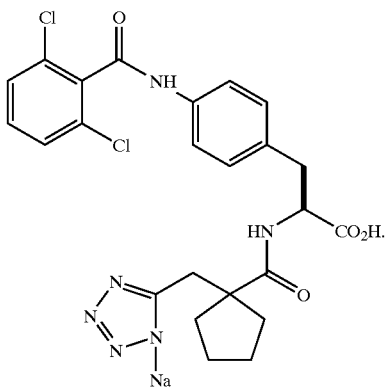

96. The compound of claim 16 wherein e is 2 whereby said compound is of the formula:

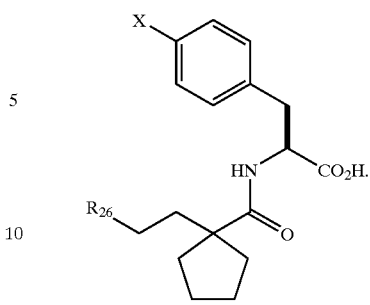

97. The compound of claim 96 wherein $R_{26}$ is —$NR_{28}R_{29}$ where $R_{28}$ and are as in claim 1.

98. The compound of claim 97 wherein $R_{23}$ and $R_{29}$ are independently hydrogen or lower alkyl.

99. The compound of claim 98 wherein a is 0 and $R_1$ is hydrogen.

100. The compound of claim 99 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

101. The compound of claim 100 wherein $R_{15}$ and $R_{16}$ are halogen.

102. The compound of claim 101 wherein $R_{15}$ and $R_{16}$ are chloro.

103. The compound of claim 102 wherein X is a group of the formula:

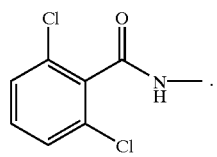

104. The compound of claim 103 having the formula:

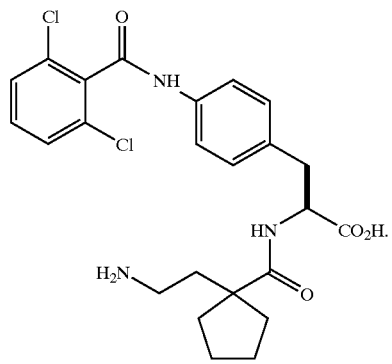

105. The compound of claim 103 having the formula:

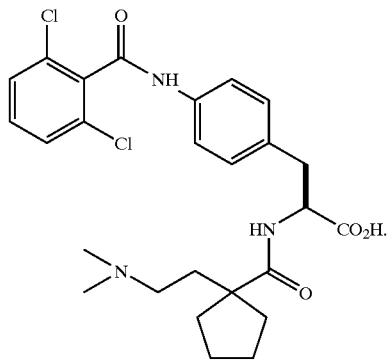

106. The compound of claim 97 wherein $R_{28}$ is hydrogen and $R_{29}$ is lower akanoyl.

107. The compound of claim 106 wherein the alkyl group of said lower alkanoyl is unsubstituted or substituted by lower alkoxy, fluoro, phenyl, cycloalkyl, lower alkoxycarbonyl, amino, or lower alkoxycarbonylamino.

108. The compound of claim 107 wherein a is 0, $R_1$ is hydrogen, and $R_{29}$ is unsubstituted or substituted lower alkanoyl.

109. The compound of claim 108 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

110. The compound of claim 109 wherein $R_{15}$ and $R_{16}$ are halogen.

111. The compound of claim 110 wherein $R_{15}$ and $R_{16}$ are chloro.

112. The compound of claim 111 wherein X is a group of the formula:

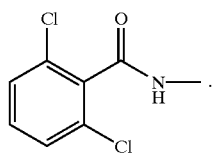

113. The compound of claim 112 having the formula:

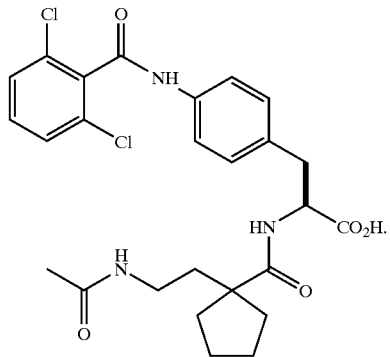

114. The compound of claim 112 having the formula:

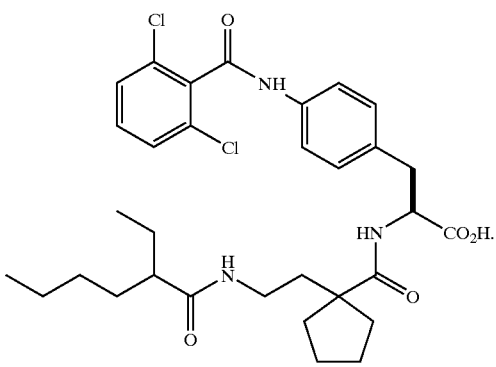

115. The compound of claim 112 having the formula:

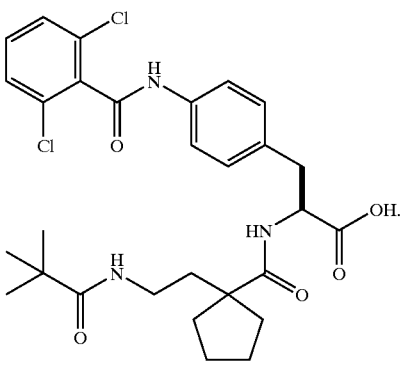

116. The compound of claim 112 having the formula:

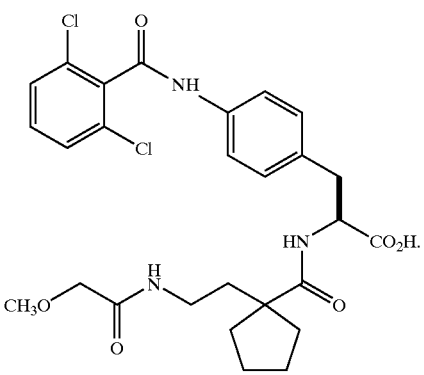

117. The compound of claim 112 having the formula:

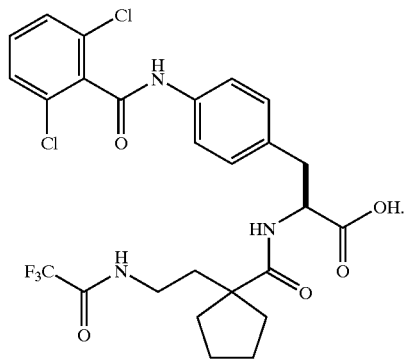

118. The compound of claim 112 having the formula:

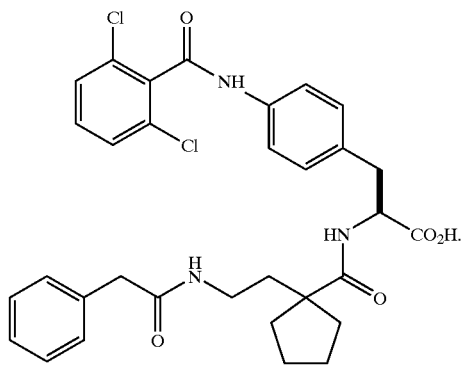

119. The compound of claim 112 having the formula:

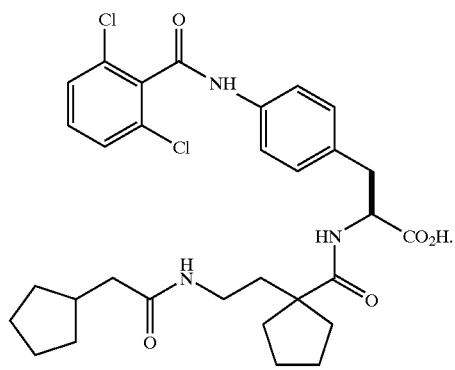

120. The compound of claim 112 having the formula:

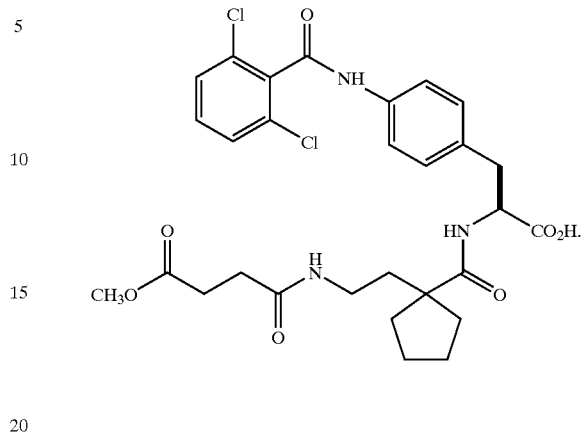

121. The compound of claim 112 having the formula:

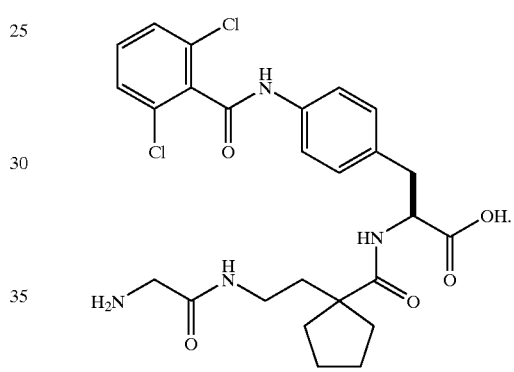

122. The compound of claim 112 having the formula:

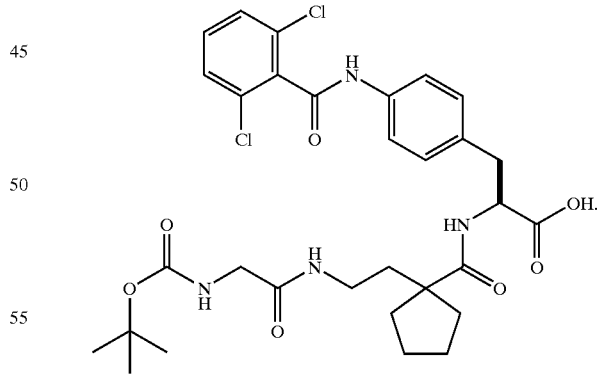

123. The compound of claim 97 wherein $R_{28}$ is hydrogen and $R_{29}$ is lower alkoxycarbonyl, lower alkylsulfonyl, heterocycloalkyl, aroyl or heteroaroyl.

124. The compound of claim 123 wherein a is 0 and $R_1$ is hydrogen.

125. The compound of claim 124 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

126. The compound of claim 125 wherein $R_{15}$ and $R_{16}$ are halogen.

127. The compound of claim 126 wherein $R_{15}$ and $R_{16}$ are chloro.

128. The compound of claim 127 wherein X is a group of the formula:

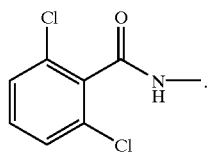

129. The compound of claim 128 having the formula:

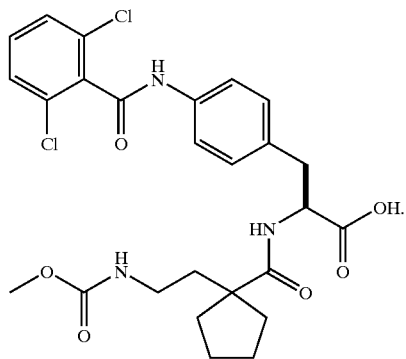

130. The compound of claim 128 having the formula:

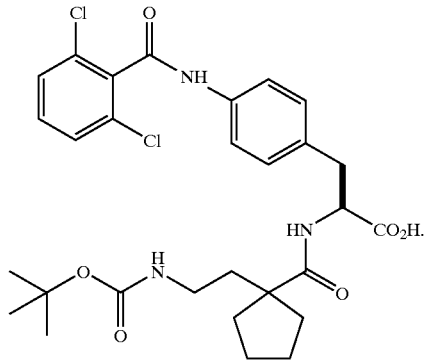

131. The compound of claim 128 having the formula:

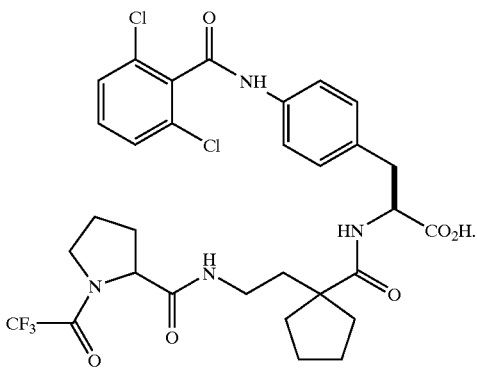

132. The compound of claim 128 having the formula:

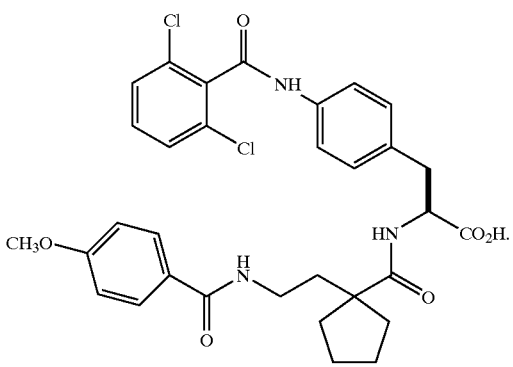

133. The compound of claim 128 having the formula:

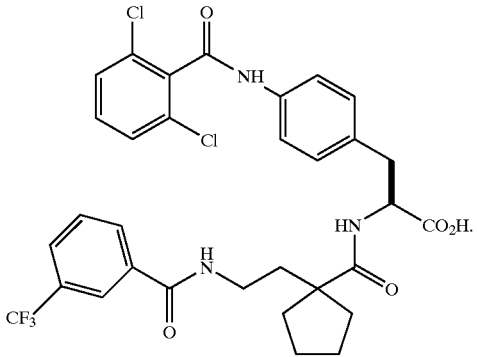

134. The compound of claim 128 having the formula:

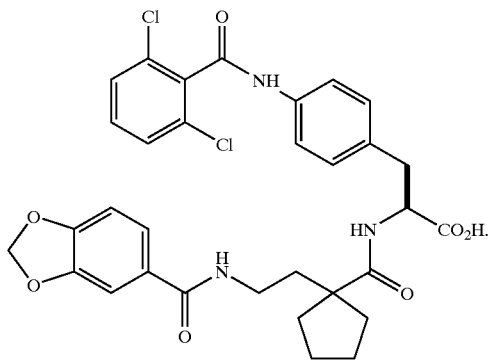

135. The compound of claim 128 having the formula:

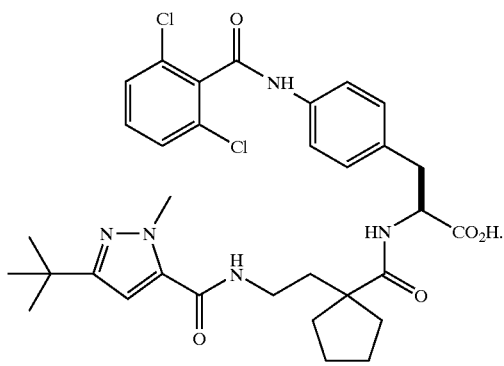

136. The compound of claim 128 having the formula:

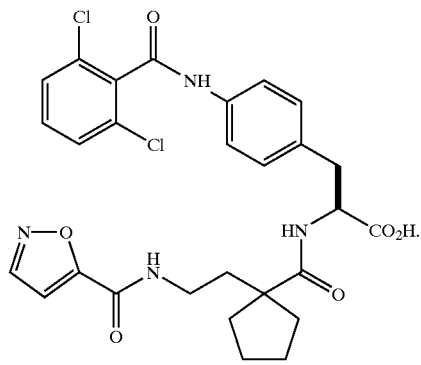

137. The compound of claim 128 having the formula:

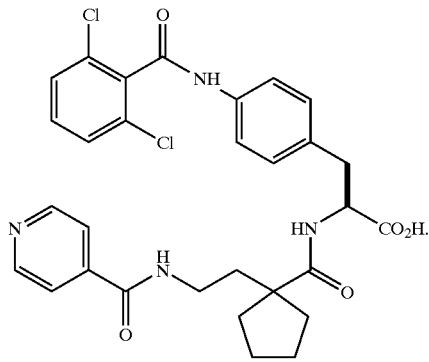

138. The compound of claim 128 having the formula:

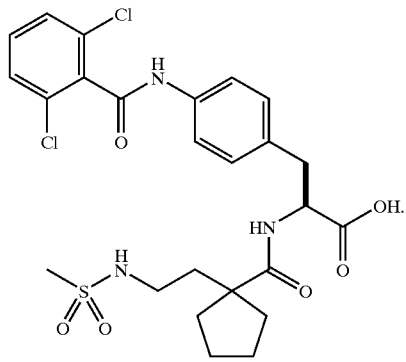

139. The compound of claim 97 wherein $R_{28}$ is hydrogen and $R_{29}$ is aminocarbonyl where said amino group is unsubstituted or substituted by lower alkyl, lower alkoxycarbonyl, monocyclic aryl or benzyl, or $R_{29}$ is lower alkylaminothiocarbonyl.

140. The compound of claim 139 wherein X is a group of the formula:

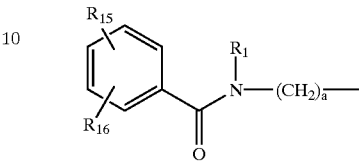

X-6 wherein $R_1$, $R_{15}$, $R_{16}$ and a are as in claim 1.

141. The compound of claim 140 wherein a is 0 and $R_1$ is hydrogen.

142. The compound of claim 141 wherein $R_{15}$ and $R_{16}$ are independently hydrogen, halogen, cyano, nitro, perfluoro lower alkyl, or lower alkyl, or $R_{15}$ is phenoxy and $R_{16}$ is hydrogen.

143. The compound of claim 142 wherein $R_{15}$ and $R_{16}$ are halogen.

144. The compound of claim 143 wherein $R_{15}$ and $R_{16}$ are chloro.

145. The compound of claim 144 wherein X is a group of the formula:

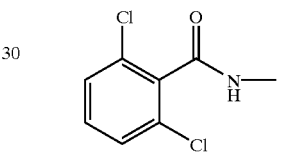

146. The compound of claim 145 having the formula:

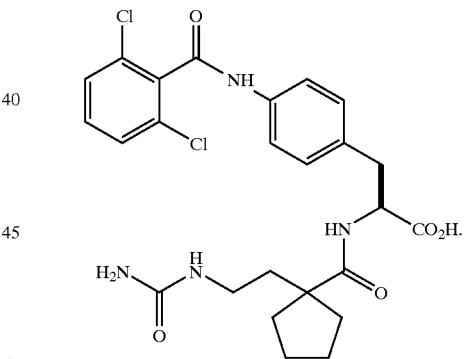

147. The compound of claim 145 having the formula:

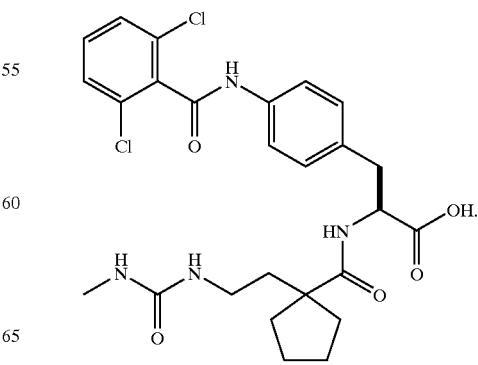

148. The compound of claim 145 having the formula:

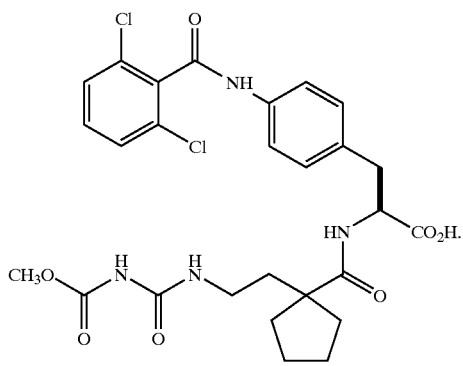

149. The compound of claim 145 having the formula:

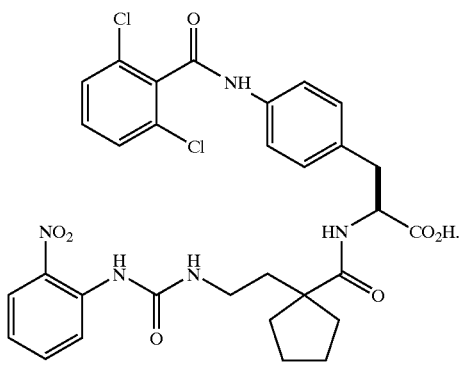

150. The compound of claim 145 having the formula:

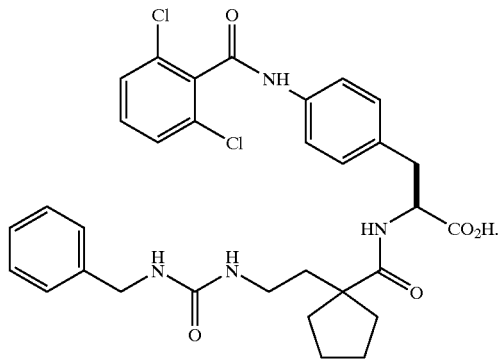

151. The compound of claim 145 having the formula:

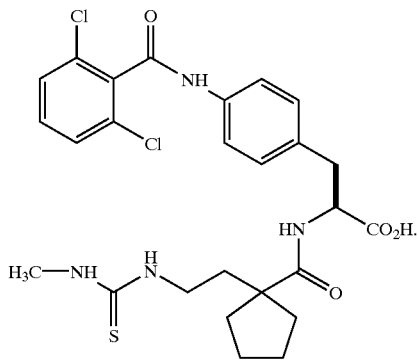

152. The compound of claim 97 wherein $R_{28}$ is lower alkyl and $R_{29}$ is lower akanoyl, lower alkoxycarbonyl or lower alkylaminocarbonyl.

153. The compound of claim 152 wherein a is 0 and $R_1$ is hydrogen.

154. The compound of claim 153 wherein $R_{15}$ and $R_{16}$ are independently hydrogen, halogen, nitro, cyano, perfluoro lower alkyl, or lower alkyl or $R_{15}$ is phenoxy and $R_{16}$ is hydrogen.

155. The compound of claim 154 wherein $R_{15}$ and $R_{16}$ are halogen.

156. The compound of claim 155 wherein $R_{15}$ and $R_{16}$ are chloro.

157. The compound of claim 156 wherein X is a group of the formula:

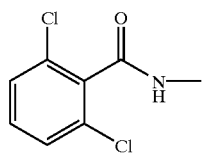

158. The compound of claim 157 having the formula:

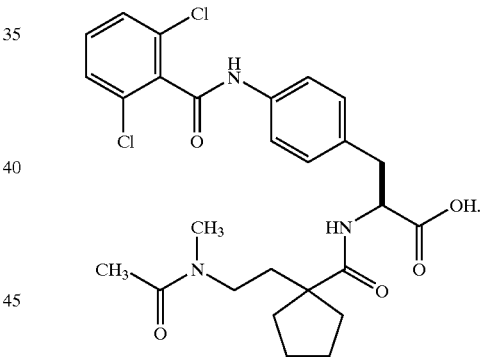

159. The compound of claim 157 having the formula:

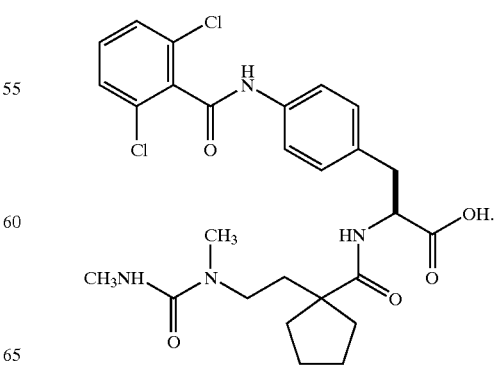

160. The compound of claim 157 having the formula:

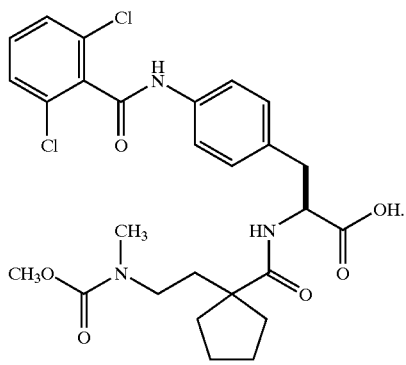

161. The compound of claim 97 wherein $R_{28}$ and $R_{29}$ taken together with the nitrogen atom to which they are attached form a morpholinyl group.

162. The compound of claim 161 wherein a is 0 and $R_1$ is hydrogen.

163. The compound of claim 162 wherein $R_{15}$ and $R_{16}$ are independently hydrogen, halogen, nitro, cyano, perfluoro lower alkyl, or lower alkyl or $R_{15}$ is phenoxy and $R_{16}$ is hydrogen.

164. The compound of claim 163 wherein $R_{15}$ and $R_{16}$ are halogen.

165. The compound of claim 164 wherein $R_{15}$ and $R_{16}$ are chloro.

166. The compound of claim 165 wherein X is a group of the formula:

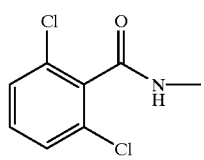

167. The compound of claim 166 having the formula:

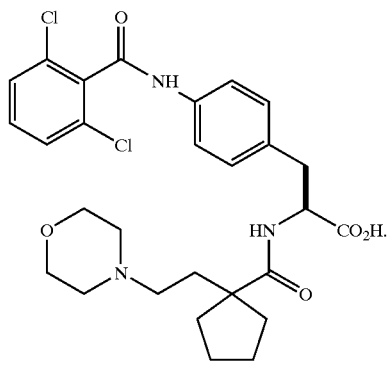

168. The compound of claim 96 wherein $R_{26}$ is lower alkyl sulfonyl, lower alkyl thio, lower alkyl sulfinyl, lower alkylthio, azido, cyano, hydroxy, lower alkoxy, lower alkanoyl or lower alkanoylamino.

169. The compound of claim 168 wherein a is 0 and $R_1$ is hydrogen.

170. The compound of claim 169 wherein $R_{15}$ and $R_{16}$ are independently hydrogen, halogen, nitro, cyano, perfluoro lower alkyl, or lower alkyl or $R_{15}$ is phenoxy and $R_{16}$ is hydrogen.

171. The compound of claim 170 wherein $R_{15}$ and $R_{16}$ are halogen.

172. The compound of claim 171 wherein $R_{15}$ and $R_{16}$ are chloro.

173. The compound of claim 172 wherein X is a group of the formula:

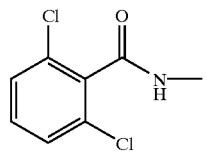

174. The compound of claim 173 having the formula:

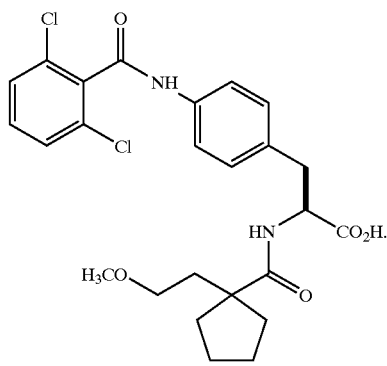

175. The compound of claim 173 having the formula:

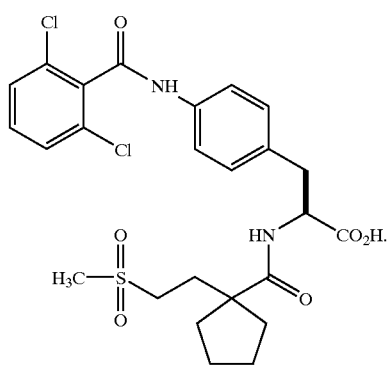

176. The compound of claim 173 having the formula:

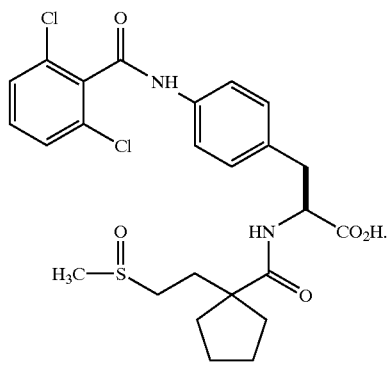

177. The compound of claim 173 having the formula:

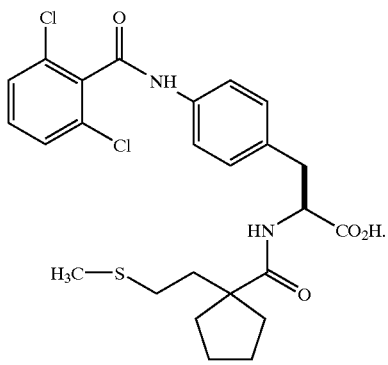

178. The compound of claim 173 having the formula:

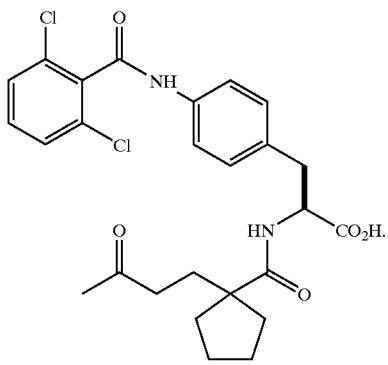

179. The compound of claim 170 wherein $R_{15}$ is cyano and $R_{16}$ is halogen.
180. The compound of claim 179 wherein $R_{16}$ is chloro.
181. The compound of claim 180 wherein X is a group of the formula:

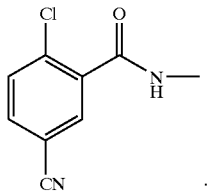

182. The compound of claim 181 having the formula:

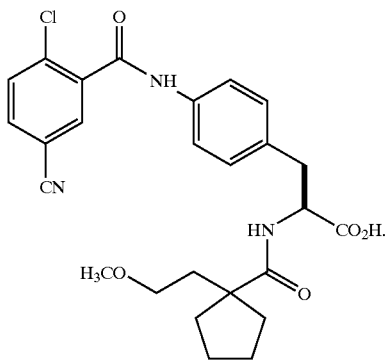

183. The compound of claim 16 wherein e is 3 whereby said compound is of the formula:

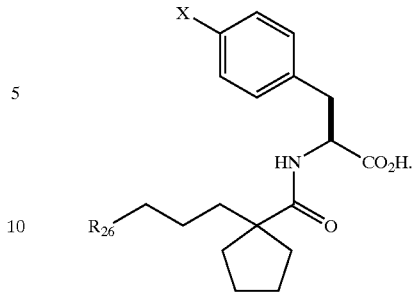

184. The compound of claim 183 wherein $R_{26}$ is lower alkyl sulfonyl, lower alkyl sulfinyl, lower alkylthio, azido, cyano, hydroxy, lower alkoxy, lower alkanoyl or lower alkanoylamino.
185. The compound of claim 184 wherein a is 0, $R_1$ is hydrogen and $R_{26}$ is lower alkylsulfonyl, lower alkylsulfinyl, lower alkylthio, cyano, lower alkanoyl or lower alkanoylamino.
186. The compound of claim 185 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.
187. The compound of claim 186 wherein $R_{15}$ and $R_{16}$ are halogen.
188. The compound of claim 187 wherein $R_{15}$ and $R_{16}$ are chloro.
189. The compound of claim 188 wherein $R_{15}$ and $R_{16}$ are o-chloro.
190. The compound of claim 189 having the formula:

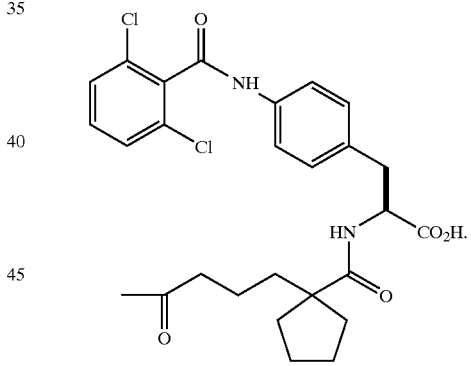

191. The compound of claim 189 having the formula:

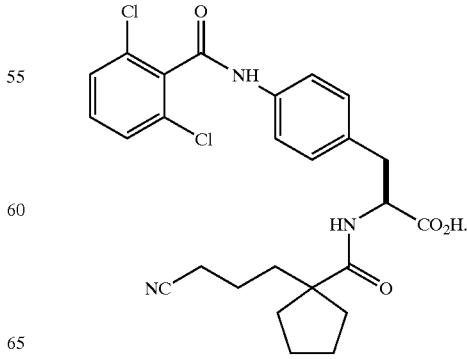

192. The compound of claim 189 having the formula:

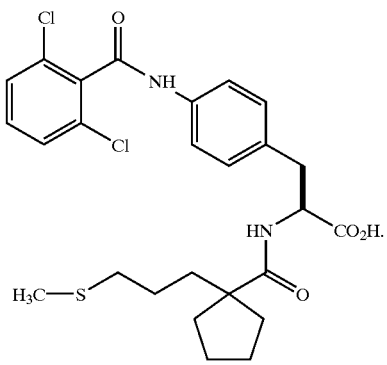

193. The compound of claim 189 having the formula:

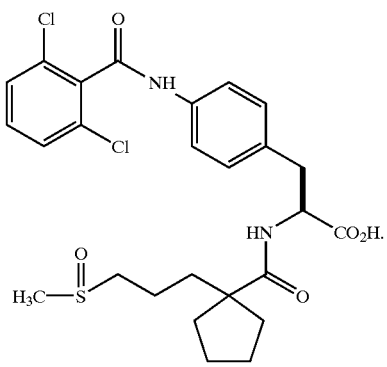

194. The compound of claim 189 having the formula:

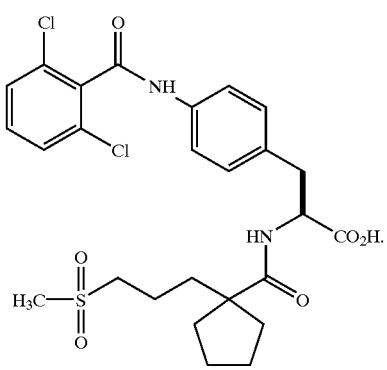

195. The compound of claim 16 wherein e is 4 whereby said compound is of the formula:

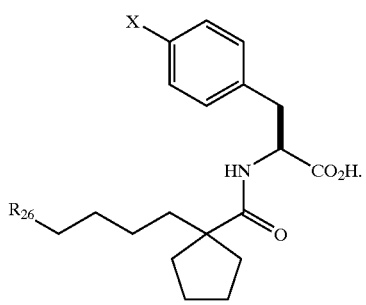

196. The compound of claim 195 wherein $R_{26}$ is lower alkyl sulfonyl, lower alkyl sulfinyl, lower alkylthio, azido, cyano, hydroxy, lower alkoxy, lower alkanoyl or lower alkanoylamino.

197. The compound of claim 196 wherein a is 0, $R_1$ is hydrogen and $R_{26}$ is lower alkylsulfonyl, lower alkylthio, azido, cyano, hydroxy, lower alkoxy or lower alkanoylamino.

198. The compound of claim 197 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

199. The compound of claim 198 wherein $R_{15}$ and $R_{16}$ are halogen.

200. The compound of claim 199 wherein $R_{15}$ and $R_{16}$ are chloro.

201. The compound of claim 200 wherein $R_{15}$ and $R_{16}$ are o-chloro.

202. The compound of claim 201 having the formula:

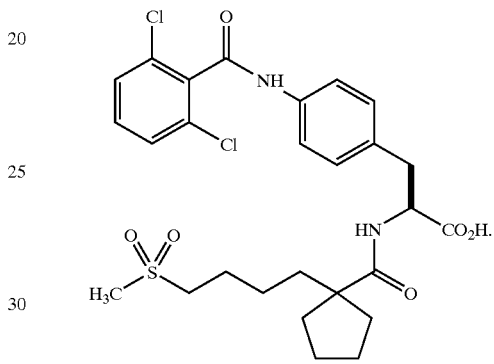

203. The compound of claim 201 having the formula:

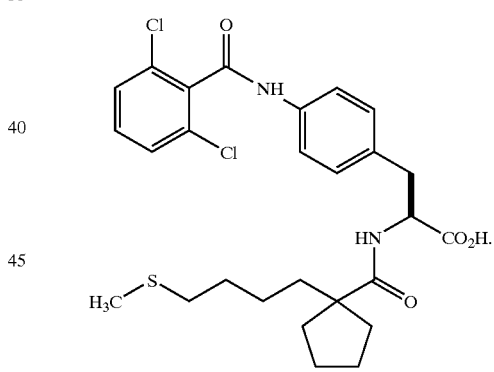

204. The compound of claim 201 having the formula:

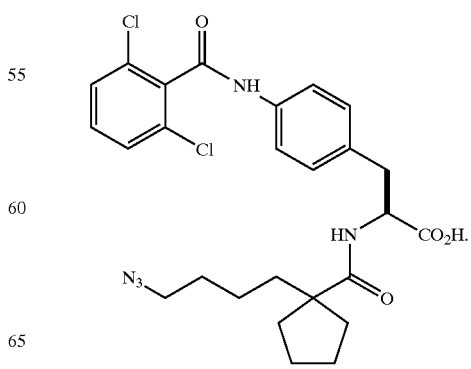

205. The compound of claim 201 having the formula:

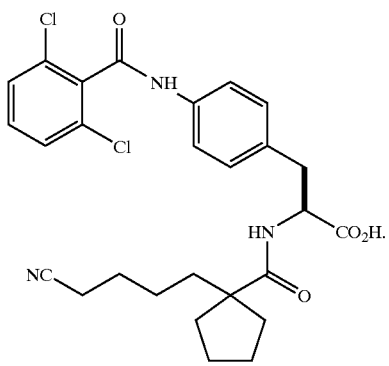

206. The compound of claim 201 having the formula:

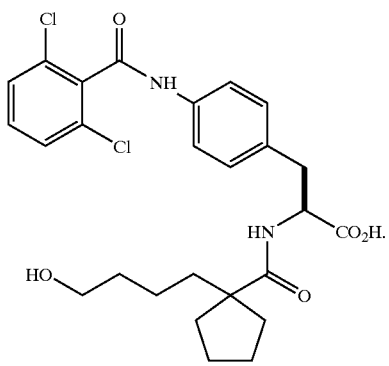

207. The compound of claim 201 having the formula:

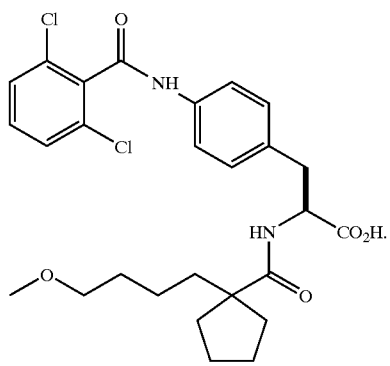

208. The compound of claim 201 having the formula:

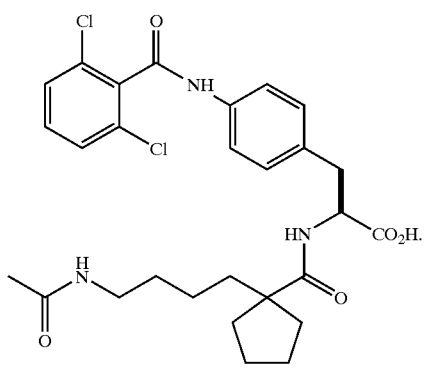

209. The compound of claim 3 wherein f is 1 whereby said compound is of the formula:

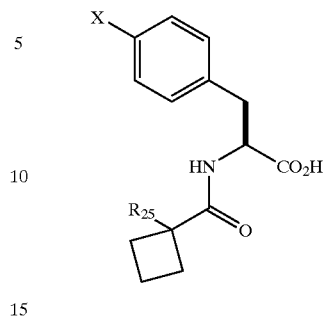

wherein $R_{25}$ is lower alkyl or a group of the formula $R_{26}$—$(CH_2)_e$— wherein $R_{26}$ and e are as in claim 1.

210. The compound of claim 209 wherein $R_{25}$ is a group of the formula $R_{26}$—$(CH_2)_e$—.

211. The compound of claim 210 wherein e is 1 whereby said compound is of the formula:

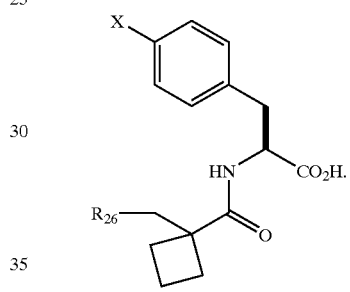

212. The compound of claim 211 wherein $R_{26}$ is lower alkoxy or aryl.

213. The compound of claim 212 wherein $R_{26}$ is methoxy or phenyl which is unsubstituted, mono-substituted by halogen, lower alkoxy, cyano or tetrazolyl which tetrazolyl is unsubstituted or monosubstituted by methyl, or disubstituted by lower alkoxy.

214. The compound of claim 213 wherein $R_{26}$ is phenyl which is monosubstituted by tetrazolyl which terazolyl is monosubstituted by methyl.

215. The compound of claim 214 wherein $R_{26}$ is of the formula:

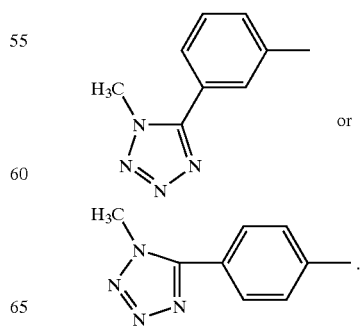

216. The compound of claim 215 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

217. The compound of claim 216 wherein $R_{15}$ and $R_{16}$ are halogen.

218. The compound of claim 217 wherein $R_{15}$ and $R_{16}$ are chloro.

219. The compound of claim 218 wherein $R_{15}$ and $R_{16}$ are o-chloro.

220. The compound of claim 219 wherein a is 0.

221. The compound of claim 220 having the formula:

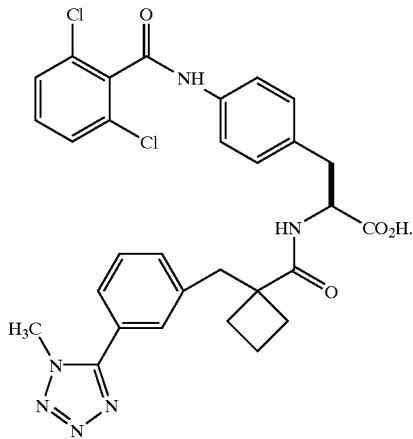

222. The compound of claim 220 having the formula:

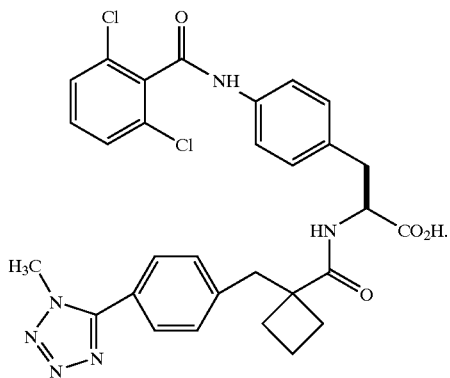

223. The compound of claim 3 wherein f is 3 and said compound is of the formula:

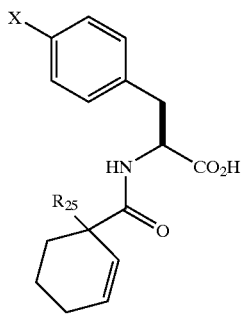

wherein $R_{25}$ and X are as in claim 1.

224. The compound of claim 223 wherein said compound is of the formula:

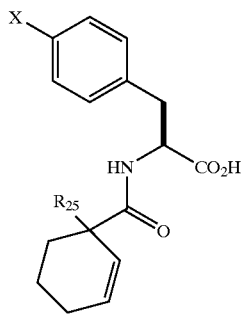

wherein $R_{25}$ and X are as in claim 1.

225. The compound of claim 223 wherein said compound is of the formula:

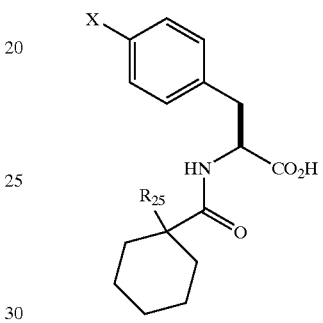

wherein $R_{25}$ and X are as in claim 1.

226. The compound of claim 225 wherein $R_{25}$ is lower alkyl.

227. The compound of claim 225 wherein $R_{25}$ is a group of the formula $R_{26}-(CH_2)_e-$ wherein $R_{26}$ and e are as in claim 1.

228. The compound of claim 227 wherein e is 0 whereby said compound is of the formula:

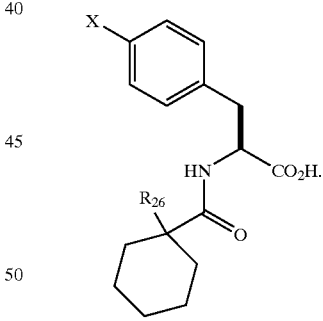

229. The compound of claim 228 wherein $R_{26}$ is lower alkoxy or aryl.

230. The compound of claim 229 wherein $R_{26}$ is methoxy, or is phenyl which is: 1) unsubstituted, 2) mono-substituted by halogen, lower alkoxy, cyano or tetrazolyl which tetrazolyl is unsubstituted or monosubstituted by methyl, or 3) disubstituted by lower alkoxy.

231. The compound of claim 230 wherein $R_{26}$ is phenyl which is unsubstituted or mono-substituted by lower alkoxy.

232. The compound of claim 231 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

233. The compound of claim 232 wherein $R_{15}$ and $R_{16}$ are halogen.

234. The compound of claim 233 wherein $R_{15}$ and $R_{16}$ are chloro.

235. The compound of claim 234 wherein $R_{15}$ and $R_{16}$ are o-chloro.

236. The compound of claim 235 wherein a is 0.

237. The compound of claim 236 having the formula:

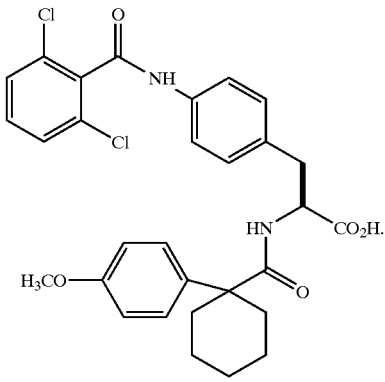

238. The compound of claim 232 wherein $R_{15}$ is halogen and $R_{16}$ is hydrogen, nitro, perfluoro lower alkyl, or lower alkyl.

239. The compound of claim 238 wherein $R_{15}$ is p-fluoro and $R_{16}$ is o-perfluoromethyl.

240. The compound of claim 239 wherein a is 0.

241. The compound of claim 240 having the formula:

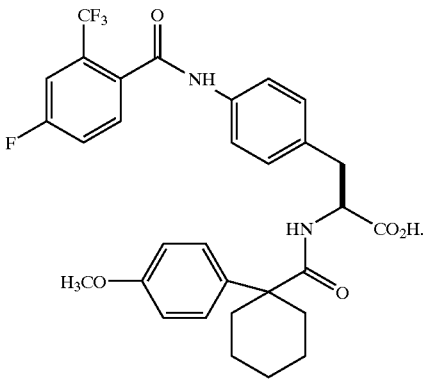

242. The compound of claim 232 wherein $R_{15}$ and $R_{16}$ are independently nitro, perfluoro lower alkyl, or lower alkyl.

243. The compound of claim 242 wherein $R_{15}$ is o-methyl and $R_{16}$ is p-nitro.

244. The compound of claim 243 wherein a is 0.

245. The compound of claim 244 having the formula:

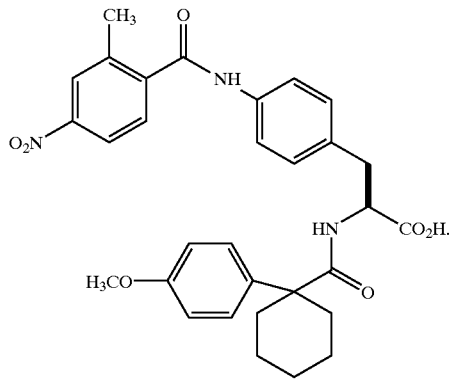

246. The compound of claim 227 wherein e is 1 whereby said compound is of the formula:

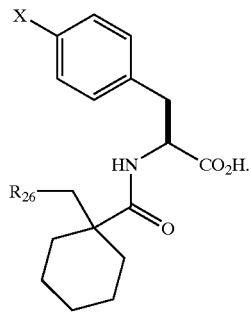

247. The compound of claim 246 wherein $R_{26}$ is lower alkoxy or aryl.

248. The compound of claim 247 wherein $R_{26}$ is methoxy, or is phenyl which is: 1) unsubstituted, 2) mono-substituted by halogen, lower alkoxy, cyano or tetrazolyl which tetrazolyl is unsubstituted or monosubstituted by methyl, or 3) disubstituted by lower alkoxy.

249. The compound of claim 248 wherein $R_{26}$ is phenyl which is unsubstituted or mono-substituted by lower alkoxy.

250. The compound of claim 249 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

251. The compound of claim 250 wherein $R_{15}$ and $R_{16}$ are halogen.

252. The compound of claim 251 wherein $R_{15}$ and $R_{16}$ are chloro.

253. The compound of claim 252 wherein $R_{15}$ and $R_{16}$ are o-chloro.

254. The compound of claim 253 wherein a is 0.

255. The compound of claim 254 having the formula:

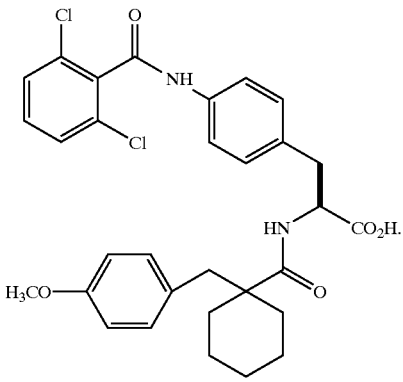

256. The compound of claim 248 wherein $R_{26}$ is phenyl monosubstituted by chloro or tetrazolyl, which tetrazolyl is unsubstituted or mono-substituted by methyl or cyano.

257. The compound of claim 256 wherein $R_{26}$ is phenyl monosubstituted by tetrazolyl, which tetrazolyl is unsubstituted or mono-substituted by methyl.

258. The compound of claim 257 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

259. The compound of claim 258 wherein $R_{15}$ and $R_{16}$ are halogen.

260. The compound of claim 259 wherein $R_{15}$ and $R_{16}$ are chloro.

261. The compound of claim 260 wherein $R_{15}$ and $R_{16}$ are o-chloro.

262. The compound of claim 261 wherein a is 0.

263. The compound of claim 262 having the formula:

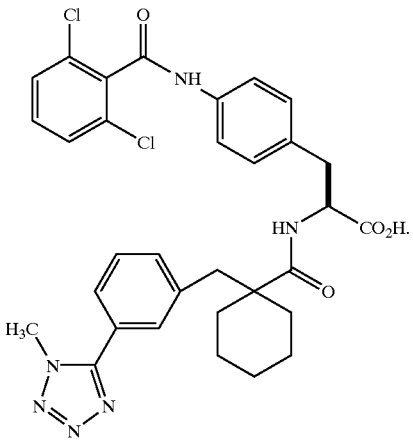

264. The compound of claim 1 having the formula:

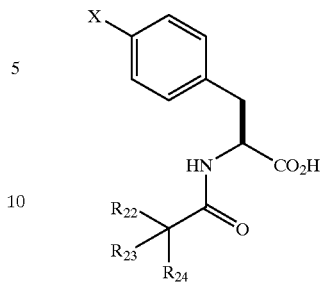

wherein X, $R_{22}$, $R_{23}$ and $R_{24}$ are as in claim 1.

265. The compound of claim 264 wherein $R_{22}$ and $R_{23}$ are independently unsubstituted phenyl or lower alkyl, and $R_{24}$ is hydrogen or unsubstituted lower alkyl or alkenyl.

266. The compound of claim 265 wherein $R_{22}$, $R_{23}$ and $R_{24}$ are lower alkyl.

267. The compound of claim 266 wherein $R_{15}$ and $R_{16}$ are independently hydrogen, halogen, nitro, cyano, perfluoro lower alkyl, or lower alkyl, or $R_{15}$ is phenoxy and $R_{16}$ is hydrogen.

268. The compound of claim 267 wherein $R_{15}$ and $R_{16}$ are halogen.

269. The compound of claim 268 wherein $R_{15}$ and $R_{16}$ are chloro.

270. The compound of claim 269 wherein $R_{15}$ and $R_{16}$ are o-chloro.

271. The compound of claim 270 wherein a is 0.

272. The compound of claim 271 wherein $R_{22}$ is methyl, $R_{23}$ is ethyl and $R_{24}$ is n-butyl.

273. The compound of claim 272 having the formula:

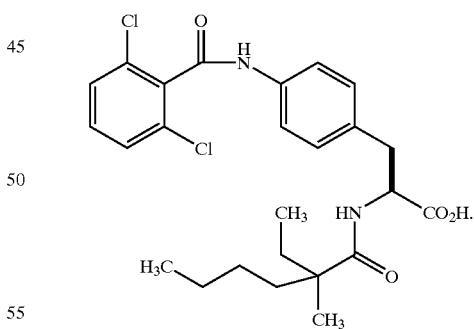

274. The compound of claim 267 wherein $R_{15}$ is lower alkyl and $R_{16}$ is nitro.

275. The compound of claim 274 wherein $R_{15}$ iso-methyl and $R_{16}$ is m-nitro.

276. The compound of claim 275 wherein a is 0.

277. The compound of claim 276 wherein $R_{22}$ is methyl, $R_{23}$ is ethyl and $R_{24}$ is n-butyl.

278. The compound of claim 277 having the formula:

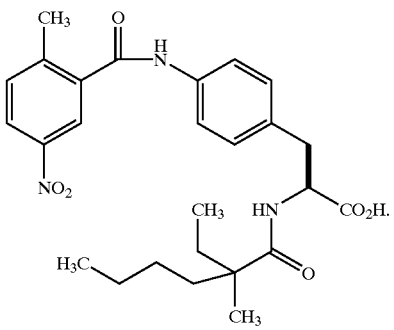

279. The compound of claim 267 wherein $R_{15}$ is perfluoro and $R_{16}$ is fluoro.

280. The compound of claim 279 wherein $R_{15}$ is p-fluoro and $R_{16}$ is o-perfluoromethyl.

281. The compound of claim 280 wherein a is 0.

282. The compound of claim 281 wherein $R_{22}$ is methyl, $R_{23}$ is ethyl and $R_{24}$ is n-butyl.

283. The compound of claim 282 having the formula:

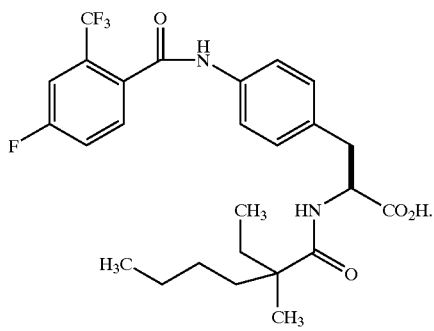

284. The compound of claim 265 wherein $R_{22}$ is unsubstituted phenyl, $R_{23}$ is lower alkyl and $R_{24}$ is hydrogen.

285. The compound of claim 265 wherein $R_{22}$ and $R_{23}$ are unsubstituted phenyl and $R_{24}$ is hydrogen.

286. The compound of claim 1 which is an ester of the formula:

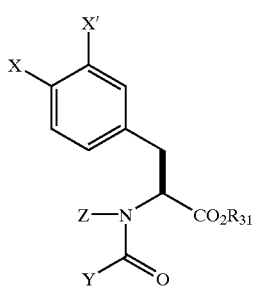

wherein:
$R_{31}$ is lower alkyl; or
$R_{31}$ a group of formula:

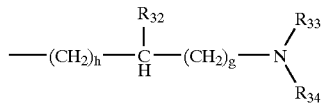

P-1 wherein:
$R_{32}$ is hydrogen or lower alkyl,
$R_{33}$ is hydrogen, lower alkyl, or aryl,
$R_{34}$ is hydrogen or lower alkyl,
h is an integer from 0 to 2,
g is an integer from 0 to 2, and
the sum of h and g is 1 to 3; or
$R_{31}$ is a group of formula:

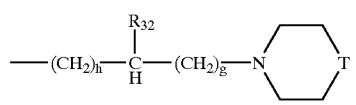

P-2 wherein:
$R_{32}$, g, and h are as above for P-1,
T is O, S, —(CH$_2$)$_j$—, a group of the formula N—$R_{35}$, or when j=0, a bond,
$R_{33}$ is hydrogen, lower alkyl, lower alkanoyl, or lower alkoxycarbonyl, and
j is 0, 1 or 2
and wherein X, X' Y and Z are as in claim 1.

287. The compound of claim 286 having the formula:

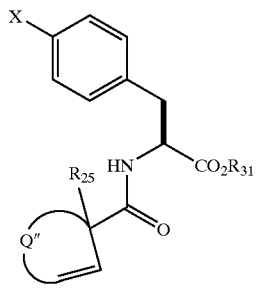

wherein Q" is unsubstituted or lower alkyl substituted —(CH$_2$)$_f$—, f is 1, 2 or 3, and X and $R_{25}$ are as in claim 1.

288. The compound of claim 287 having the formula:

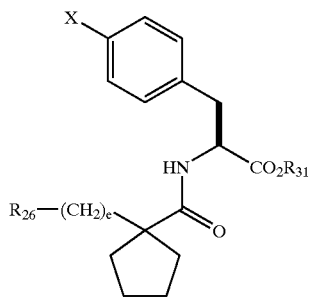

wherein X, $R_{26}$ and e are as in claim 1.

289. The compound of claim 288 wherein e is 4 whereby said compound is of the formula:

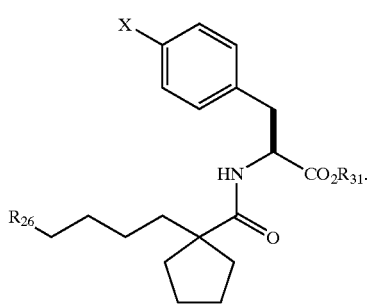

290. The compound of claim 289 wherein $R_{26}$ is lower alkyl sulfonyl, lower alkyl thio, lower alkyl sulfinyl, lower alkylthio, azido, cyano, hydroxy, lower alkoxy, lower alkanoyl or lower alkanoylamino.

291. The compound of claim 290 wherein a is 0, $R_1$ is hydrogen, $R_{26}$ is lower alkyl sulfonyl or lower alkoxy and $R_{15}$ and $R_{16}$ are o-chloro.

292. The compound of claim 291 wherein $R_{31}$ is ethyl, 2-(N,N-diethylamino)ethyl or 2-(4-morpholinyl) ethyl.

293. The compound of claim 292 having the formula:

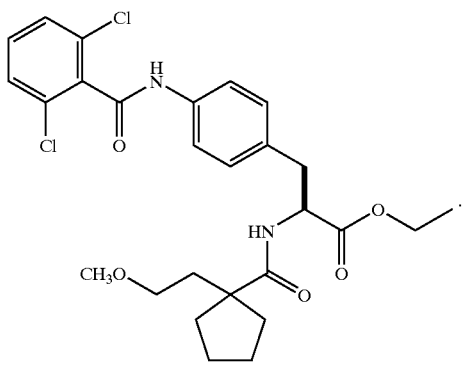

294. The compound of claim 292 having the formula:

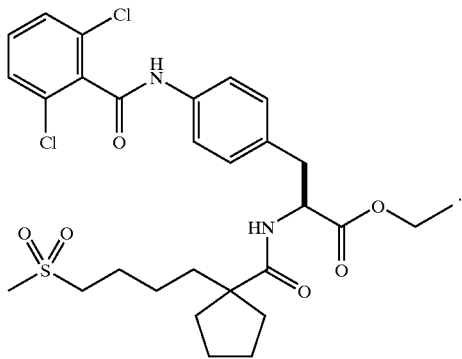

295. The compound of claim 292 having the formula:

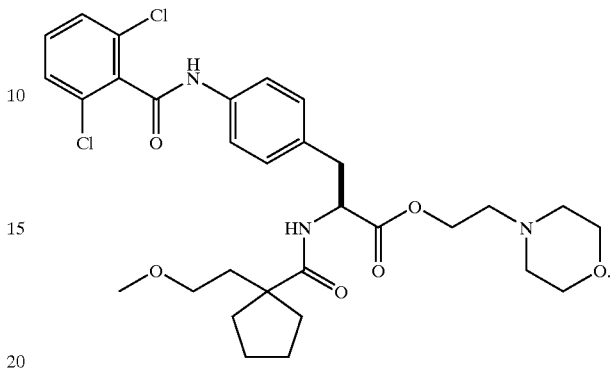

296. The compound of claim 292 having the formula:

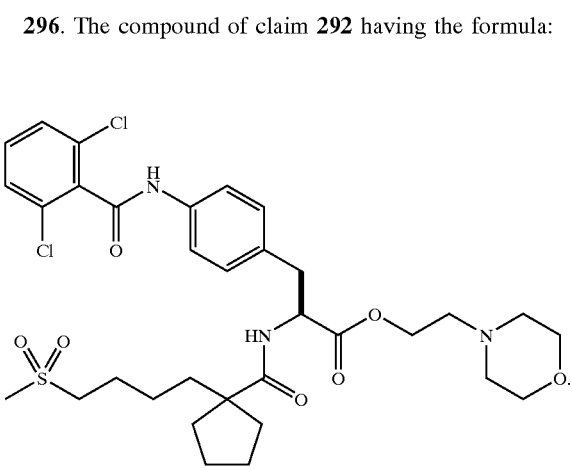

297. The compound of claim 292 having the formula:

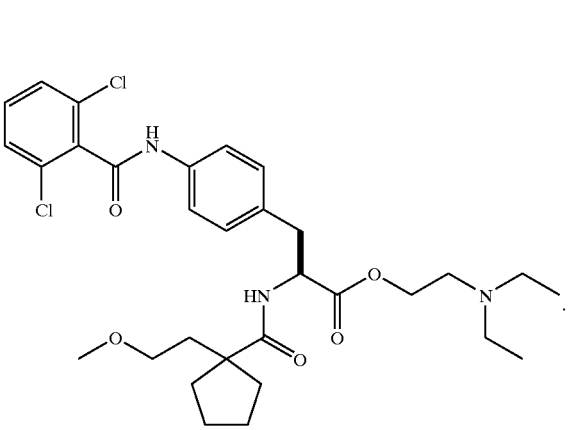

298. The compound of claim 290 wherein $R_{18}$ is phenyl wherein the phenyl ring is unsubstituted or monosubstituted by halogen, or phenyl lower alkyl, $R_{19}$ is lower alkyl, which is unsubstituted or substituted by pyridyl or phenyl wherein the phenyl ring is unsubstituted or monosubstituted by lower alkoxy or halogen, and $R_{20}$ is lower alkanoyl.

299. The compound of claim 298 wherein $R_{26}$ is lower alkyl sulfonyl or lower alkoxy.

300. The compound of claim 299 wherein $R_{31}$ is ethyl, 2-(N,N-diethylamino)ethyl or 2-(4-morpholinyl)ethyl.

301. The compound of claim 1 wherein Z is lower alkyl.

302. The compound of claim 301 having the formula:

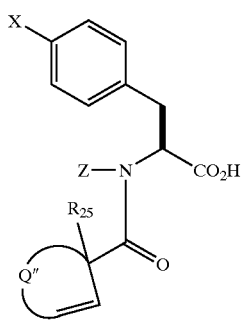

wherein Q''' is unsubstituted or lower alkyl substituted —$(CH_2)_f$—, f is 1, 2 or 3, and X and $R_{25}$ are as in claim 1.

303. The compound of claim 302 having the formula:

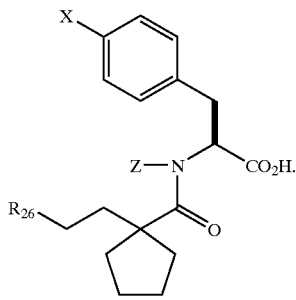

304. The compound of claim 303 wherein a is 0, $R_1$ is hydrogen and $R_{26}$ is lower alkyl sulfonyl or lower alkoxy.

305. The compound of claim 304 having the formula:

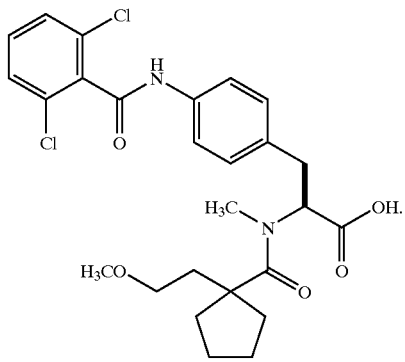

* * * * *

UNITED STATES PATENT AND TRADEMARK OFFICE
CERTIFICATE OF CORRECTION

PATENT NO. : 6,806,365 B2
DATED : October 19, 2004
INVENTOR(S) : Li Chen et al.

It is certified that error appears in the above-identified patent and that said Letters Patent is hereby corrected as shown below:

Title page,
Item [54], Title, "N-ALKANOYLPHENYLALAMINE DERIVATIVES" should be
-- N-ALKANOYLPHENYLALANINE DERIVATIVES --
Item [73], Assignee, "Hoffmann-La Rocher Inc...." should be -- Hoffmann-La Roche Inc.... --

Column 312,
Line 17, "...where $R_{28}$ and are as in claim 1." should be -- ...where $R_{28}$ and $R_{29}$ are as in claim 1. --
Line 20, "...wherein $R_{23}$ and $R_{29}$ are..." should be -- ...wherein $R_{28}$ and $R_{29}$ are... --

Column 336,
Line 62, "...wherein $R_{15}$ iso-methyl..." should be -- ...wherein $R_{15}$ is o-methyl... --

Signed and Sealed this

Twenty-second Day of February, 2005

JON W. DUDAS
*Director of the United States Patent and Trademark Office*